United States Patent
Gregg

(10) Patent No.: US 9,931,362 B2
(45) Date of Patent: Apr. 3, 2018

(54) COMPOSITION FOR CONTROLLING FISH

(71) Applicant: Kenneth William Gregg, Atlanta, GA (US)

(72) Inventor: Kenneth William Gregg, Atlanta, GA (US)

(73) Assignee: Kenneth William Gregg, Atlanta, GA (US)

( * ) Notice: Subject to any disclaimer, the term of this patent is extended or adjusted under 35 U.S.C. 154(b) by 169 days.

(21) Appl. No.: 14/729,814

(22) Filed: Jun. 3, 2015

(65) Prior Publication Data

US 2015/0265659 A1    Sep. 24, 2015

Related U.S. Application Data

(63) Continuation of application No. 12/718,506, filed on Mar. 5, 2010, now Pat. No. 9,078,458.

(60) Provisional application No. 61/158,121, filed on Mar. 6, 2009.

(51) Int. Cl.
| | | |
|---|---|---|
| *A01N 63/02* | (2006.01) | |
| *A61K 35/74* | (2015.01) | |
| *A61K 49/00* | (2006.01) | |
| *C12N 1/20* | (2006.01) | |
| *A23K 40/30* | (2016.01) | |
| *A23K 10/18* | (2016.01) | |
| *A23K 50/80* | (2016.01) | |

(52) U.S. Cl.
CPC .............. *A61K 35/74* (2013.01); *A23K 10/18* (2016.05); *A23K 40/30* (2016.05); *A23K 50/80* (2016.05); *A61K 49/0004* (2013.01); *C12N 1/20* (2013.01)

(58) Field of Classification Search
CPC ........ A23K 50/80; A23K 10/18; A23K 10/16; A61K 49/0004
See application file for complete search history.

(56) References Cited

PUBLICATIONS

Beveridge et al. "The ingestion of bacteria in suspension by common carp Cyprinus carpio L.". Journal of Fish Biology. 1991. 39, pp. 8125-8831.*
ATCC catalogue. ATCC Bacteria and Bacteriophages. 19th edition, 1996, p. 90.*
Simidu et al. "An improved medium for isolation of bacteria from marine fish". J Gen Microbiol 1968, 52, 355-360.*
Cahil, M. M. "Bacterial Flora of Fishes: a Review". Microb Ecol 1990, 19: 21-41.*

* cited by examiner

*Primary Examiner* — Vera Afremova
(74) *Attorney, Agent, or Firm* — Judy Jarecki-Black; Chad Kitchen; Merial Inc.

(57) ABSTRACT

The present invention relates to a composition for controlling fish. In particular, the composition may be an incitant, functioning as either a fish attractant or a fish repellent. The composition may be prepared by extracting bacteria from a source fish, culturing the bacteria in an appropriate media, and subsequently combining the cultured bacteria with a substrate to form the composition.

16 Claims, 11 Drawing Sheets

Figure 9

Figure 1:
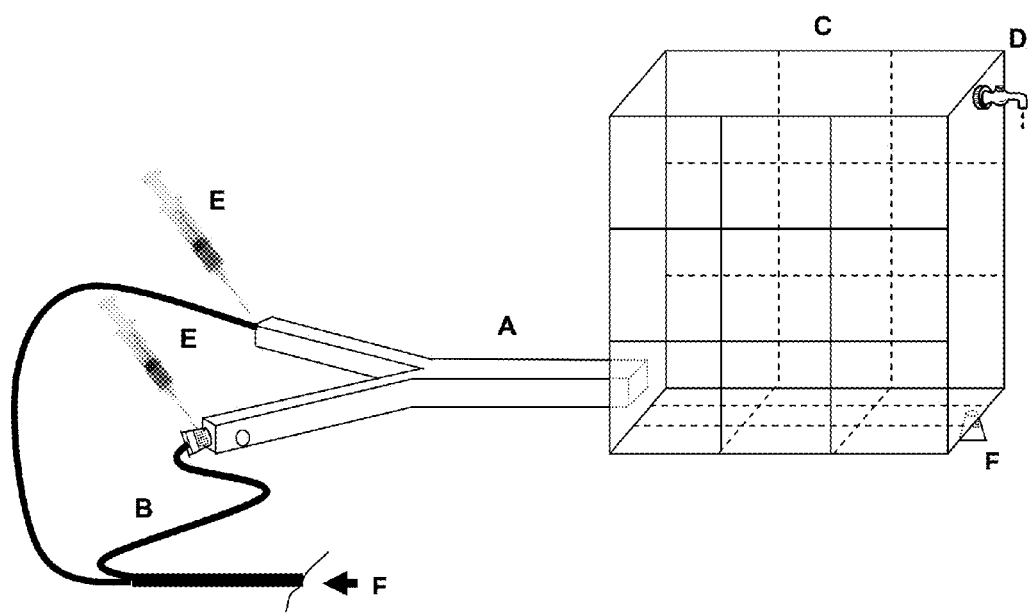

| SEQ ID NO | DNA/PRT | Description |
|---|---|---|
| 1 | DNA | Br1-1-10-27F_E10.ab1 |
| 2 | DNA | Br1-1-11-27F_E11.ab1 |
| 3 | DNA | Br1-1-12-27F_E12.ab1 |
| 4 | DNA | Br1-1-1-27F_E01.ab1 |
| 5 | DNA | Br1-1-13-27F_F01.ab1 |
| 6 | DNA | Br1-1-14-27F_F02.ab1 |
| 7 | DNA | Br1-1-15-27F_F03.ab1 |
| 8 | DNA | Br1-1-16-27F_F04.ab1 |
| 9 | DNA | Br1-1-17-27F_F05.ab1 |
| 10 | DNA | Br1-1-18-27F_F06.ab1 |
| 11 | DNA | Br1-1-19-27F_F07.ab1 |
| 12 | DNA | Br1-1-20-27F_F08.ab1 |
| 13 | DNA | Br1-1-22-27F_F10.ab1 |
| 14 | DNA | Br1-1-2-27F_E02.ab1 |
| 15 | DNA | Br1-1-23-27F_F11.ab1 |
| 16 | DNA | Br1-1-24-27F_F12.ab1 |
| 17 | DNA | Br1-1-3-27F_E03.ab1 |
| 18 | DNA | Br1-1-4-27F_E04.ab1 |
| 19 | DNA | Br1-1-5-27F_E05.ab1 |
| 20 | DNA | Br1-1-6-27F_E06.ab1 |
| 21 | DNA | Br1-1-7-27F_E07.ab1 |
| 22 | DNA | Br1-1-8-27F_E08.ab1 |
| 23 | DNA | Br1-1-9-27F_E09.ab1 |
| 24 | DNA | FM-1-10-27F_G03.ab1 |
| 25 | DNA | FM-1-11-27F_G04.ab1 |
| 26 | DNA | FM1-1-1-27F_F06.ab1 |
| 27 | DNA | FM-1-12-27F_G05.ab1 |
| 28 | DNA | FM1-1-2-27F_F07.ab1 |
| 29 | DNA | FM-1-13-27F_G06.ab1 |
| 30 | DNA | FM1-1-3-27F_F08.ab1 |
| 31 | DNA | FM-1-14-27F_G07.ab1 |
| 32 | DNA | FM1-1-4-27F_F09.ab1 |
| 33 | DNA | FM-1-15-27F_G08.ab1 |
| 34 | DNA | FM1-1-6-27F_F11.ab1 |
| 35 | DNA | FM1-1-7-27F_F12.ab1 |
| 36 | DNA | FM-1-8-27F_G01.ab1 |
| 37 | DNA | FM-1-9-27F_G02.ab1 |
| 38 | DNA | Gam1-1-10-27F_C10.ab1 |
| 39 | DNA | Gam1-1-11-27F_C11.ab1 |
| 40 | DNA | Gam1-1-12-27F_C12.ab1 |
| 41 | DNA | Gam1-1-1-27F_C01.ab1 |

Figure 9 (Continued)

| SEQ ID NO | DNA/PRT | Description |
|---|---|---|
| 42 | DNA | Gam1-1-13-27F_G06.ab1 |
| 43 | DNA | Gam1-1-15-27F_G08.ab1 |
| 44 | DNA | Gam1-1-16-27F_G09.ab1 |
| 45 | DNA | Gam1-1-17-27F_G10.ab1 |
| 46 | DNA | Gam1-1-18-27F_G11.ab1 |
| 47 | DNA | Gam1-1-19-27F_G02.ab1 |
| 48 | DNA | Gam1-1-20-27F_H01.ab1 |
| 49 | DNA | Gam1-1-21-27F_H02.ab1 |
| 50 | DNA | Gam1-1-22-27F_H03.ab1 |
| 51 | DNA | Gam1-1-2-27F_C02.ab1 |
| 52 | DNA | Gam1-1-24-27F_H05.ab1 |
| 53 | DNA | Gam1-1-25-27F_H06.ab1 |
| 54 | DNA | Gam1-1-26-27F_H07.ab1 |
| 55 | DNA | Gam1-1-27-27F_H08.ab1 |
| 56 | DNA | Gam1-1-28-27F_H09.ab1 |
| 57 | DNA | Gam1-1-29-27F_H10.ab1 |
| 58 | DNA | Gam1-1-30-27F_H11.ab1 |
| 59 | DNA | Gam1-1-32-27F_B01.ab1 |
| 60 | DNA | Gam1-1-3-27F_H02.ab1 |
| 61 | DNA | Gam1-1-33-27F_B02.ab1 |
| 62 | DNA | Gam1-1-35-27F_B04.ab1 |
| 63 | DNA | Gam1-1-36-27F_B05.ab1 |
| 64 | DNA | Gam1-1-37-27F_B06.ab1 |
| 65 | DNA | Gam1-1-38-27F_B07.ab1 |
| 66 | DNA | Gam1-1-39-27F_B08.ab1 |
| 67 | DNA | Gam1-1-40-27F_B09.ab1 |
| 68 | DNA | Gam1-1-4-27F_C04.ab1 |
| 69 | DNA | Gam1-1-5-27F_C05.ab1 |
| 70 | DNA | Gam1-1-6-27F_C06.ab1 |
| 71 | DNA | Gam1-1-7-27F_C07.ab1 |
| 72 | DNA | Gam1-1-8-27F_C08.ab1 |
| 73 | DNA | Gam1-1-9-27F_C09.ab1 |
| 74 | DNA | Gam1-1-41-27F_B10.ab1 |
| 75 | DNA | Gam1-1-42-27F_B11.ab1 |
| 76 | DNA | Gam1-1-43-27F_B12.ab1 |
| 77 | DNA | GS1-1-1-27F_H01.ab1 |
| 78 | DNA | GS1-1-2-27F_H02.ab1 |
| 79 | DNA | GS1-1-3-27F_H03.ab1 |
| 80 | DNA | GS1-1-4-27F_H04.ab1 |
| 81 | DNA | GS1-1-5-27F_H05.ab1 |

COMPOSITION FOR CONTROLLING FISH

CROSS-REFERENCE TO RELATED APPLICATIONS

This application is a continuation of, and claims priority to, U.S. application Ser. No. 12/718,506, filed on Mar. 5, 2010, which claims benefit of U.S. provisional application Ser. No. 61/158,121 filed Mar. 6, 2009.

FIELD OF THE INVENTION

The present invention is based on the development of a technology related to controlling the behavior of non-plant aquatic life. In particular, the technology may be used as an incitant to modify the feeding activities of fish. The present invention provides bacterial preparations that may be used to alter the feeding propensity of fish. The preparations may be useful for enhancing and or altering the diet preference of fish. The invention may include compositions that act as feeding incitants.

BACKGROUND OF THE INVENTION

Compositions for modifying fish behavior are well known in the art. Typically, such compositions include a liquid or particulate odor and/or taste or light attractant dispersed within a carrier material (see for example U.S. Pat. Nos. 5,097,616 and 5,393,537). Commonly used attractants include fish oils such as cod oil, herring oil, and salmon oil; extracts of various fishes and fish by-products including particulate fish parts; extracts and residues of earthworms; grubs and insects; anise oil; certain amino acids; fish egg extract; fish meal homogenate; morpholine; mineral oil; fragrances; fish scent; garlic oil; and extracts from shrimp, crabs, clams or artificial equivalents. Steroidal hormones have also been demonstrated to influence feeding behavior in fish (U.S. Pat. No. 7,335,349). Further, peptides, free amino acids, carbohydrates, organic nitrogen bases, nucleotides and nucleosides, and fatty acids may all be chemical cues/signals capable of eliciting and regulating behaviors of animals in aquatic environments (Zimmer 2008, Howe and Sheikh 1975; Pawlik 1992; Painter et al. 1998; Krug and Manzi 1999; Hardege et al. 2004; Cummins et al. 2005; Kicklighter et al. 2007).

Much research has been performed on coating compositions used as odor/taste attractants. For example, new forms of fish attracting compositions are disclosed in Meyers, U.S. Pat. No. 4,505,936, relating to an odor/taste attractant formed from shellfish waste and processed with certain additives, which prevent spoilage of the attractant; Valentincic, U.S. Pat. No. 5,185,164 relates to a catfish bait composition having at least one of a selected group of isolated amino acids; and Rittschof, U.S. Pat. No. 4,704,286 disclosing an attractant made of ground fish and certain other additives, which encourage a fish not to release bait once it has bitten it.

In addition, certain types of bacteria have been used with differing bait compositions. For instance, Ott, U.S. Pat. No. 4,369,176 relates to an insect bait composition that includes spore-producing bacteria of the genera *Bacillus*, selected because the bacterium secrets enzymes that ferment exogenous sugars yielding metabolic byproducts with insect-attractant values. Moreover, Asai, U.S. Pat. No. 4,202,905, attracts fish using luminous bait comprising a light producing bacteria.

Although many differing compositions have previously been used in attempts to attract fish, the specific use of bacteria related to or corresponding to a natural fish taste or smell has not previously been described or proposed. In addition, there is a growing need for a composition that controls specific species of fish with respect to specific dietary requirements (Naylor, Goldburg et al. 2000). Farming of carnivore/predator fishes places additional demands on the source of fish meal (e.g. marine feeder fish), and so a composition that could specifically incite feeding behavior in fishes, even in the absence of the preferred feeder fish, would be highly desirable. The present invention addresses this unmet need by providing compositions and methods to incite feeding behavior in fishes even when the preferred feeder fish is not present, either in whole or in part (i.e. fish homogenates, extracts, and the like).

Citation or identification of any document in this application is not admission that such document is available as prior art to the present invention.

SUMMARY OF THE INVENTION

The present invention relates to methods for obtaining bacteria from source aquatic animals and to methods of using said bacteria to elicit specific behaviors in target aquatic animals. Bacteria obtained according to said methods are specifically associated with, and released by, the source aquatic animals, and are responsible for the behaviors exhibited by the target aquatic animals in response to the presence of the source aquatic animals. The behavior-eliciting bacteria tend to be distinct from the bacteria commonly found in the surrounding water. The present invention further relates to behavior-eliciting compositions comprising said behavior-eliciting bacteria, which can be used to control aquatic non-plant life, including fish, crustaceans, larvae (hereinafter collectively referred to as fish), avians, and marine mammals. More particularly, the present invention provides compositions that can be incitants and/or attractants and/or repellents for fish, avians, and marine mammals depending upon the target species of fish, avian, and marine mammal and upon the composition used.

The present invention further relates to a method for preparing the behavior-eliciting compositions. The method may comprise extracting behavior-eliciting bacteria from a source fish, culturing the bacteria, then adding an effective amount of the bacteria to a substrate or carrier to produce the compositions. The compositions may comprise bacteria and may be used to modify the behavior of fish, avians, or marine mammals. Both live and inactivated bacteria may be used to produce the behavior-eliciting compositions. The bacteria may be prepared according to the methods disclosed herein, which includes the steps of extracting said bacteria from a source fish and culturing them in a suitable medium. The bacteria may be obtained from Fat Head Minnows (FHM) and be used to elicit feeding behavior in Largemouth Bass. The behavior-eliciting bacteria obtained from several common, commercially relevant source fish include those of the family Aeromonadaceae, Comamonadaceae, Enterobacteriaceae, and Moraxcellaceae, and of the genus *Acinetobacter, Aeromonas, Acidovorax*, and *Enterobacter*, though it will be obvious to those of ordinary skill in the art that the methods according to the present invention can be used to obtain and identify behavior-eliciting bacteria from any number of different source fish varieties. Any behavior-eliciting composition prepared according to the methods disclosed herein may be within the scope of the present invention.

The specific strain of the bacteria produced, such as the specific strain of *Acidovorax*, may be dependent on the type of fish from which the bacteria is extracted. Now that the methods and compositions of the present invention have been disclosed in great detail, an ordinarily skilled person or team will find it obvious to identify bacteria that may incite very specific feeding responses in specific target fish, avians, or marine mammals. For example, specific fish or feeder fish may be associated with specific strains of bacteria, and said strains may be responsible for the feeding behavior exhibited by a carnivore/predator fish, avian, or marine mammal. The extracted bacteria may be cultured in a dark environment in a minimal medium. The minimal medium may comprise organic compounds having carbon sources that may be simple and clearly defined.

Still another feature of the present invention may be that different bacterial strains may be selected based upon their ability to elicit different behavioral responses in fish, avians, or marine mammals. For example, the selected bacterial strain may either elicit feeding or avoidance behavior in a species of fish, avian, or marine mammal. Thus, the present invention provides for compositions that may be applied to artificial baits and/or incorporated into food to elicit feeding behavior in game fish, avians, or marine mammals. It will be immediately appreciated by a skilled person that with the appropriate selection of a source/feeder fish, the compositions according to the present invention may be used as a shark repellant. In addition, the compositions can be introduced into paint, and a composition-painted surface (for example, the hull of a boat or ship) may protect a boat, ship, or other vessel from, for example, barnacle attachment. Composition-painted surfaces could also cause marine mammals to avoid boats, ships or other vessels, thereby reducing injury to said mammals. In addition, the present compositions may be used to relocate spawning grounds or to alter migratory patterns.

To summarize, the present application fully discloses and describes an invention which addresses significant and long-felt needs, particularly in the field of aquaculture. Compositions according to the present application may be used to reduce or even eliminate the use of fish meal to feed fish, which addresses regulatory agency concerns of depleting wild small/feeder fish populations. The compositions may also reduce the cost of fish feed by encouraging fish to feed upon inexpensive, high quality protein sources which the fish would normally avoid due to lack of appropriate odor/taste signals. The compositions may reduce early stage mortality and optimize early stage growth, which would increase the profitability of aquaculture/farming. The compositions may also enable the farming of fish that normally would only eat "live" feed, thus producing new market opportunities. And finally, but not exhaustively, because the behavior-eliciting compositions comprise bacteria which are derived from fish already found in nature, environmental concerns are kept to a minimum, and organic labeling of fish fed the compositions should be fully supported.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Other features and advantages of the present invention will be apparent to those skilled in the art from a careful reading of the Detailed Description of a Preferred Embodiment presented below.

BRIEF DESCRIPTION OF THE DRAWINGS

The following detailed description, given by way of examples, but not intended to limit the invention solely to the specific embodiments described, may best be understood in conjunction with the accompanying drawings, in which:

FIG. 1 is a diagram of the test chamber used to quantify fish response to introduced stimuli: A=Y-shaped inflow channel; B=plastic tubing leading from water source; C=chamber with grid lines; D=drain/overflow port; E=hypodermic syringe; F=drain plug;

FIG. 2 is a graph depicting the movements of hungry largemouth bass in response to fathead minnow odor/taste;

FIG. 3 is a graph illustrating the movements of recently fed largemouth bass in response to fathead minnow odor/taste;

FIG. 4 is a graph illustrating the percent weight gain of hybrid striped bass fingerlings on four diets (TC) Trout Chow; (C) a 40/60 Trout Chow-casein mixture; (K1) Trout Chow-casein mixture coated with a low level of the behavior-eliciting composition; and (K2) Trout Chow-casein mixture coated with a high level of the present composition;

FIG. 5 is a graph illustrating the percent weight gain (g) of hybrid striped bass fingerlings in three diets: (C) casein; (C1) casein coated with a low level of the behavior-eliciting composition; and (C2) casein coated with a high level of the present composition;

FIG. 6 is a graph illustrating the percent weight gain of hybrid striped bass fingerlings on three diets: (P) and uncoated poultry diet; (P1) a poultry diet coated with low level of the present composition; and (P2) a poultry diet coated with a high level of the behavior-eliciting composition;

FIG. 7 is a graph illustrating the percent weight gain of hybrid striped bass fry after 17 days of feeding on three diets: (C) a casein diet; (C1) casein coated with a low level of the present composition containing fathead minnow bacteria; and (C2) casein coated with a high level of the present composition containing fathead minnow bacteria;

FIG. 8 is a graph illustrating the percent weight gain of the same hybrid striped bass fry as shown in FIG. 6, but weights shown are after 28 days of feeding the three diets: (C) a casein diet; (C1) casein coated with a low level of the present composition containing fathead minnow bacteria; (C2) casein coated with a high level of the present composition containing fathead minnow bacteria;

FIG. 9 is a listing of the SEQ ID NOs present in the sequence listing;

FIG. 10 is an EM photomicrograph of fish food coated with compositions according to the present invention.

DETAILED DESCRIPTION OF THE INVENTION

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicate otherwise.

Fish in general have sensitive chemoreceptors that contribute to their feeding and social behavior (Fisknes and Doving 1982; Hara 1992). In addition, different types of fish release distinct odor/taste to their surrounding waters. The distinctive odor/taste released by fish induce different responses in other nearby fish (Reutter, Boudriot et al. 2000). For example, the odor/taste of a minnow elicits a different response from surrounding fish than does that of a bass. Therefore, when a bass senses the stimulating odor/taste of a minnow, the bass will exhibit a predatory response, darting at the source of the odor/taste. In comparison, when a minnow senses the odor/taste released by a bass, the minnow responds with a fright response. The present invention is founded upon these responses to incitant stimuli i.e. odor/taste to control fish avians, or marine mammals.

In an embodiment of the present invention, certain bacteria determined to be associated with a given fish species are responsible for a distinctive odor/taste of that fish. Furthermore, such a distinctive odor/taste is normally released into the natural habitat of said fish. Upon isolation and presentation to fish, the olfactory and/or taste stimulating bacteria have been shown to affect the behavior of fish. These naturally occurring bacteria elicit responses depending on the bacterium used as the source odor/taste, and the species of the fish, avians, or marine mammal sensing the odor/taste. For example, introduction of certain bacterial strains into an environment causes a rapid, overt feeding reaction in one species of fish, while causing the opposite reaction (such as an escape reaction) in another species of fish. As expected, a fish exposed to an odor/taste of potential prey exhibit characteristic feeding behavior whereas a fish exposed to the odor/taste of a potential predator fish are repelled by the odor/taste.

As used herein, a "source fish" is hereby defined as a fish from which the bacteria are extracted. A source fish is customarily chosen because of the response it elicits from a second fish, avian, or marine mammal species. The "second species" hereby defined as the target (fish, avian, or marine mammal) is a species in which a desired response is elicited. For example, the target is the species of fish, avian, or marine mammal that is subject to incitant activity, i.e. the target is incited by the bacterial composition to exhibit either feeding or avoidance behavior. When water is used as a carrier, a mixture in the form of a suspension is formed with the bacteria. The concentration of the bacteria in the mixture is preferably at least approximately $1\times10^{12}$ bacteria per milliliter of water. This mixture can then be used, for example, to spray coat low-cost high quality protein sources to make said protein attractive to carnivore/predator fish.

It is believed that the bacteria responsible for the signal sent to carnivore/predator fish, whether it is smell, taste or both, may be largely of the genera *Acinetobacter, Aeromonas, Acidovorax*, and *Enterobacter*. The Fat Head Minnow (FHM) source fish were determined to largely harbor bacteria of the genus *Acidovorax*, though other behavior-eliciting bacteria may be associated with FHM. The data indicates that the carnivore/predator fish sense the odor/taste of these bacteria. The present invention suggests that different fish species harbor inherently different strains of *Acinetobacter, Aeromonas, Acidovorax*, and *Enterobacter* that emit different odors or tastes or signals from one another. Therefore, the specific bacteria used in the present invention are dependent on the fish species from which the bacteria are extracted. The specific bacteria are also dependent upon the desired behavior: if one wants to elicit feeding behavior, the bacteria will likely be isolated from source/feeder fish; if one wants to elicit avoidance behavior, the bacteria will likely be isolated from predator fish.

In some embodiments, the behavior-eliciting compositions may include a pharmaceutically or veterinarily acceptable carrier and/or diluent and/or excipient and bacteria.

The bacteria used in the composition according to the present invention may be of the Aeromonadaceae, Comamonadaceae, Enterobacteriaceae, or Moraxcellaceae family, or of the *Acinetobacter, Aquamonas, Aeromonas, Citrobacter, Enterobacter, Erwina, Escherichia, Plesiomonas*, and *Salmonella* genus, or of the *Acidovorax* genus. The compositions may comprise bacteria which possess specific properties that stimulate a specific, desired response or behavior in fish, avians, or marine mammals.

In some embodiments, the compositions may include bacteria from TABLE 4 which lists the names and other characteristic information of bacteria which share significant sequence homology with bacteria isolated from Bluegills (BR), Golden Shiners (GS), Fathead Minnows (FHM), and Mosquitofish (Gam). Each of these fish species (supra) are appropriate feeder/source fish for the farming of economically useful predator fish.

In some embodiments, behavior-eliciting compositions made according to the instant application may comprise *Acinetobacter* sp. WH084, *Acinetobacter* sp. WH374, *Acinetobacter tjernbergiae, Aeromonas jandaei, Aeromonas jandaei* (T), *Aeromonas* sp. ', *Aeromonas* sp. DH14, *Aeromonas* sp. DH46, *Aeromonas* sp. DH57, *Aeromonas* sp. Lgg5.7, *Aeromonas* sp. MCCB 141, *Aeromonas* sp. RC278, *Aeromonas veronii*, bacterium SL2.12, or other "equivalent bacteria" which may be associated with and released by source fish, for example BR, GS, FHM, or Gam, to elicit behaviors in fish, avians, or marine mammals. As used herein "equivalent bacteria" means bacteria that possess an inherent odor/taste that allows them to elicit a reasonably equivalent response in a fish, avian, or marine mammals. The compositions may comprise bacteria having nucleotide sequences that have greater than 80% sequence homology with the nucleotide sequences as set forth in SEQ ID NOs:1-23.

In other embodiments, the behavior-eliciting compositions may comprise *Acidovorax facilis, Acidovorax* sp. ', *Acidovorax* sp. 12M7, *Acidovorax* sp. g32, *Acidovorax* sp. MG61, *Acidovorax* sp. R-24667, *Acidovorax* sp. Z022, *Aeromonas jandaei, Aeromonas jandaei* (T), *Aeromonas* sp., *Aeromonas* sp. ', *Aeromonas* sp. DH14, *Aeromonas* sp. DH54, *Aeromonas* sp. DH57, *Aeromonas* sp. DH58, *Aeromonas* sp. DH69, *Aeromonas* sp. Lgg5.7, *Aeromonas* sp. MBRG 4.2, *Aeromonas* sp. RC278, *Aeromonas veronii*, bacterium 2AT1, bacterium c07-4b, bacterium CYB24, bacterium E8, bacterium E8, bacterium G2, bacterium SL2.12, bacterium SNR2-1, *Buttiauxella agrestis, Buttiauxella* sp. 01 WB03.2-68, *Citrobacter freundii, Citrobacter* sp. 1101-10, *Citrobacter* sp. T40, endophytic bacterium HA04, endophytic bacterium HB02, *Enterobacter asburiae, Enterobacter cloacae* subsp. *cloacae, Enterobacter* sp. 196, *Enterobacter* sp. DH40-2, *Enterobacter* sp. DW56, *Enterobacter* sp. Mn2, *Enterobacter* sp. ZXM215, Enterobacteriaceae bacterium R-31537, filamentous bacterium J8, *Klebsiella pneumoniae, Microbacterium* sp. K10, *Pantoea agglomerans, Pantoea* sp. DW39, *Pseudomonas fluorescens, Salmonella enterica, Salmonella enterica* subsp. *enterica, Serratia* sp. R-17665, uncultured *Acidovorax* sp., uncultured beta proteobacterium, uncultured *Citrobacter* sp., uncultured Comamonadaceae bacterium, uncultured *Enterobacter* sp., uncultured Enterobacteriaceae bacterium, uncultured gamma proteobacterium, uncultured *Klebsiella* sp., uncultured proteobacterium, uncultured *Serratia* sp., or other "equivalent bacteria". The compositions may comprise bacteria having nucleotide sequences that have greater than 80% sequence homology with the nucleotide sequences as set forth in SEQ ID NOs:24-37.

In yet other embodiments, the behavior-eliciting compositions may comprise *Aeromonas jandaei, Aeromonas jandaei* (T), *Aeromonas* sp., *Aeromonas* sp. ', *Aeromonas* sp. DH14, *Aeromonas* sp. DH25, *Aeromonas* sp. DH46, *Aeromonas* sp. DH54, *Aeromonas* sp. DH57, *Aeromonas* sp. DH58, *Aeromonas* sp. DH69, *Aeromonas* sp. Lgg5.7, *Aeromonas* sp. MBRG 4.2, *Aeromonas* sp. RC278, *Aeromonas veronii, bacterium* 2AT1, bacterium c07-4b, bacterium G2, bacterium SL2.12, bacterium SNR2-1, *Citrobacter freundii, Citrobacter* sp. 1101-10, *Citrobacter* sp. T40, endophytic bacterium HA04, endophytic bacterium HB02, *Enterobacter asburiae, Enterobacter cloacae* subsp. *cloacae, Enterobacter* sp. 196, *Enterobacter* sp. DH40-2, *Enterobacter* sp. DW56, *Enterobacter* sp. Mn2, *Enterobacter* sp. ZXM215, Enterobacteriaceae bacterium R-31537, *Klebsiella pneumoniae, Microbacterium* sp. K10, *Pantoea agglomerans, Pantoea* sp. DW39, *Pseudomonas fluorescens, Salmonella enterica, Salmonella enterica* subsp. *enterica, Salmonella enterica* subsp. *enterica* serovar *Dublin, Salmonella enterica* subsp. *enterica* serovar *Enteritidis, Salmonella enterica* subsp. *enterica* serovar *Typhi, Salmonella enterica* subsp. *enterica* serovar *Typhimurium, Serratia* sp. R-17665, uncultured *Citrobacter* sp., uncultured *Enterobacter* sp., uncultured Enterobacteriaceae bacterium, uncultured gamma proteobacterium, uncultured *Klebsiella* sp., uncultured proteobacterium, uncultured *Serratia* sp., or other equivalent bacteria. The compositions may comprise bacteria having nucleotide sequences that have greater than 80% sequence homology with the nucleotide sequences as set forth in SEQ ID NOs:38-76.

In other embodiments, the compositions may comprise bacterium E8, *Buttiauxella agrestis, Buttiauxella* sp. 01 WB03.2-68, Enterobacteriaceae bacterium R-31537, *Serratia* sp. R-17665, uncultured *Citrobacter* sp., uncultured *Enterobacter* sp., uncultured proteobacterium, uncultured *Serratia* sp., or other equivalent bacteria. The compositions may comprise bacteria having nucleotide sequences that have greater than 80% sequence homology with the nucleotide sequences as set forth in SEQ ID NOs:77-81.

As used herein, the terms "pharmaceutically or veterinarily acceptable carrier" and "pharmaceutically or veterinarily acceptable vehicle" and "pharmaceutically or veterinarily acceptable excipient" are interchangeable and refer to a substrate that can be consumed by a target species without significant adverse effects. Suitable pharmaceutically acceptable carriers known in the art include, but are not limited to, sterile water, saline, glucose, or buffered solutions. Carriers may include auxiliary agents including, but not limited to feed, diluents, stabilizers (i.e., sugars and amino acids), preservatives, wetting agents, emulsifying agents, pH buffering agents, viscosity enhancing additives, colors and the like. The pharmaceutically or veterinarily acceptable carriers or vehicles or excipients are well known to the one skilled in the art. For example, a pharmaceutically or veterinarily acceptable carrier or vehicle or excipient can be a NaCl (e.g., saline) solution or a phosphate buffer. In another example, the excipient, carrier or vehicle may be fish, avian or marine mammal food such as, but not limited to, meal, pellets, or slurries. Amounts and volumes are herein discussed in the general description and can also be determined by the skilled artisan from this disclosure read in conjunction with the knowledge in the art, without any undue experimentation.

In one embodiment, the bacteria of the behavior-eliciting compositions may be prepared by isolating bacteria from a species of fish (source fish) by removing an aliquot of conditioned water (water from the aquaria that the source fish have inhabited, for example, for >30 minutes), inoculating growth media with a portion of said aliquot, propagating said bacteria in growth media, streaking said bacteria to form single colony isolates on nutrient agar plates/slants, and subsequently subculturing such isolates in growth media.

To obtain a composition having a certain odor/taste, a specific species of source/feeder fish, such as fathead minnows, are placed in a container of water and allowed to swim for a sufficient amount of time, reasonably at least ten minutes. To prevent any undesirable contaminants, i.e. algae, bacteria, parasites, etc. in the final composition, the aquaria water used is initially chlorinated and is subsequently dechlorinated and passed through a 0.45 µm filter prior to the addition of subject fish. The fish will release bacteria into the dechlorinated water immediately, however, the longer the fish is exposed to the water the greater the amount of bacteria that will be released ultimately yielding the conditioned water. After a sufficient amount of time (10 minutes to 1.0 hour), a culturing medium is inoculated with an aliquot of the conditioned water.

Any suitable growth medium capable of culturing the bacteria released by the fish may be used; however a minimal medium is may be more effective. Minimal media contains the minimum nutrients possible for colony growth, generally without the presence of amino acids, and typically contains: 1) a carbon source for bacterial growth, which may be a sugar such as glucose, or a less energy-rich source like citrate; 2) various salts, which may vary amongst the specific bacterium of the composition and growing conditions; these salts generally provide essential elements such as magnesium, nitrogen, phosphorus, and sulfur to allow the bacteria to synthesize protein and nucleic acid; 3) water (Davis, Dulbecco et al. 1990). For the present invention, a suitable minimal medium may comprise: potassium phosphate-dibasic, potassium phosphate-monobasic, ammonium sulfate, sodium citrate, magnesium sulfate and deionized water. The entire volume of prepared minimal medium is then sterilized by passage through a 0.45 µm filter. The citrate of the sodium citrate is the carbon source in that particular minimal medium. In another embodiment, sterile glucose (autoclaved or sterile-filtered) is added to the above mentioned minimal medium as a carbon source.

In another embodiment of the present invention the minimal medium may comprise: potassium phosphate-dibasic, present in an amount of approximately 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, or 2.0%, frequently 0.7% by weight; potassium phosphate-monobasic, present in an amount of approximately 0.1%, 0.2%, 0.3%, 0.4%, 0.5%, 0.6%, 0.7%, 0.8%, 0.9%, or 1.0%, frequently 0.3% by weight; ammonium sulfate, present in an amount of approximately 0.01%, 0.02%, 0.03%, 0.04%, 0.05%, 0.06%, 0.07%, 0.08%, 0.09%, 0.10%, 0.20%, 0.3%, 0.4%, 0.5%, 0.6%, 0.7%, or 0.8%, frequently 0.1% by weight; sodium sulfatecitrate, present in an amount of approximately 0.005%, 0.15%, 0.20%, 0.25%, 0.30%, 0.35%, 0.40%, 0.45%, 0.50%, or 0.55%, frequently 0.051% by weight; magnesium sulfate, present in an amount between approximately 0.001%, 0.002%, 0.003%, 0.004%, 0.005%, 0.006%, 0.007%, 0.008%, 0.009%, 0.010%, 0.020%, or 0.03%, frequently 0.01% by weight; distilled water, present in an amount of approximately 70%, 71%, 72%, 73%, 74%, 75%, 76% 78%, 79%, 80%, 81%, 82%, 83%, 84%, 85%, 86% 88%, 89%, 90%, 91%, 92%, 93%, 94%, 95%, 96% 97%, 98%, or 99%, most frequently 94% by weight; and a concentrated solution of sterile glucose (about 10 to 70% w/v) diluted in the final medium to a weight volume concentration of approximately 1.0%, 2.0%, 3.0%, 4.0%, 5.0%, 6.0%, 7.0%, 8.0%, 9.0% or 10.0%, frequently 5.0%.

The bacteria (isolated as described above) were cultured in a dark environment to reduce the growth of algae that may be present in the initial sample. Bacterial growth began immediately upon inoculation of the culture medium and continued through logarithmic phase until stationary phase was reached, at approximately 48 hours post inoculation (Davis, Dulbecco et al. 1990). No adverse effects were experienced from culturing for times periods greater or less than 48 hours. Culturing for fewer than 48 hours decreased the quantity of the composition produced and culturing for more than 48 hours had little or no effect on the concentration of the final composition.

Bacteria were grown in minimal culture media for approximately 48 hours to achieve stationary phase (Davis, Dulbecco et al. 1990). Subsequently, the bacteria were killed by adding 37% formaldehyde to the culture to a final concentration of 1.0% (v/v). The bacteria were separated (pelleted) from the medium by centrifugation at 7,000×G for 10 minutes at 20° C. To ensure adequate removal of formaldehyde, the supernatant is separated from the bacterial cell pellet by filtering, decanting, or aspiration, and the pelleted bacteria were resuspended in a volume of distilled water equivalent to the volume of the initial culture. The resuspended bacteria were pelleted again using the same centrifugation parameters. The bacterial cell pellet was resuspended in distilled water. This process was repeated two (2) more times, discarding the supernatant obtained from the centrifugation step. The final cell pellet was then mixed with an appropriate volume of desired solution or excipient to form a bacterial suspension (i.e. a behavior-eliciting composition).

In another embodiment, the bacteria are resuspended with an appropriate volume of distilled water to form a composition with a bacterial concentration of approximately $1.0 \times 10^7$, $1.5 \times 10^7$, $1.0 \times 10^8$, $1.5 \times 10^8$, $1.0 \times 10^9$, $1.5 \times 10^9$, $1.0 \times 10^{19}$, $1.5 \times 10^{19}$, or $1.0 \times 10^{11}$ bacteria per milliliter. In one embodiment, the water/composition mixture is applied to an object of interest, such as fish food. Application of the mixture may be accomplished by any means known in the art, such as spraying, soaking, mixing etc. When used to enhance the attractiveness of fish food, the amount of the composition applied on, mixed with, or associated with one pound of fish food is approximately $1.0 \times 10^9$, $1.5 \times 10^9$, $1.0 \times 10^{10}$, $1.5 \times 10^{10}$, or $1.0 \times 10^{11}$, $1.0 \times 10^{10}$, $1.5 \times 10^{10}$, $1.0 \times 10^{11}$, $1.5 \times 10^{11}$, $1.0 \times 10^{12}$, $1.5 \times 10^{12}$, $1.0 \times 10^{13}$, or $1.5 \times 10^{13}$ bacteria. Alternative substrates can be used depending on the purpose of the composition. For example, the composition can be mixed with food at the time of formulation, and solutions/substrates compatible with the formulation process as necessary.

Feed is the largest production cost for commercial aquaculture (for example, most farming of salmon, other marine finfish and shrimp), and thus improving feed efficiency in industrial systems is a priority (Naylor, Goldberg et al. 2000). A primary advantage of the present invention is that the behavior-eliciting compositions can be incorporated into low cost, high protein food for fish, avians, or marine mammals. There are a number of commercial food suppliers (Purinamills, AquaMax, Gray Summit Mo.; Cargill, Aquaxcel, Franklinton La.; Zeigler Bros., Gardners Pa.) that offer low cost fish foods. Typically, such low cost high protein foods are efficient, and economically viable, (Lim and Webster 2001) but unfortunately they are usually unpalatable (Subcommittee-Fish-Nutrition 1993). For example, many types of fish refuse to eat inexpensive high protein food sources containing casein. In fact, certain bass fish will starve rather than eat casein. However, when a composition comprising cultured bacteria extracted from a normal bass prey fish, such as minnow source fishes, is applied to casein-based food, the bass will eat and sustain a reasonable amount of growth on the casein diet. Therefore, behavior-eliciting compositions according to the present invention inexpensively transform otherwise unpalatable high protein food sources into efficient palatable food sources. A further aspect of the present invention is that the bacterial compositions additionally possess inherent nutritional value.

Another feature of the present invention is the combination of the cultured bacteria and particular carriers. By combining the bacteria with low-cost protein sources, for example, fish will consume the protein whereas without the bacteria, said fish would find it unpalatable, and in some cases, they would starve. This aspect is particularly important during the process of weaning fish to commercially available fish food, where mortality can exceed 60%. Behavior-eliciting compositions according to the present invention may dramatically reduce fish mortality, thus significantly reducing aquaculture costs.

All documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

The invention will now be further described by way of the following non-limiting examples.

EXAMPLES

Without further elaboration, it is believed that one skilled in the art can, using the preceding descriptions, practice the present invention to its fullest extent. The following detailed examples are to be construed as merely illustrative, and not limitations of the preceding disclosure in any way whatsoever. Those skilled in the art will promptly recognize appropriate variations from the procedures both as to reactants and as to reaction conditions and techniques.

Example 1: Test Chamber

In the present invention, a test chamber was designed and used for quantitative analysis of feeding, predator avoidance, and other behaviors of test subjects. The test chamber shown in FIG. 1 was constructed of clear poly(methyl 2-methylpropenoate) (PLEXIGLAS) and consists of a main chamber with a "Y-shaped" inflow channel. The chamber volume is 28 cm×29 cm×27 cm and has a capacity of ~22.0

Liters. The inflow channel allows introduction of substrates and compositions of interest. Each section of the inflow channel is square in cross-section (13.69 cm$^2$) and 30.0 cm in length.

During operation, dechlorinated tap water (prepared as described below) was continuously fed through both arms of the inflow channels. The two water streams from each inflow channel converge and enter the main chamber at the bottom/center of the main chamber. The water in the main chamber overflowed through an opening near the top of the main chamber on the side opposite the inflow channels. Lines marked on the two sides and bottom of the main chamber formed nine squares on each face of the apparatus. The lines delineate 27 virtual cubic "compartments" in the main chamber.

Fish were introduced to the main chamber through the open top of the apparatus. Each time a fish moved from one of the 27 virtual cubic compartments (see above) to another, the move was recorded as an event by the observer. Substances in solution were added to the incoming water stream by penetrating a rubber septum at the entry port of either inflow arm with a hypodermic needle. Solutions and compositions of interest were added as single injections via a syringe attached to the injection needle or continuously pumped into the water stream.

Dechlorination.

A 20 Liter plastic carboy, with a bottom spigot, served as a dechlorinating vessel. Tap water flowed in to the top of the carboy through plastic tubing at a rate of 3.0 Liters per minute. A peristaltic pump was used to add 0.2 M sodium thiosulfate to the carboy at a rate of 2.5 milliliters per minute to remove the chlorine. Chlorine removal (Eaton, Clesceri et al. 1992) was monitored with a Hach Chlorine Test Kit (Hach Co., Loveland Colo., Model CN-66F).

Flow dynamics for the apparatus were tested by injecting 1.0% methylene blue into one of the inflow arms through the designated port followed by visual observation of the distribution of blue color. The degree of dilution of test substances in each cubic grid compartment of the main chamber was assessed using pH measurements. Briefly, with water flowing through the chamber, 10.0 ml volumes of 1.0 N HCl were injected through one of the inflow arms of the apparatus. At intervals, 10.0 ml samples of water were removed from the center of each cubic grid compartment with a pipette. Measurement of pH in the samples allowed calculation of dilution factors in the various grid compartments.

Water temperatures in the test chamber were adjusted to be within 1° C. of the source aquaria.

Example 2. Use of the Test Chamber

The test chamber described above (FIG. 1) was designed to allow monitoring of the swimming movements of fish in response to components in flowing water. Similar chambers have been used by others for quantitative and semi-quantitative evaluations of various kinds of fish behaviors evoked by components in solution. (Kleerekoper 1969; Bardach and Villars 1974; Pfeiffer 1982). In essence, hungry fish exhibit increased swimming movements in response to positive stimuli, i.e. natural and synthetic amino acids (Carr 1988) and extracts of prey fish specific to the fish species being observed.

In all tests, individual fish were observed during three sequential 10 minute periods. The first 10 minutes in the test chamber served as an acclimation period. The second 10 minute interval served as a control period during which only dechlorinated tap water was injected and fish movements were recorded. At the beginning of the last period, the experimental period, the composition of interest was injected and fish movements were recorded.

Results from the test chamber consist of recordings of movements for each fish through the grids within the test chamber during the control period and the experimental period. Mean movements during control and experimental periods were accompanied by standard errors. Differences between means were tested using the t-test for paired comparisons (Sokal and Rohlf 1969). This test evaluates the significance of the difference between the two means obtained in experimental condition where a significance requires a p value≤0.05.

Example 3. Determining the Response of Fish to Another Fish Species "Odor/Taste"

Figure 2:
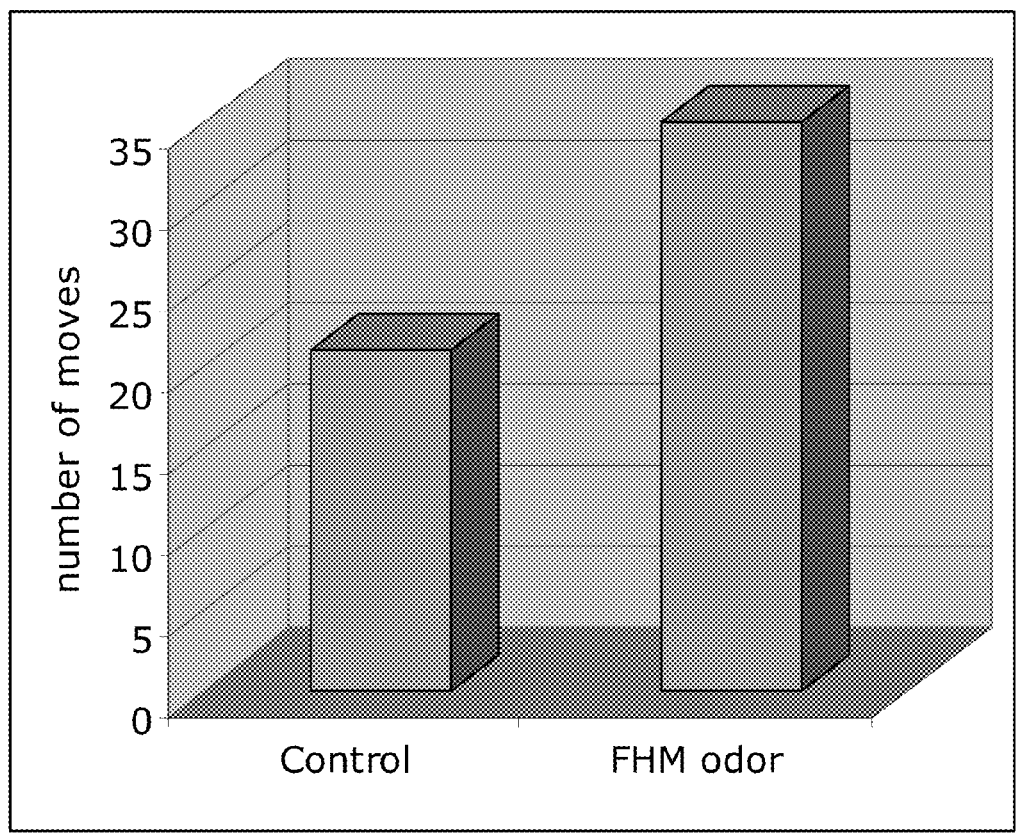
Figure 3:
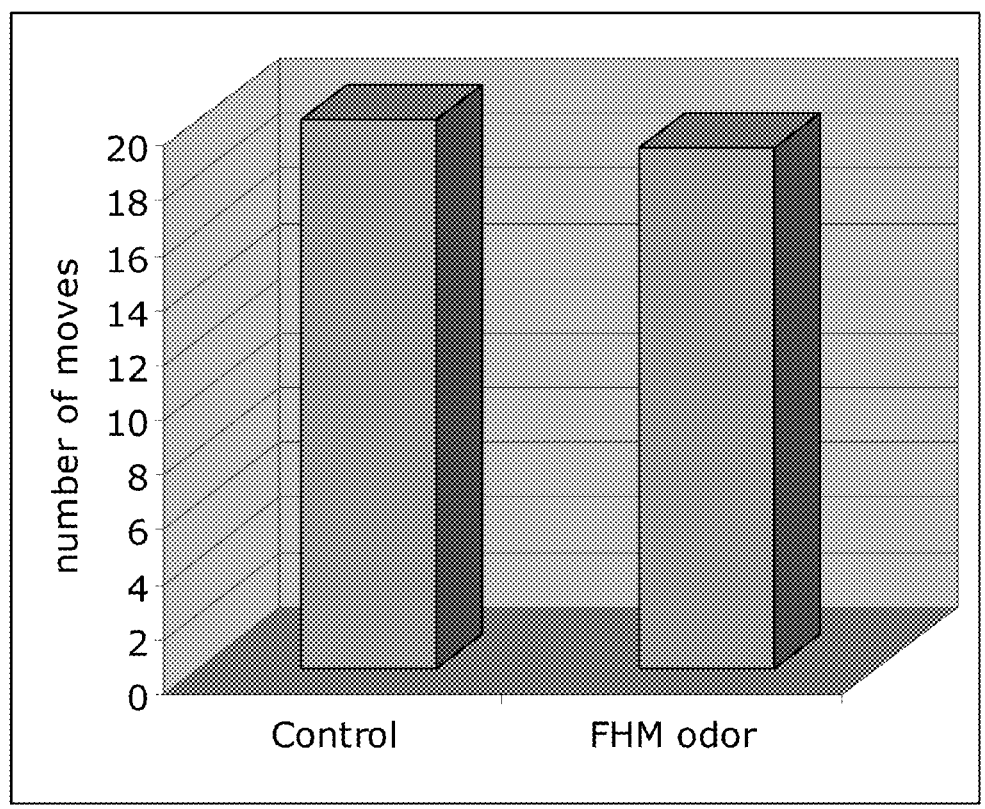

The olfactometric/taste test chamber (FIG. 1) was used to determine how largemouth bass and several species of small fish react to each other's odor/taste (measurements as per Example 2, above). It was observed that small fish (yellow fin shiner, fathead minnow) often react to bass odor/taste by becoming motionless (fright response), whereas hungry bass responded to the odor/taste of the small fish with searching movements, also referred to as exploratory feeding behavior (FIG. 2). Bass that had just been fed ignored the odor/taste of the small fish (see FIG. 3).

Characterization of the Avoidance Odor/Taste Response.

Water was taken from an aquarium which housed a largemouth bass for tests of avoidance by small fish (said water will be hereinafter referred to as "bass water" or "conditioned bass water"). The bass water was tested immediately after removal from the tank. In this embodiment, FHM and YFS were tested as described below.

Conditioned bass water was obtained from aquaria in which bass had been 1) swimming, 2) housed, or from a 3) new tank that had housed bass fish for 30 minutes. The bass were removed by netting them, and the resulting 3 types of conditioned bass water were used as described below to determine the nature of the response said water would elicit in FHM.

Behavior.

The response of each species to bass water appeared to depend on whether or not the test fish were hungry. Hungry FHM stopped swimming for between one (1) and two (2) minutes when exposed to bass water. The FHM slowly resumed swimming as the bass water was diluted. Satiated FHM exhibited a slight reduction in their swimming activity when exposed to bass water (P=0.11). Hungry YFS responded to bass water with rapid darting, followed by entry into the inflow channel in 60% of the trials. This entry was delayed until the inflow channel had been flushed of the bass water (average 7.6 min). Satiated YFS did respond to bass water with moderate swimming activity, but did not enter the inflow channel.

Filtration Removes the Bass Odor/Taste.

Conditioned bass water was sterile-filtered through a 0.45 μm filter (e.g., Millipore Corp., Billerica Mass., #SJHVM4710, 0.45 μm), and was then tested in the chamber as described above. After filtration, the FHM responses elicited by bass water were similar to those elicited by the dechlorinated control water, indicating that no avoidance. In this experiment, the FHM fish increased their movement similar to the dechlorinated tap water control. These results show that the odor/taste responsible for the avoidance behavior of FHM is particulate and can be removed by filtration.

Centrifugation.

Thirty (30.0) ml of conditioned bass water was transferred to sterile conical centrifuge tubes. The tubes were centrifuged at room temperature for 10 minutes at 7,000×G. An aliquot of the supernatant was removed from the centrifuge tube, and was used in a 'finger' bowl experiment in which one FHM fish was added to a small 'finger' bowl containing 230 ml of dechlorinated tap water. The fish was allowed to acclimate for 15 minutes and then 1.0 ml of conditioned bass water was added to the bowl and the fish motion was monitored. In the finger bowl experiments, the FHM fish increased their movement, similar to the response observed with the dechlorinated tap water controls and the 0.45 μm filtered water. Consequently, this result shows that the odor/taste responsible for the avoidance behavior in FHM can be removed from aqueous solution at low centrifugal forces that are typically used to pellet bacteria.

The Odor/Taste is Bacteria.

The experiments described above strongly suggested that bacteria were the odor/taste to which the FHM were responding. To explore this possibility, 1.0 ml of conditioned bass water was plated on sterile nutrient agar plates (agar solidified in 15 cm covered Petri dishes). Petri dishes were incubated at 25° C. for 24 hours. Plating on nutrient agar generated ~4,000 bacterial colonies per ml of conditioned bass water. Control dechlorinated tap water yielded <100 colonies per ml. Using a sterile loop, bacteria from isolated colonies on nutrient agar plates were used to inoculate: agar slants (storage copies), nutrient broth medium, and minimal medium as described above. Growth in both nutrient medium (4 days at 25° C.) and minimal medium (6 days at 25° C.) yielded bacterial growth to levels of ~$1.0 \times 10^9$ bacterial per ml. Bacterial from nutrient broth and minimal medium were diluted to $1.0 \times 10^6$ per ml. These bacteria were used in the finger bowl assay (described above) to determine the effect on FHM fish. Results showed that bacteria grown on nutrient broth had no effect on FHM response, similar to controls. More importantly, however, it was observed that in the presence of bacteria grown on minimal medium, the FHM fish froze in a typical avoidance behavior. The response was identical to that observed conditioned bass medium (described above). This finding showed that bacteria inherently associated with bass fish were sufficient to elicit the odor/taste response in FHM fish (i.e. the avoidance behavior).

Typing of the Bacterial (Composition) as *Citrobacter*.

Individual colonies that formed from streaking the minimal media agar plates were used to inoculate minimal growth medium, minimal medium agar slants, and minimal medium agar Petri dishes. The resultant bacterial cultures were used as a source for subsequent analyses. Gram staining of selected individual cultures as well as the starting culture exhibited gram-negative characteristics (Bergey 1994). Aliquots of liquid cultured material were microscopically observed using oil-immersion at 1000× magnification. The bacteria were found to be rod-shaped and typically as attached duplets. Since the bacteria were Gram negative and rod shaped (*bacillus*), the diagnostic test employed for typing was the API 20E test strip (BioMerieux, Inc., #20100 api 20E). The API 20E system consists of a plastic strip of 20 individual, miniaturized tests tubes (cupules) each containing a different reagent used to determine the metabolic capabilities, and, ultimately, the genus and species of enteric bacteria in the family Enterobacteraceae. Single colonies from six different cultures were used to inoculate a 0.85% saline solution, and after mixing, the inoculated saline solution was applied to API 20E strips rehydrating the dried reagent in each tube on the strip. Some of the tubes are completely filled (tests CIT, VP and GEL), whereas others were topped off with mineral oil so that the anaerobic reactions (reactions that occur in the absence of oxygen) could be carried out (tests ADH, LDC, ODC, H2S, URE). The strips were then incubated in a small, plastic humidity chamber for 18-24 hours at 37° C. Living bacteria produce metabolites and wastes as part of the business of being a functioning cell. The reagents in the cupules are specifically designed to test for the presence of products of bacterial metabolism specific to certain kinds of bacteria. After incubation, each tube (an individual test) was assessed for a specific color change indicating the presence of a metabolic reaction that sheds light on the microbe's identity. Some of the cupule contents changed color due to pH differences, others contained end products that must be identified using additional reagents. Interpretation of the 20 reactions, in addition to the oxidase reaction (which was done separately), was converted to a seven-digit code. Results of the analysis yielded an API code of 0604532 that corresponded to the bacterial identifier *Citrobacter freundii*.

Odor/Taste is Ubiquitous in Fish Species Tested.

In a manner similar to that described above, bacteria specific to a given fish species can be shown to be the causative agent for avoidance or attraction to a second fish, avian, or marine mammal. For example, FHM fish (prey fish) were found to harbor bacteria that elicit feeding behavior in bass fish (predator fish). As illustrated by FIG. 2, hungry largemouth bass moved significantly more in response to the fathead minnow (FHM) odor/taste, as compared to control water. In contrast, recently fed largemouth bass do not respond significantly differently to fathead minnow odor/taste, as compared to control water (FIG. 2). In sum, these results indicated that bass preferentially responded to FHM odor/taste only when they were hungry. Bass also responded equally well to formaldehyde-inactivated bacteria.

FHM responses were then tested using samples of the minimal medium containing bass bacteria (with appropriate controls) as well as formaldehyde-fixed, washed bacteria. Both kinds of samples caused fright responses in the minnows, just as fresh bass water had. These results showed that the bacteria did not have to be live to elicit behavioral responses from the minnows. Therefore, the present application is intended to encompass compositions which comprise bacteria that have been inactivated by any well-known method that still preserve the ability of the bacteria to elicit a desired behavior in a target fish, avian or marine mammal. The ability to use either live or inactivated bacteria offers a clear advantage to customers that may exhibit a preference for one over the other.

Example 4. Preparation of the Bacteria (Composition)

The Seed Culture.

The behavior-eliciting composition was obtained by allowing fathead minnows (FHM) to swim in a container of sterile dechlorinated tap water for between 15 minutes to one (1) hour. After this time period, a 1.0 ml aliquot of this water was removed using a sterile pipette and is subsequently transferred to 1.0 L of minimal medium (prepared according to the ingredients listed in TABLE 1) in a 3.0 L Erlenmeyer flask.

TABLE 1 components of the minimal medium.

| Component | Amount |
|---|---|
| Potassium Phosphate - Dibasic | 7.0 gm |
| Potassium Phosphate - Monobasic | 3.0 gm |
| Ammonium Sulfate | 1.0 gm |
| Sodium Citrate | 0.5 gm |
| Magnesium sulfate | 0.1 gm |
| Distilled Water | 950.0 ml |

The prepared medium was stored in covered 3.0 L Erlenmeyer flasks and was sterilized in a suitable apparatus, preferably an autoclave. After sterilization, 50.0 milliliters of a sterilized 4% glucose solution was aseptically added to the sterilized culture medium to form the preferred minimal medium.

Growth of the Composition.

A 1.0 ml aliquot of the seed bacteria (see above) was subsequently added to 1.0 L of the preferred minimal medium in a 3.0 L flask. The flask was placed in a dark environment at 20° C. for 48 hours, to avoid or minimize any possible algal growth. After 48 hours of growth, the bacteria (composition) were fixed, centrifuged, and washed at least 2 times with an appropriate volume of distilled water. Bacteria were centrifuged a final time, the supernatant discarded, and the packed cells resuspended with water to form a behavior-eliciting composition having a bacterial concentration of $1.0 \times 10^{12}$ bacteria per milliliter.

Example 5

In view of the response elicited by the fathead minnow, Example 5 demonstrates how bacteria extracted from prey fish might be useful in enhancing the acceptability of fish chows, potentially allowing a reduction in the cost of the chow without affecting the growth of the fish. Feeding experiments using hybrid striped bass fingerlings and fry were conducted using various mixtures of Trout Chow and casein.

Figure 10:
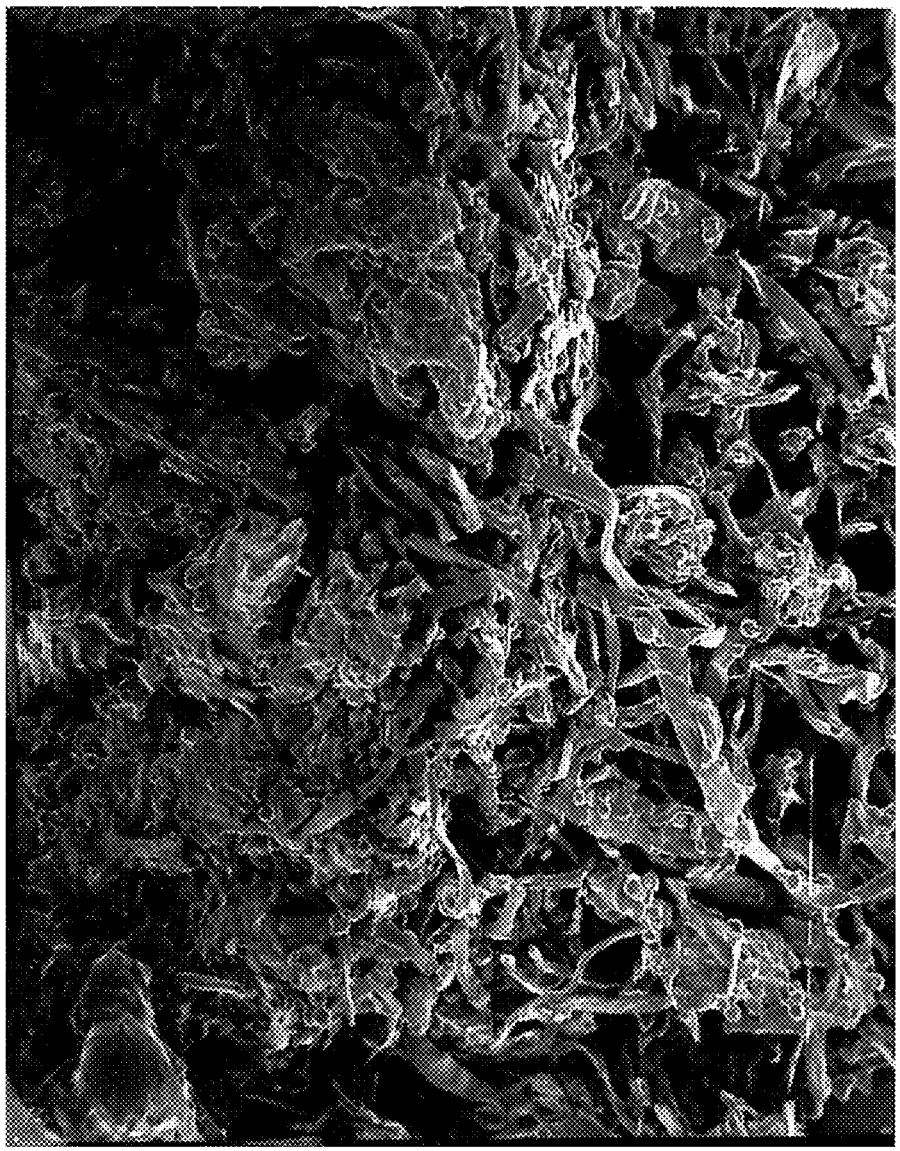

For all the feeding experiments, approximately 24 pounds of feed was coated in two 12 pound lots—one was to receive the high level of behavior-eliciting composition/coating, and the other would receive the low level of composition/coating. For the coating, 22 liters of FHM-derived bacterial culture was grown and then concentrated and washed to a final packed volume of 900 ml. The 900 ml was divided into 600 ml for the high coating and 300 ml for the low coating. Each aliquot was resuspended in about 1 liter and hand sprayed onto the pellets of feed using a standard garden-type sprayer. The pellets were carefully mixed and spread on aluminum foil to dry overnight. A representative microphotograph of coated feed is presented in FIG. 10.

Four (4) different diets were tested. Three tanks of ten fish were fed Trout Chow (TC). Other groups of three tanks were fed the 60% casein/40% Trout Chow mixture without any top-coating (C) (see TABLE 2 for the contents of the casein formula), the 60% casein/40% Trout Chow mixture coated with a low level of the present composition (chosen arbitrarily and designated K1); and the 60% casein/40% Trout Chow mixture coated with a high level of the present composition, which was twice the level of the low level (K2). It had already been determined that the hybrid striped bass did not gain much weight on the Trout Chow/Casein diet alone. The behavior-eliciting composition was prepared as described and comprised inactivated bacteria that had been extracted from fathead minnows (FHM).

Figure 4:
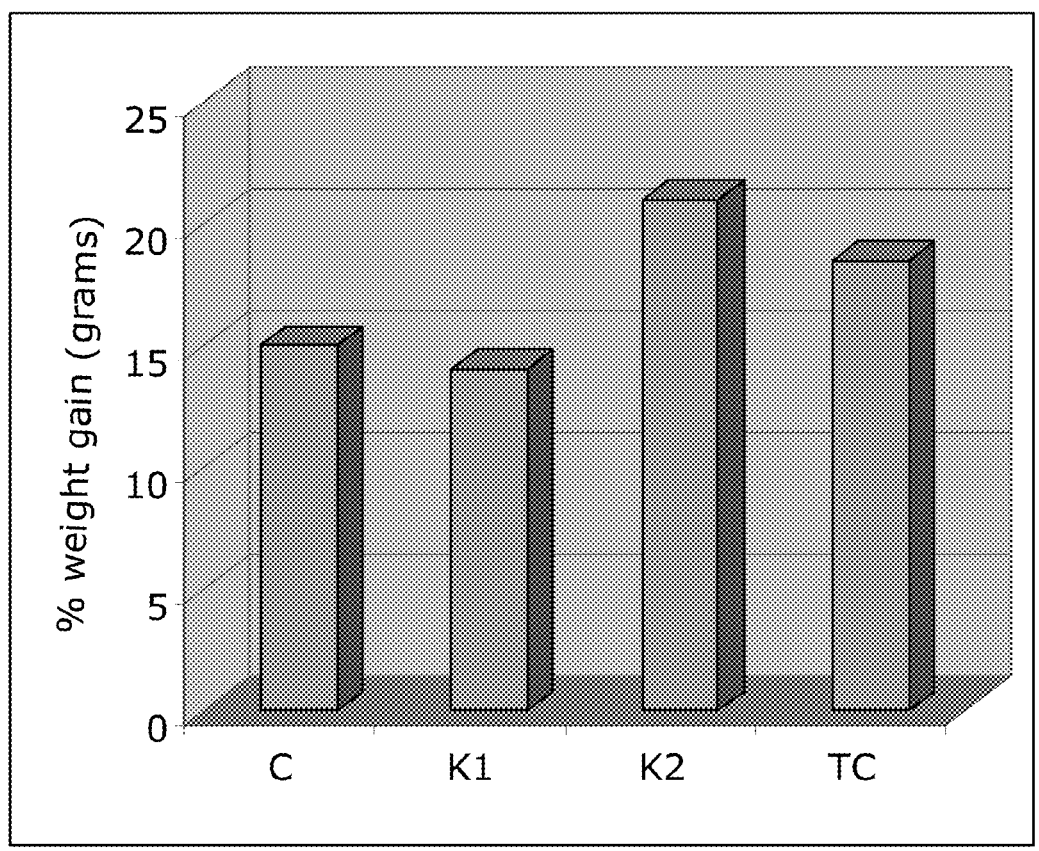

One hundred-twenty hybrid striped bass fingerlings were distributed among twelve tanks supplied with recirculating water. The fish were fed 90 grams of food per day for 28 days. They were weighed at the beginning and end of the experiment. Fish eating the casein/TC diet with the high level of coating gained 14.13±2.83 g, compared to the weight gain on Trout Chow of 12.14±2.62 g. Weight gains on the uncoated and medium-level coated casein/TC diet were 10.36±1.47 g and 10.21±0.63 g, respectively. FIG. 4 shows the percent weight gains of the hybrid striped bass on each of the diets. This experiment illustrates that the fish eating the casein/TC diet with the high level of coating not only gained more weight than those on the uncoated diet, but also gained more weight than those fish eating Trout Chow.

TABLE 2

| Casein diet composition (g/100 g)* | |
|---|---|
| Casein | 36.50 |
| Cornstarch | 4.60 |
| Cellulose | 32.40 |
| Fed. Vit. #30 | 0.20 |
| Ascorbic Acid (coated) | 0.10 |
| Chlorine Cl | 0.20 |
| NaCl | 0.75 |
| USWF Mineral | 0.05 |
| Menhaden oil | 14.20 |
| CMC | 2.00 |

*Experiments with 40/60 Trout Chow/Casein Diet

The above mentioned diets had a protein level of 35% and contained 3.5 kcal/g.

Example 6

Figure 5:
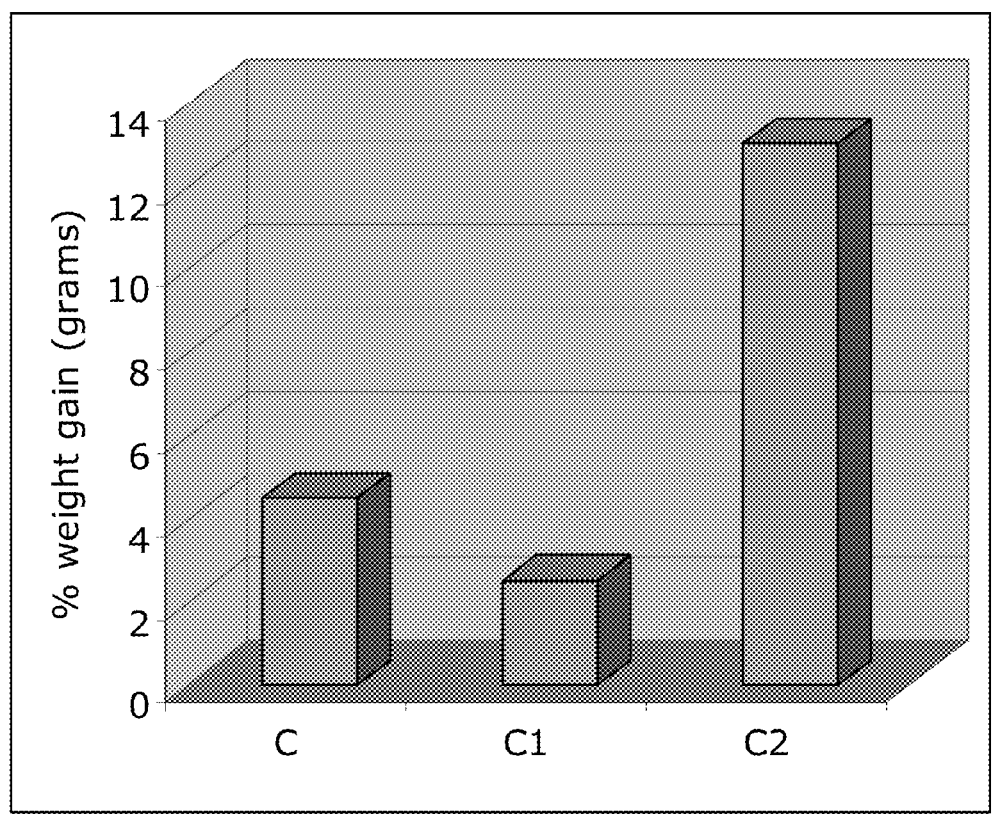

A casein diet (with no added Trout Chow) was coated with the fathead minnow (FHM) derived behavior-eliciting composition, and a poultry meal diet was coated similarly or with a 2-fold diluted FHM composition. Weight gains on these diets were compared to weight gains by fish eating uncoated diets. The ingredients of the poultry diet are listed in Table 3. Twenty four tanks of 10 hybrid striped bass fingerlings each were used. Three tanks of fish were fed Trout Chow (Purina Mills LLC, AQUAMAX). It should be noted that the fish had already become acclimated to a Trout Chow diet, so the latter three groups of fish did not require any time to adjust to a new diet. Groups of 3 tanks were fed the casein diet with no coating (C); an intermediate level of coating with the present invention (C1); and a high level of coating with the present invention (C2). The coating levels were the same as those used in Example 5. The experiment was continued for 34 days. The results are shown in FIG. 5.

Figure 6:
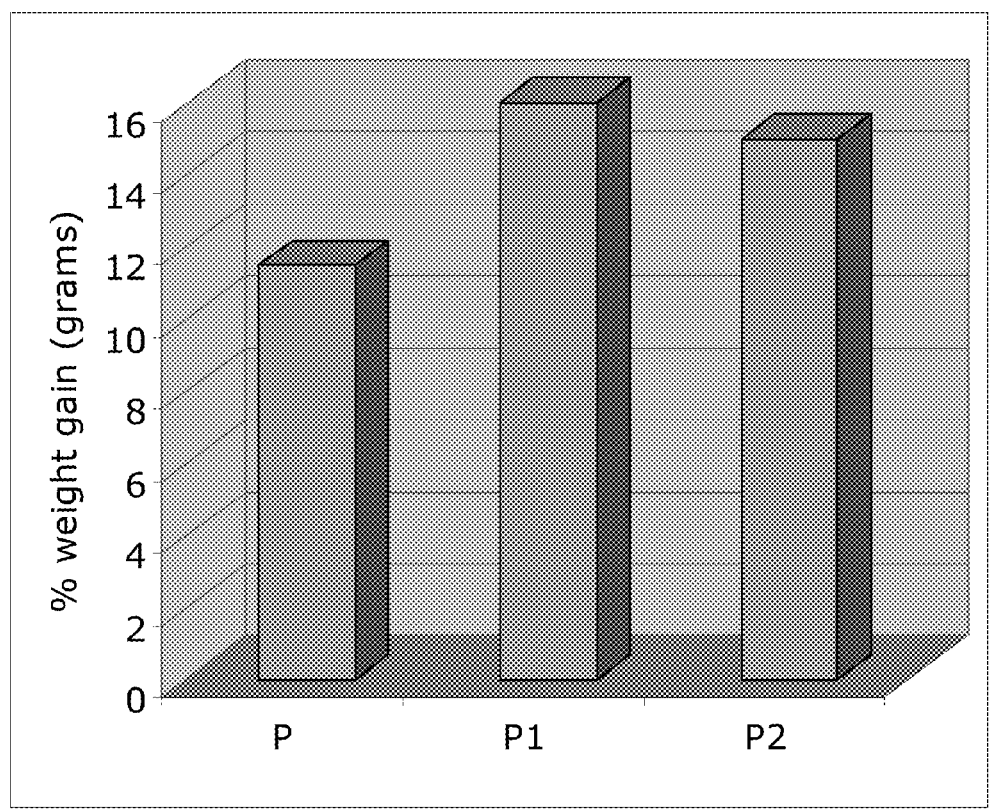

Although the fish did quite well on the Trout Chow, as expected, the primary experiment was to determine the effect the behavior-eliciting composition coating had on the lower-cost, less-palatable casein and poultry diets. Three tanks of fish were fed Poultry pellets (Ziegler Brothers, Gardeners Pa.). Groups of 3 tanks were fed the Poultry diet with no coating (P); an intermediate level of coating with the present invention (P1); and a high level of coating with the present invention (P2). The coating levels were the same as those used in Example 5. The experiment/feeding was continued for 34 days. There was significant filamentous growth in the tanks, likely the result of low-level fungal or bacterial contamination of the Poultry pellets not controlled in the manufacture of the pellets (Ziegler Brothers, Gardeners Pa.). However, as shown in FIG. 6, the fish did gain more weight on the poultry diet as a function of the behavior-eliciting coating the Poultry pellets with the composition. Fish eating the Poultry diet did gain slightly less weight on the diet with the high level of coating compared to those eating the Poultry diet with the lower level coating, but the difference was not significant. Both levels of coating exhibited ~2% weight gains over uncoated diet. FIGS. 5 and 6 summarize the above mentioned data.

TABLE 3

Poultry diet composition (g/100 g)*

| Poultry meal | 52.00 |
|---|---|
| Wheat middlings | 28.00 |
| Fed. Vit. #30 | 0.20 |
| Ascorbic acid | 0.10 |
| Chlorine Cl | 0.20 |
| NaCl | 0.75 |
| USWF Mineral | 0.05 |
| Menhaden oil | 15.00 |
| CMC | 2.00 |

*amounts of poultry meal, salt and menhaden oil varied as a function of the protein, lipid and fiber levels of ingredients used The above diet had a protein level of 35% and contained 3.5 kcal/g.

Example 7

Figure 7:
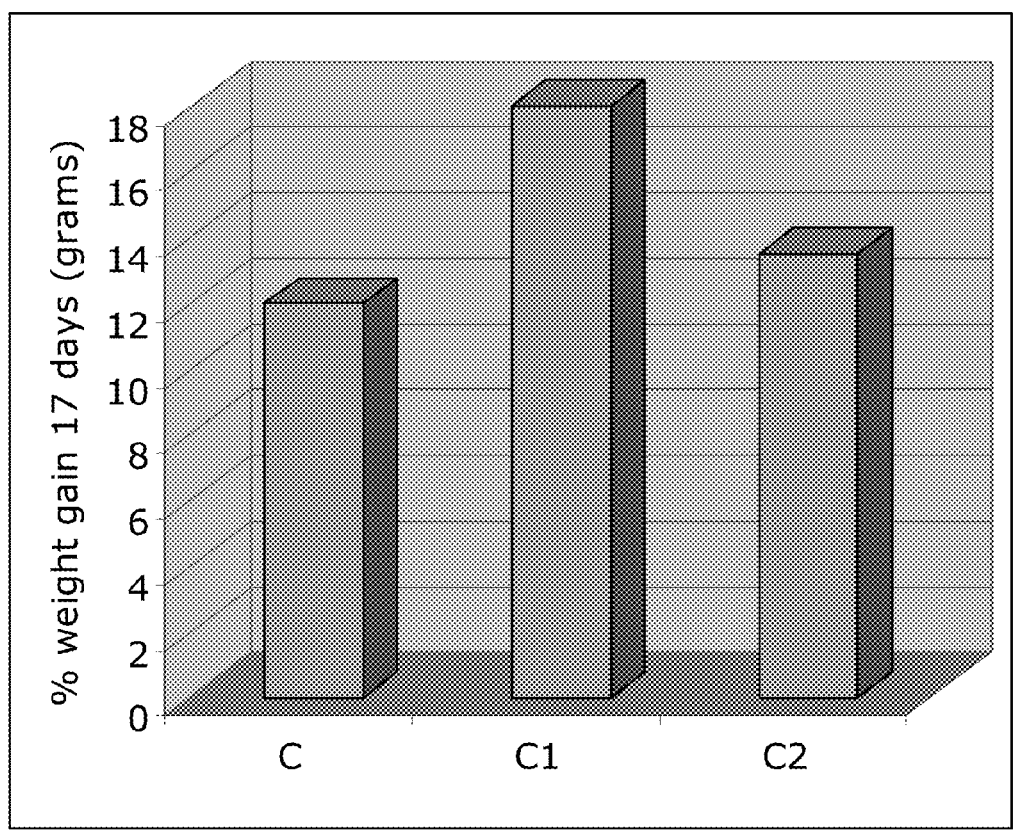
Figure 8:
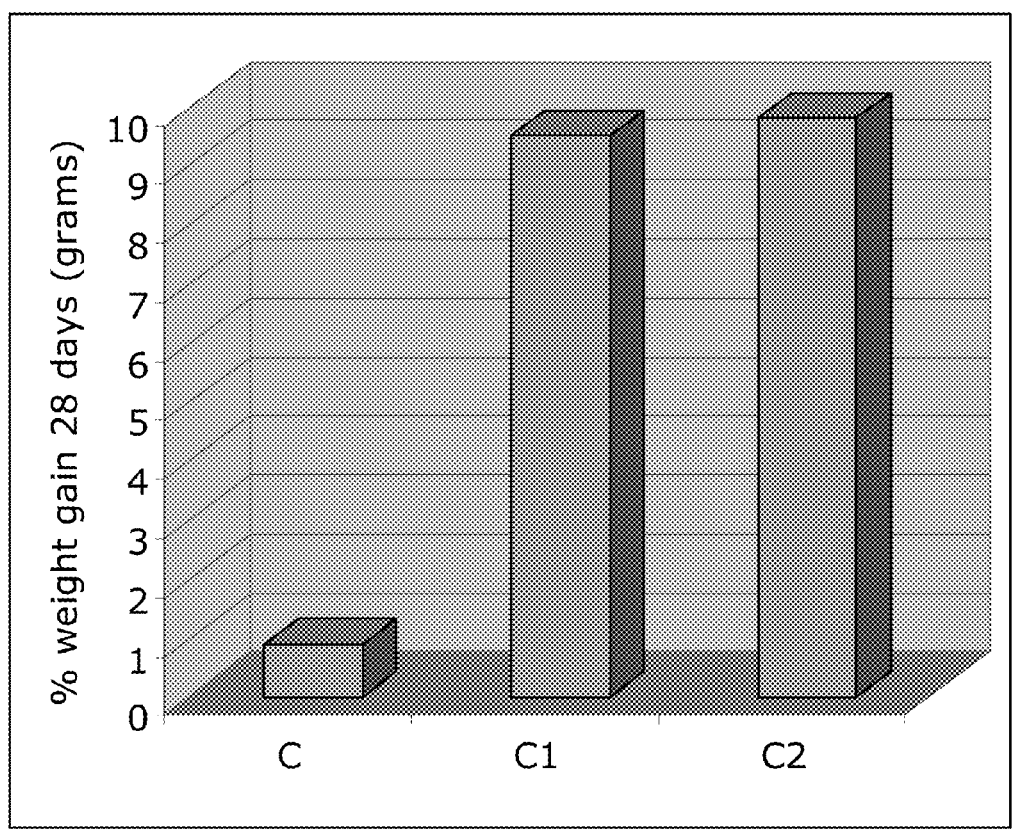

The tests of the casein diet used in Example 5 (no Trout Chow mixed with it) were repeated but with smaller fish (beginning weights about 0.6 g compared to the average beginning weight of about 10 g in Example 5. Ninety fish were weighed and distributed among 9 tanks Groups of 3 tanks were fed either the plain casein pellets (C) or top-coated pellets at low (C1) and high levels (C2). Fish were weighed at the end of 17 days (FIG. 7) and 28 days (FIG. 8).

The experiment was terminated at the end of 28 days because the fish were beginning to appear unhealthy on this diet. The coated casein pellets allowed greater weight gain at 17 days (FIG. 7) and greater weight retention at 28 days (FIG. 8). In contrast, those fish on the uncoated diet lost almost all the weight they had gained previously.

Example 8—Sequences Encoding Portions of 16S RNA Obtained from Bacteria Isolated According to the Present Invention Bacteria were isolated from Bluegills (BR), Fathead Minnows (FHM), Mosquitofish (Gam), and Golden Shiners (GS) in accordance with the techniques described in the instant application. DNA was amplified and PCR products were sequenced essentially as previously described (see Bano et al., 2007). Briefly, bacteria were collected from incubations by filtration through 0.22 μm pore size Sterivex cartridge filters (Millipore; Billerica, Mass.). DNA extraction was completed using the MoBio PowerSoil DNA Extraction Kit. DNA was amplified using Bacteria-specific 16S rRNA primers 27F/1492R (Baker et al., 2003), cloned with the TOPO TA cloning kit (Invitrogen; Carlsbad, Calif.) using vector and *E. coli* competent cells. Clones were selected randomly and sequenced by Genewiz (South Plainfield, N.J.).

Results were compared to the sequences available at the Ribosomal Database Project website (http://rdp.cme.msu.edu/, Cole et al., 2008)

TABLE 4 presents summary data for the bacteria that were associated with the indicated fish. SEQ ID NOs:1-23 are sequences obtained from "Br" or bluegill-associated bacteria. SEQ ID NOs:24-37 are from "FHM" or fathead minnow-associated bacteria. SEQ ID NOs:38-76 are from "Gam" or mosquitofish, or *Gambusia*-associated bacteria. SEQ ID NOs:77-81 are from "GS" is golden shiner-associated bacteria. For each SEQ ID NO, the names and accession numbers for 10 of the closest matching 16S RNA sequences are indicated.

TABLE 4

| SEQ | RDP_ID | Identity | Match Name | Match Name | Access. # |
|---|---|---|---|---|---|
| 1 | S000967841 | 99.224 | *Aeromonas* sp. DH46 | | EU260226 |
| 1 | S000967819 | 99.187 | *Aeromonas* sp. DH14 | | EU260204 |
| 1 | S000705518 | 93.356 | uncult. bac. | aab57c04 | DQ813907 |
| 1 | S000705477 | 93.356 | uncult. bac. | aaa26g10 | DQ813866 |
| 1 | S000705469 | 93.356 | uncult. bac. | aaa25h11 | DQ813858 |
| 1 | S000438730 | 93.356 | *Aeromonas* sp. ' | CDC 787-80' | U88662 |
| 1 | S000428865 | 93.356 | *Aeromonas jandaei* | B10 | AF099026 |
| 1 | S000428864 | 93.356 | *Aeromonas jandaei* | M34 | AF099025 |
| 1 | S000008085 | 93.356 | *Aeromonas jandaei* (T) | ATCC 49568T | X74678 |
| 1 | S000005395 | 93.356 | *Aeromonas* sp. RC278 | RC278(MM85) | AF063003 |
| 2 | S000705798 | 93.266 | uncult. bac. | aab65b03 | DQ814187 |
| 2 | S000705528 | 93.266 | uncult. bac. | aab57d03 | DQ813917 |
| 2 | S000705518 | 93.266 | uncult. bac. | aab57c04 | DQ813907 |
| 2 | S000705469 | 93.266 | uncult. bac. | aaa25h11 | DQ813858 |
| 2 | S000438730 | 93.266 | *Aeromonas* sp. ' | CDC 787-80' | U88662 |
| 2 | S000428865 | 93.266 | *Aeromonas jandaei* | B10 | AF099026 |
| 2 | S000428864 | 93.266 | *Aeromonas jandaei* | M34 | AF099025 |
| 2 | S000008085 | 93.266 | *Aeromonas jandaei* (T) | ATCC 49568T | X74678 |
| 2 | S000005395 | 93.266 | *Aeromonas* sp. RC278 | RC278(MM85) | AF063003 |
| 2 | S000705477 | 93.154 | uncult. bac. | aaa26g10 | DQ813866 |
| 3 | S000967819 | 99.674 | *Aeromonas* sp. DH14 | | EU260204 |
| 3 | S000456820 | 99.365 | *Aeromonas* sp. ' | 10.5 MW-3' | AY826604 |

TABLE 4-continued

| SEQ | RDP_ID | Identity | Match Name | Match Name | Access. # |
|---|---|---|---|---|---|
| 3 | S000967841 | 99.214 | *Aeromonas* sp. DH46 | EU260226 | |
| 3 | S000458103 | 99.005 | *Aeromonas veronii* | N63 | AB182225 |
| 3 | S000458050 | 99.005 | *Aeromonas veronii* | N09 | AB182172 |
| 3 | S000458110 | 99 | *Aeromonas veronii* | N70 | AB182232 |
| 3 | S000458040 | 99 | *Aeromonas veronii* | 105F | AB182099 |
| 3 | S000458039 | 99 | *Aeromonas veronii* | 104F | AB182098 |
| 3 | S000458034 | 99 | *Aeromonas veronii* | 99F | AB182093 |
| 3 | S000706450 | 96.34 | uncult. bac. | aab54c05 | DQ814839 |
| 4 | S000967819 | 100 | *Aeromonas* sp. DH14 | EU260204 | |
| 4 | S000967841 | 99.843 | *Aeromonas* sp. DH46 | EU260226 | |
| 4 | S000705528 | 94.138 | uncult. bac. | aab57d03 | DQ813917 |
| 4 | S000705518 | 94.138 | uncult. bac. | aab57c04 | DQ813907 |
| 4 | S000705469 | 94.138 | uncult. bac. | aaa25h11 | DQ813858 |
| 4 | S000438730 | 94.138 | *Aeromonas* sp. ' | CDC 787-80' | U88662 |
| 4 | S000428865 | 94.138 | *Aeromonas jandaei* | B10 | AF099026 |
| 4 | S000428864 | 94.138 | *Aeromonas jandaei* | M34 | AF099025 |
| 4 | S000005395 | 94.138 | *Aeromonas* sp. RC278 | RC278(MM85) | AF063003 |
| 4 | S000705477 | 94.025 | uncult. bac. | aaa26g10 | DQ813866 |
| 5 | S000705798 | 98.405 | uncult. bac. | aab65b03 | DQ814187 |
| 5 | S000705528 | 98.405 | uncult. bac. | aab57d03 | DQ813917 |
| 5 | S000705518 | 98.405 | uncult. bac. | aab57c04 | DQ813907 |
| 5 | S000705477 | 98.405 | uncult. bac. | aaa26g10 | DQ813866 |
| 5 | S000705469 | 98.405 | uncult. bac. | aaa25h11 | DQ813858 |
| 5 | S000438730 | 98.405 | *Aeromonas* sp. ' | CDC 787-80' | U88662 |
| 5 | S000428865 | 98.405 | *Aeromonas jandaei* | B10 | AF099026 |
| 5 | S000428864 | 98.405 | *Aeromonas jandaei* | M34 | AF099025 |
| 5 | S000008085 | 98.405 | *Aeromonas jandaei* (T) | ATCC 49568T | X74678 |
| 5 | S000005395 | 98.405 | *Aeromonas* sp. RC278 | RC278(MM85) | AF063003 |
| 6 | S000705798 | 97.816 | uncult. bac. | aab65b03 | DQ814187 |
| 6 | S000705528 | 97.816 | uncult. bac. | aab57d03 | DQ813917 |
| 6 | S000705518 | 97.816 | uncult. bac. | aab57c04 | DQ813907 |
| 6 | S000705477 | 97.816 | uncult. bac. | aaa26g10 | DQ813866 |
| 6 | S000705469 | 97.816 | uncult. bac. | aaa25h11 | DQ813858 |
| 6 | S000438730 | 97.816 | *Aeromonas* sp. ' | CDC 787-80' | U88662 |
| 6 | S000428865 | 97.816 | *Aeromonas jandaei* | B10 | AF099026 |
| 6 | S000428864 | 97.816 | *Aeromonas jandaei* | M34 | AF099025 |
| 6 | S000008085 | 97.816 | *Aeromonas jandaei* (T) | ATCC 49568T | X74678 |
| 6 | S000005395 | 97.816 | *Aeromonas* sp. RC278 | RC278(MM85) | AF063003 |
| 7 | S000967819 | 100 | *Aeromonas* sp. DH14 | EU260204 | |
| 7 | S000705518 | 92.189 | uncult. bac. | aab57c04 | DQ813907 |
| 7 | S000705477 | 92.189 | uncult. bac. | aaa26g10 | DQ813866 |
| 7 | S000705469 | 92.189 | uncult. bac. | aaa25h11 | DQ813858 |
| 7 | S000438730 | 92.189 | *Aeromonas* sp. ' | CDC 787-80' | U88662 |
| 7 | S000428865 | 92.189 | *Aeromonas jandaei* | B10 | AF099026 |
| 7 | S000428864 | 92.189 | *Aeromonas jandaei* | M34 | AF099025 |
| 7 | S000008085 | 92.189 | *Aeromonas jandaei* (T) | ATCC 49568T | X74678 |
| 7 | S000005395 | 92.189 | *Aeromonas* sp. RC278 | RC278(MM85) | AF063003 |
| 7 | S000705497 | 92.061 | uncult. bac. | aaa28h03 | DQ813886 |
| 8 | S000967819 | 100 | *Aeromonas* sp. DH14 | EU260204 | |
| 8 | S000705518 | 90.805 | uncult. bac. | aab57c04 | DQ813907 |
| 8 | S000705477 | 90.805 | uncult. bac. | aaa26g10 | DQ813866 |
| 8 | S000705469 | 90.805 | uncult. bac. | aaa25h11 | DQ813858 |
| 8 | S000438730 | 90.805 | *Aeromonas* sp. ' | CDC 787-80' | U88662 |
| 8 | S000428865 | 90.805 | *Aeromonas jandaei* | B10 | AF099026 |
| 8 | S000428864 | 90.805 | *Aeromonas jandaei* | M34 | AF099025 |
| 8 | S000008085 | 90.805 | *Aeromonas jandaei* (T) | ATCC 49568T | X74678 |
| 8 | S000005395 | 90.805 | *Aeromonas* sp. RC278 | RC278(MM85) | AF063003 |
| 8 | S000705497 | 90.69 | uncult. bac. | aaa28h03 | DQ813886 |
| 9 | S000967841 | 99.689 | *Aeromonas* sp. DH46 | EU260226 | |
| 9 | S000967819 | 99.674 | *Aeromonas* sp. DH14 | EU260204 | |
| 9 | S001265172 | 91.716 | *Aeromonas* sp. MCCB 141 | FJ573178 | |
| 9 | S000705477 | 91.716 | uncult. bac. | aaa26g10 | DQ813866 |
| 9 | S000705469 | 91.716 | uncult. bac. | aaa25h11 | DQ813858 |
| 9 | S000438730 | 91.716 | *Aeromonas* sp. ' | CDC 787-80' | U88662 |
| 9 | S000428865 | 91.716 | *Aeromonas jandaei* | B10 | AF099026 |
| 9 | S000428864 | 91.716 | *Aeromonas jandaei* | M34 | AF099025 |
| 9 | S000008085 | 91.716 | *Aeromonas jandaei* (T) | ATCC 49568T | X74678 |
| 9 | S000005395 | 91.716 | *Aeromonas* sp. RC278 | RC278(MM85) | AF063003 |
| 10 | S000967841 | 99.844 | *Aeromonas* sp. DH46 | EU260226 | |
| 10 | S000967819 | 99.837 | *Aeromonas* sp. DH14 | EU260204 | |
| 10 | S000705518 | 97.419 | uncult. bac. | aab57c04 | DQ813907 |
| 10 | S000705477 | 97.419 | uncult. bac. | aaa26g10 | DQ813866 |
| 10 | S000705469 | 97.419 | uncult. bac. | aaa25h11 | DQ813858 |
| 10 | S000438730 | 97.419 | *Aeromonas* sp. ' | CDC 787-80' | U88662 |
| 10 | S000428865 | 97.419 | *Aeromonas jandaei* | B10 | AF099026 |
| 10 | S000428864 | 97.419 | *Aeromonas jandaei* | M34 | AF099025 |
| 10 | S000008085 | 97.419 | *Aeromonas jandaei* (T) | ATCC 49568T | X74678 |
| 10 | S000005395 | 97.419 | *Aeromonas* sp. RC278 | RC278(MM85) | AF063003 |

TABLE 4-continued

| SEQ | RDP_ID | Identity | Match Name | Match Name | Access. # |
|---|---|---|---|---|---|
| 11 | S000705888 | 96.709 | uncult. bac. | aab66d03 | DQ814277 |
| 11 | S000705518 | 96.709 | uncult. bac. | aab57c04 | DQ813907 |
| 11 | S000705477 | 96.709 | uncult. bac. | aaa26g10 | DQ813866 |
| 11 | S000705469 | 96.709 | uncult. bac. | aaa25h11 | DQ813858 |
| 11 | S000438730 | 96.709 | *Aeromonas* sp. ' | CDC 787-80' | U88662 |
| 11 | S000428865 | 96.709 | *Aeromonas jandaei* | B10 | AF099026 |
| 11 | S000428864 | 96.709 | *Aeromonas jandaei* | M34 | AF099025 |
| 11 | S000008085 | 96.709 | *Aeromonas jandaei* (T) | ATCC 49568T | X74678 |
| 11 | S000005395 | 96.709 | *Aeromonas* sp. RC278 | RC278(MM85) | AF063003 |
| 11 | S000706024 | 96.587 | uncult. bac. | aab68c10 | DQ814413 |
| 12 | S000705528 | 97.335 | uncult. bac. | aab57d03 | DQ813917 |
| 12 | S000705518 | 97.335 | uncult. bac. | aab57c04 | DQ813907 |
| 12 | S000705477 | 97.335 | uncult. bac. | aaa26g10 | DQ813866 |
| 12 | S000705469 | 97.335 | uncult. bac. | aaa25h11 | DQ813858 |
| 12 | S000438730 | 97.335 | *Aeromonas* sp. ' | CDC 787-80' | U88662 |
| 12 | S000428865 | 97.335 | *Aeromonas jandaei* | B10 | AF099026 |
| 12 | S000428864 | 97.335 | *Aeromonas jandaei* | M34 | AF099025 |
| 12 | S000008085 | 97.335 | *Aeromonas jandaei* (T) | ATCC 49568T | X74678 |
| 12 | S000005395 | 97.335 | *Aeromonas* sp. RC278 | RC278(MM85) | AF063003 |
| 12 | S000705633 | 97.208 | uncult. bac. | aab58e12 | DQ814022 |
| 13 | S000705798 | 97.576 | uncult. bac. | aab65b03 | DQ814187 |
| 13 | S000705528 | 97.576 | uncult. bac. | aab57d03 | DQ813917 |
| 13 | S000705518 | 97.576 | uncult. bac. | aab57c04 | DQ813907 |
| 13 | S000705477 | 97.576 | uncult. bac. | aaa26g10 | DQ813866 |
| 13 | S000705469 | 97.576 | uncult. bac. | aaa25h11 | DQ813858 |
| 13 | S000438730 | 97.576 | *Aeromonas* sp. ' | CDC 787-80' | U88662 |
| 13 | S000428865 | 97.576 | *Aeromonas jandaei* | B10 | AF099026 |
| 13 | S000428864 | 97.576 | *Aeromonas jandaei* | M34 | AF099025 |
| 13 | S000008085 | 97.576 | *Aeromonas jandaei* (T) | ATCC 49568T | X74678 |
| 13 | S000005395 | 97.576 | *Aeromonas* sp. RC278 | RC278(MM85) | AF063003 |
| 14 | S000967819 | 100 | *Aeromonas* sp. DH14 | | EU260204 |
| 14 | S000708278 | 93.132 | uncult. bac. | aaa97a08 | DQ816667 |
| 14 | S000705477 | 93.132 | uncult. bac. | aaa26g10 | DQ813866 |
| 14 | S000705469 | 93.132 | uncult. bac. | aaa25h11 | DQ813858 |
| 14 | S000438730 | 93.132 | *Aeromonas* sp. ' | CDC 787-80' | U88662 |
| 14 | S000428865 | 93.132 | *Aeromonas jandaei* | B10 | AF099026 |
| 14 | S000428864 | 93.132 | *Aeromonas jandaei* | M34 | AF099025 |
| 14 | S000008085 | 93.132 | *Aeromonas jandaei* (T) | ATCC 49568T | X74678 |
| 14 | S000005395 | 93.132 | *Aeromonas* sp. RC278 | RC278(MM85) | AF063003 |
| 14 | S001185126 | 93.122 | uncult. bac. | Bul2ab09 | FJ228813 |
| 15 | S000705769 | 97.845 | uncult. bac. | aab60f07 | DQ814158 |
| 15 | S000705528 | 97.845 | uncult. bac. | aab57d03 | DQ813917 |
| 15 | S000705518 | 97.845 | uncult. bac. | aab57c04 | DQ813907 |
| 15 | S000705477 | 97.845 | uncult. bac. | aaa26g10 | DQ813866 |
| 15 | S000705469 | 97.845 | uncult. bac. | aaa25h11 | DQ813858 |
| 15 | S000438730 | 97.845 | *Aeromonas* sp. ' | CDC 787-80' | U88662 |
| 15 | S000428865 | 97.845 | *Aeromonas jandaei* | B10 | AF099026 |
| 15 | S000428864 | 97.845 | *Aeromonas jandaei* | M34 | AF099025 |
| 15 | S000008085 | 97.845 | *Aeromonas jandaei* (T) | ATCC 49568T | X74678 |
| 15 | S000005395 | 97.845 | *Aeromonas* sp. RC278 | RC278(MM85) | AF063003 |
| 16 | S000705528 | 96.658 | uncult. bac. | aab57d03 | DQ813917 |
| 16 | S000705518 | 96.658 | uncult. bac. | aab57c04 | DQ813907 |
| 16 | S000705477 | 96.658 | uncult. bac. | aaa26g10 | DQ813866 |
| 16 | S000705469 | 96.658 | uncult. bac. | aaa25h11 | DQ813858 |
| 16 | S000438730 | 96.658 | *Aeromonas* sp. ' | CDC 787-80' | U88662 |
| 16 | S000428865 | 96.658 | *Aeromonas jandaei* | B10 | AF099026 |
| 16 | S000428864 | 96.658 | *Aeromonas jandaei* | M34 | AF099025 |
| 16 | S000008085 | 96.658 | *Aeromonas jandaei* (T) | ATCC 49568T | X74678 |
| 16 | S000005395 | 96.658 | *Aeromonas* sp. RC278 | RC278(MM85) | AF063003 |
| 16 | S000705497 | 96.53 | uncult. bac. | aaa28h03 | DQ813886 |
| 17 | S000456820 | 99.365 | *Aeromonas* sp. ' | 10.5 MW-3' | AY826604 |
| 17 | S000705528 | 91.825 | uncult. bac. | aab57d03 | DQ813917 |
| 17 | S000705518 | 91.825 | uncult. bac. | aab57c04 | DQ813907 |
| 17 | S000705469 | 91.825 | uncult. bac. | aaa25h11 | DQ813858 |
| 17 | S000438730 | 91.825 | *Aeromonas* sp. ' | CDC 787-80' | U88662 |
| 17 | S000428865 | 91.825 | *Aeromonas jandaei* | B10 | AF099026 |
| 17 | S000428864 | 91.825 | *Aeromonas jandaei* | M34 | AF099025 |
| 17 | S000393862 | 91.825 | *Aeromonas veronii* | LMG13695 | 2 |
| 17 | S000008085 | 91.825 | *Aeromonas jandaei* (T) | ATCC 49568T | X74678 |
| 17 | S000005395 | 91.825 | *Aeromonas* sp. RC278 | RC278(MM85) | AF063003 |
| 18 | S000456820 | 99.365 | *Aeromonas* sp. ' | 10.5 MW-3' | AY826604 |
| 18 | S001549380 | 94.731 | *Aeromonas jandaei* | pW23 | FJ940830 |
| 18 | S001549354 | 94.731 | *Aeromonas jandaei* | 4pM28 | FJ940804 |
| 18 | S000705469 | 94.731 | uncult. bac. | aaa25h11 | DQ813858 |
| 18 | S000438730 | 94.731 | *Aeromonas* sp. ' | CDC 787-80' | U88662 |
| 18 | S000428865 | 94.731 | *Aeromonas jandaei* | B10 | AF099026 |
| 18 | S000428864 | 94.731 | *Aeromonas jandaei* | M34 | AF099025 |
| 18 | S000393862 | 94.731 | *Aeromonas veronii* | LMG13695 | 2 |

TABLE 4-continued

| SEQ | RDP_ID | Identity | Match Name | Match Name | Access. # |
|---|---|---|---|---|---|
| 18 | S000008085 | 94.731 | *Aeromonas jandaei* (T) | ATCC 49568T | X74678 |
| 18 | S000005395 | 94.731 | *Aeromonas* sp. RC278 | RC278(MM85) | AF063003 |
| 19 | S000035980 | 99.751 | *Aeromonas* sp. Lgg5.7 | AJ489337 | |
| 19 | S000456820 | 99.365 | *Aeromonas* sp. ' | 10.5 MW-3' | AY826604 |
| 19 | S000458104 | 98.993 | *Aeromonas veronii* | N64 | AB182226 |
| 19 | S000458117 | 98.99 | *Aeromonas veronii* | N77 | AB182239 |
| 19 | S000458074 | 98.988 | *Aeromonas veronii* | N34 | AB182196 |
| 19 | S000458025 | 98.986 | *Aeromonas veronii* | 90F | AB182084 |
| 19 | S000691722 | 98.942 | bacterium SL2.12 | DQ517031 | |
| 19 | S000030133 | 98.936 | *Aeromonas veronii* | S4M13 | AF472504 |
| 19 | S000458071 | 98.921 | *Aeromonas veronii* | N31 | AB182193 |
| 19 | S000967819 | 98.042 | *Aeromonas* sp. DH14 | EU260204 | |
| 20 | S000967841 | 99.844 | *Aeromonas* sp. DH46 | EU260226 | |
| 20 | S000967819 | 99.837 | *Aeromonas* sp. DH14 | EU260204 | |
| 20 | S000967846 | 99.701 | *Aeromonas* sp. DH57 | EU260231 | |
| 20 | S000705518 | 98.307 | uncult. bac. | aab57c04 | DQ813907 |
| 20 | S000705469 | 98.307 | uncult. bac. | aaa25h11 | DQ813858 |
| 20 | S000438730 | 98.307 | *Aeromonas* sp. ' | CDC 787-80' | U88662 |
| 20 | S000428865 | 98.307 | *Aeromonas jandaei* | B10 | AF099026 |
| 20 | S000428864 | 98.307 | *Aeromonas jandaei* | M34 | AF099025 |
| 20 | S000008085 | 98.307 | *Aeromonas jandaei* (T) | ATCC 49568T | X74678 |
| 20 | S000005395 | 98.307 | *Aeromonas* sp. RC278 | RC278(MM85) | AF063003 |
| 21 | S000967819 | 99.674 | *Aeromonas* sp. DH14 | EU260204 | |
| 21 | S000708720 | 91.071 | uncult. bac. | aaa95h10 | DQ817109 |
| 21 | S000705518 | 90.96 | uncult. bac. | aab57c04 | DQ813907 |
| 21 | S000705469 | 90.96 | uncult. bac. | aaa25h11 | DQ813858 |
| 21 | S000438730 | 90.96 | *Aeromonas* sp. ' | CDC 787-80' | U88662 |
| 21 | S000428865 | 90.96 | *Aeromonas jandaei* | B10 | AF099026 |
| 21 | S000428864 | 90.96 | *Aeromonas jandaei* | M34 | AF099025 |
| 21 | S000008085 | 90.96 | *Aeromonas jandaei* (T) | ATCC 49568T | X74678 |
| 21 | S000005395 | 90.96 | *Aeromonas* sp. RC278 | RC278(MM85) | AF063003 |
| 21 | S000705477 | 90.848 | uncult. bac. | aaa26g10 | DQ813866 |
| 22 | S000967819 | 99.349 | *Aeromonas* sp. DH14 | EU260204 | |
| 22 | S000705477 | 89.047 | uncult. bac. | aaa26g10 | DQ813866 |
| 22 | S000705528 | 88.938 | uncult. bac. | aab57d03 | DQ813917 |
| 22 | S000705469 | 88.938 | uncult. bac. | aaa25h11 | DQ813858 |
| 22 | S000438730 | 88.938 | *Aeromonas* sp. ' | CDC 787-80' | U88662 |
| 22 | S000428865 | 88.938 | *Aeromonas jandaei* | B10 | AF099026 |
| 22 | S000428864 | 88.938 | *Aeromonas jandaei* | M34 | AF099025 |
| 22 | S000008085 | 88.938 | *Aeromonas jandaei* (T) | ATCC 49568T | X74678 |
| 22 | S000005395 | 88.938 | *Aeromonas* sp. RC278 | RC278(MM85) | AF063003 |
| 22 | S000705518 | 88.828 | uncult. bac. | aab57c04 | DQ813907 |
| 23 | S000409954 | 99.267 | uncult. bac. | ABW-130 | AY456860 |
| 23 | S000619307 | 98.504 | uncult. bac. | BPH1050 | DQ221371 |
| 23 | S001352807 | 97.796 | *Acinetobacter* sp. WH084 | FJ866707 | |
| 23 | S001014738 | 97.758 | *Acinetobacter tjernbergiae* | DSM14971 | EF611415 |
| 23 | S000619314 | 97.525 | uncult. bac. | BPH2C9003 | DQ221378 |
| 23 | S000619245 | 97.5 | uncult. bac. | BPH1C15001 | DQ221309 |
| 23 | S000619246 | 97.5 | uncult. bac. | BPH1C15002 | DQ221310 |
| 23 | S001352761 | 97.4 | *Acinetobacter* sp. WH374 | FJ866661 | |
| 23 | S000619249 | 97 | uncult. bac. | BPH1C15005 | DQ221313 |
| 23 | S000619262 | 96.509 | uncult. bac. | BPH1C20002 | DQ221326 |
| 24 | S000915376 | 99.767 | uncult. beta proteobacterium | MS158A1_C01 | EF705161 |
| 24 | S000386190 | 99.569 | *Acidovorax* sp. 12M7 | AB120338 | |
| 24 | S000912964 | 99.551 | uncult. beta proteobacterium | MS089A1_C09 | EF702749 |
| 24 | S000915409 | 99.549 | uncult. beta proteobacterium | MS158A1_F06 | EF705194 |
| 24 | S000608601 | 98.901 | uncult. bac. | Ri222 | AM110029 |
| 24 | S001331720 | 96.092 | *Acidovorax* sp. Z022 | FN293049 | |
| 24 | S001517497 | 95.687 | uncult. bac. | nbw346a08c1 | GQ091433 |
| 24 | S001525581 | 95.573 | uncult. bac. | nbw511f09c1 | GQ099517 |
| 24 | S001519854 | 95.573 | uncult. bac. | nbw425b04c1 | GQ093790 |
| 24 | S001513669 | 95.46 | uncult. bac. | nbw304e10c1 | GQ087605 |
| 25 | S000915376 | 99.767 | uncult. beta proteobacterium | MS158A1_C01 | EF705161 |
| 25 | S000386190 | 99.569 | *Acidovorax* sp. 12M7 | AB120338 | |
| 25 | S001082320 | 98.983 | uncult. *Acidovorax* sp. | NSR3Q1b11 | EU629817 |
| 25 | S000608601 | 98.901 | uncult. bac. | Ri222 | AM110029 |
| 25 | S000915409 | 98.799 | uncult. beta proteobacterium | MS158A1_F06 | EF705194 |
| 25 | S001331720 | 95.243 | *Acidovorax* sp. Z022 | FN293049 | |
| 25 | S001517497 | 94.537 | uncult. bac. | nbw346a08c1 | GQ091433 |
| 25 | S001522360 | 94.537 | uncult. bac. | nbw446b08c1 | GQ096296 |
| 25 | S001525581 | 94.537 | uncult. bac. | nbw511f09c1 | GQ099517 |
| 25 | S001040152 | 91.828 | uncult. bac. | PA31 | EU743899 |
| 26 | S000894766 | 99.58 | uncult. *Acidovorax* sp. | 40_4 | AM779871 |

TABLE 4-continued

| SEQ | RDP_ID | Identity | Match Name | Match Name | Access. # |
|---|---|---|---|---|---|
| 26 | S000915376 | 99.534 | uncult. beta proteobacterium | MS158A1_C01 | EF705161 |
| 26 | S000386190 | 99.353 | *Acidovorax* sp. 12M7 | AB120338 | |
| 26 | S000912964 | 99.254 | uncult. beta proteobacterium | MS089A1_C09 | EF702749 |
| 26 | S001082320 | 98.99 | uncult. *Acidovorax* sp. | NSR3Q1b11 | EU629817 |
| 26 | S000608601 | 98.901 | uncult. bac. | Ri222 | AM110029 |
| 26 | S001331720 | 97.333 | *Acidovorax* sp. Z022 | FN293049 | |
| 26 | S001517497 | 96.981 | uncult. bac. | nbw346a08c1 | GQ091433 |
| 26 | S000999969 | 96.977 | uncult. bac. | Oh3137A12D | EU137452 |
| 26 | S001513669 | 96.739 | uncult. bac. | nbw304e10c1 | GQ087605 |
| 27 | S000915376 | 99.767 | uncult. beta proteobacterium | MS158A1_C01 | EF705161 |
| 27 | S000386190 | 99.569 | *Acidovorax* sp. 12M7 | AB120338 | |
| 27 | S000915409 | 99.099 | uncult. beta proteobacterium | MS158A1_F06 | EF705194 |
| 27 | S000608601 | 98.901 | uncult. bac. | Ri222 | AM110029 |
| 27 | S001331720 | 95.103 | *Acidovorax* sp. Z022 | FN293049 | |
| 27 | S001034645 | 94.773 | uncult. *Acidovorax* sp. | 1P-2-I01 | EU705064 |
| 27 | S001034587 | 94.773 | uncult. *Acidovorax* sp. | 1P-2-E06 | EU705006 |
| 27 | S001517497 | 94.576 | uncult. bac. | nbw346a08c1 | GQ091433 |
| 27 | S001525581 | 94.463 | uncult. bac. | nbw511f09c1 | GQ099517 |
| 27 | S001513669 | 94.35 | uncult. bac. | nbw304e10c1 | GQ087605 |
| 28 | S000915376 | 99.767 | uncult. beta proteobacterium | MS158A1_C01 | EF705161 |
| 28 | S000678674 | 99.658 | uncult. beta proteobacterium | MTAG33 | AJ964947 |
| 28 | S000386190 | 99.569 | *Acidovorax* sp. 12M7 | AB120338 | |
| 28 | S000915409 | 99.549 | uncult. beta proteobacterium | MS158A1_F06 | EF705194 |
| 28 | S000425538 | 99.451 | uncult. *Acidovorax* sp. | CDBL_D6 | AY734546 |
| 28 | S000910961 | 99.425 | uncult. beta proteobacterium | MS001A1_A05 | EF700746 |
| 28 | S000912964 | 99.402 | uncult. beta proteobacterium | MS089A1_C09 | EF702749 |
| 28 | S000608601 | 98.901 | uncult. bac. | Ri222 | AM110029 |
| 28 | S001331720 | 93.964 | *Acidovorax* sp. Z022 | FN293049 | |
| 28 | S001040152 | 92.735 | uncult. bac. | PA31 | EU743899 |
| 29 | S000915376 | 99.767 | uncult. beta proteobacterium | MS158A1_C01 | EF705161 |
| 29 | S000386190 | 99.569 | *Acidovorax* sp. 12M7 | AB120338 | |
| 29 | S000912964 | 99.552 | uncult. beta proteobacterium | MS089A1_C09 | EF702749 |
| 29 | S000915409 | 99.549 | uncult. beta proteobacterium | MS158A1_F06 | EF705194 |
| 29 | S000678674 | 99.487 | uncult. beta proteobacterium | MTAG33 | AJ964947 |
| 29 | S000910961 | 99.283 | uncult. beta proteobacterium | MS001A1_A05 | EF700746 |
| 29 | S000907725 | 99.263 | uncult. beta proteobacterium | MS074A1_A03 | EF697510 |
| 29 | S000608601 | 98.901 | uncult. bac. | Ri222 | AM110029 |
| 29 | S001331720 | 95.991 | *Acidovorax* sp. Z022 | FN293049 | |
| 29 | S001040152 | 92.751 | uncult. bac. | PA31 | EU743899 |
| 30 | S000915376 | 99.534 | uncult. beta proteobacterium | MS158A1_C01 | EF705161 |
| 30 | S000915409 | 99.398 | uncult. beta proteobacterium | MS158A1_F06 | EF705194 |
| 30 | S001331720 | 96.045 | *Acidovorax* sp. Z022 | FN293049 | |
| 30 | S001517497 | 95.608 | uncult. bac. | nbw346a08c1 | GQ091433 |
| 30 | S001525581 | 95.495 | uncult. bac. | nbw511f09c1 | GQ099517 |
| 30 | S001527914 | 95.495 | uncult. bac. | nbw500a08c1 | GQ101850 |
| 30 | S001000142 | 95.495 | uncult. bac. | Oh3127A10C | EU137625 |
| 30 | S000607908 | 95.495 | *Acidovorax* sp. R-24667 | AM084010 | |
| 30 | S001513669 | 95.383 | uncult. bac. | nbw304e10c1 | GQ087605 |
| 30 | S000976862 | 95.383 | uncult. *Acidovorax* sp. | AV_8R-S-F03 | EU341283 |
| 31 | S000915376 | 99.534 | uncult. beta proteobacterium | MS158A1_C01 | EF705161 |
| 31 | S000894766 | 99.37 | uncult. *Acidovorax* sp. | 40_4 | AM779871 |
| 31 | S000386190 | 99.353 | *Acidovorax* sp. 12M7 | AB120338 | |
| 31 | S000915409 | 99.245 | uncult. beta proteobacterium | MS158A1_F06 | EF705194 |
| 31 | S000456780 | 99.176 | *Acidovorax* sp. '14.5 MW-16' | 14.5 MW-16' | AY826564 |
| 31 | S000894761 | 99.111 | uncult. *Acidovorax* sp. | 14_2 | AM779866 |
| 31 | S000912964 | 99.103 | uncult. beta proteobacterium | MS089A1_C09 | EF702749 |
| 31 | S001082320 | 98.99 | uncult. *Acidovorax* sp. | NSR3Q1b11 | EU629817 |
| 31 | S000608601 | 98.901 | uncult. bac. | Ri222 | AM110029 |

TABLE 4-continued

| SEQ | RDP_ID | Identity | Match Name | Match Name | Access. # |
|---|---|---|---|---|---|
| 31 | S000741955 | 98.687 | uncult. bac. | GL-GLY3 | EF014934 |
| 32 | S000915376 | 99.767 | uncult. beta proteobacterium | MS158A1_C01 | EF705161 |
| 32 | S000386190 | 99.569 | Acidovorax sp. 12M7 | AB120338 | |
| 32 | S000912964 | 99.402 | uncult. beta proteobacterium | MS089A1_C09 | EF702749 |
| 32 | S000915409 | 99.249 | uncult. beta proteobacterium | MS158A1_F06 | EF705194 |
| 32 | S000608601 | 98.901 | uncult. bac. | Ri222 | AM110029 |
| 32 | S001331720 | 97.578 | Acidovorax sp. Z022 | FN293049 | |
| 32 | S001517497 | 97.126 | uncult. bac. | nbw346a08c1 | GQ091433 |
| 32 | S001522360 | 97.126 | uncult. bac. | nbw446b08c1 | GQ096296 |
| 32 | S000999969 | 97.123 | uncult. bac. | Oh3137A12D | EU137452 |
| 32 | S001525581 | 97.011 | uncult. bac. | nbw511f09c1 | GQ099517 |
| 33 | S000422185 | 100 | bacterium CYB24 | 97619 | AY702867 |
| 33 | S000456855 | 100 | Acidovorax sp. ' | 6.5 MW-10' | AY826639 |
| 33 | S000911498 | 99.814 | uncult. beta proteobacterium | MS032A1_A10 | EF701283 |
| 33 | S000751146 | 99.807 | filamentous bacterium J8 | EF016509 | |
| 33 | S000333966 | 99.774 | uncult. bac. | CYB236 | AY645488 |
| 33 | S001277787 | 96.579 | uncult. Comamonadaceae bacterium | LW18m-1-58 | EU642288 |
| 33 | S000995842 | 96.579 | Acidovorax sp. g32 | EU375647 | |
| 33 | S001576976 | 96.267 | Acidovorax facilis | TSWCSN46 | GQ284412 |
| 33 | S000354541 | 96.267 | uncult. bac. | GOUTB4 | AY050592 |
| 33 | S000087791 | 96.267 | unidentified | Ben05B | X86071 |
| 34 | S000915376 | 99.767 | uncult. beta proteobacterium | MS158A1_C01 | EF705161 |
| 34 | S000386190 | 99.569 | Acidovorax sp. 12M7 | AB120338 | |
| 34 | S000912964 | 99.402 | uncult. beta proteobacterium | MS089A1_C09 | EF702749 |
| 34 | S000915409 | 99.398 | uncult. beta proteobacterium | MS158A1_F06 | EF705194 |
| 34 | S000608601 | 98.901 | uncult. bac. | Ri222 | AM110029 |
| 34 | S001331720 | 97.988 | Acidovorax sp. Z022 | FN293049 | |
| 34 | S001517497 | 97.524 | uncult. bac. | nbw346a08c1 | GQ091433 |
| 34 | S001525581 | 97.406 | uncult. bac. | nbw511f09c1 | GQ099517 |
| 34 | S001527914 | 97.406 | uncult. bac. | nbw500a08c1 | GQ101850 |
| 34 | S001513669 | 97.288 | uncult. bac. | nbw304e10c1 | GQ087605 |
| 35 | S000386190 | 99.569 | Acidovorax sp. 12M7 | AB120338 | |
| 35 | S000915376 | 99.534 | uncult. beta proteobacterium | MS158A1_C01 | EF705161 |
| 35 | S000636683 | 99.414 | uncult. bac. | RBL5-15 | DQ323099 |
| 35 | S000915409 | 99.398 | uncult. beta proteobacterium | MS158A1_F06 | EF705194 |
| 35 | S000456780 | 99.176 | Acidovorax sp. ' | 14.5 MW-16' | AY826564 |
| 35 | S000894766 | 99.16 | uncult. Acidovorax sp. | 40_4 | AM779871 |
| 35 | S000912964 | 99.103 | uncult. beta proteobacterium | MS089A1_C09 | EF702749 |
| 35 | S001082320 | 98.983 | uncult. Acidovorax sp. | NSR3Q1b11 | EU629817 |
| 35 | S000608601 | 98.901 | uncult. bac. | Ri222 | AM110029 |
| 35 | S000678674 | 98.291 | uncult. beta proteobacterium | MTAG33 | AJ964947 |
| 36 | S000915376 | 99.534 | uncult. beta proteobacterium | MS158A1_C01 | EF705161 |
| 36 | S000608601 | 98.901 | uncult. bac. | Ri222 | AM110029 |
| 36 | S001331720 | 92.042 | Acidovorax sp. Z022 | FN293049 | |
| 36 | S001034645 | 91.799 | uncult. Acidovorax sp. | 1P-2-I01 | EU705064 |
| 36 | S001034587 | 91.799 | uncult. Acidovorax sp. | 1P-2-E06 | EU705006 |
| 36 | S001517497 | 91.59 | uncult. bac. | nbw346a08c1 | GQ091433 |
| 36 | S001513669 | 91.459 | uncult. bac. | nbw304e10c1 | GQ087605 |
| 36 | S001527916 | 91.459 | uncult. bac. | nbw500a10c1 | GQ101852 |
| 36 | S000607908 | 91.459 | Acidovorax sp. R-24667 | AM084010 | |
| 36 | S000484095 | 91.459 | Acidovorax sp. MG61 | AJ746118 | |
| 37 | S000915376 | 99.767 | uncult. beta proteobacterium | MS158A1_C01 | EF705161 |
| 37 | S000386190 | 99.569 | Acidovorax sp. 12M7 | AB120338 | |
| 37 | S000894766 | 99.37 | uncult. Acidovorax sp. | 40_4 | AM779871 |
| 37 | S000456780 | 99.176 | Acidovorax sp. ' | 14.5 MW-16' | AY826564 |
| 37 | S000894761 | 99.111 | uncult. Acidovorax sp. | 14_2 | AM779866 |
| 37 | S000907725 | 99.079 | uncult. beta proteobacterium | MS074A1_A03 | EF697510 |
| 37 | S001082320 | 98.99 | uncult. Acidovorax sp. | NSR3Q1b11 | EU629817 |
| 37 | S000608601 | 98.901 | uncult. bac. | Ri222 | AM110029 |
| 37 | S000915409 | 98.496 | uncult. beta proteobacterium | MS158A1_F06 | EF705194 |
| 37 | S001331720 | 95.326 | Acidovorax sp. Z022 | FN293049 | |
| 38 | S000705798 | 94.387 | uncult. bac. | aab65b03 | DQ814187 |

TABLE 4-continued

| SEQ | RDP_ID | Identity | Match Name | Match Name | Access. # |
|---|---|---|---|---|---|
| 38 | S000705528 | 94.387 | uncult. bac. | aab57d03 | DQ813917 |
| 38 | S000705518 | 94.387 | uncult. bac. | aab57c04 | DQ813907 |
| 38 | S000705477 | 94.387 | uncult. bac. | aaa26g10 | DQ813866 |
| 38 | S000705469 | 94.387 | uncult. bac. | aaa25h11 | DQ813858 |
| 38 | S000438730 | 94.387 | *Aeromonas* sp. ' | CDC 787-80' | U88662 |
| 38 | S000428865 | 94.387 | *Aeromonas jandaei* | B10 | AF099026 |
| 38 | S000428864 | 94.387 | *Aeromonas jandaei* | M34 | AF099025 |
| 38 | S000008085 | 94.387 | *Aeromonas jandaei* (T) | ATCC 49568T | X74678 |
| 38 | S000005395 | 94.387 | *Aeromonas* sp. RC278 | RC278(MM85) | AF063003 |
| 39 | S000386208 | 99.784 | *Microbacterium* sp. K10 | AB120356 | |
| 39 | S001568795 | 99.722 | uncult. bac. | P1_13 | GQ293382 |
| 39 | S001421174 | 99.639 | uncult. bac. | N2_12E14f | AB484430 |
| 39 | S001420942 | 99.639 | uncult. bac. | N2_E2L18f | AB484198 |
| 39 | S001420929 | 99.639 | uncult. bac. | N2_E2J16f | AB484185 |
| 39 | S001420717 | 99.639 | uncult. bac. | N2_EN17f | AB483973 |
| 39 | S001420716 | 99.639 | uncult. bac. | N2_EI10f | AB483972 |
| 39 | S001420309 | 99.639 | uncult. bac. | C2_S4L20f | AB483565 |
| 39 | S001419652 | 99.639 | uncult. bac. | C2_13H15f | AB482908 |
| 39 | S001419651 | 99.639 | uncult. bac. | C2_13G16f | AB482907 |
| 40 | S000967819 | 99.672 | *Aeromonas* sp. DH14 | EU260204 | |
| 40 | S000035980 | 99.501 | *Aeromonas* sp. Lgg5.7 | AJ489337 | |
| 40 | S000967841 | 99.222 | *Aeromonas* sp. DH46 | EU260226 | |
| 40 | S000967846 | 99.104 | *Aeromonas* sp. DH57 | EU260231 | |
| 40 | S000456820 | 99.048 | *Aeromonas* sp. ' | 10.5 MW-3' | AY826604 |
| 40 | S000428536 | 98.679 | *Aeromonas veronii* | HM231 | AF079301 |
| 40 | S000428535 | 98.679 | *Aeromonas veronii* | HM221 | AF079300 |
| 40 | S000708457 | 96.552 | uncult. bac. | aab00d02 | DQ816846 |
| 40 | S000707859 | 96.433 | uncult. bac. | aaa78f03 | DQ816248 |
| 40 | S000706822 | 96.433 | uncult. bac. | aab51f04 | DQ815211 |
| 41 | S000394358 | 100 | *Citrobacter* sp. T40 | AF451253 | |
| 41 | S001156083 | 99.804 | *Citrobacter freundii* | CLOC1 | EU880504 |
| 41 | S000708013 | 97.092 | uncult. bac. | aab17f05 | DQ816402 |
| 41 | S000707984 | 97.092 | uncult. bac. | aab17b12 | DQ816373 |
| 41 | S000707945 | 97.092 | uncult. bac. | aaa80e03 | DQ816334 |
| 41 | S000707907 | 97.092 | uncult. bac. | aaa79e07 | DQ816296 |
| 41 | S000707639 | 97.092 | uncult. bac. | aaa86b06 | DQ816028 |
| 41 | S000707619 | 97.092 | uncult. bac. | aaa85g06 | DQ816008 |
| 41 | S000625863 | 97.092 | *Citrobacter freundii* | 7 | DQ294285 |
| 41 | S000599313 | 97.092 | uncult. bac. | s4w18-9 | DQ068918 |
| 42 | S000979075 | 100 | Enterobacteriaceae bacterium R-31537 | AM403612 | |
| 42 | S000145384 | 99.762 | *Enterobacter asburiae* | ATCC 35953 | AJ417483 |
| 42 | S000619315 | 99.75 | uncult. bac. | BPH2C10006 | DQ221379 |
| 42 | S000619234 | 99.75 | uncult. bac. | BPH1C10005 | DQ221298 |
| 42 | S000877290 | 99.722 | uncult. *Enterobacter* sp. | Grias22 | EF548003 |
| 42 | S000619317 | 99.5 | uncult. bac. | BPH2C10008 | DQ221381 |
| 42 | S000619316 | 99.5 | uncult. bac. | BPH2C10007 | DQ221380 |
| 42 | S000619233 | 99.5 | uncult. bac. | BPH1C10004 | DQ221297 |
| 42 | S001044221 | 99.369 | *Pseudomonas fluorescens* | DDBNJ508 | AY874157 |
| 42 | S000459010 | 98.491 | *Enterobacter* sp. DW56 | AJ534854 | |
| 43 | S000979075 | 99.709 | Enterobacteriaceae bacterium R-31537 | AM403612 | |
| 43 | S001044221 | 99.369 | *Pseudomonas fluorescens* | DDBNJ508 | AY874157 |
| 43 | S001195043 | 99.355 | uncult. *Serratia* sp. | C33BI24 | FJ372794 |
| 43 | S000877290 | 99.135 | uncult. *Enterobacter* sp. | Grias22 | EF548003 |
| 43 | S001568795 | 98.889 | uncult. bac. | P1_13 | GQ293382 |
| 43 | S000038165 | 98.854 | *Pantoea agglomerans* | AH16 | AJ010096 |
| 43 | S000425616 | 98.361 | *Klebsiella pneumoniae* | AY736552 | |
| 43 | S000400130 | 97.548 | *Serratia* sp. R-17665 | AY178563 | |
| 43 | S000703369 | 96.13 | uncult. gamma proteobacterium | PA-C03 | DQ295393 |
| 43 | S000967710 | 95.622 | bacterium 2AT1 | EU259710 | |
| 44 | S000394358 | 100 | *Citrobacter* sp. T40 | AF451253 | |
| 44 | S001156083 | 99.804 | *Citrobacter freundii* | CLOC1 | EU880504 |
| 44 | S000916333 | 99.744 | uncult. proteobacterium | MS030A1_E07 | EF706118 |
| 44 | S001602034 | 94.731 | uncult. *Citrobacter* sp. | F4jan.7 | GQ417907 |
| 44 | S001602032 | 94.731 | uncult. *Citrobacter* sp. | F4jan.5 | GQ417905 |
| 44 | S001093072 | 94.731 | uncult. *Citrobacter* sp. | KLOND10 | EU704221 |
| 44 | S000735520 | 94.731 | *Citrobacter* sp. I101-10 | DQ192061 | |
| 44 | S000599206 | 94.731 | uncult. bac. | f5s7 | DQ068811 |
| 44 | S000599202 | 94.619 | uncult. bac. | f5s3 | DQ068807 |
| 44 | S000966748 | 94.619 | bacterium SNR2-1 | EU195910 | |
| 45 | S000967819 | 99.837 | *Aeromonas* sp. DH14 | EU260204 | |
| 45 | S000967841 | 99.379 | *Aeromonas* sp. DH46 | EU260226 | |
| 45 | S000705477 | 93.08 | uncult. bac. | aaa26g10 | DQ813866 |
| 45 | S000705518 | 92.969 | uncult. bac. | aab57c04 | DQ813907 |
| 45 | S000705469 | 92.969 | uncult. bac. | aaa25h11 | DQ813858 |
| 45 | S000438730 | 92.969 | *Aeromonas* sp. ' | CDC 787-80' | U88662 |

TABLE 4-continued

| SEQ | RDP_ID | Identity | Match Name | Match Name | Access. # |
|---|---|---|---|---|---|
| 45 | S000428865 | 92.969 | *Aeromonas jandaei* | B10 | AF099026 |
| 45 | S000428864 | 92.969 | *Aeromonas jandaei* | M34 | AF099025 |
| 45 | S000008085 | 92.969 | *Aeromonas jandaei* (T) | ATCC 49568T | X74678 |
| 45 | S000005395 | 92.969 | *Aeromonas* sp. RC278 | RC278(MM85) | AF063003 |
| 46 | S000979075 | 100 | Enterobacteriaceae bacterium R-31537 | AM403612 | |
| 46 | S000145384 | 99.762 | *Enterobacter asburiae* | ATCC 35953 | AJ417483 |
| 46 | S000619315 | 99.75 | uncult. bac. | BPH2C10006 | DQ221379 |
| 46 | S000619234 | 99.75 | uncult. bac. | BPH1C10005 | DQ221298 |
| 46 | S000877290 | 99.722 | uncult. *Enterobacter* sp. | Grias22 | EF548003 |
| 46 | S000619317 | 99.5 | uncult. bac. | BPH2C10008 | DQ221381 |
| 46 | S000619316 | 99.5 | uncult. bac. | BPH2C10007 | DQ221380 |
| 46 | S000619233 | 99.5 | uncult. bac. | BPH1C10004 | DQ221297 |
| 46 | S001419008 | 99.284 | uncult. bac. | C2_EG04f | AB482264 |
| 46 | S000459010 | 98.491 | *Enterobacter* sp. DW56 | AJ534854 | |
| 47 | S000979075 | 100 | Enterobacteriaceae bacterium R-31537 | AM403612 | |
| 47 | S001421178 | 99.642 | uncult. bac. | N2_12O07f | AB484434 |
| 47 | S001420929 | 99.642 | uncult. bac. | N2_E2J16f | AB484185 |
| 47 | S001420717 | 99.642 | uncult. bac. | N2_EN17f | AB483973 |
| 47 | S001420716 | 99.642 | uncult. bac. | N2_EI10f | AB483972 |
| 47 | S001420309 | 99.642 | uncult. bac. | C2_S4L20f | AB483565 |
| 47 | S001419652 | 99.642 | uncult. bac. | C2_13H15f | AB482908 |
| 47 | S001419651 | 99.642 | uncult. bac. | C2_13G16f | AB482907 |
| 47 | S000459010 | 98.491 | *Enterobacter* sp. DW56 | AJ534854 | |
| 47 | S001188791 | 97.157 | endophytic bacterium HB02 | FJ205659 | |
| 48 | S000979075 | 100 | Enterobacteriaceae bacterium R-31537 | AM403612 | |
| 48 | S000386208 | 99.569 | *Microbacterium* sp. K10 | AB120356 | |
| 48 | S001421178 | 99.284 | uncult. bac. | N2_12O07f | AB484434 |
| 48 | S001420716 | 99.284 | uncult. bac. | N2_EI10f | AB483972 |
| 48 | S001420309 | 99.284 | uncult. bac. | C2_S4L20f | AB483565 |
| 48 | S001419652 | 99.284 | uncult. bac. | C2_13H15f | AB482908 |
| 48 | S001419651 | 99.284 | uncult. bac. | C2_13G16f | AB482907 |
| 48 | S001329319 | 99.074 | *Enterobacter* sp. Mn2 | FJ668636 | |
| 48 | S000877290 | 98.889 | uncult. *Enterobacter* sp. | Grias22 | EF548003 |
| 48 | S000459010 | 98.491 | *Enterobacter* sp. DW56 | AJ534854 | |
| 49 | S000386208 | 99.784 | *Microbacterium* sp. K10 | AB120356 | |
| 49 | S001568795 | 99.722 | uncult. bac. | P1_13 | GQ293382 |
| 49 | S000979075 | 99.709 | Enterobacteriaceae bacterium R-31537 | AM403612 | |
| 49 | S000619321 | 99.5 | uncult. bac. | BPH2C10012 | DQ221385 |
| 49 | S000619320 | 99.5 | uncult. bac. | BPH2C10011 | DQ221384 |
| 49 | S001329319 | 99.074 | *Enterobacter* sp. Mn2 | FJ668636 | |
| 49 | S000367749 | 99 | uncult. bac. | AP1-28 | AY119425 |
| 49 | S000459010 | 98.679 | *Enterobacter* sp. DW56 | AJ534854 | |
| 49 | S001188788 | 96.694 | endophytic bacterium HA04 | FJ205656 | |
| 49 | S000140489 | 96.694 | bacterium G2 | AY345398 | |
| 50 | S000619317 | 99.75 | uncult. bac. | BPH2C10008 | DQ221381 |
| 50 | S000916333 | 99.746 | uncult. proteobacterium | MS030A1_E07 | EF706118 |
| 50 | S000443769 | 99.667 | uncult. Enterobacteriaceae bacterium | DGGE band 10AF | AY761018 |
| 50 | S000771259 | 99.615 | uncult. bac. | ADPs2_10A | DQ342589 |
| 50 | S000619315 | 99.5 | uncult. bac. | BPH2C10006 | DQ221379 |
| 50 | S000619234 | 99.5 | uncult. bac. | BPH1C10005 | DQ221298 |
| 50 | S000771374 | 99.401 | uncult. bac. | PSAD1_10A | DQ342704 |
| 50 | S000619316 | 99.25 | uncult. bac. | BPH2C10007 | DQ221380 |
| 50 | S000619233 | 99.25 | uncult. bac. | BPH1C10004 | DQ221297 |
| 50 | S001242141 | 99.2 | *Enterobacter* sp. ZXM215 | FJ436752 | |
| 51 | S000386208 | 99.784 | *Microbacterium* sp. K10 | AB120356 | |
| 51 | S000619321 | 99.5 | uncult. bac. | BPH2C10012 | DQ221385 |
| 51 | S000619320 | 99.5 | uncult. bac. | BPH2C10011 | DQ221384 |
| 51 | S001568795 | 99.438 | uncult. bac. | P1_13 | GQ293382 |
| 51 | S000979075 | 99.412 | Enterobacteriaceae bacterium R-31537 | AM403612 | |
| 51 | S000147111 | 99.292 | *Enterobacter cloacae* subsp. *cloacae* | No 19 | AJ417467 |
| 51 | S001329319 | 99.074 | *Enterobacter* sp. Mn2 | FJ668636 | |
| 51 | S000893850 | 98.985 | *Pantoea agglomerans* | V1S7 | EU040249 |
| 51 | S000367749 | 98.802 | uncult. bac. | AP1-28 | AY119425 |
| 51 | S001095631 | 97.222 | *Enterobacter* sp. 196 | EU244779 | |
| 52 | S000967841 | 99.689 | *Aeromonas* sp. DH46 | EU260226 | |
| 52 | S000967819 | 99.675 | *Aeromonas* sp. DH14 | EU260204 | |
| 52 | S000967846 | 99.553 | *Aeromonas* sp. DH57 | EU260231 | |
| 52 | S000967847 | 99.424 | *Aeromonas* sp. DH58 | EU260232 | |
| 52 | S000967843 | 99.415 | *Aeromonas* sp. DH54 | EU260228 | |

TABLE 4-continued

| SEQ | RDP_ID | Identity | Match Name | Match Name | Access. # |
|---|---|---|---|---|---|
| 52 | S000967852 | 99.303 | *Aeromonas* sp. DH69 | EU260237 | |
| 52 | S000967828 | 99.266 | *Aeromonas* sp. DH25 | EU260213 | |
| 52 | S000111085 | 97.047 | *Aeromonas* sp. MBRG 4.2 | AJ508692 | |
| 52 | S000705526 | 96.437 | uncult. bac. | aab57d01 | DQ813915 |
| 52 | S001558743 | 93.249 | uncult. bac. | p2h3 | FJ897440 |
| 53 | S000360228 | 99.526 | uncult. bac. | mdb68d09 | AY537938 |
| 53 | S000458103 | 99.502 | *Aeromonas veronii* | N63 | AB182225 |
| 53 | S000458050 | 99.502 | *Aeromonas veronii* | N09 | AB182172 |
| 53 | S000458040 | 99.5 | *Aeromonas veronii* | 105F | AB182099 |
| 53 | S000458039 | 99.5 | *Aeromonas veronii* | 104F | AB182098 |
| 53 | S000458034 | 99.5 | *Aeromonas veronii* | 99F | AB182093 |
| 53 | S000495374 | 99.4 | *Aeromonas veronii* | KIN103 | AY136084 |
| 53 | S000967841 | 99.222 | *Aeromonas* sp. DH46 | EU260226 | |
| 53 | S000967819 | 99.186 | *Aeromonas* sp. DH14 | EU260204 | |
| 53 | S001558743 | 93.446 | uncult. bac. | p2h3 | FJ897440 |
| 54 | S001421178 | 99.463 | uncult. bac. | N2_12O07f | AB484434 |
| 54 | S001421174 | 99.463 | uncult. bac. | N2_12E14f | AB484430 |
| 54 | S001420942 | 99.463 | uncult. bac. | N2_E2L18f | AB484198 |
| 54 | S001420929 | 99.463 | uncult. bac. | N2_E2J16f | AB484185 |
| 54 | S001420717 | 99.463 | uncult. bac. | N2_EN17f | AB483973 |
| 54 | S001420716 | 99.463 | uncult. bac. | N2_EI10f | AB483972 |
| 54 | S001420309 | 99.463 | uncult. bac. | C2_S4L20f | AB483565 |
| 54 | S001419652 | 99.463 | uncult. bac. | C2_13H15f | AB482908 |
| 54 | S001419651 | 99.463 | uncult. bac. | C2_13G16f | AB482907 |
| 54 | S000459022 | 99.439 | *Pantoea* sp. DW39 | AJ534866 | |
| 55 | S001421175 | 99.463 | uncult. bac. | N2_12G22f | AB484431 |
| 55 | S001421174 | 99.463 | uncult. bac. | N2_12E14f | AB484430 |
| 55 | S001420942 | 99.463 | uncult. bac. | N2_E2L18f | AB484198 |
| 55 | S001420929 | 99.463 | uncult. bac. | N2_E2J16f | AB484185 |
| 55 | S001420717 | 99.463 | uncult. bac. | N2_EN17f | AB483973 |
| 55 | S001420716 | 99.463 | uncult. bac. | N2_EI10f | AB483972 |
| 55 | S001420309 | 99.463 | uncult. bac. | C2_S4L20f | AB483565 |
| 55 | S001419652 | 99.463 | uncult. bac. | C2_13H15f | AB482908 |
| 55 | S001419651 | 99.463 | uncult. bac. | C2_13G16f | AB482907 |
| 55 | S000459010 | 98.679 | *Enterobacter* sp. DW56 | AJ534854 | |
| 56 | S000979075 | 100 | Enterobacteriaceae bacterium R-31537 | AM403612 | |
| 56 | S000145384 | 99.762 | *Enterobacter asburiae* | ATCC 35953 | AJ417483 |
| 56 | S000619315 | 99.75 | uncult. bac. | BPH2C10006 | DQ221379 |
| 56 | S000619234 | 99.75 | uncult. bac. | BPH1C10005 | DQ221298 |
| 56 | S000877290 | 99.722 | uncult. *Enterobacter* sp. | Grias22 | EF548003 |
| 56 | S000619317 | 99.5 | uncult. bac. | BPH2C10008 | DQ221381 |
| 56 | S000619316 | 99.5 | uncult. bac. | BPH2C10007 | DQ221380 |
| 56 | S000619233 | 99.5 | uncult. bac. | BPH1C10004 | DQ221297 |
| 56 | S001044221 | 99.369 | *Pseudomonas fluorescens* | DDBNJ508 | AY874157 |
| 56 | S000459010 | 98.302 | *Enterobacter* sp. DW56 | AJ534854 | |
| 57 | S000691722 | 99.471 | bacterium SL2.12 | DQ517031 | |
| 57 | S000030133 | 99.468 | *Aeromonas veronii* | S4M13 | AF472504 |
| 57 | S000458071 | 99.46 | *Aeromonas veronii* | N31 | AB182193 |
| 57 | S000428536 | 99.434 | *Aeromonas veronii* | HM231 | AF079301 |
| 57 | S000428535 | 99.434 | *Aeromonas veronii* | HM221 | AF079300 |
| 57 | S000497364 | 99.429 | bacterium c07-4b | AB198050 | |
| 57 | S000457969 | 99.341 | *Aeromonas veronii* | 34F | AB182028 |
| 57 | S000039286 | 99.333 | *Aeromonas* sp. | BB8 | Z48271 |
| 57 | S000039271 | 99.333 | *Aeromonas* sp. | BB6 | Z48266 |
| 57 | S000892761 | 99.203 | *Aeromonas veronii* | 9T1LB41 | EF634231 |
| 58 | S001421176 | 99.821 | uncult. bac. | N2_12H21f | AB484432 |
| 58 | S001421175 | 99.821 | uncult. bac. | N2_12G22f | AB484431 |
| 58 | S001421174 | 99.821 | uncult. bac. | N2_12E14f | AB484430 |
| 58 | S001420942 | 99.821 | uncult. bac. | N2_E2L18f | AB484198 |
| 58 | S001420929 | 99.821 | uncult. bac. | N2_E2J16f | AB484185 |
| 58 | S001420717 | 99.821 | uncult. bac. | N2_EN17f | AB483973 |
| 58 | S001420716 | 99.821 | uncult. bac. | N2_EI10f | AB483972 |
| 58 | S001420309 | 99.821 | uncult. bac. | C2_S4L20f | AB483565 |
| 58 | S001419652 | 99.821 | uncult. bac. | C2_13H15f | AB482908 |
| 58 | S001419651 | 99.821 | uncult. bac. | C2_13G16f | AB482907 |
| 59 | S000979075 | 100 | Enterobacteriaceae bacterium R-31537 | AM403612 | |
| 59 | S001421368 | 99.821 | uncult. bac. | N2_13O20f | AB484624 |
| 59 | S001421367 | 99.821 | uncult. bac. | N2_13J21f | AB484623 |
| 59 | S001420939 | 99.821 | uncult. bac. | N2_E2L12f | AB484195 |
| 59 | S001420878 | 99.821 | uncult. bac. | N2_E2B02f | AB484134 |
| 59 | S001420730 | 99.821 | uncult. bac. | N2_EP08f | AB483986 |
| 59 | S001420729 | 99.821 | uncult. bac. | N2_EO06f | AB483985 |
| 59 | S001420728 | 99.821 | uncult. bac. | N2_EL16f | AB483984 |
| 59 | S001420727 | 99.821 | uncult. bac. | N2_EJ05f | AB483983 |
| 59 | S001419008 | 99.821 | uncult. bac. | C2_EG04f | AB482264 |
| 60 | S000771394 | 100 | uncult. bac. | S1-7f | DQ342724 |

TABLE 4-continued

| SEQ | RDP_ID | Identity | Match Name | Match Name | Access. # |
|---|---|---|---|---|---|
| 60 | S000771149 | 100 | uncult. bac. | AD1F4D | DQ342479 |
| 60 | S000771044 | 99.837 | uncult. bac. | AD1-2F12B | DQ342374 |
| 60 | S000619317 | 99.75 | uncult. bac. | BPH2C10008 | DQ221381 |
| 60 | S000771139 | 99.676 | uncult. bac. | AD1F12H | DQ342469 |
| 60 | S001420728 | 99.642 | uncult. bac. | N2_EL16f | AB483984 |
| 60 | S001420727 | 99.642 | uncult. bac. | N2_EJ05f | AB483983 |
| 60 | S001419008 | 99.642 | uncult. bac. | C2_EG04f | AB482264 |
| 60 | S000917259 | 99.518 | uncult. proteobacterium | MS168A1_G07 | EF707044 |
| 60 | S001600253 | 98.485 | uncult. *Citrobacter* sp. | F5jun.13 | GQ416126 |
| 61 | S001420942 | 100 | uncult. bac. | N2_E2L18f | AB484198 |
| 61 | S001420929 | 100 | uncult. bac. | N2_E2J16f | AB484185 |
| 61 | S001420717 | 100 | uncult. bac. | N2_EN17f | AB483973 |
| 61 | S001420716 | 100 | uncult. bac. | N2_EI10f | AB483972 |
| 61 | S001420309 | 100 | uncult. bac. | C2_S4L20f | AB483565 |
| 61 | S001419652 | 100 | uncult. bac. | C2_13H15f | AB482908 |
| 61 | S001419651 | 100 | uncult. bac. | C2_13G16f | AB482907 |
| 61 | S000459010 | 98.679 | *Enterobacter* sp. DW56 | AJ534854 | |
| 61 | S001188788 | 96.364 | endophytic bacterium HA04 | FJ205656 | |
| 61 | S000140489 | 96.364 | bacterium G2 | AY345398 | |
| 62 | S000979075 | 100 | Enterobacteriaceae bacterium R-31537 | AM403612 | |
| 62 | S000145384 | 99.762 | *Enterobacter asburiae* | ATCC 35953 | AJ417483 |
| 62 | S000619315 | 99.75 | uncult. bac. | BPH2C10006 | DQ221379 |
| 62 | S000619234 | 99.75 | uncult. bac. | BPH1C10005 | DQ221298 |
| 62 | S000877290 | 99.722 | uncult. *Enterobacter* sp. | Grias22 | EF548003 |
| 62 | S000619317 | 99.5 | uncult. bac. | BPH2C10008 | DQ221381 |
| 62 | S000619316 | 99.5 | uncult. bac. | BPH2C10007 | DQ221380 |
| 62 | S000619233 | 99.5 | uncult. bac. | BPH1C10004 | DQ221297 |
| 62 | S000619231 | 99.5 | uncult. bac. | BPH1C10002 | DQ221295 |
| 62 | S001044221 | 99.369 | *Pseudomonas fluorescens* | DDBNJ508 | AY874157 |
| 63 | S000979075 | 99.709 | Enterobacteriaceae bacterium R-31537 | AM403612 | |
| 63 | S001421178 | 99.642 | uncult. bac. | N2_12O07f | AB484434 |
| 63 | S001420716 | 99.642 | uncult. bac. | N2_EI10f | AB483972 |
| 63 | S001420309 | 99.642 | uncult. bac. | C2_S4L20f | AB483565 |
| 63 | S001419652 | 99.642 | uncult. bac. | C2_13H15f | AB482908 |
| 63 | S001419651 | 99.642 | uncult. bac. | C2_13G16f | AB482907 |
| 63 | S001188791 | 98.333 | endophytic bacterium HB02 | FJ205659 | |
| 63 | S000711290 | 98.205 | *Pantoea agglomerans* | WAB1872 | AM184214 |
| 63 | S000140489 | 98.205 | bacterium G2 | AY345398 | |
| 63 | S000599273 | 98.077 | uncult. bac. | bb2s2 | DQ068878 |
| 64 | S000979075 | 100 | Enterobacteriaceae bacterium R-31537 | AM403612 | |
| 64 | S001421368 | 99.821 | uncult. bac. | N2_13O20f | AB484624 |
| 64 | S001421367 | 99.821 | uncult. bac. | N2_13J21f | AB484623 |
| 64 | S001420939 | 99.821 | uncult. bac. | N2_E2L12f | AB484195 |
| 64 | S001420878 | 99.821 | uncult. bac. | N2_E2B02f | AB484134 |
| 64 | S001420730 | 99.821 | uncult. bac. | N2_EP08f | AB483986 |
| 64 | S001420729 | 99.821 | uncult. bac. | N2_EO06f | AB483985 |
| 64 | S001420728 | 99.821 | uncult. bac. | N2_EL16f | AB483984 |
| 64 | S001420727 | 99.821 | uncult. bac. | N2_EJ05f | AB483983 |
| 64 | S001419008 | 99.821 | uncult. bac. | C2_EG04f | AB482264 |
| 65 | S001421367 | 99.821 | uncult. bac. | N2_13J21f | AB484623 |
| 65 | S001420939 | 99.821 | uncult. bac. | N2_E2L12f | AB484195 |
| 65 | S001420878 | 99.821 | uncult. bac. | N2_E2B02f | AB484134 |
| 65 | S001420730 | 99.821 | uncult. bac. | N2_EP08f | AB483986 |
| 65 | S001420729 | 99.821 | uncult. bac. | N2_EO06f | AB483985 |
| 65 | S001420728 | 99.821 | uncult. bac. | N2_EL16f | AB483984 |
| 65 | S001420727 | 99.821 | uncult. bac. | N2_EJ05f | AB483983 |
| 65 | S001419008 | 99.821 | uncult. bac. | C2_EG04f | AB482264 |
| 65 | S001488489 | 91.346 | uncult. bac. | nbw32d08c1 | GQ062425 |
| 65 | S001488415 | 91.346 | uncult. bac. | nbw31e02c1 | GQ062351 |
| 66 | S001421176 | 100 | uncult. bac. | N2_12H21f | AB484432 |
| 66 | S001421175 | 100 | uncult. bac. | N2_12G22f | AB484431 |
| 66 | S001421174 | 100 | uncult. bac. | N2_12E14f | AB484430 |
| 66 | S001420942 | 100 | uncult. bac. | N2_E2L18f | AB484198 |
| 66 | S001420929 | 100 | uncult. bac. | N2_E2J16f | AB484185 |
| 66 | S001420717 | 100 | uncult. bac. | N2_EN17f | AB483973 |
| 66 | S001420716 | 100 | uncult. bac. | N2_EI10f | AB483972 |
| 66 | S001420309 | 100 | uncult. bac. | C2_S4L20f | AB483565 |
| 66 | S001419652 | 100 | uncult. bac. | C2_13H15f | AB482908 |
| 66 | S001419651 | 100 | uncult. bac. | C2_13G16f | AB482907 |
| 67 | S000979075 | 99.709 | Enterobacteriaceae bacterium R-31537 | AM403612 | |
| 67 | S001421178 | 99.642 | uncult. bac. | N2_12O07f | AB484434 |
| 67 | S001420717 | 99.642 | uncult. bac. | N2_EN17f | AB483973 |

TABLE 4-continued

| SEQ | RDP_ID | Identity | Match Name | Match Name | Access. # |
|---|---|---|---|---|---|
| 67 | S001420716 | 99.642 | uncult. bac. | N2_EI10f | AB483972 |
| 67 | S001420309 | 99.642 | uncult. bac. | C2_S4L20f | AB483565 |
| 67 | S001419652 | 99.642 | uncult. bac. | C2_13H15f | AB482908 |
| 67 | S001419651 | 99.642 | uncult. bac. | C2_13G16f | AB482907 |
| 67 | S001188791 | 96.654 | endophytic bacterium HB02 | FJ205659 | |
| 67 | S000711290 | 96.525 | *Pantoea agglomerans* | WAB1872 | AM184214 |
| 67 | S000140489 | 96.525 | bacterium G2 | AY345398 | |
| 68 | S001195043 | 98.387 | uncult. *Serratia* sp. | C33BI24 | FJ372794 |
| 68 | S000038165 | 98.286 | *Pantoea agglomerans* | AH16 | AJ010096 |
| 68 | S000360061 | 98.264 | uncult. bac. | 2F06 | AY537762 |
| 68 | S000360017 | 98.258 | uncult. bac. | 1G08 | AY537716 |
| 68 | S000979075 | 98.256 | Enterobacteriaceae bacterium R-31537 | AM403612 | |
| 68 | S001044221 | 98.113 | *Pseudomonas fluorescens* | DDBNJ508 | AY874157 |
| 68 | S000425616 | 98.033 | *Klebsiella pneumoniae* | AY736552 | |
| 68 | S001082253 | 97.351 | uncult. *Klebsiella* sp. | NSR3Q1b71 | EU629750 |
| 68 | S000359995 | 97.213 | uncult. bac. | 1D06 | AY537693 |
| 68 | S000360189 | 96.117 | uncult. bac. | 2B12 | AY537895 |
| 69 | S000979075 | 99.709 | Enterobacteriaceae bacterium R-31537 | AM403612 | |
| 69 | S000386208 | 99.353 | *Microbacterium* sp. K10 | AB120356 | |
| 69 | S001568795 | 99.167 | uncult. bac. | P1_13 | GQ293382 |
| 69 | S001044221 | 99.054 | *Pseudomonas fluorescens* | DDBNJ508 | AY874157 |
| 69 | S001329319 | 98.843 | Enterobacter sp. Mn2 | FJ668636 | |
| 69 | S000877290 | 98.611 | uncult. *Enterobacter* sp. | Grias22 | EF548003 |
| 69 | S000459010 | 98.302 | *Enterobacter* sp. DW56 | AJ534854 | |
| 69 | S001188791 | 93.722 | endophytic bacterium HB02 | FJ205659 | |
| 69 | S000140489 | 93.612 | bacterium G2 | AY345398 | |
| 69 | S000599273 | 93.502 | uncult. bac. | bb2s2 | DQ068878 |
| 70 | S001421176 | 100 | uncult. bac. | N2_12H21f | AB484432 |
| 70 | S001421175 | 100 | uncult. bac. | N2_12G22f | AB484431 |
| 70 | S001421174 | 100 | uncult. bac. | N2_12E14f | AB484430 |
| 70 | S001420942 | 100 | uncult. bac. | N2_E2L18f | AB484198 |
| 70 | S001420929 | 100 | uncult. bac. | N2_E2J16f | AB484185 |
| 70 | S001420717 | 100 | uncult. bac. | N2_EN17f | AB483973 |
| 70 | S001420716 | 100 | uncult. bac. | N2_EI10f | AB483972 |
| 70 | S001420309 | 100 | uncult. bac. | C2_S4L20f | AB483565 |
| 70 | S001419652 | 100 | uncult. bac. | C2_13H15f | AB482908 |
| 70 | S001419651 | 100 | uncult. bac. | C2_13G16f | AB482907 |
| 71 | S000145384 | 100 | *Enterobacter asburiae* | ATCC 35953 | AJ417483 |
| 71 | S000619315 | 100 | uncult. bac. | BPH2C10006 | DQ221379 |
| 71 | S000619234 | 100 | uncult. bac. | BPH1C10005 | DQ221298 |
| 71 | S000619317 | 99.75 | uncult. bac. | BPH2C10008 | DQ221381 |
| 71 | S001420730 | 99.643 | uncult. bac. | N2_EP08f | AB483986 |
| 71 | S001420729 | 99.643 | uncult. bac. | N2_EO06f | AB483985 |
| 71 | S001420728 | 99.643 | uncult. bac. | N2_EL16f | AB483984 |
| 71 | S001420727 | 99.643 | uncult. bac. | N2_EJ05f | AB483983 |
| 71 | S001419008 | 99.643 | uncult. bac. | C2_EG04f | AB482264 |
| 71 | S000459010 | 98.679 | *Enterobacter* sp. DW56 | AJ534854 | |
| 72 | S000035980 | 99.751 | *Aeromonas* sp. Lgg5.7 | AJ489337 | |
| 72 | S000456820 | 99.365 | *Aeromonas* sp. ' | 10.5 MW-3' | AY826604 |
| 72 | S000967841 | 99.07 | *Aeromonas* sp. DH46 | EU260226 | |
| 72 | S000967819 | 99.026 | *Aeromonas* sp. DH14 | EU260204 | |
| 72 | S000691722 | 98.942 | bacterium SL2.12 | DQ517031 | |
| 72 | S000030133 | 98.936 | *Aeromonas veronii* | S4M13 | AF472504 |
| 72 | S000458071 | 98.921 | *Aeromonas veronii* | N31 | AB182193 |
| 72 | S000428536 | 98.868 | *Aeromonas veronii* | HM231 | AF079301 |
| 72 | S000428535 | 98.868 | *Aeromonas veronii* | HM221 | AF079300 |
| 72 | S000967846 | 97.774 | *Aeromonas* sp. DH57 | EU260231 | |
| 73 | S000386208 | 99.784 | *Microbacter.* sp. K10 | AB120356 | |
| 73 | S001568795 | 99.722 | uncult. bac. | P1_13 | GQ293382 |
| 73 | S000979075 | 99.709 | Enterobacteriaceae bacterium R-31537 | AM403612 | |
| 73 | S001420929 | 98.566 | uncult. bac. | N2_E2J16f | AB484185 |
| 73 | S001420717 | 98.566 | uncult. bac. | N2_EN17f | AB483973 |
| 73 | S001420716 | 98.566 | uncult. bac. | N2_EI10f | AB483972 |
| 73 | S001420309 | 98.566 | uncult. bac. | C2_S4L20f | AB483565 |
| 73 | S001419652 | 98.566 | uncult. bac. | C2_13H15f | AB482908 |
| 73 | S001419651 | 98.566 | uncult. bac. | C2_13G16f | AB482907 |
| 73 | S000459010 | 98.308 | *Enterobacter* sp. DW56 | AJ534854 | |
| 74 | S000804928 | 98.773 | *Salmonella enterica* subsp. *enterica* serovar Typhimurium | LT2 | D12814 |
| 74 | S000804927 | 98.773 | *Salmonella enterica* subsp. *enterica* serovar Typhi | D12813 | |
| 74 | S000804926 | 98.773 | *Salmonella enterica* subsp. | D12812 | |

TABLE 4-continued

| SEQ | RDP_ID | Identity | Match Name | Match Name | Access. # |
|---|---|---|---|---|---|
| | | | enterica | | |
| 74 | S000804925 | 98.773 | Salmonella enterica subsp. enterica serovar Enteritidis | D12811 | |
| 74 | S000804924 | 98.773 | Salmonella enterica subsp. enterica serovar Dublin | D12810 | |
| 74 | S000804923 | 98.773 | Salmonella enterica | D12809 | |
| 74 | S000832411 | 97.971 | uncult. bac. | VT70 | EF063971 |
| 74 | S000832410 | 97.971 | uncult. bac. | VT65 | EF063970 |
| 74 | S000832409 | 97.971 | uncult. bac. | VT40 | EF063969 |
| 74 | S000967880 | 96.161 | Enterobacter sp. DH40-2 | | EU260265 |
| 75 | S000979075 | 100 | Enterobacteriaceae bacterium R-31537 | | AM403612 |
| 75 | S000145384 | 99.762 | Enterobacter asburiae | ATCC 35953 | AJ417483 |
| 75 | S000619315 | 99.75 | uncult. bac. | BPH2C10006 | DQ221379 |
| 75 | S000619234 | 99.75 | uncult. bac. | BPH1C10005 | DQ221298 |
| 75 | S000877290 | 99.722 | uncult. Enterobacter sp. | Grias22 | EF548003 |
| 75 | S000619317 | 99.5 | uncult. bac. | BPH2C10008 | DQ221381 |
| 75 | S000619316 | 99.5 | uncult. bac. | BPH2C10007 | DQ221380 |
| 75 | S000619233 | 99.5 | uncult. bac. | BPH1C10004 | DQ221297 |
| 75 | S000619231 | 99.5 | uncult. bac. | BPH1C10002 | DQ221295 |
| 75 | S001044221 | 99.369 | Pseudomonas fluorescens | DDBNJ508 | AY874157 |
| 76 | S001421176 | 100 | uncult. bac. | N2_12H21f | AB484432 |
| 76 | S001421175 | 100 | uncult. bac. | N2_12G22f | AB484431 |
| 76 | S001421174 | 100 | uncult. bac. | N2_12E14f | AB484430 |
| 76 | S001420942 | 100 | uncult. bac. | N2_E2L18f | AB484198 |
| 76 | S001420929 | 100 | uncult. bac. | N2_E2J16f | AB484185 |
| 76 | S001420717 | 100 | uncult. bac. | N2_EN17f | AB483973 |
| 76 | S001420716 | 100 | uncult. bac. | N2_EI10f | AB483972 |
| 76 | S001420309 | 100 | uncult. bac. | C2_S4L20f | AB483565 |
| 76 | S001419652 | 100 | uncult. bac. | C2_13H15f | AB482908 |
| 76 | S001419651 | 100 | uncult. bac. | C2_13G16f | AB482907 |
| 77 | S000619324 | 99.75 | uncult. bac. | BPH2C12003 | DQ221388 |
| 77 | S001419009 | 99.463 | uncult. bac. | C2_EI14f | AB482265 |
| 77 | S000911957 | 99.275 | uncult. proteobacterium | MS043A1_F01 | EF701742 |
| 77 | S000619239 | 99.25 | uncult. bac. | BPH1C12001 | DQ221303 |
| 77 | S001419303 | 99.106 | uncult. bac. | C2_E2M04f | AB482559 |
| 77 | S001419265 | 99.106 | uncult. bac. | C2_E2I11f | AB482521 |
| 77 | S001231817 | 99.026 | uncult. bac. | gb3_HZ1B12 | FJ454745 |
| 77 | S000619326 | 98.5 | uncult. bac. | BPH2C12005 | DQ221390 |
| 77 | S000619325 | 98.5 | uncult. bac. | BPH2C12004 | DQ221389 |
| 77 | S000619323 | 98.5 | uncult. bac. | BPH2C12002 | DQ221387 |
| 78 | S001419009 | 99.284 | uncult. bac. | C2_EI14f | AB482265 |
| 78 | S000619324 | 99.25 | uncult. bac. | BPH2C12003 | DQ221388 |
| 78 | S001419303 | 98.927 | uncult. bac. | C2_E2M04f | AB482559 |
| 78 | S001419265 | 98.927 | uncult. bac. | C2_E2I11f | AB482521 |
| 78 | S000619239 | 98.75 | uncult. bac. | BPH1C12001 | DQ221303 |
| 78 | S000400130 | 98.634 | Serratia sp. R-17665 | | AY178563 |
| 78 | S000619326 | 98.5 | uncult. bac. | BPH2C12005 | DQ221390 |
| 78 | S000619325 | 98.5 | uncult. bac. | BPH2C12004 | DQ221389 |
| 78 | S000619323 | 98.5 | uncult. bac. | BPH2C12002 | DQ221387 |
| 78 | S000979075 | 97.965 | Enterobacteriaceae bacterium R-31537 | | AM403612 |
| 79 | S001419009 | 99.821 | uncult. bac. | C2_EI14f | AB482265 |
| 79 | S000619324 | 99.75 | uncult. bac. | BPH2C12003 | DQ221388 |
| 79 | S001419303 | 99.463 | uncult. bac. | C2_E2M04f | AB482559 |
| 79 | S001419265 | 99.463 | uncult. bac. | C2_E2I11f | AB482521 |
| 79 | S000911957 | 99.275 | uncult. proteobacterium | MS043A1_F01 | EF701742 |
| 79 | S000619239 | 99.25 | uncult. bac. | BPH1C12001 | DQ221303 |
| 79 | S000751165 | 98.785 | bacterium E8 | | EF016528 |
| 79 | S000619326 | 98.5 | uncult. bac. | BPH2C12005 | DQ221390 |
| 79 | S000619325 | 98.5 | uncult. bac. | BPH2C12004 | DQ221389 |
| 79 | S000619323 | 98.5 | uncult. bac. | BPH2C12002 | DQ221387 |
| 80 | S001419009 | 99.642 | uncult. bac. | C2_EI14f | AB482265 |
| 80 | S001419303 | 99.284 | uncult. bac. | C2_E2M04f | AB482559 |
| 80 | S001419265 | 99.284 | uncult. bac. | C2_E2I11f | AB482521 |
| 80 | S000836340 | 99.087 | uncult. bac. | 042_48h_JTSP | EF494584 |
| 80 | S000911957 | 99.034 | uncult. proteobacterium | MS043A1_F01 | EF701742 |
| 80 | S000619324 | 99 | uncult. bac. | BPH2C12003 | DQ221388 |
| 80 | S001046945 | 98.933 | Buttiauxella sp. 01WB03.2-68 | | FM161460 |
| 80 | S000979075 | 98.529 | Enterobacteriaceae bacterium R-31537 | | AM403612 |
| 80 | S001195043 | 98.058 | uncult. Serratia sp. | C33BI24 | FJ372794 |
| 80 | S000877290 | 98.056 | uncult. Enterobacter sp. | Grias22 | EF548003 |
| 81 | S001419009 | 99.821 | uncult. bac. | C2_EI14f | AB482265 |
| 81 | S001419303 | 99.463 | uncult. bac. | C2_E2M04f | AB482559 |
| 81 | S001419265 | 99.463 | uncult. bac. | C2_E2I11f | AB482521 |
| 81 | S000619324 | 99.25 | uncult. bac. | BPH2C12003 | DQ221388 |

TABLE 4-continued

| SEQ | RDP_ID | Identity | Match Name | Match Name | Access. # |
|---|---|---|---|---|---|
| 81 | S000836340 | 99.097 | uncult. bac. | 042_48h_JTSP | EF494584 |
| 81 | S001046945 | 98.95 | *Buttiauxella* sp. 01WB03.2-68 | FM161460 | |
| 81 | S000751165 | 98.58 | bacterium E8 | EF016528 | |
| 81 | S001156171 | 98.462 | *Buttiauxella agrestis* | KesE3 | EU884312 |
| 81 | S001323632 | 97.489 | uncult. *Citrobacter* sp. | TTGE gel band C2 | FJ719116 |
| 81 | S000969150 | 94.881 | uncult. bac. | fl3 | AB291632 |

TABLE 5 summarizes the bacterial Family and Genus dominance that may be concluded in view of the TABLE 4 results. "Br" is bluegill; "FHM" is fathead minnow; "Gam" is mosquitofish, or *Gambusia*; and "GS" is golden shiner.

TABLE 5

| Source Fish | SEQ ID NOs. from sequenced bacteria | Family | Genus |
|---|---|---|---|
| "Br" | 1-23 | Aeromonadaceae/ Moraxcellaceae | *Aeromonas*/ *Acinetobacter* |
| "FHM" | 24-37 | Comamonadaceae | *Acidovorax* |
| "Gam" | 38-76 | Aeromonadaceae/ Enterobacteriaceae | *Aeromonas*/*Enterobacter* |
| "GS" | 77-81 | Enterobacteriaceae | *Enterobacter* |

Behavior-eliciting compositions according to the present invention may include bacteria of the dominant families and genera indicated in TABLE 5. For example, if a predator fish preferentially exhibits feeding behavior in the presence of Bluegills, adding bacteria of the family Aeromonadaceae and the genus *Aeromonas* to compositions in accordance with the present invention may be effective in eliciting feeding behavior in said predator fish. Now that the inventors have disclosed the association between the source fish (Br, FHM, Gam, and GS) and the dominant bacterial families and genera, skilled artisans will instantly appreciate that it may be advantageous to add specific bacteria to compositions in order to influence the behavior of fish, avians, or marine mammals.

In another embodiment, compositions according to the present invention may include non-dominant bacteria. The methods disclosed by the instant application enable one of skill to isolate and test novel bacteria for their ability to elicit feeding responses in fish, avians, and marine mammals. The fish, avians, and marines animals may be responding to the dominant bacteria, or they may be responding to less well-represented bacteria. In either case, routine experimentation, as fully disclosed and described by the instant application, can be used to establish a correlation between specific bacteria (isolated from a source fish) and a feeding response exhibited by said fish, avians, or marine mammals.

It will be clear to those skilled in the art of fish modifying compositions that many modifications and substitutions can be made to the composition and its various methods of preparation and use described above without departing from the spirit and scope of the invention, which is defined by the appended claims.

CITED REFERENCES

Baker G C, Smith J J, Cowan D A. Review and re-analysis of domain-specific 16S primers. J Microbiol Methods. 2003 December; 55(3):541-55.

Bano, N., W. A. Bennett, A. deR. Smith, L. Vasquez and J. T. Hollibaugh. 2007. Dominance of *Mycoplasma* in the guts of the Long-Jawed Mudsucker, *Gillichthys mirabilis*, from five California salt marshes. Environmental Microbiology 9: 2636-2631.

Bardach, J. E. and T. Villars (1974). The chemical senses of fishes. *Chemoreception in Marine Organisms*. P. T. Grant and A. M. Mackie. New York, Academic Press. 1: 49-104.

Bergey, D. H. (1994). *Bergey's Manual of Determinative Bacteriology*. Baltimore, Lippincott Williams & Wilkins.

Carr, W. E. S. (1988). The molecular nature of chemical stimuli in the aquatic environment. *Sensory Biology of Aquatic Animals*. J. Atema. New York, Springer-Verlag: 3-27.

COLE et al. Nucleic Acids Res. 2009 January; 37 (Database issue):D141-5. Epub 2008 Nov. 12.

CUMMINS, S. E., SCHEIN, C. H., X U, Y., BRAUN, W., and NAGLE, G. T. 2005. Molluscan attractins: A family of water-borne protein pheromones with interspecific attractiveness. Peptides 26: 121-129.

Davis, B. D., R. Dulbecco, et al. (1990). *Microbiology*. Philadelphia, Lippencott Williams & Wilkins.

Eaton, A. D., L. S. Clesceri, et al. (1992). Method 4500-Cl. *Standard Methods for the Examination of Water & Wastewater*, American Public Health Association.

Fisknes, B. and K. Doving (1982). "Olfactory sensitivity to group-specific substances in Atlantic salmon." *Journal of Chemical Ecology* 8(8): 1083-1091.

Hara, T. J. (1992). *Fish Chemoreception*. London, Chapman & Hall.

HARDEGE, J., BARTELS-HARDEGE, H., MULLER, C. T., and BECKMANN, M. 2004. Peptide pheromones in female *Nereis succinea*. Peptides 9:1517-1522.

HOWE, N. R., and SHEIKH, Y. M. 1975. Anthopleurine: A sea anemone alarm pheromone. Science 189:386-388.

KICKLIGHTER, C. E., GERMANN, M., KAMIO, M., and DERBY, C. D. 2007. Molecular identification of alarm cues in the defensive secretions of the sea hare *Aplysia californica*. Anim. Behav. 74:1481-1492.

Kleerekoper, H. (1969). Olfaction in Fishes. Bloomington, Ind. University Press.

KRUG, P. J., and MANZI, A. E. 1999. Waterborne and surface-associated carbohydrates as settlement cues for larvae of the specialist marine herbivore, *Alderia modesta*. Biol. Bull. 197: 94-103.

Lim, C. and C. D. Webster (2001). *Nutrition and Fish Health*. Philadelphia, Haworth Press.

Naylor, R. L., R. J. Goldberg, et al. (2000). "Effect of aquaculture on world fish supplies." *Nature* 405(6790): 1017-1024.

PAINTER, S. D., CLOUGH, B., GARDEN, R. W., SWEEDLER, J. V., and NAGLE, G. T. 1998. Characterization of *Aplysia* attractin, the first waterborne peptide pheromone in invertebrates. Biol. Bull. 194:120-131.

PAWLIK, J. R., and BUTMAN, C. A. 1993. Settlement of a marine tube worm as a function of current velocity: Interacting effects of hydrodynamics and behavior. Limnol. Oceanogr. 38:1730-1740.

Pfeiffer, W. (1982). Chemical signals in communication. *Chemorecption in Fishes*. T. J. Hara. New York, Elsevier Sci. Publ. Co.: 307-326.

Reutter, K., F. Boudriot, et al. (2000). "Heterogeneity of Fish Taste Bud Ultrastructure as Demonstrated in the Holosteans Amia calva and Lepisosteus oculatus." *Philosophical Transactions: Biological Sciences* 355(1401): 1225-1228.

Sokal, R. F. and F. J. Rohlf (1969). *Biometry*. San Francisco, W. H. Freeman & Co.

Subcommittee-Fish-Nutrition (1993). *Nutrient Requirements of Fish*. Washington, D.C., The National Academies Press.

Zimmer and Zimmer. (2008) Dynamic Scaling in Chemical Ecology. J Chem Ecol 34:822-836.

What is claimed is:

1. A method for isolating and identifying persistent feeding behavior-eliciting bacteria from the gill, mouth or skin mucosa of an aquatic prey animal, or for isolating and identifying avoidance behavior-eliciting bacteria from the gill, mouth and/or skin mucosa of an aquatic predator animal;

wherein the isolated feeding behavior-eliciting bacteria and the aquatic prey animal each elicit the same persistent feeding behavior in the prey animal's normal aquatic predator animal; or wherein the isolated avoidance behavior-eliciting bacteria and the aquatic predator animal each elicit the same avoidance behavior in the aquatic predator animal's normal aquatic prey animal, comprising the steps of:

a. providing the aquatic predator animal or the aquatic prey animal;
b. placing the animal in a container that contains water;
c. not feeding the animal for a period of time;
d. placing the animal in sub-micron filtered or otherwise sterilized or distilled water;
e. allowing the behavior-eliciting bacteria from the prey or predator animal's gill, mouth and/or skin mucosa to enter the water, over a period of at least about 10 minutes, thereby producing conditioned water, which contains the behavior-eliciting bacteria;
f. inoculating minimal media with an aliquot of the conditioned water, which contains the behavior-eliciting bacteria, then propagating the bacteria, and finally streaking the bacteria on nutrient agar and allowing single colony isolates to form thereon;
g. subculturing the isolates until there is a substantial increase of the bacterial biomass, then chemically fixing and washing the bacteria;
h. exposing the prey animal's normal predator animal to the fixed and washed bacteria isolated from the prey animal, or exposing the predator animal's normal prey animal to the fixed and washed bacteria isolated from the predator animal;
i. allowing the prey animal sufficient time to manifest the avoidance behavior, or the predator animal sufficient time to manifest the persistent feeding behavior; and
j. identifying the isolated bacteria as being capable of eliciting the persistent feeding behavior when the predator animal from step i manifests the persistent feeding behavior; or, identifying the isolated bacteria as being capable of eliciting the avoidance behavior when the prey animal from step i exhibits the avoidance behavior, thereby isolating and identifying the persistent feeding behavior-eliciting bacteria from the aquatic prey animal or the avoidance behavior-eliciting bacteria from the aquatic predator animal.

2. The method of claim 1, wherein the culturing step g is done in the dark to avoid the growth of algae and other photosynthetic organisms.

3. The method of claim 1, wherein the prey or predator animal is not fed in step c for at least about 24 hours and is also rinsed at least one time prior to being placed in the water in the placing step d.

4. The method of claim 1, wherein the culturing step g is done in the dark, the prey or predator animal is not fed in step c for at least about 24 hours, and the source animal is rinsed at least once prior to being placed in the water in the placing step d.

5. The method of claim 4, wherein the culturing step g is conducted in minimal media comprising a mixture of potassium phosphate-dibasic, potassium phosphate-monobasic, ammonium sulfate, sodium sulfate, magnesium sulfate and distilled water.

6. The method of claim 5, wherein the culturing step g is conducted in minimal media comprising a mixture of potassium phosphate-dibasic, potassium phosphate-monobasic, ammonium sulfate, sodium sulfate, magnesium sulfate, distilled water, and glucose.

7. The method of claim 6, wherein the minimal media comprises the following components in the indicated amounts, expressed as percent by weight of total media: potassium phosphate-dibasic, present in an amount between approximately 0.1% to 2.0%; potassium phosphate-monobasic, present in an amount between approximately 0.1% to 1.0%; ammonium sulfate, present in an amount between approximately 0.01% to 0.8%; sodium sulfate citrate, present in an amount between approximately 0.005% to 0.55%; magnesium sulfate, present in an amount between approximately 0.001% to 0.03%; distilled water, present in an amount between approximately 70% to 99%; and a concentrated solution of sterile glucose between approximately 1.0% to 10.0%.

8. The method of claim 6, wherein said culturing step g continues until there is a substantial increase of the bacterial biomass or is performed for approximately 48 hours.

9. The method of claim 1, wherein the prey animal is a fathead minnow (FHM), a bluegill, a golden shiner or a mosquitofish.

10. The method of claim 1, wherein the bacteria of exposing step h are comprised of a mixture of at least two different genera.

11. The method of claim 10, wherein the bacteria of exposing step h are comprised of a mixture of at least three different genera.

12. A method for eliciting a persistent feeding behavior in an aquatic predator animal, or an avoidance behavior in an aquatic prey animal, comprising the step of exposing the predator or prey animal to an effective amount of a composition comprising the feeding behavior-eliciting or avoidance behavior-eliciting bacteria identified in step j of the method of claim 1, thereby eliciting the behavior.

13. The method of claim 12, wherein the aquatic predator or prey animal exhibits the persistent feeding behavior or avoidance behavior within less than about 30 minutes of being exposed to the composition.

14. The method of claim 13, wherein the predator or prey animal exhibits the behavior within less than about 10 minutes of being exposed to the composition.

15. The method of claim 13, wherein the predator animal responds to the composition in substantially the same way as the predator animal would respond to the presence of the aquatic prey animal from which the behavior-eliciting bacteria were isolated.

16. The method of claim 13, wherein the prey animal responds to the composition in substantially the same way as the prey animal would respond to the presence of the aquatic predator animal from which the behavior-eliciting bacteria were isolated.

* * * * *

SEQUENCE LISTING

```
<160> NUMBER OF SEQ ID NOS: 81

<210> SEQ ID NO 1
<211> LENGTH: 879
<212> TYPE: DNA
<213> ORGANISM: Artificial Sequence
<220> FEATURE:
<223> OTHER INFORMATION: Br1-1-10-27F_E10.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (614)..(616)
<223> OTHER INFORMATION: n is a, c, g, or t
<220> FEATURE:
<221> NAME/KEY: misc_feature
<222> LOCATION: (637)..(637)
<223> OTHER INFORMATION: n is a, c, g, or t
<220> FEATURE:
<221> NAME/KEY: misc_feature
<222> LOCATION: (713)..(714)
<223> OTHER INFORMATION: n is a, c, g, or t
<220> FEATURE:
<221> NAME/KEY: misc_feature
<222> LOCATION: (717)..(717)
<223> OTHER INFORMATION: n is a, c, g, or t
<220> FEATURE:
<221> NAME/KEY: misc_feature
<222> LOCATION: (719)..(720)
<223> OTHER INFORMATION: n is a, c, g, or t
<220> FEATURE:
<221> NAME/KEY: misc_feature
<222> LOCATION: (722)..(724)
<223> OTHER INFORMATION: n is a, c, g, or t
<220> FEATURE:
<221> NAME/KEY: misc_feature
<222> LOCATION: (727)..(727)
<223> OTHER INFORMATION: n is a, c, g, or t
<220> FEATURE:
<221> NAME/KEY: misc_feature
<222> LOCATION: (758)..(758)
<223> OTHER INFORMATION: n is a, c, g, or t
<220> FEATURE:
<221> NAME/KEY: misc_feature
<222> LOCATION: (775)..(777)
<223> OTHER INFORMATION: n is a, c, g, or t
<220> FEATURE:
<221> NAME/KEY: misc_feature
<222> LOCATION: (787)..(788)
<223> OTHER INFORMATION: n is a, c, g, or t
<220> FEATURE:
<221> NAME/KEY: misc_feature
<222> LOCATION: (791)..(791)
<223> OTHER INFORMATION: n is a, c, g, or t
<220> FEATURE:
<221> NAME/KEY: misc_feature
<222> LOCATION: (797)..(797)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
```

<221> NAME/KEY: misc_feature
<222> LOCATION: (810)..(810)
<223> OTHER INFORMATION: n is a, c, g, or t
<220> FEATURE:
<221> NAME/KEY: misc_feature
<222> LOCATION: (813)..(814)
<223> OTHER INFORMATION: n is a, c, g, or t
<220> FEATURE:
<221> NAME/KEY: misc_feature
<222> LOCATION: (816)..(817)
<223> OTHER INFORMATION: n is a, c, g, or t
<220> FEATURE:
<221> NAME/KEY: misc_feature
<222> LOCATION: (837)..(837)
<223> OTHER INFORMATION: n is a, c, g, or t
<220> FEATURE:
<221> NAME/KEY: misc_feature
<222> LOCATION: (842)..(844)
<223> OTHER INFORMATION: n is a, c, g, or t
<220> FEATURE:
<221> NAME/KEY: misc_feature
<222> LOCATION: (847)..(854)
<223> OTHER INFORMATION: n is a, c, g, or t
<220> FEATURE:
<221> NAME/KEY: misc_feature
<222> LOCATION: (856)..(857)
<223> OTHER INFORMATION: n is a, c, g, or t
<220> FEATURE:
<221> NAME/KEY: misc_feature
<222> LOCATION: (859)..(859)
<223> OTHER INFORMATION: n is a, c, g, or t
<220> FEATURE:
<221> NAME/KEY: misc_feature
<222> LOCATION: (861)..(861)
<223> OTHER INFORMATION: n is a, c, g, or t
<220> FEATURE:
<221> NAME/KEY: misc_feature
<222> LOCATION: (863)..(863)
<223> OTHER INFORMATION: n is a, c, g, or t
<220> FEATURE:
<221> NAME/KEY: misc_feature
<222> LOCATION: (875)..(876)
<223> OTHER INFORMATION: n is a, c, g, or t

<400> SEQUENCE: 1

```
tacnntgcag tcgagcggca gcgggaaagt agcttgctac ttttgccggc gagcggcgga      60
cgggtgagta atgcctgggg atctgcccag tcgaggggga taactactgg aaacggtagc     120
taataccgca tacgccctac gggggaaagc agggaccttc gggccttgcg cgattggat     180
gaacccaggt gggattagct agttggtgag gtaacggctc accaaggcga cgatccctag     240
ctggtctgag aggatgatca gccacactgg aactgagaca cggtccagac tcctacggga     300
ggcagcagtg gggaatattg cacaatgggg gaaaccctga tgcagccatg ccgcgtgtgt     360
gaagaaggcc ttcgggttgt aaagcacttt cagcgaggag gaaaggtcag tagctaatat     420
ctgctggctg tgacgttact cgcagaagaa gcaccggcta actccgtgcc agcagccgcg     480
gtaatacgga gggtgcaagc gttaatcgga attactgggc gtaaagcgca cgcaggcggt     540
tggataagtt agatgtgaaa gccccgggct caacctggga attgcattta aaactgtcca     600
gctagagtct tgannnggggg ggtagaattc caggtgntag cggtgaaatg cgtagagatc     660
tggaggaata ccgtggcga aggcggcccc ctgggacaaa gactgacgcc tcnngtngnn     720
annnagncgt ggggagcaac aggattagat accctggnag tccacgccgt aaacnnnatg     780
tcgattnnga ngctgtntct tganacgtgn ctnngnncta cgcgttaaat cgaccgnctg     840
gnnntannnn nnnngnnang ntnaactcaa tgaannacg                            879
```

<210> SEQ ID NO 2
<211> LENGTH: 896

```
<212> TYPE: DNA
<213> ORGANISM: Artificial Sequence
<220> FEATURE:
<223> OTHER INFORMATION: Br1-1-11-27F_E11.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (615)..(616)
<223> OTHER INFORMATION: n is a, c, g, or t
<220> FEATURE:
<221> NAME/KEY: misc_feature
<222> LOCATION: (640)..(640)
<223> OTHER INFORMATION: n is a, c, g, or t
<220> FEATURE:
<221> NAME/KEY: misc_feature
<222> LOCATION: (659)..(661)
<223> OTHER INFORMATION: n is a, c, g, or t
<220> FEATURE:
<221> NAME/KEY: misc_feature
<222> LOCATION: (698)..(698)
<223> OTHER INFORMATION: n is a, c, g, or t
<220> FEATURE:
<221> NAME/KEY: misc_feature
<222> LOCATION: (715)..(715)
<223> OTHER INFORMATION: n is a, c, g, or t
<220> FEATURE:
<221> NAME/KEY: misc_feature
<222> LOCATION: (764)..(764)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
<220> FEATURE:
<221> NAME/KEY: misc_feature
<222> LOCATION: (794)..(794)
<223> OTHER INFORMATION: n is a, c, g, or t
<220> FEATURE:
<221> NAME/KEY: misc_feature
<222> LOCATION: (804)..(805)
<223> OTHER INFORMATION: n is a, c, g, or t
<220> FEATURE:
<221> NAME/KEY: misc_feature
<222> LOCATION: (810)..(811)
<223> OTHER INFORMATION: n is a, c, g, or t
<220> FEATURE:
<221> NAME/KEY: misc_feature
<222> LOCATION: (815)..(816)
<223> OTHER INFORMATION: n is a, c, g, or t
<220> FEATURE:
<221> NAME/KEY: misc_feature
<222> LOCATION: (818)..(818)
<223> OTHER INFORMATION: n is a, c, g, or t
<220> FEATURE:
<221> NAME/KEY: misc_feature
<222> LOCATION: (820)..(822)
<223> OTHER INFORMATION: n is a, c, g, or t
<220> FEATURE:
<221> NAME/KEY: misc_feature
<222> LOCATION: (832)..(833)
<223> OTHER INFORMATION: n is a, c, g, or t
<220> FEATURE:
<221> NAME/KEY: misc_feature
<222> LOCATION: (836)..(838)
<223> OTHER INFORMATION: n is a, c, g, or t
<220> FEATURE:
<221> NAME/KEY: misc_feature
<222> LOCATION: (840)..(842)
<223> OTHER INFORMATION: n is a, c, g, or t
<220> FEATURE:
<221> NAME/KEY: misc_feature
<222> LOCATION: (848)..(852)
<223> OTHER INFORMATION: n is a, c, g, or t
<220> FEATURE:
<221> NAME/KEY: misc_feature
<222> LOCATION: (855)..(858)
```

<223> OTHER INFORMATION: n is a, c, g, or t
<220> FEATURE:
<221> NAME/KEY: misc_feature
<222> LOCATION: (862)..(862)
<223> OTHER INFORMATION: n is a, c, g, or t
<220> FEATURE:
<221> NAME/KEY: misc_feature
<222> LOCATION: (865)..(865)
<223> OTHER INFORMATION: n is a, c, g, or t
<220> FEATURE:
<221> NAME/KEY: misc_feature
<222> LOCATION: (868)..(868)
<223> OTHER INFORMATION: n is a, c, g, or t
<220> FEATURE:
<221> NAME/KEY: misc_feature
<222> LOCATION: (874)..(875)
<223> OTHER INFORMATION: n is a, c, g, or t
<220> FEATURE:
<221> NAME/KEY: misc_feature
<222> LOCATION: (883)..(885)
<223> OTHER INFORMATION: n is a, c, g, or t
<220> FEATURE:
<221> NAME/KEY: misc_feature
<222> LOCATION: (891)..(891)
<223> OTHER INFORMATION: n is a, c, g, or t

<400> SEQUENCE: 2

```
tacnntgcaa gtcgagcggc agcgggaaag tagcttgcta cttttgccgg cgagcggcgg      60
acgggtgagt aatgcctggg gatctgccca gtcgaggggg ataactactg gaaacggtag     120
ctaataccgc atacgcccta cggggggaaag caggggacct tcgggccttg cgcgattgga    180
tgaacccagg tgggattagc tagttggtga ggtaacggct caccaaggcg acgatcccta    240
gctggtctga gaggatgatc agccacactg gaactgagac acggtccaga ctcctacggg    300
aggcagcagt ggggaatatt gcacaatggg ggaaaccctg atgcagccat gccgcgtgtg    360
tgaagaaggc cttcgggttg taaagcactt tcagcgagga ggaaaggtca gtagctaata    420
tctgctggct gtgacgttac tcgcagaaga agcaccggct aactccgtgc cagcagccgc    480
ggtaatacgg agggtgcaag cgttaatcgg aattactggg cgtaaagcgc acgcaggcgg    540
ttggataagt tagatgtgaa agccccgggc tcaacctggg aattgcattt aaaactgtcc    600
agctagagtc ttgannaggg ggggtagaat tccaggtgtn agcggtgaaa tgcgtagann    660
nctggaggaa taccgggtgg cgaaaggcgg cccccctgnac aaagactgac gctcngtgcg    720
aaagcgtggg gagcaaacag gattagatac cctggtagtc cacnccgtaa acgatgtcga    780
tttggaggct gngntcttga gacnnggctn ncggnnantn nnagcgctta anntcnnncn    840
nngtgggnnn nntannnncc cncanggnta aaanntcaaa tgnnnttgac nggggg         896
```

<210> SEQ ID NO 3
<211> LENGTH: 851
<212> TYPE: DNA
<213> ORGANISM: Artificial Sequence
<220> FEATURE:
<223> OTHER INFORMATION: Br1-1-12-27F_E12.ab1
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (644)..(645)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (673)..(676)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (690)..(692)
<223> OTHER INFORMATION: n is a, c, g, or t
<220> FEATURE:
<221> NAME/KEY: misc_feature
<222> LOCATION: (704)..(706)
<223> OTHER INFORMATION: n is a, c, g, or t
<220> FEATURE:
<221> NAME/KEY: misc_feature
<222> LOCATION: (810)..(812)
<223> OTHER INFORMATION: n is a, c, g, or t
<220> FEATURE:
<221> NAME/KEY: misc_feature
<222> LOCATION: (832)..(832)
<223> OTHER INFORMATION: n is a, c, g, or t

<400> SEQUENCE: 3
gcggcntann catgcagtcg agcggcagcg ggaaagtagc ttgctacttt tgccggcgag      60
cggcggacgg gtgagtaatg cctggggatc tgcccagtcg aggggggataa ctactggaaa    120 cggtagctaa taccgcatac gccctacggg ggaaagcagg ggaccttcgg gccttgcgcg    180
attggatgaa cccaggtggg attagctagt tggtgaggta acggctcacc aaggcgacga    240
tccctagctg gtctgagagg atgatcagcc acactggaac tgagacacgg tccagactcc    300
tacgggaggc agcagtgggg aatattgcac aatgggggaa accctgatgc agccatgccg    360
cgtgtgtgaa gaaggccttc gggttgtaaa gcactttcag cgaggaggaa aggtcagtag    420
ctaatatctg ctggctgtga cgttactcgc agaagaagca ccggctaact ccgtgccagc    480
agccgcggta atacggaggg tgcaagcgtt aatcggaatt actgggcgta aagcgcacgc    540
aggcggttgg ataagttaga tgtgaaagcc ccgggctcaa cctggaatt gcatttaaaa     600 ctgtccagct agagtcttgt agaggggggt agaattccag gtgnngcggt ggaaatgcgt    660
agagcnctgg agnnnnccgg tggncgaagn nnggccccct ggannnagac tgacgctcag    720
gtgcgaaagc gtggggagca aacaggatta gataccctgg tagtccacgc cgtaaacgat    780
gtcgatttgg gaggctgtgt ccttgagacn nngccttccg ggagcctaac gncgttaaat    840
tcgacccgcc c                                                          851

<210> SEQ ID NO 4
<211> LENGTH: 892
<212> TYPE: DNA
<213> ORGANISM: Artificial Sequence
<220> FEATURE:
<223> OTHER INFORMATION: Br1-1-1-27F_E01.ab1
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:

<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (674)..(680)
<223> OTHER INFORMATION: n is a, c, g, or t
<220> FEATURE:
<221> NAME/KEY: misc_feature
<222> LOCATION: (692)..(693)
<223> OTHER INFORMATION: n is a, c, g, or t
<220> FEATURE:
<221> NAME/KEY: misc_feature
<222> LOCATION: (695)..(695)
<223> OTHER INFORMATION: n is a, c, g, or t
<220> FEATURE:
<221> NAME/KEY: misc_feature
<222> LOCATION: (697)..(697)
<223> OTHER INFORMATION: n is a, c, g, or t
<220> FEATURE:
<221> NAME/KEY: misc_feature
<222> LOCATION: (717)..(717)
<223> OTHER INFORMATION: n is a, c, g, or t
<220> FEATURE:
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (796)..(796)
<223> OTHER INFORMATION: n is a, c, g, or t
<220> FEATURE:
<221> NAME/KEY: misc_feature
<222> LOCATION: (804)..(805)
<223> OTHER INFORMATION: n is a, c, g, or t
<220> FEATURE:
<221> NAME/KEY: misc_feature
<222> LOCATION: (810)..(811)
<223> OTHER INFORMATION: n is a, c, g, or t
<220> FEATURE:
<221> NAME/KEY: misc_feature
<222> LOCATION: (815)..(815)
<223> OTHER INFORMATION: n is a, c, g, or t
<220> FEATURE:
<221> NAME/KEY: misc_feature
<222> LOCATION: (817)..(823)
<223> OTHER INFORMATION: n is a, c, g, or t
<220> FEATURE:
<221> NAME/KEY: misc_feature
<222> LOCATION: (834)..(834)
<223> OTHER INFORMATION: n is a, c, g, or t
<220> FEATURE:
<221> NAME/KEY: misc_feature
<222> LOCATION: (844)..(845)
<223> OTHER INFORMATION: n is a, c, g, or t
<220> FEATURE:
<221> NAME/KEY: misc_feature
<222> LOCATION: (852)..(852)
<223> OTHER INFORMATION: n is a, c, g, or t
<220> FEATURE:
<221> NAME/KEY: misc_feature
<222> LOCATION: (863)..(865)
<223> OTHER INFORMATION: n is a, c, g, or t
<220> FEATURE:
<221> NAME/KEY: misc_feature
<222> LOCATION: (879)..(879)
<223> OTHER INFORMATION: n is a, c, g, or t
<220> FEATURE:
<221> NAME/KEY: misc_feature
<222> LOCATION: (882)..(884)
<223> OTHER INFORMATION: n is a, c, g, or t

<400> SEQUENCE: 4
cgnngntncn ntgcaagtcg agcggcagcg ggaaagtagc ttgctacttt tgccggcgag     60
cggcggacgg gtgagtaatg cctggggatc tgcccagtcg aggggggataa ctactggaaa    120 cggtagctaa taccgcatac gccctacggg ggaaagcagg ggaccttcgg gccttgcgcg    180

```
attggatgaa cccaggtggg attagctagt tggtgaggta acggctcacc aaggcgacga    240
tccctagctg gtctgagagg atgatcagcc acactggaac tgagacacgg tccagactcc    300
tacgggaggc agcagtgggg aatattgcac aatgggggaa accctgatgc agccatgccg    360
cgtgtgtgaa gaaggccttc gggttgtaaa gcactttcag cgaggaggaa aggtcagtag    420
ctaatatctg ctggctgtga cgttactcgc agaagaagca ccggctaact ccgtgccagc    480
agccgcggta atacggaggg tgcaagcgtt aatcggaatt actgggcgta aagcgcacgc    540
aggcggttgg ataagttaga tgtgaaagcc ccgggctcaa cctgggaatt gcatttaaaa    600
ctgtccagct agagtcttgt agaggggggt agaattccag gtgtagcggt gaaacgcgta    660
gagatctgga ggannnnnnn ggggagggcg gnncncntgg acaaagactg acgctcngcg    720
cgaaagcgtg gggangcaaa caggattaga taccctggta gtccacgccg taaacgatgt    780
cgatttggaa ggctgngtcc ttgnnaacgn ngacntnnnn nnnggagcta cgcntaaatc    840
gacnnctggg gngtacggcc gcnnnttaaa actcaaatna annnacgggg gc    892
```

<210> SEQ ID NO 5
<211> LENGTH: 815
<212> TYPE: DNA
<213> ORGANISM: Artificial Sequence
<220> FEATURE:
<223> OTHER INFORMATION: Br1-1-13-27F_F01.ab1
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (677)..(677)
<223> OTHER INFORMATION: n is a, c, g, or t
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (712)..(715)
<223> OTHER INFORMATION: n is a, c, g, or t
<220> FEATURE:
<221> NAME/KEY: misc_feature
<222> LOCATION: (796)..(797)
<223> OTHER INFORMATION: n is a, c, g, or t
<220> FEATURE:
<221> NAME/KEY: misc_feature
<222> LOCATION: (800)..(800)
<223> OTHER INFORMATION: n is a, c, g, or t
<220> FEATURE:
<221> NAME/KEY: misc_feature
<222> LOCATION: (805)..(805)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
<220> FEATURE:
<221> NAME/KEY: misc_feature
<222> LOCATION: (809)..(809)
<223> OTHER INFORMATION: n is a, c, g, or t

<400> SEQUENCE: 5

```
tgcnagtcga gcggcagcgg gaaagtagct tgctactttt gccggcgagc ggcggacggg     60
tgagtaatgc ctggggatct gcccagtcga gggggataac tactggaaac ggtagctaat    120
accgcatacg ccctacgggg gaaagcaggg gaccttcggg ccttgcgcga ttggatgaac    180
ccaggtggga ttagctagtt ggtgaggtaa cggctcacca aggcgacgat ccctagctgg    240
```

| | | |
|---|---|---|
| tctgagagga tgatcagcca cactggaact gagacacggt ccagactcct acgggaggca | 300 |
| gcagtgggga atattgcaca atgggggaaa ccctgatgca gccatgccgc gtgtgtgaag | 360 |
| aaggccttcg ggttgtaaag cactttcagc gaggaggaaa ggtcagtagc taatatctgc | 420 |
| tggctgtgac gttactcgca gaagaagcac cggctaactc cgtgccagca gccgcggtaa | 480 |
| tacggagggt gcaagcgtta atcggaatta ctgggcgtaa agcgcacgca ggcggttgga | 540 |
| taagttagat gtgaaagccc cgggctcaac ctgggaattg catttaaaac tgtccagcta | 600 |
| gagtcttgta gagggggggta gaattccagg tgtagcggtg aaatgcgtag agatctggag | 660 |
| gaataccggt ggcgaangcg gccccctgga caaagactga cgctcangtg cnnnngcgtg | 720 |
| gggagcaaac aggattagat accctggtag tccacgccgt aaacgatgtc gatttggagg | 780 |
| ctgtgtcctt gagacnnggn ttccngnanc taacg | 815 |

<210> SEQ ID NO 6
<211> LENGTH: 824
<212> TYPE: DNA
<213> ORGANISM: Artificial Sequence
<220> FEATURE:
<223> OTHER INFORMATION: Br1-1-14-27F_F02.ab1
<220> FEATURE:
<221> NAME/KEY: misc_feature
<222> LOCATION: (677)..(677)
<223> OTHER INFORMATION: n is a, c, g, or t
<220> FEATURE:
<221> NAME/KEY: misc_feature
<222> LOCATION: (700)..(710)
<223> OTHER INFORMATION: n is a, c, g, or t
<220> FEATURE:
<221> NAME/KEY: misc_feature
<222> LOCATION: (781)..(781)
<223> OTHER INFORMATION: n is a, c, g, or t
<220> FEATURE:
<221> NAME/KEY: misc_feature
<222> LOCATION: (794)..(794)
<223> OTHER INFORMATION: n is a, c, g, or t
<220> FEATURE:
<221> NAME/KEY: misc_feature
<222> LOCATION: (806)..(807)
<223> OTHER INFORMATION: n is a, c, g, or t
<220> FEATURE:
<221> NAME/KEY: misc_feature
<222> LOCATION: (809)..(809)
<223> OTHER INFORMATION: n is a, c, g, or t
<220> FEATURE:
<221> NAME/KEY: misc_feature
<222> LOCATION: (820)..(820)
<223> OTHER INFORMATION: n is a, c, g, or t

<400> SEQUENCE: 6

| | | |
|---|---|---|
| tgcaagtcga gcggcagcgg gaaagtagct tgctactttt gccggcgagc ggcggacggg | 60 |
| tgagtaatgc ctggggatct gcccagtcga ggggggataac tactgaaac ggtagctaat | 120 |
| accgcatacg ccctacgggg gaaagcaggg gaccttcggg ccttgcgcga ttggatgaac | 180 |
| ccaggtggga ttagctagtt ggtgaggtaa cggctcacca aggcgacgat ccctagctgg | 240 |
| tctgagagga tgatcagcca cactggaact gagacacggt ccagactcct acgggaggca | 300 |
| gcagtgggga atattgcaca atgggggaaa ccctgatgca gccatgccgc gtgtgtgaag | 360 |
| aaggccttcg ggttgtaaag cactttcagc gaggaggaaa ggtcagtagc taatatctgc | 420 |
| tggctgtgac gttactcgca gaagaagcac cggctaactc cgtgccagca gccgcggtaa | 480 |
| tacggagggt gcaagcgtta atcggaatta ctgggcgtaa agcgcacgca ggcggttgga | 540 |
| taagttagat gtgaaagccc cgggctcaac ctgggaattg catttaaaac tgtccagcta | 600 |
| gagtcttgta gagggggggta gaattccagg tgtagcggtg aaatgcgtag agatctggag | 660 |

| | | | |
|---|---|---|---|
| gaataccggt ggcgaangcg gcccccctgga caaagactgn nnnnnnnnnn gcgaaagcgt | | | 720 |
| ggggagcaaa caggattaga taccctggta gtccacgccg taaacgatgt cgatttggag | | | 780 |
| nctgtgtcct tganacgtgg cttccnnanc taacgcgttn aatc | | | 824 |

```
<210> SEQ ID NO 7
<211> LENGTH: 780
<212> TYPE: DNA
<213> ORGANISM: Artificial Sequence
<220> FEATURE:
<223> OTHER INFORMATION: Br1-1-15-27F_F03.ab1
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (660)..(660)
<223> OTHER INFORMATION: n is a, c, g, or t
<220> FEATURE:
<221> NAME/KEY: misc_feature
<222> LOCATION: (676)..(678)
<223> OTHER INFORMATION: n is a, c, g, or t
<220> FEATURE:
<221> NAME/KEY: misc_feature
<222> LOCATION: (690)..(698)
<223> OTHER INFORMATION: n is a, c, g, or t
<220> FEATURE:
<221> NAME/KEY: misc_feature
<222> LOCATION: (700)..(702)
<223> OTHER INFORMATION: n is a, c, g, or t
<220> FEATURE:
<221> NAME/KEY: misc_feature
<222> LOCATION: (704)..(708)
<223> OTHER INFORMATION: n is a, c, g, or t
<220> FEATURE:
<221> NAME/KEY: misc_feature
<222> LOCATION: (712)..(719)
<223> OTHER INFORMATION: n is a, c, g, or t
<220> FEATURE:
<221> NAME/KEY: misc_feature
<222> LOCATION: (723)..(734)
<223> OTHER INFORMATION: n is a, c, g, or t
<220> FEATURE:
<221> NAME/KEY: misc_feature
<222> LOCATION: (736)..(744)
<223> OTHER INFORMATION: n is a, c, g, or t
<220> FEATURE:
<221> NAME/KEY: misc_feature
<222> LOCATION: (748)..(748)
<223> OTHER INFORMATION: n is a, c, g, or t
<220> FEATURE:
<221> NAME/KEY: misc_feature
<222> LOCATION: (751)..(752)
<223> OTHER INFORMATION: n is a, c, g, or t
<220> FEATURE:
<221> NAME/KEY: misc_feature
<222> LOCATION: (754)..(754)
<223> OTHER INFORMATION: n is a, c, g, or t
<220> FEATURE:
<221> NAME/KEY: misc_feature
<222> LOCATION: (775)..(775)
<223> OTHER INFORMATION: n is a, c, g, or t

<400> SEQUENCE: 7
```

| | | | |
|---|---|---|---|
| tgcangtcga gcggcagcgg gaaagcagct tgctactttt gccggcgagc ggcggacggg | | | 60 |
| tgagtaatgc ctggggatct gcccagtcga ggggataac tactgaaaac ggtagctaat | | | 120 |
| accgcatacg ccctacgggg gaaagcaggg gaccttcggg ccttgcgcga ttggatgaac | | | 180 |
| ccaggtggga ttagctagtt ggtgaggtaa cggctcacca aggcgacgat ccctagctgg | | | 240 |
| tctgagagga tgatcagcca cactggaact gagacacggt ccagactcct acgggaggca | | | 300 |

```
gcagtgggga atattgcaca atgggggaaa ccctgatgca gccatgccgc gtgtgtgaag    360
aaggccttcg ggttgtaaag cactttcagc gaggaggaaa ggtcagtagc taatatctgc    420
tggctgtgac gttactcgca gaagaagcac cggctaactc cgtgccagca gccgcggtaa    480
tacggagggt gcaagcgtta atcggaatta ctgggcgtaa agcgcacgca ggcggttgga    540
taagttagat gtgaaagccc cgggctcaac ctgggaattg catttaaaac tgtccagcta    600
gagtcttgta gaggggggta gaattccagg tgtagcggtg aaatgcgtag agatctggan    660
gaataccggt ggcgannngg cccctggan nnnnnnnngn nncnnnnngt gnnnnnnnng    720
ggnnnnnnnn nnnngnnnnn nnncccngg nnantccacg ccgtaaacga tgtcnatttg    780
```

<210> SEQ ID NO 8
<211> LENGTH: 875
<212> TYPE: DNA
<213> ORGANISM: Artificial Sequence
<220> FEATURE:
<223> OTHER INFORMATION: Br1-1-16-27F_F04.ab1
<220> FEATURE:
<221> NAME/KEY: misc_feature
<222> LOCATION: (3)..(6)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (656)..(656)
<223> OTHER INFORMATION: n is a, c, g, or t
<220> FEATURE:
<221> NAME/KEY: misc_feature
<222> LOCATION: (672)..(676)
<223> OTHER INFORMATION: n is a, c, g, or t
<220> FEATURE:
<221> NAME/KEY: misc_feature
<222> LOCATION: (679)..(681)
<223> OTHER INFORMATION: n is a, c, g, or t
<220> FEATURE:
<221> NAME/KEY: misc_feature
<222> LOCATION: (686)..(687)
<223> OTHER INFORMATION: n is a, c, g, or t
<220> FEATURE:
<221> NAME/KEY: misc_feature
<222> LOCATION: (689)..(689)
<223> OTHER INFORMATION: n is a, c, g, or t
<220> FEATURE:
<221> NAME/KEY: misc_feature
<222> LOCATION: (693)..(699)
<223> OTHER INFORMATION: n is a, c, g, or t
<220> FEATURE:
<221> NAME/KEY: misc_feature
<222> LOCATION: (704)..(704)
<223> OTHER INFORMATION: n is a, c, g, or t
<220> FEATURE:
<221> NAME/KEY: misc_feature
<222> LOCATION: (712)..(712)
<223> OTHER INFORMATION: n is a, c, g, or t
<220> FEATURE:
<221> NAME/KEY: misc_feature
<222> LOCATION: (715)..(716)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (739)..(745)
<223> OTHER INFORMATION: n is a, c, g, or t
<220> FEATURE:
<221> NAME/KEY: misc_feature
<222> LOCATION: (750)..(752)
<223> OTHER INFORMATION: n is a, c, g, or t

```
<220> FEATURE:
<221> NAME/KEY: misc_feature
<222> LOCATION: (754)..(761)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (770)..(770)
<223> OTHER INFORMATION: n is a, c, g, or t
<220> FEATURE:
<221> NAME/KEY: misc_feature
<222> LOCATION: (775)..(775)
<223> OTHER INFORMATION: n is a, c, g, or t
<220> FEATURE:
<221> NAME/KEY: misc_feature
<222> LOCATION: (778)..(779)
<223> OTHER INFORMATION: n is a, c, g, or t
<220> FEATURE:
<221> NAME/KEY: misc_feature
<222> LOCATION: (785)..(785)
<223> OTHER INFORMATION: n is a, c, g, or t
<220> FEATURE:
<221> NAME/KEY: misc_feature
<222> LOCATION: (790)..(790)
<223> OTHER INFORMATION: n is a, c, g, or t
<220> FEATURE:
<221> NAME/KEY: misc_feature
<222> LOCATION: (808)..(808)
<223> OTHER INFORMATION: n is a, c, g, or t
<220> FEATURE:
<221> NAME/KEY: misc_feature
<222> LOCATION: (812)..(812)
<223> OTHER INFORMATION: n is a, c, g, or t
<220> FEATURE:
<221> NAME/KEY: misc_feature
<222> LOCATION: (816)..(817)
<223> OTHER INFORMATION: n is a, c, g, or t
<220> FEATURE:
<221> NAME/KEY: misc_feature
<222> LOCATION: (832)..(832)
<223> OTHER INFORMATION: n is a, c, g, or t
<220> FEATURE:
<221> NAME/KEY: misc_feature
<222> LOCATION: (850)..(851)
<223> OTHER INFORMATION: n is a, c, g, or t
<220> FEATURE:
<221> NAME/KEY: misc_feature
<222> LOCATION: (856)..(856)
<223> OTHER INFORMATION: n is a, c, g, or t
<220> FEATURE:
<221> NAME/KEY: misc_feature
<222> LOCATION: (867)..(868)
<223> OTHER INFORMATION: n is a, c, g, or t
<220> FEATURE:
<221> NAME/KEY: misc_feature
<222> LOCATION: (871)..(871)
<223> OTHER INFORMATION: n is a, c, g, or t
<220> FEATURE:
<221> NAME/KEY: misc_feature
<222> LOCATION: (874)..(874)
<223> OTHER INFORMATION: n is a, c, g, or t

<400> SEQUENCE: 8
ctnnnntgcn agtcgagcgg cagcgggaaa gtagcttgct acttttgccg gcgagcggcg      60
gacgggtgag taatgcctgg ggatctgccc agtcgagggg gataactact ggaaacggta     120
gctaataccg catacgccct acggggggaaa gcagggggacc ttcgggcctt gcgcgattgg    180
atgaacccag gtgggattag ctagttggtg aggtaacggc tcaccaaggc gacgatccct     240
agctggtctg agaggatgat cagccacact ggaactgaga cacggtccag actcctacgg     300
gaggcagcag tggggaatat tgcacaatgg gggaaaccct gatgcagcca tgccgcgtgt     360
```

```
gtgaagaagg ccttcgggtt gtaaagcact ttcagcgagg aggaaaggtc agtagctaat    420
atctgctggc tgtgacgtta ctcgcagaag aagcaccggc taactccgtg ccagcagccg    480
cggtaatacg gagggtgcaa gcgttaatcg gaattactgg gcgtaaagcg cacgcaggcg    540
gttggataag ttagatgtga aagccccggg ctcaacctgg gaattgcatt taaaactgtc    600
cagctagagt cttgtagagg ggggtagaat tccaggtgta gcggtgaaat gcgtanagat    660
ctggaggata cnnnnnggnn nagagnngnc ccnnnnnnna aaanactgac gntcnntgcg    720
aaagcgtgng ggagcaaann nnnnntaaan nncnnnnnnn ncccncccn aaaanaanna    780 tgtcnatttn ggaggctgtg tccttganac gnggcnntcc gggagctaac gncgttaaat    840
cgaccgcccn ngggggnagta cgggccnnca nggnt                              875
```

<210> SEQ ID NO 9
<211> LENGTH: 843
<212> TYPE: DNA
<213> ORGANISM: Artificial Sequence
<220> FEATURE:
<223> OTHER INFORMATION: Br1-1-17-27F_F05.ab1
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (689)..(708)
<223> OTHER INFORMATION: n is a, c, g, or t
<220> FEATURE:
<221> NAME/KEY: misc_feature
<222> LOCATION: (710)..(715)
<223> OTHER INFORMATION: n is a, c, g, or t
<220> FEATURE:
<221> NAME/KEY: misc_feature
<222> LOCATION: (718)..(723)
<223> OTHER INFORMATION: n is a, c, g, or t
<220> FEATURE:
<221> NAME/KEY: misc_feature
<222> LOCATION: (725)..(725)
<223> OTHER INFORMATION: n is a, c, g, or t
<220> FEATURE:
<221> NAME/KEY: misc_feature
<222> LOCATION: (728)..(733)
<223> OTHER INFORMATION: n is a, c, g, or t
<220> FEATURE:
<221> NAME/KEY: misc_feature
<222> LOCATION: (753)..(753)
<223> OTHER INFORMATION: n is a, c, g, or t
<220> FEATURE:
<221> NAME/KEY: misc_feature
<222> LOCATION: (780)..(780)
<223> OTHER INFORMATION: n is a, c, g, or t
<220> FEATURE:
<221> NAME/KEY: misc_feature
<222> LOCATION: (785)..(785)
<223> OTHER INFORMATION: n is a, c, g, or t
<220> FEATURE:
<221> NAME/KEY: misc_feature
<222> LOCATION: (788)..(788)
<223> OTHER INFORMATION: n is a, c, g, or t
<220> FEATURE:
<221> NAME/KEY: misc_feature
<222> LOCATION: (790)..(790)
<223> OTHER INFORMATION: n is a, c, g, or t
<220> FEATURE:
<221> NAME/KEY: misc_feature
<222> LOCATION: (798)..(799)
<223> OTHER INFORMATION: n is a, c, g, or t
<220> FEATURE:
<221> NAME/KEY: misc_feature
<222> LOCATION: (802)..(802)
<223> OTHER INFORMATION: n is a, c, g, or t
<220> FEATURE:
<221> NAME/KEY: misc_feature
<222> LOCATION: (805)..(814)
<223> OTHER INFORMATION: n is a, c, g, or t
<220> FEATURE:
<221> NAME/KEY: misc_feature
<222> LOCATION: (816)..(816)
<223> OTHER INFORMATION: n is a, c, g, or t
<220> FEATURE:
<221> NAME/KEY: misc_feature
<222> LOCATION: (826)..(827)
<223> OTHER INFORMATION: n is a, c, g, or t
<220> FEATURE:
<221> NAME/KEY: misc_feature
<222> LOCATION: (835)..(835)
<223> OTHER INFORMATION: n is a, c, g, or t
<220> FEATURE:
<221> NAME/KEY: misc_feature
<222> LOCATION: (837)..(837)
<223> OTHER INFORMATION: n is a, c, g, or t
<220> FEATURE:
<221> NAME/KEY: misc_feature
<222> LOCATION: (839)..(839)
<223> OTHER INFORMATION: n is a, c, g, or t

<400> SEQUENCE: 9

```
tgcaagtcga gcggcagcgg gaaagtagct tgctactttt gccggcgagc ggcggacggg     60
tgagtaatgc ctggggatct gcccagtcga ggggggataac tactgaaaac ggtagctaat   120
accgcatacg ccctacgggg gaaagcaggg gaccttcggg ccttgcgcga ttggatgaac    180
ccaggtggga ttagctagtt ggtgaggtaa cggctcacca aggcgacgat ccctagctgg    240
tctgagagga tgatcagcca cactggaact gagacacggt ccagactcct acgggaggca    300
gcggtgggga atattgcaca atgggggaaa ccctgatgca gccatgccgc gtgtgtgaag    360
aaggccttcg ggttgtaaag cactttcagc gaggaggaaa ggtcagtagc tattatctgc    420
tggctgtgac gttactcgca gaagaagcac cggctaactc cgtgccagca gccgcggtaa    480
tacggagggt gcaagcgtta atcggaatta ctgggcgtaa agcgcacgca ggcggttgga    540
taagttagat gtgaaagccc cgggctcaac ctgggaattg catttaaaac tgtccagcta    600
gagtcttgta gaggggggta gaattccagg tgtagcggtg aaatgcgtag agatctggag    660
gaataccggt ggcgaagcgg nccctggnn nnnnnnnnn nnnnnnnngn nnnnaannn       720
nnngnggnnn nncaaacag gattagatac ccngggtagt ccacgccgta aacgatgtcn    780
attngangn tgtgtccnng anacnnnnnn nnnnanctaa cgcgtnnaat cgacngncng    840
ggg                                                                 843
```

<210> SEQ ID NO 10
<211> LENGTH: 774
<212> TYPE: DNA
<213> ORGANISM: Artificial Sequence
<220> FEATURE:
<223> OTHER INFORMATION: Br1-1-18-27F_F06.ab1
<220> FEATURE:
<221> NAME/KEY: misc_feature
<222> LOCATION: (677)..(677)
<223> OTHER INFORMATION: n is a, c, g, or t
<220> FEATURE:
<221> NAME/KEY: misc_feature
<222> LOCATION: (689)..(692)
<223> OTHER INFORMATION: n is a, c, g, or t
<220> FEATURE:
<221> NAME/KEY: misc_feature
<222> LOCATION: (695)..(697)
<223> OTHER INFORMATION: n is a, c, g, or t
<220> FEATURE:
<221> NAME/KEY: misc_feature
<222> LOCATION: (706)..(708)
<223> OTHER INFORMATION: n is a, c, g, or t
<220> FEATURE:

```
<221> NAME/KEY: misc_feature
<222> LOCATION: (731)..(731)
<223> OTHER INFORMATION: n is a, c, g, or t
<220> FEATURE:
<221> NAME/KEY: misc_feature
<222> LOCATION: (733)..(733)
<223> OTHER INFORMATION: n is a, c, g, or t
<220> FEATURE:
<221> NAME/KEY: misc_feature
<222> LOCATION: (761)..(763)
<223> OTHER INFORMATION: n is a, c, g, or t

<400> SEQUENCE: 10
tgcaagtcga gcggcagcgg gaaagtagct tgctacttttt gccggcgagc ggcggacggg    60
tgagtaatgc ctggggatct gcccagtcga gggggataac tactggaaac ggtagctaat   120
accgcatacg ccctacgggg gaaagcaggg gaccttcggg ccttgcgcga ttggatgaac   180
ccaggtggga ttagctagtt ggtgaggtaa cggctcacca aggcgacgat ccctagctgg   240
tctgagagga tgatcagcca cactggaact gagacacggt ccagactcct acgggaggca   300
gcagtgggga atattgcaca atgggggaaa ccctgatgca gccatgccgc gtgtgtgaag   360
aaggccttcg ggttgtaaag cactttcagc gaggaggaaa ggtcagtagc taatatctgc   420
tggctgtgac gttactcgca gaagaagcac cggctaactc cgtgccagca gccgcggtaa   480
tacggagggt gcaagcgttg atcggaatta ctgggcgtaa agcgcacgca ggcggttgga   540
taagttagat gtgaaagccc cgggctcaac ctgggaattg catttaaaac tgtccagcta   600
gagtcttgta gaggggggta gaattccagg tgtagcggtg aaatgcgtag agatctggag   660
gaataccggt ggcgaagcg gcccccctgnn nnaannntga cgctcnnntg cgaaagcgtg   720
gggagcaaac ngnattagat accccggtag tccgcgccgt nnngatgtcg attt         774

<210> SEQ ID NO 11
<211> LENGTH: 790
<212> TYPE: DNA
<213> ORGANISM: Artificial Sequence
<220> FEATURE:
<223> OTHER INFORMATION: Br1-1-19-27F_F07.ab1
<220> FEATURE:
<221> NAME/KEY: misc_feature
<222> LOCATION: (672)..(677)
<223> OTHER INFORMATION: n is a, c, g, or t
<220> FEATURE:
<221> NAME/KEY: misc_feature
<222> LOCATION: (679)..(679)
<223> OTHER INFORMATION: n is a, c, g, or t
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (692)..(693)
<223> OTHER INFORMATION: n is a, c, g, or t
<220> FEATURE:
<221> NAME/KEY: misc_feature
<222> LOCATION: (707)..(713)
<223> OTHER INFORMATION: n is a, c, g, or t
<220> FEATURE:
<221> NAME/KEY: misc_feature
<222> LOCATION: (731)..(732)
<223> OTHER INFORMATION: n is a, c, g, or t
<220> FEATURE:
<221> NAME/KEY: misc_feature
<222> LOCATION: (749)..(749)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
```

<220> FEATURE:
<221> NAME/KEY: misc_feature
<222> LOCATION: (777)..(777)
<223> OTHER INFORMATION: n is a, c, g, or t
<220> FEATURE:
<221> NAME/KEY: misc_feature
<222> LOCATION: (779)..(779)
<223> OTHER INFORMATION: n is a, c, g, or t
<220> FEATURE:
<221> NAME/KEY: misc_feature
<222> LOCATION: (781)..(781)
<223> OTHER INFORMATION: n is a, c, g, or t

<400> SEQUENCE: 11

```
tgcaagtcga gcggcagcgg gaaagtagct tgctactttt gccggcgagc ggcggacggg    60
tgagtaatgc ctggggatct gcccagtcga gggggataac tactggaaac ggtagctaat   120
accgcatacg ccctacgggg gaaagcaggg gaccttcggg ccttgcgcga ttggatgaac   180
ccaggtggga ttagctagtt ggtgaggtaa cggctcacca aggcgacgat ccctagctgg   240
tctgagagga tgatcagcca cactggaact gagacacggt ccagactcct acgggaggca   300
gcagtgggga atattgcaca atgggggaaa ccctgatgca gccatgccgc gtgtgtgaag   360
aaggccttcg ggttgtaaag cactttcagc gaggaggaaa ggtcagtagc taatatctgc   420
tggctgtgac gttactcgca gaagaagcac cggctaactc cgtgccagca gccgcggtaa   480
tacggtgggt gcaagcgtta atcggaatta ctgggcgtaa agcgcacgca ggcggttgga   540
taagttagat gtgaaagccc cgggctcaac ctgggaattg catttaaaac tgtccagcta   600
gagtcttgta gaggggggta gaattccagg tgtagcggtg aaatgcgtag agatctggag   660
gaataccggt gnnnnnngng gccccngggg annaagactg acgctcnnnn nnaaagcgt   720
ggggagcaaa nnggattaga taccctggna gtccacgccg taaacgangt cgatttngna   780
ngctgtgtcc                                                          790
```

<210> SEQ ID NO 12
<211> LENGTH: 787
<212> TYPE: DNA
<213> ORGANISM: Artificial Sequence
<220> FEATURE:
<223> OTHER INFORMATION: Br1-1-20-27F_F08.ab1
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (677)..(677)
<223> OTHER INFORMATION: n is a, c, g, or t
<220> FEATURE:
<221> NAME/KEY: misc_feature
<222> LOCATION: (706)..(707)
<223> OTHER INFORMATION: n is a, c, g, or t
<220> FEATURE:
<221> NAME/KEY: misc_feature
<222> LOCATION: (726)..(726)
<223> OTHER INFORMATION: n is a, c, g, or t
<220> FEATURE:
<221> NAME/KEY: misc_feature
<222> LOCATION: (731)..(734)
<223> OTHER INFORMATION: n is a, c, g, or t
<220> FEATURE:
<221> NAME/KEY: misc_feature
<222> LOCATION: (738)..(738)
<223> OTHER INFORMATION: n is a, c, g, or t
<220> FEATURE:
<221> NAME/KEY: misc_feature
<222> LOCATION: (747)..(748)
<223> OTHER INFORMATION: n is a, c, g, or t
<220> FEATURE:

<221> NAME/KEY: misc_feature
<222> LOCATION: (762)..(763)
<223> OTHER INFORMATION: n is a, c, g, or t
<220> FEATURE:
<221> NAME/KEY: misc_feature
<222> LOCATION: (770)..(770)
<223> OTHER INFORMATION: n is a, c, g, or t
<220> FEATURE:
<221> NAME/KEY: misc_feature
<222> LOCATION: (775)..(776)
<223> OTHER INFORMATION: n is a, c, g, or t
<220> FEATURE:
<221> NAME/KEY: misc_feature
<222> LOCATION: (778)..(778)
<223> OTHER INFORMATION: n is a, c, g, or t
<220> FEATURE:
<221> NAME/KEY: misc_feature
<222> LOCATION: (781)..(781)
<223> OTHER INFORMATION: n is a, c, g, or t
<220> FEATURE:
<221> NAME/KEY: misc_feature
<222> LOCATION: (785)..(785)
<223> OTHER INFORMATION: n is a, c, g, or t

<400> SEQUENCE: 12

```
tgnaagtcga gcggcagcgg gaaagtagct tgctactttt gccggcgagc ggcggacggg      60
tgagtaatgc ctggggatct gcccagtcga gggggataac tactgaaaac ggtagctaat     120
accgcatacg ccctacgggg gaaagcaggg gaccttcggg ccttgcgcga ttggatgaac     180
ccaggtggga ttagctagtt ggtgaggtaa cggctcacca aggcgacgat ccctagctgg     240
tctgagagga tgatcagcca cactggaact gagacacggt ccagactcct acgggaggca     300
gcagtgggga atattgcaca atgggggaaa ccctgatgca gccatgccgc gtgtgtgaag     360
aaggccttcg ggttgtaaag cactttcagc gaggaggaaa ggtcagtagc taatatctgc     420
tggctgtgac gttactcgca gaagaagcac cggctaactc cgtgccagca gccgcggtaa     480
tacggagggt gcaagcgtta atcggaatta ctgggcgtaa agcgcacgca ggcggttgga     540
taagttagat gtgaaagccc cgggctcaac ctgggaattg catttaaaac tgtccagcta     600
gagtcttgta gaggggggta gaattccagg tgtagcggtg aaatgcgtag agatctggag     660
gaataccggt ggcgaangcg gcccctgga caaagactga cgctcnngtg cgaaagcgtg     720
gggagnaaac nnnnttanat accctgnnag tccacgccgt anngatgtcn atttnnangc     780 ngtgncc                                                               787
```

<210> SEQ ID NO 13
<211> LENGTH: 823
<212> TYPE: DNA
<213> ORGANISM: Artificial Sequence
<220> FEATURE:
<223> OTHER INFORMATION: Br1-1-22-27F_F10.ab1
<220> FEATURE:
<221> NAME/KEY: misc_feature
<222> LOCATION: (677)..(677)
<223> OTHER INFORMATION: n is a, c, g, or t
<220> FEATURE:
<221> NAME/KEY: misc_feature
<222> LOCATION: (701)..(701)
<223> OTHER INFORMATION: n is a, c, g, or t
<220> FEATURE:
<221> NAME/KEY: misc_feature
<222> LOCATION: (703)..(703)
<223> OTHER INFORMATION: n is a, c, g, or t
<220> FEATURE:
<221> NAME/KEY: misc_feature
<222> LOCATION: (707)..(709)
<223> OTHER INFORMATION: n is a, c, g, or t
<220> FEATURE:
<221> NAME/KEY: misc_feature
<222> LOCATION: (762)..(762)
<223> OTHER INFORMATION: n is a, c, g, or t
<220> FEATURE:
<221> NAME/KEY: misc_feature
<222> LOCATION: (778)..(778)
<223> OTHER INFORMATION: n is a, c, g, or t
<220> FEATURE:
<221> NAME/KEY: misc_feature
<222> LOCATION: (785)..(785)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
<220> FEATURE:
<221> NAME/KEY: misc_feature
<222> LOCATION: (795)..(796)
<223> OTHER INFORMATION: n is a, c, g, or t
<220> FEATURE:
<221> NAME/KEY: misc_feature
<222> LOCATION: (799)..(799)
<223> OTHER INFORMATION: n is a, c, g, or t
<220> FEATURE:
<221> NAME/KEY: misc_feature
<222> LOCATION: (802)..(802)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (806)..(806)
<223> OTHER INFORMATION: n is a, c, g, or t
<220> FEATURE:
<221> NAME/KEY: misc_feature
<222> LOCATION: (808)..(808)
<223> OTHER INFORMATION: n is a, c, g, or t
<220> FEATURE:
<221> NAME/KEY: misc_feature
<222> LOCATION: (819)..(819)
<223> OTHER INFORMATION: n is a, c, g, or t

<400> SEQUENCE: 13

```
tgcaagtcga gcggcagcgg gaaagtagct tgctactttt gccggcgagc ggcggacggg    60
tgagtaatgc ctggggatct gcccagtcga gggggataac tactggaaac ggtagctaat   120
accgcatacg ccctacgggg gaaagcaggg gaccttcggg ccttgcgcga ttggatgaac   180
ccaggtggga ttagctagtt ggtgaggtaa cggctcacca aggcgacgat ccctagctgg   240
tctgagagga tgatcagcca cactggaact gagacacggt ccagactcct acgggaggca   300
gcagtgggga atattgcaca atgggggaaa ccctgatgca gccatgccgc gtgtgtgaag   360
aaggccttcg ggttgtaaag cactttcagc gaggaggaaa ggtcagtagc taatatctgc   420
tggctgtgac gttactcgca gaagaagcac cggctaactc cgtgccagca gccgcggtaa   480
tacggagggt gcaagcgtta atcggaatta ctgggcgtaa agcgcacgca ggcggttgga   540
taagttagat gtgaaagccc cgggctcaac ctgggaattg catttaaaac tgtccagcta   600
gagtcttgta gaggggggta gaattccagg tgtagcggtg aaatgcgtag agatctggag   660
gaataccggt ggcgaangcg gcccctgga caaagactga ncnctcnnng cgaaagcgtg   720
gggagcaaac aggattagat accctggtag tccacgccgt ancgatgtcg atttggangc   780
tgtgnccttg anacnnggnt tncngnanct aacgcgttna atc                    823
```

<210> SEQ ID NO 14
<211> LENGTH: 870
<212> TYPE: DNA
<213> ORGANISM: Artificial Sequence
<220> FEATURE:

```
<223> OTHER INFORMATION: Br1-1-2-27F_E02.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (647)..(648)
<223> OTHER INFORMATION: n is a, c, g, or t
<220> FEATURE:
<221> NAME/KEY: misc_feature
<222> LOCATION: (650)..(650)
<223> OTHER INFORMATION: n is a, c, g, or t
<220> FEATURE:
<221> NAME/KEY: misc_feature
<222> LOCATION: (652)..(654)
<223> OTHER INFORMATION: n is a, c, g, or t
<220> FEATURE:
<221> NAME/KEY: misc_feature
<222> LOCATION: (656)..(658)
<223> OTHER INFORMATION: n is a, c, g, or t
<220> FEATURE:
<221> NAME/KEY: misc_feature
<222> LOCATION: (660)..(661)
<223> OTHER INFORMATION: n is a, c, g, or t
<220> FEATURE:
<221> NAME/KEY: misc_feature
<222> LOCATION: (663)..(671)
<223> OTHER INFORMATION: n is a, c, g, or t
<220> FEATURE:
<221> NAME/KEY: misc_feature
<222> LOCATION: (673)..(679)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (684)..(686)
<223> OTHER INFORMATION: n is a, c, g, or t
<220> FEATURE:
<221> NAME/KEY: misc_feature
<222> LOCATION: (688)..(691)
<223> OTHER INFORMATION: n is a, c, g, or t
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (726)..(726)
<223> OTHER INFORMATION: n is a, c, g, or t
<220> FEATURE:
<221> NAME/KEY: misc_feature
<222> LOCATION: (730)..(730)
<223> OTHER INFORMATION: n is a, c, g, or t
<220> FEATURE:
<221> NAME/KEY: misc_feature
<222> LOCATION: (732)..(732)
<223> OTHER INFORMATION: n is a, c, g, or t
<220> FEATURE:
<221> NAME/KEY: misc_feature
<222> LOCATION: (736)..(739)
<223> OTHER INFORMATION: n is a, c, g, or t
<220> FEATURE:
<221> NAME/KEY: misc_feature
<222> LOCATION: (741)..(742)
<223> OTHER INFORMATION: n is a, c, g, or t
<220> FEATURE:
<221> NAME/KEY: misc_feature
<222> LOCATION: (750)..(750)
<223> OTHER INFORMATION: n is a, c, g, or t
<220> FEATURE:
<221> NAME/KEY: misc_feature
<222> LOCATION: (753)..(754)
<223> OTHER INFORMATION: n is a, c, g, or t
<220> FEATURE:
<221> NAME/KEY: misc_feature
```

```
<222> LOCATION: (764)..(765)
<223> OTHER INFORMATION: n is a, c, g, or t
<220> FEATURE:
<221> NAME/KEY: misc_feature
<222> LOCATION: (769)..(771)
<223> OTHER INFORMATION: n is a, c, g, or t
<220> FEATURE:
<221> NAME/KEY: misc_feature
<222> LOCATION: (775)..(776)
<223> OTHER INFORMATION: n is a, c, g, or t
<220> FEATURE:
<221> NAME/KEY: misc_feature
<222> LOCATION: (789)..(790)
<223> OTHER INFORMATION: n is a, c, g, or t
<220> FEATURE:
<221> NAME/KEY: misc_feature
<222> LOCATION: (796)..(796)
<223> OTHER INFORMATION: n is a, c, g, or t
<220> FEATURE:
<221> NAME/KEY: misc_feature
<222> LOCATION: (802)..(802)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
<220> FEATURE:
<221> NAME/KEY: misc_feature
<222> LOCATION: (814)..(814)
<223> OTHER INFORMATION: n is a, c, g, or t
<220> FEATURE:
<221> NAME/KEY: misc_feature
<222> LOCATION: (816)..(816)
<223> OTHER INFORMATION: n is a, c, g, or t
<220> FEATURE:
<221> NAME/KEY: misc_feature
<222> LOCATION: (823)..(823)
<223> OTHER INFORMATION: n is a, c, g, or t
<220> FEATURE:
<221> NAME/KEY: misc_feature
<222> LOCATION: (830)..(830)
<223> OTHER INFORMATION: n is a, c, g, or t
<220> FEATURE:
<221> NAME/KEY: misc_feature
<222> LOCATION: (832)..(835)
<223> OTHER INFORMATION: n is a, c, g, or t
<220> FEATURE:
<221> NAME/KEY: misc_feature
<222> LOCATION: (841)..(842)
<223> OTHER INFORMATION: n is a, c, g, or t
<220> FEATURE:
<221> NAME/KEY: misc_feature
<222> LOCATION: (846)..(846)
<223> OTHER INFORMATION: n is a, c, g, or t
<220> FEATURE:
<221> NAME/KEY: misc_feature
<222> LOCATION: (851)..(851)
<223> OTHER INFORMATION: n is a, c, g, or t
<220> FEATURE:
<221> NAME/KEY: misc_feature
<222> LOCATION: (858)..(859)
<223> OTHER INFORMATION: n is a, c, g, or t
<220> FEATURE:
<221> NAME/KEY: misc_feature
<222> LOCATION: (863)..(863)
<223> OTHER INFORMATION: n is a, c, g, or t
<220> FEATURE:
<221> NAME/KEY: misc_feature
<222> LOCATION: (865)..(866)
<223> OTHER INFORMATION: n is a, c, g, or t

<400> SEQUENCE: 14
tacnntgcaa gtcgagcggc agcgggaaag tagcttgcta cttttgccgg cgagcggcgg      60
```

```
acgggtgagt aatgcctggg gatctgccca gtcgagggg ataactactg gaaacggtag     120
ctaataccgc atacgccta cggggaaag cagggacct tcgggccttg cgcgattgga      180
tgaacccagg tgggattagc tagttggtga ggtaacggct caccaaggcg acgatccta    240 gctggtctga gaggatgatc agccacactg gaactgagac acggtccaga ctcctacggg   300
aggcagcagt ggggaatatt gcacaatggg ggaaaccctg atgcagccat gccgcgtgtg   360
tgaagaaggc cttcgggttg taaagcactt tcagcgagga ggaaaggtca gtagctaata   420
tctgctggct gtgacgttac tcgcagaaga agcaccggct aactccgtgc cagcagccgc   480
ggtaatacgg agggtgcaag cgttaatcgg aattactggg cgtaaagcgc acgcaggcgg   540
ttggataagt tagatgtgaa agccccggc tcaacctggg aattgcattt aaaactgtcc    600
agctagagtc ttgtagaggg gggtagaatt ccaggtgtag cggtganntn annnannngn   660
ngnnnnnnnn nannnnnnna naannntnnn nanctgacgc tcagtgcgaa agcgtgggga   720
gcaacngatn ancgtnnnnc nnacagcatn ganngtcctt aaanngtnn nggannaccg    780 tttaaattnn ccgccnggga ananggnccc gagngntaaa agnttcaaan tnnnntatgg   840
nnagtntgga ncgggggnnc cgncnncaaa                                    870
```

<210> SEQ ID NO 15
<211> LENGTH: 789
<212> TYPE: DNA
<213> ORGANISM: Artificial Sequence
<220> FEATURE:
<223> OTHER INFORMATION: Br1-1-23-27F_F11.ab1
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (677)..(677)
<223> OTHER INFORMATION: n is a, c, g, or t
<220> FEATURE:
<221> NAME/KEY: misc_feature
<222> LOCATION: (706)..(708)
<223> OTHER INFORMATION: n is a, c, g, or t
<220> FEATURE:
<221> NAME/KEY: misc_feature
<222> LOCATION: (711)..(712)
<223> OTHER INFORMATION: n is a, c, g, or t
<220> FEATURE:
<221> NAME/KEY: misc_feature
<222> LOCATION: (731)..(731)
<223> OTHER INFORMATION: n is a, c, g, or t
<220> FEATURE:
<221> NAME/KEY: misc_feature
<222> LOCATION: (733)..(733)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (776)..(776)
<223> OTHER INFORMATION: n is a, c, g, or t
<220> FEATURE:
<221> NAME/KEY: misc_feature
<222> LOCATION: (780)..(780)
<223> OTHER INFORMATION: n is a, c, g, or t
<220> FEATURE:
<221> NAME/KEY: misc_feature
<222> LOCATION: (784)..(786)
<223> OTHER INFORMATION: n is a, c, g, or t

<400> SEQUENCE: 15

```
tgcnagtcga gcggcagcgg gaaagtagct tgctactttt gccggcgagc ggcggacggg    60
```

```
tgagtaatgc ctggggatct gcccagtcga gggggataac tactggaaac ggtagctaat    120
accgcatacg ccctacgggg gaaagcaggg gaccttcggg ccttgcgcga ttggatgaac    180
ccaggtggga ttagctagtt ggtgaggtaa cggctcacca aggcgacgat ccctagctgg    240
tctgagagga tgatcagcca cactggaact gagacacggt ccagactcct acgggaggca    300
gcagtgggga atattgcaca atgggggaaa ccctgatgca gccatgccgc gtgtgtgaag    360
aaggccttcg ggttgtaaag cactttcagc gaggaggaaa ggtcagtagc taatatctgc    420
tggctgtgac gttactcgca gaagaagcac cggctaactc cgtgccagca gccgcggtaa    480 tacgagggt gcaagcgtta atcgaatta ctgggcgtaa agcgcacgca ggcggttgga    540
taagttagat gtgaaagccc cgggctcaac ctgggaattg catttaaaac tgtccagcta    600
gagtcttgta gaggggggta gaattccagg tgtagcggtg aaatgcgtag agatctggag    660
gaataccggt ggcgaangcg gcccctgga caaagactga cgctcnnngc nnaaagcgtg    720
gggagcaaac ngattagat accctggtag tccacgccgt aaacnatgtc gatttngagn    780 ctgnnncct                                                            789
```

<210> SEQ ID NO 16
<211> LENGTH: 777
<212> TYPE: DNA
<213> ORGANISM: Artificial Sequence
<220> FEATURE:
<223> OTHER INFORMATION: Br1-1-24-27F_F12.ab1
<220> FEATURE:
<221> NAME/KEY: misc_feature
<222> LOCATION: (605)..(605)
<223> OTHER INFORMATION: n is a, c, g, or t
<220> FEATURE:
<221> NAME/KEY: misc_feature
<222> LOCATION: (607)..(607)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (644)..(644)
<223> OTHER INFORMATION: n is a, c, g, or t
<220> FEATURE:
<221> NAME/KEY: misc_feature
<222> LOCATION: (671)..(672)
<223> OTHER INFORMATION: n is a, c, g, or t
<220> FEATURE:
<221> NAME/KEY: misc_feature
<222> LOCATION: (700)..(702)
<223> OTHER INFORMATION: n is a, c, g, or t
<220> FEATURE:
<221> NAME/KEY: misc_feature
<222> LOCATION: (714)..(718)
<223> OTHER INFORMATION: n is a, c, g, or t
<220> FEATURE:
<221> NAME/KEY: misc_feature
<222> LOCATION: (725)..(725)
<223> OTHER INFORMATION: n is a, c, g, or t
<220> FEATURE:
<221> NAME/KEY: misc_feature
<222> LOCATION: (727)..(728)
<223> OTHER INFORMATION: n is a, c, g, or t
<220> FEATURE:
<221> NAME/KEY: misc_feature
<222> LOCATION: (747)..(747)
<223> OTHER INFORMATION: n is a, c, g, or t
<220> FEATURE:
<221> NAME/KEY: misc_feature
<222> LOCATION: (749)..(749)
<223> OTHER INFORMATION: n is a, c, g, or t
<220> FEATURE:

<221> NAME/KEY: misc_feature
<222> LOCATION: (751)..(752)
<223> OTHER INFORMATION: n is a, c, g, or t
<220> FEATURE:
<221> NAME/KEY: misc_feature
<222> LOCATION: (760)..(760)
<223> OTHER INFORMATION: n is a, c, g, or t
<220> FEATURE:
<221> NAME/KEY: misc_feature
<222> LOCATION: (764)..(764)
<223> OTHER INFORMATION: n is a, c, g, or t
<220> FEATURE:
<221> NAME/KEY: misc_feature
<222> LOCATION: (769)..(769)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t

<400> SEQUENCE: 16
tcgagcggca gcgggaaagt agcttgctac ttttgccggc gagcggcgga cgggtgagta      60
atgcctgggg atctgcccag tcgaggggga taactactgg aaacggtagc taataccgca     120
tacgccctac gggggaaagc agggaccctt cgggccttgc gcgattggat gaacccaggt     180
gggattagct agttggtgag gtaacggctc accaaggcga cgatccctag ctggtctgag     240
aggatgatca gccacactgg aactgagaca cggtccagac tcctacggga ggcagcagtg     300
gggaatattg cacaatgggg gaaaccctga tgcagccatg ccgcgtgtgt gaagaaggcc     360
ttcgggttgt aaagcacttt cagcgaggag gaaaggtcag tagctaatat ctgctggctg     420
tgacgttact cgcagaagaa gcaccggcta actccgtgcc agcagccgcg gtaataccgga    480 gggtgcaagc gttaatcgga attactgggc gtaaagcgca cgcaggcggt tggataagtt     540
agatgtgaaa gccccgggct caacctggga attgcattta aaactgtcca gctagagtct     600
tgtananggg ggtagaantc caggtgtagc ggtgaaatgc gtanagatct ggaggaatac     660
cggtggcgaa nncggccccc tggacaaaga ctgacgctcn nngcgaaagc gtgnnnnnca     720
aacangnnta gataccctgg tagtccncnc nntaaacgan gtcnatttng naggctg       777

<210> SEQ ID NO 17
<211> LENGTH: 887
<212> TYPE: DNA
<213> ORGANISM: Artificial Sequence
<220> FEATURE:
<223> OTHER INFORMATION: Br1-1-3-27F_E03.ab1
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (587)..(587)
<223> OTHER INFORMATION: n is a, c, g, or t
<220> FEATURE:
<221> NAME/KEY: misc_feature
<222> LOCATION: (589)..(589)
<223> OTHER INFORMATION: n is a, c, g, or t

```
<220> FEATURE:
<221> NAME/KEY: misc_feature
<222> LOCATION: (594)..(597)
<223> OTHER INFORMATION: n is a, c, g, or t
<220> FEATURE:
<221> NAME/KEY: misc_feature
<222> LOCATION: (599)..(599)
<223> OTHER INFORMATION: n is a, c, g, or t
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (605)..(607)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (611)..(613)
<223> OTHER INFORMATION: n is a, c, g, or t
<220> FEATURE:
<221> NAME/KEY: misc_feature
<222> LOCATION: (615)..(618)
<223> OTHER INFORMATION: n is a, c, g, or t
<220> FEATURE:
<221> NAME/KEY: misc_feature
<222> LOCATION: (620)..(623)
<223> OTHER INFORMATION: n is a, c, g, or t
<220> FEATURE:
<221> NAME/KEY: misc_feature
<222> LOCATION: (703)..(704)
<223> OTHER INFORMATION: n is a, c, g, or t
<220> FEATURE:
<221> NAME/KEY: misc_feature
<222> LOCATION: (708)..(712)
<223> OTHER INFORMATION: n is a, c, g, or t
<220> FEATURE:
<221> NAME/KEY: misc_feature
<222> LOCATION: (715)..(719)
<223> OTHER INFORMATION: n is a, c, g, or t
<220> FEATURE:
<221> NAME/KEY: misc_feature
<222> LOCATION: (721)..(721)
<223> OTHER INFORMATION: n is a, c, g, or t
<220> FEATURE:
<221> NAME/KEY: misc_feature
<222> LOCATION: (730)..(731)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t

<400> SEQUENCE: 17
gntnnncntg caagtcgagc ggcagcggga aagtagcttg ctacttttgc cggcgagcgg      60
cggacgggtg agtaatgcct ggggatctgc ccagtcgagg gggataacta ctggaaacgg     120
tagctaatac cgcatacgcc ctacggggga aagcagggga ccttcgggcc ttgcgcgatt     180
ggatgaaccc aggtgggatt agctagttgg tgaggtaacg gctcaccaag gcgacgatcc     240
ctagctggtc tgagaggatg atcagccaca ctggaactga gacacggtcc agactcctac     300
gggaggcagc agtggggaat attgcacaat gggggaaacc ctgatgcagc catgccgcgt     360
gtgtgaagaa ggccttcggg ttgtaaagca ctttcagcga ggaggaaagg tcagtagcta     420
atatctgctg gctgtgacgt tactcgcaga agaagcaccg gctaactccg tgccagcagc     480
cgcggtaata cggagggtgc aagcgttaat cggaattact gggcgtaaag cgcacgcagg     540
cggttggata agttagatgt gaaagccccg ggctcaacct gggtntnanc tgtnnnnang     600
```

```
tnggnnngnt nnngnnnnan nnnggtagcg gtgaaatgcg tagagatctg gaggaatacc    660
ggtggcgaag gcggcccct ggacaaagac tgacgctcag tgnnaaannn nnggnnnnna     720
ncaagacagn nattagatac cctggtagtc caccgccgta aacgatgtcg attatgntag    780
gatgctgtgt ccttgagacg tggcttccgg agctaacgcg ttaaatcgac gcctggggag    840
tacggccgca aggttaaaac tcaaatgaat tgacgggggc cccgcca                  887
```

<210> SEQ ID NO 18
<211> LENGTH: 882
<212> TYPE: DNA
<213> ORGANISM: Artificial Sequence
<220> FEATURE:
<223> OTHER INFORMATION: Br1-1-4-27F_E04.ab1
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (608)..(608)
<223> OTHER INFORMATION: n is a, c, g, or t
<220> FEATURE:
<221> NAME/KEY: misc_feature
<222> LOCATION: (644)..(647)
<223> OTHER INFORMATION: n is a, c, g, or t
<220> FEATURE:
<221> NAME/KEY: misc_feature
<222> LOCATION: (697)..(697)
<223> OTHER INFORMATION: n is a, c, g, or t
<220> FEATURE:
<221> NAME/KEY: misc_feature
<222> LOCATION: (715)..(715)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (787)..(787)
<223> OTHER INFORMATION: n is a, c, g, or t
<220> FEATURE:
<221> NAME/KEY: misc_feature
<222> LOCATION: (810)..(812)
<223> OTHER INFORMATION: n is a, c, g, or t
<220> FEATURE:
<221> NAME/KEY: misc_feature
<222> LOCATION: (839)..(839)
<223> OTHER INFORMATION: n is a, c, g, or t
<220> FEATURE:
<221> NAME/KEY: misc_feature
<222> LOCATION: (849)..(851)
<223> OTHER INFORMATION: n is a, c, g, or t
<220> FEATURE:
<221> NAME/KEY: misc_feature
<222> LOCATION: (854)..(855)
<223> OTHER INFORMATION: n is a, c, g, or t
<220> FEATURE:
<221> NAME/KEY: misc_feature
<222> LOCATION: (869)..(869)
<223> OTHER INFORMATION: n is a, c, g, or t

<400> SEQUENCE: 18

```
tanncntgca agtcgagcgg cagcgggaaa gtagcttgct acttttgccg gcgagcggcg    60
gacgggtgag taatgcctgg ggatctgccc agtcgagggg gataactact ggaaacggta   120
```

```
gctaataccg catacgccct acggggggaaa gcagggggacc ttcgggcctt gcgcgattgg    180
atgaacccag gtgggattag ctagttggtg aggtaacggc tcaccaaggc gacgatcccg    240
agctggtctg agaggatgat cagccacact ggaactgaga cacggtccag actcctacgg    300
gaggcagcag tggggaatat tgcacaatgg gggaaaccct gatgcagcca tgccgcgtgt    360
gtgaagaagg ccttcgggtt gtaaagcact ttcagcgagg aggaaaggtc agtagctaat    420
atctgctgac tgtgacgtta ctcgcagaag aagcaccggc taactccgtg ccagcagccg    480
cggtaatacg gagggtgcaa gcgttaatcg gaattactgg gcgtaaagcg cacgcaggcg    540
gttggataag ttagatgtga aagccccggg ctcaacctgg gaattgcttt taaaactgtc    600
tngctaanag tcttgtagag gggggtagaa ttccaggtgt agcnnnngaa atgcgtagag    660
atctggagga ataccggtgg cgaaggcggc ccctggnaca aaaactgacg ctcangtgcg    720
aaaaaagcgt ggggagcaaa caggattaga taccctggna gtccacgccg taaacgatgt    780
cgattgngga ggctgtgtcc ttgagacgtn nntccggagc taacgcgtta atcgacgcng    840
gggagtacnn ncannaaaact caaatgaang acggggggccc gc    882
```

<210> SEQ ID NO 19
<211> LENGTH: 888
<212> TYPE: DNA
<213> ORGANISM: Artificial Sequence
<220> FEATURE:
<223> OTHER INFORMATION: Br1-1-5-27F_E05.ab1
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (635)..(635)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (641)..(642)
<223> OTHER INFORMATION: n is a, c, g, or t
<220> FEATURE:
<221> NAME/KEY: misc_feature
<222> LOCATION: (659)..(659)
<223> OTHER INFORMATION: n is a, c, g, or t
<220> FEATURE:
<221> NAME/KEY: misc_feature
<222> LOCATION: (682)..(682)
<223> OTHER INFORMATION: n is a, c, g, or t
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (698)..(698)
<223> OTHER INFORMATION: n is a, c, g, or t
<220> FEATURE:
<221> NAME/KEY: misc_feature
<222> LOCATION: (701)..(703)
<223> OTHER INFORMATION: n is a, c, g, or t
<220> FEATURE:
<221> NAME/KEY: misc_feature
<222> LOCATION: (705)..(705)
<223> OTHER INFORMATION: n is a, c, g, or t
<220> FEATURE:
<221> NAME/KEY: misc_feature
<222> LOCATION: (709)..(709)
<223> OTHER INFORMATION: n is a, c, g, or t
<220> FEATURE:

-continued

```
<221> NAME/KEY: misc_feature
<222> LOCATION: (715)..(718)
<223> OTHER INFORMATION: n is a, c, g, or t
<220> FEATURE:
<221> NAME/KEY: misc_feature
<222> LOCATION: (721)..(722)
<223> OTHER INFORMATION: n is a, c, g, or t
<220> FEATURE:
<221> NAME/KEY: misc_feature
<222> LOCATION: (727)..(729)
<223> OTHER INFORMATION: n is a, c, g, or t
<220> FEATURE:
<221> NAME/KEY: misc_feature
<222> LOCATION: (739)..(740)
<223> OTHER INFORMATION: n is a, c, g, or t
<220> FEATURE:
<221> NAME/KEY: misc_feature
<222> LOCATION: (751)..(751)
<223> OTHER INFORMATION: n is a, c, g, or t
<220> FEATURE:
<221> NAME/KEY: misc_feature
<222> LOCATION: (754)..(754)
<223> OTHER INFORMATION: n is a, c, g, or t
<220> FEATURE:
<221> NAME/KEY: misc_feature
<222> LOCATION: (763)..(763)
<223> OTHER INFORMATION: n is a, c, g, or t
<220> FEATURE:
<221> NAME/KEY: misc_feature
<222> LOCATION: (775)..(776)
<223> OTHER INFORMATION: n is a, c, g, or t
<220> FEATURE:
<221> NAME/KEY: misc_feature
<222> LOCATION: (783)..(783)
<223> OTHER INFORMATION: n is a, c, g, or t
<220> FEATURE:
<221> NAME/KEY: misc_feature
<222> LOCATION: (787)..(787)
<223> OTHER INFORMATION: n is a, c, g, or t
<220> FEATURE:
<221> NAME/KEY: misc_feature
<222> LOCATION: (798)..(800)
<223> OTHER INFORMATION: n is a, c, g, or t
<220> FEATURE:
<221> NAME/KEY: misc_feature
<222> LOCATION: (802)..(802)
<223> OTHER INFORMATION: n is a, c, g, or t
<220> FEATURE:
<221> NAME/KEY: misc_feature
<222> LOCATION: (804)..(805)
<223> OTHER INFORMATION: n is a, c, g, or t
<220> FEATURE:
<221> NAME/KEY: misc_feature
<222> LOCATION: (812)..(813)
<223> OTHER INFORMATION: n is a, c, g, or t
<220> FEATURE:
<221> NAME/KEY: misc_feature
<222> LOCATION: (816)..(819)
<223> OTHER INFORMATION: n is a, c, g, or t
<220> FEATURE:
<221> NAME/KEY: misc_feature
<222> LOCATION: (825)..(825)
<223> OTHER INFORMATION: n is a, c, g, or t
<220> FEATURE:
<221> NAME/KEY: misc_feature
<222> LOCATION: (828)..(830)
<223> OTHER INFORMATION: n is a, c, g, or t
<220> FEATURE:
<221> NAME/KEY: misc_feature
<222> LOCATION: (839)..(843)
<223> OTHER INFORMATION: n is a, c, g, or t
<220> FEATURE:
<221> NAME/KEY: misc_feature
<222> LOCATION: (845)..(845)
<223> OTHER INFORMATION: n is a, c, g, or t
<220> FEATURE:
<221> NAME/KEY: misc_feature
<222> LOCATION: (848)..(848)
<223> OTHER INFORMATION: n is a, c, g, or t
```

<220> FEATURE:
<221> NAME/KEY: misc_feature
<222> LOCATION: (850)..(850)
<223> OTHER INFORMATION: n is a, c, g, or t
<220> FEATURE:
<221> NAME/KEY: misc_feature
<222> LOCATION: (853)..(853)
<223> OTHER INFORMATION: n is a, c, g, or t
<220> FEATURE:
<221> NAME/KEY: misc_feature
<222> LOCATION: (859)..(859)
<223> OTHER INFORMATION: n is a, c, g, or t
<220> FEATURE:
<221> NAME/KEY: misc_feature
<222> LOCATION: (861)..(861)
<223> OTHER INFORMATION: n is a, c, g, or t
<220> FEATURE:
<221> NAME/KEY: misc_feature
<222> LOCATION: (863)..(864)
<223> OTHER INFORMATION: n is a, c, g, or t
<220> FEATURE:
<221> NAME/KEY: misc_feature
<222> LOCATION: (866)..(867)
<223> OTHER INFORMATION: n is a, c, g, or t
<220> FEATURE:
<221> NAME/KEY: misc_feature
<222> LOCATION: (874)..(874)
<223> OTHER INFORMATION: n is a, c, g, or t
<220> FEATURE:
<221> NAME/KEY: misc_feature
<222> LOCATION: (877)..(877)
<223> OTHER INFORMATION: n is a, c, g, or t
<220> FEATURE:
<221> NAME/KEY: misc_feature
<222> LOCATION: (882)..(882)
<223> OTHER INFORMATION: n is a, c, g, or t
<220> FEATURE:
<221> NAME/KEY: misc_feature
<222> LOCATION: (886)..(886)
<223> OTHER INFORMATION: n is a, c, g, or t

<400> SEQUENCE: 19

```
gctacnntgc aagtcgagcg gcagcgggaa agtagcttgc tacttttgcc ggcgagcggc      60
ggacgggtga gtaatgcctg gggatctgcc cagtcgaggg ggataactac tggaaacggt     120
agctaatacc gcatacgccc tacgggggaa agcaggggac cttcgggcct tgcgcgattg     180
gatgaaccca ggtgggatta gctagttggt gaggtaacgg ctcaccaagg cgacgatccc     240
tagctggtct gagaggatga tcagccacac tggaactgag acacggtcca gactcctacg     300
ggaggcagca gtggggaata ttgcacaatg ggggaaaccc tgatgcagcc atgccgcgtg     360
tgtgaagaag gccttcgggt tgtaaagcac tttcagcgag gaggaaaggt cagtagctaa     420
tatctgctgg ctgtgacgtt actcgcagaa gaagcaccgg ctaactccgt gccagcagcc     480
gcggtaatac ggagggtgca agcgttaatc ggaattactg ggcgtaaagc gcacgcaggc     540
ggttggataa gttagatgtg aaagccccgg gctcaacctg gaattgcatt taaaactgt      600
ccagctagag tcttgtagag ggggtaaaaa tcagngggna nncgggtaaa tggctaaana     660
tcctgaagaa ttacggtggg cnaaggngcc cctggacnaa nnnanggang cttcnnnngc     720
nnaagcnnng ggggaagcnn accaggatta ngantaccct ggnagtccac gccgnnaacg     780
atngtcnatt tggagctnnn gncnnagaac gnngcnnnna gctangcnnn atcgacgcnn     840
nnntncgncn cangtaaant nannannacg gggnccncaa ancggngg                  888
```

<210> SEQ ID NO 20
<211> LENGTH: 905
<212> TYPE: DNA
<213> ORGANISM: Artificial Sequence
<220> FEATURE:

<223> OTHER INFORMATION: Br1-1-6-27F_E06.ab1
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (713)..(713)
<223> OTHER INFORMATION: n is a, c, g, or t
<220> FEATURE:
<221> NAME/KEY: misc_feature
<222> LOCATION: (739)..(739)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
<220> FEATURE:
<221> NAME/KEY: misc_feature
<222> LOCATION: (822)..(823)
<223> OTHER INFORMATION: n is a, c, g, or t
<220> FEATURE:
<221> NAME/KEY: misc_feature
<222> LOCATION: (840)..(842)
<223> OTHER INFORMATION: n is a, c, g, or t
<220> FEATURE:
<221> NAME/KEY: misc_feature
<222> LOCATION: (852)..(852)
<223> OTHER INFORMATION: n is a, c, g, or t
<220> FEATURE:
<221> NAME/KEY: misc_feature
<222> LOCATION: (893)..(893)
<223> OTHER INFORMATION: n is a, c, g, or t
<220> FEATURE:
<221> NAME/KEY: misc_feature
<222> LOCATION: (895)..(898)
<223> OTHER INFORMATION: n is a, c, g, or t
<220> FEATURE:
<221> NAME/KEY: misc_feature
<222> LOCATION: (901)..(901)
<223> OTHER INFORMATION: n is a, c, g, or t

<400> SEQUENCE: 20

```
ctacnntgca agtcgagcgg cagcgggaaa gtagcttgct acttttgccg gcgagcggcg      60
gacgggtgag taatgcctgg gaatctgccc agtcgagggg gataactact ggaaacggta     120
gctaataccg catacgccct acggggggaaa gcagggggacc ttcgggcctt gcgcgattgg    180
atgaacccag gtgggattag ctagttggtg aggtaacggc tcaccaaggc gacgatccct     240
agctggtctg agaggatgat cagccacact ggaactgaga cacggtccag actcctacgg     300
gaggcagcag tggggaatat tgcacaatgg gggaaaccct gatgcagcca tgccgcgtgt     360
gtgaagaagg ccttcgggtt gtaaagcact ttcagcgagg aggaaaggtc agtagctaat     420
atctgctggc tgtgacgtta ctcgcagaag aagcaccggc taactccgtg ccagcagccg     480
cggtaatacg gagggtgcaa gcgttaatcg gaattactgg gcgtaaagcg cacgcaggcg     540
gttggataag ttagatgtga aagccccggg ctcaacctgg gaattgcatt taaaactgtc     600
cagctagagt cttgtagagg ggggtagaat tccaggtgta gcggtgaaat gcgtagagat     660
ctggaggaat accggtggcg aaggcggccc cctggacaaa gactgacgct cangtgcgaa     720
agcgtgggga gcaaacagng attagatacc ctggtagtcc acgccgtaaa cgatgtcgat     780
ttggaggctg tgtccttgag acgtggnttc cggagctaac gnngttaaat cgaccgcctn     840
nnagtaccgg cngccaaggt taaaacctca aatgaatttg acggggcccc ggncnnnnag     900
ncggg                                                                 905
```

<210> SEQ ID NO 21
<211> LENGTH: 913

```
<212> TYPE: DNA
<213> ORGANISM: Artificial Sequence
<220> FEATURE:
<223> OTHER INFORMATION: Br1-1-7-27F_E07.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (652)..(652)
<223> OTHER INFORMATION: n is a, c, g, or t
<220> FEATURE:
<221> NAME/KEY: misc_feature
<222> LOCATION: (654)..(654)
<223> OTHER INFORMATION: n is a, c, g, or t
<220> FEATURE:
<221> NAME/KEY: misc_feature
<222> LOCATION: (656)..(662)
<223> OTHER INFORMATION: n is a, c, g, or t
<220> FEATURE:
<221> NAME/KEY: misc_feature
<222> LOCATION: (666)..(668)
<223> OTHER INFORMATION: n is a, c, g, or t
<220> FEATURE:
<221> NAME/KEY: misc_feature
<222> LOCATION: (671)..(680)
<223> OTHER INFORMATION: n is a, c, g, or t
<220> FEATURE:
<221> NAME/KEY: misc_feature
<222> LOCATION: (694)..(698)
<223> OTHER INFORMATION: n is a, c, g, or t
<220> FEATURE:
<221> NAME/KEY: misc_feature
<222> LOCATION: (755)..(755)
<223> OTHER INFORMATION: n is a, c, g, or t
<220> FEATURE:
<221> NAME/KEY: misc_feature
<222> LOCATION: (765)..(768)
<223> OTHER INFORMATION: n is a, c, g, or t
<220> FEATURE:
<221> NAME/KEY: misc_feature
<222> LOCATION: (770)..(770)
<223> OTHER INFORMATION: n is a, c, g, or t
<220> FEATURE:
<221> NAME/KEY: misc_feature
<222> LOCATION: (774)..(775)
<223> OTHER INFORMATION: n is a, c, g, or t
<220> FEATURE:
<221> NAME/KEY: misc_feature
<222> LOCATION: (778)..(778)
<223> OTHER INFORMATION: n is a, c, g, or t
<220> FEATURE:
<221> NAME/KEY: misc_feature
<222> LOCATION: (780)..(780)
<223> OTHER INFORMATION: n is a, c, g, or t
<220> FEATURE:
<221> NAME/KEY: misc_feature
<222> LOCATION: (784)..(784)
<223> OTHER INFORMATION: n is a, c, g, or t
<220> FEATURE:
<221> NAME/KEY: misc_feature
<222> LOCATION: (786)..(787)
<223> OTHER INFORMATION: n is a, c, g, or t
<220> FEATURE:
<221> NAME/KEY: misc_feature
<222> LOCATION: (789)..(794)
<223> OTHER INFORMATION: n is a, c, g, or t
<220> FEATURE:
<221> NAME/KEY: misc_feature
<222> LOCATION: (796)..(799)
<223> OTHER INFORMATION: n is a, c, g, or t
<220> FEATURE:
<221> NAME/KEY: misc_feature
<222> LOCATION: (801)..(807)
<223> OTHER INFORMATION: n is a, c, g, or t
<220> FEATURE:
<221> NAME/KEY: misc_feature
<222> LOCATION: (811)..(812)
```

<223> OTHER INFORMATION: n is a, c, g, or t
<220> FEATURE:
<221> NAME/KEY: misc_feature
<222> LOCATION: (816)..(816)
<223> OTHER INFORMATION: n is a, c, g, or t
<220> FEATURE:
<221> NAME/KEY: misc_feature
<222> LOCATION: (819)..(819)
<223> OTHER INFORMATION: n is a, c, g, or t
<220> FEATURE:
<221> NAME/KEY: misc_feature
<222> LOCATION: (842)..(842)
<223> OTHER INFORMATION: n is a, c, g, or t
<220> FEATURE:
<221> NAME/KEY: misc_feature
<222> LOCATION: (856)..(856)
<223> OTHER INFORMATION: n is a, c, g, or t
<220> FEATURE:
<221> NAME/KEY: misc_feature
<222> LOCATION: (884)..(884)
<223> OTHER INFORMATION: n is a, c, g, or t
<220> FEATURE:
<221> NAME/KEY: misc_feature
<222> LOCATION: (898)..(900)
<223> OTHER INFORMATION: n is a, c, g, or t
<220> FEATURE:
<221> NAME/KEY: misc_feature
<222> LOCATION: (902)..(905)
<223> OTHER INFORMATION: n is a, c, g, or t
<220> FEATURE:
<221> NAME/KEY: misc_feature
<222> LOCATION: (908)..(910)
<223> OTHER INFORMATION: n is a, c, g, or t

<400> SEQUENCE: 21

```
tacnntgcaa gtcgagcggc agcgggaaag tagcttgcta cttttgccgg cgagcggcgg       60
acgggtgagt aatacctggg gatctgccca gtcgaggggg ataactactg gaaacggtag      120
ctaataccgc atacgcccta cggggggaaag caggggaccc tcgggccttg cgcgattgga     180
tgaacccagg tgggattagc tagttggtga ggtaacggct caccaaggcg acgatcccta     240
gctggtctga gaggatgatc agccacactg gaactgagac acggtccaga ctcctacggg     300
aggcagcagt ggggaatatt gcacaatggg ggaaaccctg atgcagccat gccgcgtgtg     360
tgaagaaggc cttcgggttg taaagcactt tcagcgagga ggaaaggtca gtagctaata     420
tctgctggct gtgacgttac tcgcagaaga agcaccggct aactccgtgc cagcagccgc     480
ggtaatacgg agggtgcaag cgttaatcgg aattactggg cgtaaagcgc acgcaggcgg     540
ttggataagt tagatgtgaa agccccgggc tcaacctggg agttgcattt aaaactgtcc     600
agctagagtc ttgtagaggg gggtagaatt ccaggtgtag cggtgaaatg cnanannnnn     660
nngggnnntc nnnnnnnnnn gccccctggg acannnnntg acgctcaggt gcgaaagcgt     720
ggggagcaaa caggattaga taccctggta gtccncgccg taaannnnan gtcnnttngn     780
gagngnngnn nnnntnnnna nnnnnnncct nncgtnccng agctaacgcg ttaaatcgac     840
gnctgggga gtacgnccgc aaggttaaaa ctcaaatgaa tttnacgggg gcccgccnnn      900
annnnggnnn ggg                                                         913
```

<210> SEQ ID NO 22
<211> LENGTH: 903
<212> TYPE: DNA
<213> ORGANISM: Artificial Sequence
<220> FEATURE:
<223> OTHER INFORMATION: Br1-1-8-27F_E08.ab1
<220> FEATURE:
<221> NAME/KEY: misc_feature
<222> LOCATION: (4)..(5)
<223> OTHER INFORMATION: n is a, c, g, or t -continued

```
<220> FEATURE:
<221> NAME/KEY: misc_feature
<222> LOCATION: (597)..(600)
<223> OTHER INFORMATION: n is a, c, g, or t
<220> FEATURE:
<221> NAME/KEY: misc_feature
<222> LOCATION: (664)..(665)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (686)..(689)
<223> OTHER INFORMATION: n is a, c, g, or t
<220> FEATURE:
<221> NAME/KEY: misc_feature
<222> LOCATION: (695)..(697)
<223> OTHER INFORMATION: n is a, c, g, or t
<220> FEATURE:
<221> NAME/KEY: misc_feature
<222> LOCATION: (699)..(700)
<223> OTHER INFORMATION: n is a, c, g, or t
<220> FEATURE:
<221> NAME/KEY: misc_feature
<222> LOCATION: (718)..(719)
<223> OTHER INFORMATION: n is a, c, g, or t
<220> FEATURE:
<221> NAME/KEY: misc_feature
<222> LOCATION: (740)..(740)
<223> OTHER INFORMATION: n is a, c, g, or t
<220> FEATURE:
<221> NAME/KEY: misc_feature
<222> LOCATION: (745)..(745)
<223> OTHER INFORMATION: n is a, c, g, or t
<220> FEATURE:
<221> NAME/KEY: misc_feature
<222> LOCATION: (750)..(751)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (764)..(764)
<223> OTHER INFORMATION: n is a, c, g, or t
<220> FEATURE:
<221> NAME/KEY: misc_feature
<222> LOCATION: (770)..(771)
<223> OTHER INFORMATION: n is a, c, g, or t
<220> FEATURE:
<221> NAME/KEY: misc_feature
<222> LOCATION: (774)..(775)
<223> OTHER INFORMATION: n is a, c, g, or t
<220> FEATURE:
<221> NAME/KEY: misc_feature
<222> LOCATION: (787)..(788)
<223> OTHER INFORMATION: n is a, c, g, or t
<220> FEATURE:
<221> NAME/KEY: misc_feature
<222> LOCATION: (791)..(792)
<223> OTHER INFORMATION: n is a, c, g, or t
<220> FEATURE:
<221> NAME/KEY: misc_feature
<222> LOCATION: (802)..(802)
<223> OTHER INFORMATION: n is a, c, g, or t
<220> FEATURE:
<221> NAME/KEY: misc_feature
<222> LOCATION: (806)..(806)
<223> OTHER INFORMATION: n is a, c, g, or t
<220> FEATURE:
<221> NAME/KEY: misc_feature
<222> LOCATION: (812)..(813)
<223> OTHER INFORMATION: n is a, c, g, or t
<220> FEATURE:
<221> NAME/KEY: misc_feature
<222> LOCATION: (815)..(815)
```

```
<223> OTHER INFORMATION: n is a, c, g, or t
<220> FEATURE:
<221> NAME/KEY: misc_feature
<222> LOCATION: (817)..(818)
<223> OTHER INFORMATION: n is a, c, g, or t
<220> FEATURE:
<221> NAME/KEY: misc_feature
<222> LOCATION: (820)..(820)
<223> OTHER INFORMATION: n is a, c, g, or t
<220> FEATURE:
<221> NAME/KEY: misc_feature
<222> LOCATION: (822)..(823)
<223> OTHER INFORMATION: n is a, c, g, or t
<220> FEATURE:
<221> NAME/KEY: misc_feature
<222> LOCATION: (825)..(825)
<223> OTHER INFORMATION: n is a, c, g, or t
<220> FEATURE:
<221> NAME/KEY: misc_feature
<222> LOCATION: (827)..(827)
<223> OTHER INFORMATION: n is a, c, g, or t
<220> FEATURE:
<221> NAME/KEY: misc_feature
<222> LOCATION: (836)..(836)
<223> OTHER INFORMATION: n is a, c, g, or t
<220> FEATURE:
<221> NAME/KEY: misc_feature
<222> LOCATION: (838)..(838)
<223> OTHER INFORMATION: n is a, c, g, or t
<220> FEATURE:
<221> NAME/KEY: misc_feature
<222> LOCATION: (848)..(848)
<223> OTHER INFORMATION: n is a, c, g, or t
<220> FEATURE:
<221> NAME/KEY: misc_feature
<222> LOCATION: (850)..(850)
<223> OTHER INFORMATION: n is a, c, g, or t
<220> FEATURE:
<221> NAME/KEY: misc_feature
<222> LOCATION: (852)..(853)
<223> OTHER INFORMATION: n is a, c, g, or t
<220> FEATURE:
<221> NAME/KEY: misc_feature
<222> LOCATION: (858)..(861)
<223> OTHER INFORMATION: n is a, c, g, or t
<220> FEATURE:
<221> NAME/KEY: misc_feature
<222> LOCATION: (864)..(865)
<223> OTHER INFORMATION: n is a, c, g, or t
<220> FEATURE:
<221> NAME/KEY: misc_feature
<222> LOCATION: (867)..(868)
<223> OTHER INFORMATION: n is a, c, g, or t
<220> FEATURE:
<221> NAME/KEY: misc_feature
<222> LOCATION: (870)..(870)
<223> OTHER INFORMATION: n is a, c, g, or t
<220> FEATURE:
<221> NAME/KEY: misc_feature
<222> LOCATION: (877)..(877)
<223> OTHER INFORMATION: n is a, c, g, or t
<220> FEATURE:
<221> NAME/KEY: misc_feature
<222> LOCATION: (879)..(883)
<223> OTHER INFORMATION: n is a, c, g, or t
<220> FEATURE:
<221> NAME/KEY: misc_feature
<222> LOCATION: (896)..(896)
<223> OTHER INFORMATION: n is a, c, g, or t
<220> FEATURE:
<221> NAME/KEY: misc_feature
<222> LOCATION: (901)..(901)
<223> OTHER INFORMATION: n is a, c, g, or t

<400> SEQUENCE: 22
tacnntgcaa gtcgagcggc agcgggaaag tagcttgcta cttttgccgg cgagcggcgg      60
acgggtgagt aatgcctggg gatctgccca gtcgaggggg ataactactg gaaacggtag     120
```

```
ctaataccgc atacgcccta cgggggaaag caggggacct tcgggccttg cgcgattgga    180
tgaacccagg tgggattagc tagttggtga ggtaacggct caccaaggcg acgatccta     240 gctggtctga gaggatgatc agccacactg gaactgagac acggtccaga ctcctacggg    300
aggcagcagt ggggaatatt gcacaatggg ggaaaccctg atgcagccat gccgcgtgtg    360
tgaagaaggc cttcggggttg taaagcactt tcagcgagga ggaaaggtca gtagctaata   420
tctgctggct gtgacgttac tcgcagaaga agcaccggct aactccgtgc cagcagccgc    480
ggtaatacgg agggtgcaag cgttaatcgg aattactggg cgtaaagcgc acgcaggcgg    540
ttggataagt tagatgtgaa agccccgggc tcaacctggg aattgcattt aaaactnnnn    600
agctagagtc ttgtagaggg gggtagaatt ccaggtgtag cggtgaaatg cgtagagatc    660
tggnngggaa taccggtggc naaggnnnnc cctcnnngnn acaaaagact gacgctcnnt    720
gcgaaagcgt ggggagcaan caggnttaan naccctcgng atanctacan nccnnacaca    780
gatgtcnntt nnggaggctg gntccntgag annangnntn cnncngnagc tactcntnaa    840
tcgacgcngn gnntacgnnn nagnnanntn aatgaangnn nnngcccgca cagcgntgga    900 nca                                                                  903
```

```
<210> SEQ ID NO 23
<211> LENGTH: 899
<212> TYPE: DNA
<213> ORGANISM: Artificial Sequence
<220> FEATURE:
<223> OTHER INFORMATION: Br1-1-9-27F_E09.ab1
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (6)..(8)
<223> OTHER INFORMATION: n is a, c, g, or t
<220> FEATURE:
<221> NAME/KEY: misc_feature
<222> LOCATION: (628)..(632)
<223> OTHER INFORMATION: n is a, c, g, or t
<220> FEATURE:
<221> NAME/KEY: misc_feature
<222> LOCATION: (668)..(669)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (705)..(705)
<223> OTHER INFORMATION: n is a, c, g, or t
<220> FEATURE:
<221> NAME/KEY: misc_feature
<222> LOCATION: (712)..(712)
<223> OTHER INFORMATION: n is a, c, g, or t
<220> FEATURE:
<221> NAME/KEY: misc_feature
<222> LOCATION: (715)..(715)
<223> OTHER INFORMATION: n is a, c, g, or t
<220> FEATURE:
<221> NAME/KEY: misc_feature
<222> LOCATION: (717)..(717)
<223> OTHER INFORMATION: n is a, c, g, or t
<220> FEATURE:
<221> NAME/KEY: misc_feature
<222> LOCATION: (722)..(723)
<223> OTHER INFORMATION: n is a, c, g, or t
<220> FEATURE:
<221> NAME/KEY: misc_feature
<222> LOCATION: (753)..(755)
```

```
<223> OTHER INFORMATION: n is a, c, g, or t
<220> FEATURE:
<221> NAME/KEY: misc_feature
<222> LOCATION: (774)..(774)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t
<220> FEATURE:
<221> NAME/KEY: misc_feature
<222> LOCATION: (781)..(781)
<223> OTHER INFORMATION: n is a, c, g, or t
<220> FEATURE:
<221> NAME/KEY: misc_feature
<222> LOCATION: (784)..(784)
<223> OTHER INFORMATION: n is a, c, g, or t
<220> FEATURE:
<221> NAME/KEY: misc_feature
<222> LOCATION: (786)..(786)
<223> OTHER INFORMATION: n is a, c, g, or t
<220> FEATURE:
<221> NAME/KEY: misc_feature
<222> LOCATION: (791)..(792)
<223> OTHER INFORMATION: n is a, c, g, or t
<220> FEATURE:
<221> NAME/KEY: misc_feature
<222> LOCATION: (794)..(796)
<223> OTHER INFORMATION: n is a, c, g, or t
<220> FEATURE:
<221> NAME/KEY: misc_feature
<222> LOCATION: (798)..(798)
<223> OTHER INFORMATION: n is a, c, g, or t
<220> FEATURE:
<221> NAME/KEY: misc_feature
<222> LOCATION: (800)..(800)
<223> OTHER INFORMATION: n is a, c, g, or t
<220> FEATURE:
<221> NAME/KEY: misc_feature
<222> LOCATION: (815)..(817)
<223> OTHER INFORMATION: n is a, c, g, or t
<220> FEATURE:
<221> NAME/KEY: misc_feature
<222> LOCATION: (819)..(821)
<223> OTHER INFORMATION: n is a, c, g, or t
<220> FEATURE:
<221> NAME/KEY: misc_feature
<222> LOCATION: (830)..(832)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
<221> NAME/KEY: misc_feature
<222> LOCATION: (848)..(850)
<223> OTHER INFORMATION: n is a, c, g, or t
<220> FEATURE:
<221> NAME/KEY: misc_feature
<222> LOCATION: (853)..(856)
<223> OTHER INFORMATION: n is a, c, g, or t
<220> FEATURE:
<221> NAME/KEY: misc_feature
<222> LOCATION: (859)..(861)
<223> OTHER INFORMATION: n is a, c, g, or t
<220> FEATURE:
<221> NAME/KEY: misc_feature
<222> LOCATION: (869)..(869)
<223> OTHER INFORMATION: n is a, c, g, or t
<220> FEATURE:
<221> NAME/KEY: misc_feature
<222> LOCATION: (872)..(873)
<223> OTHER INFORMATION: n is a, c, g, or t
<220> FEATURE:
<221> NAME/KEY: misc_feature
<222> LOCATION: (892)..(893)
<223> OTHER INFORMATION: n is a, c, g, or t
<220> FEATURE:
<221> NAME/KEY: misc_feature
```

<222> LOCATION: (895)..(895)
<223> OTHER INFORMATION: n is a, c, g, or t
<220> FEATURE:
<221> NAME/KEY: misc_feature
<222> LOCATION: (897)..(897)
<223> OTHER INFORMATION: n is a, c, g, or t

<400> SEQUENCE: 23

```
gnttannntg cagtcgagcg gagatgaggt gcttgcacct tatcttagcg gcggacgggt      60
gagtaatgct taggaatctg ccatttagtg ggggacaaca ttccgaaagg aatgctaata     120
ccgcatacgt cgtacgggag aaagcagggg atcttcggac cttgcgctaa atgatgagcc    180
taagtcggat tagctagttg gtggggtaaa ggcctaccaa ggcgacgatc tgtagcgggt    240
ctgagaggat gatccgccac actgggactg agacacggcc cagactccta cgggaggcag    300
cagtggggaa tattggacaa tgggcggaag cctgatccag ccatgccgcg tgtgtgaaga    360
aggccttttg gttgtaaagc actttaagcg aggaggaggc tactagtact aatactactg    420
gatagtggac gttactcgca gaataagcac cggctaactc tgtgccagca gccgcggtaa    480
tacggagggt gcaagcgtta atcggaatta ctgggcgtaa agcgcacgca ggcggttgga    540
taagttagat gtgaaagccc cgggctcaac ctgggaattg catttaaaac tgtccagcta    600
gagtcttgta gaggggggta gaattccnnn nntagcggtg aaatgcgtag agatctggag    660
gaataccnng tggcgaaggc ggcccctgg ataaanactg acgcnctcag gngcnanagc    720
gnnggtgggg gagcaaacag gattagatac ccnnngatag tccacgccgt aacnatngtc    780
natntntagg nngnnngngn tctttagaag acgtnnntnn nagctacgcn nnaatcgacc    840
gcntgggnnn tannnncann naactcaang annacggggc cgccacagc gnngnanca      899
```

<210> SEQ ID NO 24
<211> LENGTH: 881
<212> TYPE: DNA
<213> ORGANISM: Artificial Sequence
<220> FEATURE:
<223> OTHER INFORMATION: FM-1-10-27F_G03.ab1
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (694)..(696)
<223> OTHER INFORMATION: n is a, c, g, or t
<220> FEATURE:
<221> NAME/KEY: misc_feature
<222> LOCATION: (698)..(704)
<223> OTHER INFORMATION: n is a, c, g, or t
<220> FEATURE:
<221> NAME/KEY: misc_feature
<222> LOCATION: (706)..(706)
<223> OTHER INFORMATION: n is a, c, g, or t
<220> FEATURE:
<221> NAME/KEY: misc_feature
<222> LOCATION: (748)..(748)
<223> OTHER INFORMATION: n is a, c, g, or t
<220> FEATURE:
<221> NAME/KEY: misc_feature
<222> LOCATION: (758)..(762)
<223> OTHER INFORMATION: n is a, c, g, or t
<220> FEATURE:
<221> NAME/KEY: misc_feature
<222> LOCATION: (780)..(780)
<223> OTHER INFORMATION: n is a, c, g, or t
<220> FEATURE:
<221> NAME/KEY: misc_feature
<222> LOCATION: (831)..(831)
<223> OTHER INFORMATION: n is a, c, g, or t
<220> FEATURE:

```
<221> NAME/KEY: misc_feature
<222> LOCATION: (833)..(833)
<223> OTHER INFORMATION: n is a, c, g, or t
<220> FEATURE:
<221> NAME/KEY: misc_feature
<222> LOCATION: (844)..(844)
<223> OTHER INFORMATION: n is a, c, g, or t
<220> FEATURE:
<221> NAME/KEY: misc_feature
<222> LOCATION: (846)..(847)
<223> OTHER INFORMATION: n is a, c, g, or t
<220> FEATURE:
<221> NAME/KEY: misc_feature
<222> LOCATION: (850)..(850)
<223> OTHER INFORMATION: n is a, c, g, or t
<220> FEATURE:
<221> NAME/KEY: misc_feature
<222> LOCATION: (857)..(858)
<223> OTHER INFORMATION: n is a, c, g, or t
<220> FEATURE:
<221> NAME/KEY: misc_feature
<222> LOCATION: (861)..(862)
<223> OTHER INFORMATION: n is a, c, g, or t

<400> SEQUENCE: 24
ggctgcctta ccntgcaagt cgaacggtaa caggtcttcg gatgctgacg agtggcgaac      60
gggtgagtaa tacatcggaa cgtgcccgat cgtgggggat aacgaagcga aagctttgct     120
aataccgcat aagatctaag gatgaaagca ggggaccgca aggccttgcg cgaacggagc     180
ggccgatggc agattaggta gttggtggga taaaagctta ccaagccgac gatctgtagc     240
tggtctgaga ggacgaccag ccacactggg actgagacac ggcccagact cctacgggag     300
gcagcagtgg ggaattttgg acaatgggcg aaagcctgat ccagccatgc cgcgtgcagg     360
atgaaggcct tcgggttgta aactgctttt gtacggaacg aaaagactct ggttaatacc     420
tggggtccat gacggtaccg taagaataag caccggctaa ctacgtgcca gcagccgcgg     480
taatacgtag ggtgcaagcg ttaatcggaa ttactgggcg taaagcgtgc gcaggcggtt     540
atataagaca gatgtgaaat ccccgggctc aacctgggaa ctgcatttgt gactgtatag     600
ctagagtacg gtagaggggg atggaattcc gcgtgtagca gtgaaatgcg tagatatgcg     660
gaggaacacc gatggcgaag gcaatcccct ggannngnnn nnnncnctca tgcacgaaag     720
cgtggggacc aacaggatta gatacccngg tagtccannn nntaaacgat gtcaactggn     780
ttgttgggtc ttcactgact cagtaacgaa gctaacgcgt gaagttgacc ncngggagt     840
acgncnncan ggttganntc nnaggaattg acggggacc c                        881

<210> SEQ ID NO 25
<211> LENGTH: 893
<212> TYPE: DNA
<213> ORGANISM: Artificial Sequence
<220> FEATURE:
<223> OTHER INFORMATION: FM-1-11-27F_G04.ab1
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (657)..(660)
<223> OTHER INFORMATION: n is a, c, g, or t
<220> FEATURE:
<221> NAME/KEY: misc_feature
<222> LOCATION: (747)..(754)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
```

```
<220> FEATURE:
<221> NAME/KEY: misc_feature
<222> LOCATION: (769)..(769)
<223> OTHER INFORMATION: n is a, c, g, or t
<220> FEATURE:
<221> NAME/KEY: misc_feature
<222> LOCATION: (775)..(775)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t
<220> FEATURE:
<221> NAME/KEY: misc_feature
<222> LOCATION: (787)..(787)
<223> OTHER INFORMATION: n is a, c, g, or t
<220> FEATURE:
<221> NAME/KEY: misc_feature
<222> LOCATION: (791)..(791)
<223> OTHER INFORMATION: n is a, c, g, or t
<220> FEATURE:
<221> NAME/KEY: misc_feature
<222> LOCATION: (797)..(797)
<223> OTHER INFORMATION: n is a, c, g, or t
<220> FEATURE:
<221> NAME/KEY: misc_feature
<222> LOCATION: (799)..(799)
<223> OTHER INFORMATION: n is a, c, g, or t
<220> FEATURE:
<221> NAME/KEY: misc_feature
<222> LOCATION: (831)..(831)
<223> OTHER INFORMATION: n is a, c, g, or t
<220> FEATURE:
<221> NAME/KEY: misc_feature
<222> LOCATION: (835)..(835)
<223> OTHER INFORMATION: n is a, c, g, or t
<220> FEATURE:
<221> NAME/KEY: misc_feature
<222> LOCATION: (839)..(839)
<223> OTHER INFORMATION: n is a, c, g, or t
<220> FEATURE:
<221> NAME/KEY: misc_feature
<222> LOCATION: (841)..(841)
<223> OTHER INFORMATION: n is a, c, g, or t
<220> FEATURE:
<221> NAME/KEY: misc_feature
<222> LOCATION: (845)..(845)
<223> OTHER INFORMATION: n is a, c, g, or t
<220> FEATURE:
<221> NAME/KEY: misc_feature
<222> LOCATION: (847)..(847)
<223> OTHER INFORMATION: n is a, c, g, or t
<220> FEATURE:
<221> NAME/KEY: misc_feature
<222> LOCATION: (884)..(884)
<223> OTHER INFORMATION: n is a, c, g, or t
<220> FEATURE:
<221> NAME/KEY: misc_feature
<222> LOCATION: (887)..(888)
<223> OTHER INFORMATION: n is a, c, g, or t

<400> SEQUENCE: 25
gccttanntg cagtcgaacg gtaacaggtc ttcggatgct gacgagtggc gaacgggtga      60
gtaatacatc ggaacgtgcc cgatcgtggg ggataacgaa gcgaaagctt tgctaatacc     120
gcataagatc taaggatgaa agcaggggac cgcaaggcct tgcgcgaacg gagcggccga     180
tggcagatta ggtagttggt gggataaaag cttaccaagc cgacgatctg tagctggtct     240
gagaggacga ccagccacac tgggactgag acacggccca gactcctacg ggaggcagca     300
gtggggaatt ttggacaatg ggcgaaagcc tgatccagcc atgccgcgtg caggatgaag     360
gccttcgggt tgtaaactgc ttttgtacgg aacgaaaaga ctctggttaa tacctggggt     420
ccatgacggt accgtaagaa taagcaccgg ctaactacgt gccagcagcc gcggtaatac     480
```

| gtagggtgca agcgttaatc ggaattactg ggcgtaaagc gtgcgcaggc ggttatataa | 540 |
| gacagatgtg aaatccccgg gctcaacctg ggaactgcat ttgtgactgt atagctagag | 600 |
| tacggtagag ggggatggaa ttccgcgtgt agcagtgaaa tgcgtagata tgcggannnn | 660 |
| acacggatgg cgaaggcaat ccctggacc tgtactgacg ctcatgcacg aaagcgtggg | 720 |
| gagcaaacag gattagatac cctggtnnnn nnnnccctaa acgangtcna ctggntngtt | 780 |
| gggtctnctc ngtgaantna gtaacgaagc taacgcgtga agttgaccgc ngggngtang | 840 |
| ngcangntga aactcaaagg aattgacggg aacccgccac aagnggnngg aat | 893 |

```
<210> SEQ ID NO 26
<211> LENGTH: 835
<212> TYPE: DNA
<213> ORGANISM: Artificial Sequence
<220> FEATURE:
<223> OTHER INFORMATION: FM1-1-1-27F_F06.ab1
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (668)..(668)
<223> OTHER INFORMATION: n is a, c, g, or t
<220> FEATURE:
<221> NAME/KEY: misc_feature
<222> LOCATION: (681)..(682)
<223> OTHER INFORMATION: n is a, c, g, or t
<220> FEATURE:
<221> NAME/KEY: misc_feature
<222> LOCATION: (724)..(724)
<223> OTHER INFORMATION: n is a, c, g, or t
<220> FEATURE:
<221> NAME/KEY: misc_feature
<222> LOCATION: (762)..(762)
<223> OTHER INFORMATION: n is a, c, g, or t
<220> FEATURE:
<221> NAME/KEY: misc_feature
<222> LOCATION: (769)..(769)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t
<220> FEATURE:
<221> NAME/KEY: misc_feature
<222> LOCATION: (778)..(780)
<223> OTHER INFORMATION: n is a, c, g, or t
<220> FEATURE:
<221> NAME/KEY: misc_feature
<222> LOCATION: (782)..(782)
<223> OTHER INFORMATION: n is a, c, g, or t
<220> FEATURE:
<221> NAME/KEY: misc_feature
<222> LOCATION: (792)..(793)
<223> OTHER INFORMATION: n is a, c, g, or t
<220> FEATURE:
<221> NAME/KEY: misc_feature
<222> LOCATION: (797)..(797)
<223> OTHER INFORMATION: n is a, c, g, or t
<220> FEATURE:
<221> NAME/KEY: misc_feature
<222> LOCATION: (814)..(818)
<223> OTHER INFORMATION: n is a, c, g, or t

<400> SEQUENCE: 26
```

| cgntgcttac ctgcaagtcg aacggtaaca ggtcttcgga tgctgacgag tggcgaacgg | 60 |
| gtgagtaata catcggaacg tgcccgatcg tgggggataa cgaagcgaaa gctttgctaa | 120 |
| taccgcataa gatctaagga tgaaagcagg ggaccgcaag gccttgcgcg aacgagcgg | 180 |
| ccgatggcag attaggtagt tggtgggata aaagcttacc aagccgacga tctgtagctg | 240 |

```
gtctgagagg acgaccagcc acactgggac tgagacacgg cccagactcc tacgggaggc    300
agcagtgggg aattttggac aatgggcgaa agcctgatcc agccatgccg cgtgcaggat    360
gaaggccttc gggttgtaaa ctgcttttgt acggaacgaa aagactctgg ttaatacctg    420
gggtccatga cggtaccgta agaataagca ccggctaact acgtgccagc agccgcggta    480
atacgtaggg tgcgagcgtt aatcggaatt actgggcgta aagcgtgcgc aggcggttat    540
ataagacaga tgtgaaatcc ccgggctcaa cctgggaact gcatttgtga ctgtatagct    600
agagtacggt agaggggggat ggaattccgc gtgtagcagt gaaatgcgta gatatgcgga    660
ggaacacncg atggcgaaag nnatcccctg gacctgtact gacgctcatg cacgaaagcg    720
tggngagcaa acaggattag atacctggt agtccacgcc cnaaacgang ncaactgnnn    780
gntgggtctt cnntgantca gtacgaagct aacnnnnnga agttgaccgc ctggg         835
```

<210> SEQ ID NO 27
<211> LENGTH: 899
<212> TYPE: DNA
<213> ORGANISM: Artificial Sequence
<220> FEATURE:
<223> OTHER INFORMATION: FM-1-12-27F_G05.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (657)..(658)
<223> OTHER INFORMATION: n is a, c, g, or t
<220> FEATURE:
<221> NAME/KEY: misc_feature
<222> LOCATION: (704)..(704)
<223> OTHER INFORMATION: n is a, c, g, or t
<220> FEATURE:
<221> NAME/KEY: misc_feature
<222> LOCATION: (714)..(717)
<223> OTHER INFORMATION: n is a, c, g, or t
<220> FEATURE:
<221> NAME/KEY: misc_feature
<222> LOCATION: (734)..(734)
<223> OTHER INFORMATION: n is a, c, g, or t
<220> FEATURE:
<221> NAME/KEY: misc_feature
<222> LOCATION: (744)..(744)
<223> OTHER INFORMATION: n is a, c, g, or t
<220> FEATURE:
<221> NAME/KEY: misc_feature
<222> LOCATION: (810)..(810)
<223> OTHER INFORMATION: n is a, c, g, or t
<220> FEATURE:
<221> NAME/KEY: misc_feature
<222> LOCATION: (822)..(822)
<223> OTHER INFORMATION: n is a, c, g, or t
<220> FEATURE:
<221> NAME/KEY: misc_feature
<222> LOCATION: (832)..(832)
<223> OTHER INFORMATION: n is a, c, g, or t
<220> FEATURE:
<221> NAME/KEY: misc_feature
<222> LOCATION: (834)..(836)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
<221> NAME/KEY: misc_feature
<222> LOCATION: (846)..(846)
<223> OTHER INFORMATION: n is a, c, g, or t
<220> FEATURE:
<221> NAME/KEY: misc_feature
<222> LOCATION: (850)..(851)

<223> OTHER INFORMATION: n is a, c, g, or t
<220> FEATURE:
<221> NAME/KEY: misc_feature
<222> LOCATION: (853)..(853)
<223> OTHER INFORMATION: n is a, c, g, or t
<220> FEATURE:
<221> NAME/KEY: misc_feature
<222> LOCATION: (855)..(855)
<223> OTHER INFORMATION: n is a, c, g, or t
<220> FEATURE:
<221> NAME/KEY: misc_feature
<222> LOCATION: (857)..(858)
<223> OTHER INFORMATION: n is a, c, g, or t
<220> FEATURE:
<221> NAME/KEY: misc_feature
<222> LOCATION: (861)..(863)
<223> OTHER INFORMATION: n is a, c, g, or t
<220> FEATURE:
<221> NAME/KEY: misc_feature
<222> LOCATION: (865)..(865)
<223> OTHER INFORMATION: n is a, c, g, or t
<220> FEATURE:
<221> NAME/KEY: misc_feature
<222> LOCATION: (869)..(869)
<223> OTHER INFORMATION: n is a, c, g, or t
<220> FEATURE:
<221> NAME/KEY: misc_feature
<222> LOCATION: (874)..(875)
<223> OTHER INFORMATION: n is a, c, g, or t
<220> FEATURE:
<221> NAME/KEY: misc_feature
<222> LOCATION: (879)..(883)
<223> OTHER INFORMATION: n is a, c, g, or t
<220> FEATURE:
<221> NAME/KEY: misc_feature
<222> LOCATION: (888)..(888)
<223> OTHER INFORMATION: n is a, c, g, or t

<400> SEQUENCE: 27

```
ttanntgcag tcgaacggta acaggtcttc ggatgctgac gagtggcgaa cgggtgagta      60
atacatcgga acgtgcccga tcgtggggga taacgaagcg aaagctttgc taataccgca     120
taagatctaa ggatgaaagc aggggaccgc aaggccttgc gcgaacggag cggccgatgg     180
cagattaggt agttggtggg ataaaagctt accaagccga cgatctgtag ctggtctgag     240
aggacgacca gccacactgg gactgagaca cggcccagac tcctacggga ggcagcagtg     300
gggaattttg gacaatgggc gaaagcctga tccagccatg ccgcgtgcag gatgaaggcc     360
ttcgggttgt aaactgcttt tgtacggaac gaaaagactc tggttaatac ctggggtcca     420
tgacggtacc gtaagaataa gcaccggcta actacgtgcc agcagccgcg gtaatacgta     480
gggtgcaagc gttaatcgga attactgggc gtaaagcgtg cgcaggcggt tatataagac     540
agatgtgaaa tccccgggct caacctggga actgcatttg tgactgtata gctagagtac     600
ggtagagggg gatggaattc cgcgtgtagc agtgaaatgc gtagatatgc ggaggannac     660
cgatgggcga aggcaatccc ctggacctgt actgacgctc atgnccgaaa gcgnnnngag     720
caaacaggat ttanataccc tggnagtcca cgccctaaac gatgtcaact ggttgttggg     780
tcttcactga ctcagtaacg aagctaacgn cgtgaagttg ancgcctggg gngnnncggg     840
ccncanggtn nananannct nnnanggant tggnngggnn nnncccgnca ccaagccgg     899
```

<210> SEQ ID NO 28
<211> LENGTH: 882
<212> TYPE: DNA
<213> ORGANISM: Artificial Sequence
<220> FEATURE:
<223> OTHER INFORMATION: FM1-1-2-27F_F07.ab1
<220> FEATURE:
<221> NAME/KEY: misc_feature
<222> LOCATION: (746)..(746)
<223> OTHER INFORMATION: n is a, c, g, or t
<220> FEATURE:
<221> NAME/KEY: misc_feature
<222> LOCATION: (760)..(760)
<223> OTHER INFORMATION: n is a, c, g, or t
<220> FEATURE:
<221> NAME/KEY: misc_feature
<222> LOCATION: (773)..(775)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t
<220> FEATURE:
<221> NAME/KEY: misc_feature
<222> LOCATION: (787)..(787)
<223> OTHER INFORMATION: n is a, c, g, or t
<220> FEATURE:
<221> NAME/KEY: misc_feature
<222> LOCATION: (802)..(802)
<223> OTHER INFORMATION: n is a, c, g, or t
<220> FEATURE:
<221> NAME/KEY: misc_feature
<222> LOCATION: (809)..(810)
<223> OTHER INFORMATION: n is a, c, g, or t
<220> FEATURE:
<221> NAME/KEY: misc_feature
<222> LOCATION: (816)..(816)
<223> OTHER INFORMATION: n is a, c, g, or t
<220> FEATURE:
<221> NAME/KEY: misc_feature
<222> LOCATION: (828)..(829)
<223> OTHER INFORMATION: n is a, c, g, or t
<220> FEATURE:
<221> NAME/KEY: misc_feature
<222> LOCATION: (831)..(836)
<223> OTHER INFORMATION: n is a, c, g, or t
<220> FEATURE:
<221> NAME/KEY: misc_feature
<222> LOCATION: (838)..(849)
<223> OTHER INFORMATION: n is a, c, g, or t
<220> FEATURE:
<221> NAME/KEY: misc_feature
<222> LOCATION: (860)..(860)
<223> OTHER INFORMATION: n is a, c, g, or t
<220> FEATURE:
<221> NAME/KEY: misc_feature
<222> LOCATION: (873)..(875)
<223> OTHER INFORMATION: n is a, c, g, or t
<220> FEATURE:
<221> NAME/KEY: misc_feature
<222> LOCATION: (877)..(877)
<223> OTHER INFORMATION: n is a, c, g, or t

<400> SEQUENCE: 28

```
tgccttacct gcagtcgaac ggtaacaggt cttcggatgc tgacgagtgg cgaacgggtg     60
agtaatacat cggaacgtgc ccgatcgtgg gggataacga agcgaaagct tgctaatac    120 cgcataagat ctaaggatga aagcagggga ccgcaaggcc ttgcgcgaac ggagcggccg    180
atggcagatt aggtagttgg tgggataaaa gcttaccaag ccgacgatct gtagctggtc    240
tgagaggacg accagccaca ctgggactga gacacggccc agactcctac gggaggcagc    300
agtggggaat tttggacaat gggcgaaagc ctgatccagc catgccgcgt gcaggatgaa    360
ggccttcggg ttgtaaactg cttttgtacg gaacgaaaag actctggtta atacctgggg    420
tccatgacgg taccgtaaga ataagcaccg gctaactacg tgccagcagc cgcggtaata    480
cgtagggtgc aagcgttaat cggaattact gggcgtaaag cgtgcgcagg cggttatata    540
agacagatgt gaaatccccg ggctcaacct gggaactgca tttgtgactg tatagctaga    600
gtacggtaga gggggatgga attccgcgtg tagcagtgaa atgcgtagat atgcggagga    660
```

```
acaccgatgg cgaaggcaat ccctggacc tgtactgacg ctcatgcacg aaagcgtggg      720
gagcaaacag gattagatac cctggnagtc cacgccctan cgatgtcaac tgnnngntgg    780
gtcttcnctg actccagtaa cnaacgcann tacgcntgag ttgaccgnnt nnnnnnannn    840
nnnnnnnnna aactcaagan tgacgggacc cgnnncnagc gg                       882
```

<210> SEQ ID NO 29
<211> LENGTH: 874
<212> TYPE: DNA
<213> ORGANISM: Artificial Sequence
<220> FEATURE:
<223> OTHER INFORMATION: FM-1-13-27F_G06.ab1
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (762)..(762)
<223> OTHER INFORMATION: n is a, c, g, or t
<220> FEATURE:
<221> NAME/KEY: misc_feature
<222> LOCATION: (775)..(777)
<223> OTHER INFORMATION: n is a, c, g, or t
<220> FEATURE:
<221> NAME/KEY: misc_feature
<222> LOCATION: (814)..(815)
<223> OTHER INFORMATION: n is a, c, g, or t
<220> FEATURE:
<221> NAME/KEY: misc_feature
<222> LOCATION: (831)..(834)
<223> OTHER INFORMATION: n is a, c, g, or t
<220> FEATURE:
<221> NAME/KEY: misc_feature
<222> LOCATION: (838)..(842)
<223> OTHER INFORMATION: n is a, c, g, or t
<220> FEATURE:
<221> NAME/KEY: misc_feature
<222> LOCATION: (844)..(847)
<223> OTHER INFORMATION: n is a, c, g, or t
<220> FEATURE:
<221> NAME/KEY: misc_feature
<222> LOCATION: (857)..(857)
<223> OTHER INFORMATION: n is a, c, g, or t

<400> SEQUENCE: 29

```
tgccttacct gcaagtcgaa cggtaacagg tcttcggatg ctgacgagtg gcgaacgggt    60
gagtaataca tcggaacgtg cccgatcgtg ggggataacg aagcgaaagc tttgctaata   120
ccgcataaga tctaaggatg aaagcagggg accgcaaggc cttgcgcgaa cggagcggcc   180
gatggcagat taggtagttg gtgggataaa agcttaccaa gccgacgatc tgtagctggt   240
ctgagaggac gaccagccac actgggactg agacacggcc cagactccta cgggaggcag   300
cagtggggaa ttttggacaa tgggcgaaag cctgatccag ccatgccgcg tgcaggatga   360
aggccttcgg gttgtaaact gcttttgtac ggaacgaaaa gactctggtt aatacctggg   420
gtccatgacg gtaccgtaag aataagcacc ggctaactac gtgccagcag ccgcggtaat   480
acgtagggtg caagcgttaa tcggaattac tgggcgtaaa gcgtgcgcag gcggttatat   540
aagacagatg tgaaatcccc gggctcaacc tgggaactgc atttgtgact gtatagctag   600
agtacggtag aggggatgg aattccgcgt gtagcagtga aatgcgtaga tatgcggagg   660
aacaccgatg gcgaaggcaa tccctggac ctgtactgac gctcatgnca cgaaagcgtg    720
gggagcaaac aggattagat accctggtag tccacgccct ancgatgtca actgnnngtt    780
gggtcttcac tgactcagta cgaagctaac gccnntgaag ttgaccgcct nnnngtannn   840
nncnnnnaaa ctcaagnttg acgggacccg ccac                               874
```

```
<210> SEQ ID NO 30
<211> LENGTH: 891
<212> TYPE: DNA
<213> ORGANISM: Artificial Sequence
<220> FEATURE:
<223> OTHER INFORMATION: FM1-1-3-27F_F08.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (729)..(730)
<223> OTHER INFORMATION: n is a, c, g, or t
<220> FEATURE:
<221> NAME/KEY: misc_feature
<222> LOCATION: (743)..(743)
<223> OTHER INFORMATION: n is a, c, g, or t
<220> FEATURE:
<221> NAME/KEY: misc_feature
<222> LOCATION: (772)..(772)
<223> OTHER INFORMATION: n is a, c, g, or t
<220> FEATURE:
<221> NAME/KEY: misc_feature
<222> LOCATION: (808)..(808)
<223> OTHER INFORMATION: n is a, c, g, or t
<220> FEATURE:
<221> NAME/KEY: misc_feature
<222> LOCATION: (810)..(810)
<223> OTHER INFORMATION: n is a, c, g, or t
<220> FEATURE:
<221> NAME/KEY: misc_feature
<222> LOCATION: (824)..(828)
<223> OTHER INFORMATION: n is a, c, g, or t
<220> FEATURE:
<221> NAME/KEY: misc_feature
<222> LOCATION: (831)..(831)
<223> OTHER INFORMATION: n is a, c, g, or t
<220> FEATURE:
<221> NAME/KEY: misc_feature
<222> LOCATION: (836)..(836)
<223> OTHER INFORMATION: n is a, c, g, or t
<220> FEATURE:
<221> NAME/KEY: misc_feature
<222> LOCATION: (839)..(840)
<223> OTHER INFORMATION: n is a, c, g, or t
<220> FEATURE:
<221> NAME/KEY: misc_feature
<222> LOCATION: (845)..(845)
<223> OTHER INFORMATION: n is a, c, g, or t
<220> FEATURE:
<221> NAME/KEY: misc_feature
<222> LOCATION: (851)..(851)
<223> OTHER INFORMATION: n is a, c, g, or t
<220> FEATURE:
<221> NAME/KEY: misc_feature
<222> LOCATION: (853)..(853)
<223> OTHER INFORMATION: n is a, c, g, or t
<220> FEATURE:
<221> NAME/KEY: misc_feature
<222> LOCATION: (863)..(863)
<223> OTHER INFORMATION: n is a, c, g, or t
<220> FEATURE:
<221> NAME/KEY: misc_feature
<222> LOCATION: (865)..(865)
<223> OTHER INFORMATION: n is a, c, g, or t
<220> FEATURE:
<221> NAME/KEY: misc_feature
<222> LOCATION: (868)..(868)
<223> OTHER INFORMATION: n is a, c, g, or t
<220> FEATURE:
<221> NAME/KEY: misc_feature
<222> LOCATION: (870)..(870)
<223> OTHER INFORMATION: n is a, c, g, or t
<220> FEATURE:
<221> NAME/KEY: misc_feature
<222> LOCATION: (879)..(879)
```

<223> OTHER INFORMATION: n is a, c, g, or t
<220> FEATURE:
<221> NAME/KEY: misc_feature
<222> LOCATION: (882)..(882)
<223> OTHER INFORMATION: n is a, c, g, or t
<220> FEATURE:
<221> NAME/KEY: misc_feature
<222> LOCATION: (887)..(888)
<223> OTHER INFORMATION: n is a, c, g, or t

<400> SEQUENCE: 30

```
ttanntgcaa gtcgaacggt aacaggtctt cggatgctga cgagtggcga acgggtgagt     60
aatacatcgg aacgtgcccg atcgtggggg ataacgaagc gaaagctttg ctaataccgc    120
ataagatcta aggatgaaag caggggaccg caaggccttg cgcgaacgga gcggccgatg    180
gcagattagg tagttggtgg gataaaagct taccaagccg acgatctgta gctggtctga    240
gaggacgacc agccacactg ggactgagac acggcccaga ctcctacggg aggcagcagt    300
ggggaatttt ggacaatggg cgaaagcctg atccagccat gccgcgtgca ggatgaaggc    360 cttcggttg taaactgctt ttgtacgaa cggaaagact ctggttaata cctgggtcc       420 atgacggtac cgtaagaata agcaccggct aactacgtgc cagcagccgc ggtaatacgt    480
agggtgcaag cgttaatcgg aattactggg cgtaaagcgt gcgcaggcgg ttatataaga    540
cagatgtgaa atccccgggc tcaacctggg aactgcattt gtgactgtat agctagagta    600
cggtagaggg ggatggaatt ccgcgtgtag cagtgaaatg cgtagatatg cggaggaaca    660
ccgatggcga aggcaatccc ctggacctgt actgacgctc atgcacgaaa gcgtggggag    720
caaacaggnn tagataccct ggnagtccac gccctaaacg atgtcaactg gnttgttggg    780
tcttcactga ctcagtaacg aagctaangn ggtgaagttg accnnnnngg nagtancgnn    840
cgcangagtg nanacatact canangnan ttgacgggng anccgcnnaa g              891
```

<210> SEQ ID NO 31
<211> LENGTH: 938
<212> TYPE: DNA
<213> ORGANISM: Artificial Sequence
<220> FEATURE:
<223> OTHER INFORMATION: FM-1-14-27F_G07.ab1
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (671)..(671)
<223> OTHER INFORMATION: n is a, c, g, or t
<220> FEATURE:
<221> NAME/KEY: misc_feature
<222> LOCATION: (706)..(709)
<223> OTHER INFORMATION: n is a, c, g, or t
<220> FEATURE:
<221> NAME/KEY: misc_feature
<222> LOCATION: (824)..(824)
<223> OTHER INFORMATION: n is a, c, g, or t
<220> FEATURE:
<221> NAME/KEY: misc_feature
<222> LOCATION: (841)..(842)
<223> OTHER INFORMATION: n is a, c, g, or t
<220> FEATURE:
<221> NAME/KEY: misc_feature
<222> LOCATION: (867)..(867)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t
<220> FEATURE:
<221> NAME/KEY: misc_feature
<222> LOCATION: (880)..(880)
<223> OTHER INFORMATION: n is a, c, g, or t
<220> FEATURE:
<221> NAME/KEY: misc_feature
<222> LOCATION: (888)..(888)
<223> OTHER INFORMATION: n is a, c, g, or t
<220> FEATURE:
<221> NAME/KEY: misc_feature
<222> LOCATION: (901)..(901)
<223> OTHER INFORMATION: n is a, c, g, or t
<220> FEATURE:
<221> NAME/KEY: misc_feature
<222> LOCATION: (903)..(903)
<223> OTHER INFORMATION: n is a, c, g, or t
<220> FEATURE:
<221> NAME/KEY: misc_feature
<222> LOCATION: (924)..(924)
<223> OTHER INFORMATION: n is a, c, g, or t

<400> SEQUENCE: 31

```
tgccttannt gcaagtcgaa cggtaacagg tcttcggatg ctgacgagtg gcgaacgggt    60
gagtaataca tcggaacgtg cccgatcgtg ggggataacg aagcgaaagc tttgctaata   120
ccgcataaga tctaaggatg aaagcagggg accgcaaggc cttgcgcgaa cggagcggcc   180
gatggcagat taggtagttg gtgggataaa agcttaccaa gccgacgatc tgtagctggt   240
ctgagaggac gaccagccac actgggactg agacacggcc cagactccta cgggaggcag   300
cagtggggaa ttttggacaa tgggcgaaag cctgatccag ccatgccgcg tgcaggatga   360
aggccttcgg gttgtaaact gcttttgtac ggaacgaaaa gactctggtt aatacctggg   420
gtccatgacg gtaccgtaag aataagcacc ggctaactac gtgccagcag ccgcggtaat   480
acgtagggtg cgagcgttaa tcggaattac tgggcgtaaa gcgtgcgcag gcggttatat   540
aagacagatg tgaaatcccc gggctcaacc tgggaactgc atttgtgact gtatagctag   600
agtacggtag aggggggatgg aattccgcgt gtagcagtga aatgcgtaga tatgcggagg   660
aacaccgatg ncgaagggca atcccctggg acctgtactg accccnnnnc aacgaaagcg   720
tggggagcaa acaggattaa gattaccctg gttagtccac cgcccctaaa cgatgtcaac   780
tggtttgttg ggttcttcac ctgacttcag taacgaagct aacngcgtgg aagttgaacg   840
nncctggggg agtacggccg ccagcgnttg aatganaacn tcgaaagnga acttggacgg   900
ngngaacccc gcaccaagcc gggngggaat ggaatggt                           938
```

<210> SEQ ID NO 32
<211> LENGTH: 871
<212> TYPE: DNA
<213> ORGANISM: Artificial Sequence
<220> FEATURE:
<223> OTHER INFORMATION: FM1-1-4-27F_F09.ab1
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (676)..(676)
<223> OTHER INFORMATION: n is a, c, g, or t
<220> FEATURE:
<221> NAME/KEY: misc_feature
<222> LOCATION: (746)..(746)
<223> OTHER INFORMATION: n is a, c, g, or t
<220> FEATURE:
<221> NAME/KEY: misc_feature
<222> LOCATION: (811)..(811)
<223> OTHER INFORMATION: n is a, c, g, or t
<220> FEATURE:
<221> NAME/KEY: misc_feature
<222> LOCATION: (834)..(841)

<223> OTHER INFORMATION: n is a, c, g, or t
<220> FEATURE:
<221> NAME/KEY: misc_feature
<222> LOCATION: (843)..(845)
<223> OTHER INFORMATION: n is a, c, g, or t

<400> SEQUENCE: 32

```
ccttanntgc aagtcgaacg gtaacaggtc ttcggatgct gacgagtggc gaacgggtga     60
gtaatacatc ggaacgtgcc cgatcgtggg ggataacgaa gcgaaagctt tgctaatacc    120
gcataagatc taaggatgaa agcaggggac cgcaaggcct tgcgcgaacg gagcggccga    180
tggcagatta ggtagttggt gggataaaag cttaccaagc cgacgatctg tagctggtct    240
gagaggacga ccagccacac tgggactgag acacggccca gactcctacg ggaggcagca    300
gtggggaatt ttggacaatg ggcgaaagcc tgatccagcc atgccgcgtg caggatgaag    360
gccttcgggt tgtaaactgc ttttgtacgg aacgaaaaga ctctggttaa tacctggggt    420
ccatgacggt accgtaagaa taagcaccgg ctaactacgt gccagcagcc gcggtaatac    480
gtagggtgca agcgttaatc ggaattactg ggcgtaaagc gtgcgcaggc ggttatataa    540
gacagatgtg aaatccccgg gctcaacctg gaactgcat ttgtgactgt atagctagag    600
tacggtagag ggggatggaa ttccgcgtgt agcagtgaaa tgcgtagata tgcggaggaa    660
caccgatggc gaaagncaat cccctggacc tgtactgacg ctcatgcacg aaagcgtggg    720
gagcaaacag gattagatac cctggnagtc cacgccctaa acgatgtcaa ctggttgttg    780
ggtcttcact gactcagtac gaagctaacg ngtgaagttg accgcctggg gagnnnnnnn    840
nannngaaac tcaaaggaat tgacgggaac c                                   871
```

<210> SEQ ID NO 33
<211> LENGTH: 882
<212> TYPE: DNA
<213> ORGANISM: Artificial Sequence
<220> FEATURE:
<223> OTHER INFORMATION: FM-1-15-27F_G08.ab1
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (743)..(743)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t
<220> FEATURE:
<221> NAME/KEY: misc_feature
<222> LOCATION: (810)..(810)
<223> OTHER INFORMATION: n is a, c, g, or t
<220> FEATURE:
<221> NAME/KEY: misc_feature
<222> LOCATION: (821)..(823)
<223> OTHER INFORMATION: n is a, c, g, or t
<220> FEATURE:
<221> NAME/KEY: misc_feature
<222> LOCATION: (828)..(829)
<223> OTHER INFORMATION: n is a, c, g, or t
<220> FEATURE:
<221> NAME/KEY: misc_feature
<222> LOCATION: (834)..(836)
<223> OTHER INFORMATION: n is a, c, g, or t
<220> FEATURE:
<221> NAME/KEY: misc_feature
<222> LOCATION: (838)..(841)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
<221> NAME/KEY: misc_feature
<222> LOCATION: (864)..(865)
<223> OTHER INFORMATION: n is a, c, g, or t
<220> FEATURE:
<221> NAME/KEY: misc_feature
<222> LOCATION: (868)..(870)
<223> OTHER INFORMATION: n is a, c, g, or t
<220> FEATURE:
<221> NAME/KEY: misc_feature
<222> LOCATION: (874)..(874)
<223> OTHER INFORMATION: n is a, c, g, or t
<220> FEATURE:
<221> NAME/KEY: misc_feature
<222> LOCATION: (878)..(879)
<223> OTHER INFORMATION: n is a, c, g, or t

<400> SEQUENCE: 33

```
cttanntgca gtcgaacggt aacaggtctt cggatgctga cgagtggcga acgggtgagt      60
aatacatcgg aacgtgcccg agagtggggg ataacgaagc gaaagctttg ctaataccgc     120
atacgatctc aggatgaaag caggggaccg caaggccttg cgctcacgga gcggccgatg     180
gcagattagg tagttggtgg gataaaagct taccaagccg acgatctgta gctggtctga     240
gaggacgacc agccacactg ggactgagac acggcccaga ctcctacggg aggcagcagt     300
ggggaatttt ggacaatggg cgcaagcctg atccagccat gccgcgtgca ggatgaaggc     360
cttcggggttg taaactgctt ttgtacggaa cgaaaagact ctggttaata cctggggtcc    420
atgacggtac cgtaagaata agcaccggct aactacgtgc cagcagccgc ggtaatacgt     480
agggtgcgag cgttaatcgg aattactggg cgtaaagcgt gcgcaggcgg ttatataaga    540
cagatgtgaa atccccgggc tcaacctggg aactgcattt gtgactgtat agctagagta    600
cggcagaggg ggatggaatt ccgcgtgtag cagtgaaatg cgtagatatg cggaggaaca    660
ccgatggcga aggcaatccc ctgggcctgt actgacgctc atgcacgaaa gcgtggggag    720
caaacaggat tagataccct ggnagtccac gccctaacga tgtcaactgg ntgttgggtc    780
ttcactgact cagtaacgaa gctaacgcgn gaagttgacc nnnggggnnt acgnnncnnn    840
ntnaactcaa ggaattgacg gggnnccnnn caancggnng gg                       882
```

<210> SEQ ID NO 34
<211> LENGTH: 850
<212> TYPE: DNA
<213> ORGANISM: Artificial Sequence
<220> FEATURE:
<223> OTHER INFORMATION: FM1-1-6-27F_F11.ab1
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (675)..(675)
<223> OTHER INFORMATION: n is a, c, g, or t
<220> FEATURE:
<221> NAME/KEY: misc_feature
<222> LOCATION: (746)..(746)
<223> OTHER INFORMATION: n is a, c, g, or t
<220> FEATURE:
<221> NAME/KEY: misc_feature
<222> LOCATION: (751)..(751)
<223> OTHER INFORMATION: n is a, c, g, or t
<220> FEATURE:
<221> NAME/KEY: misc_feature
<222> LOCATION: (771)..(773)
<223> OTHER INFORMATION: n is a, c, g, or t
<220> FEATURE:

<221> NAME/KEY: misc_feature
<222> LOCATION: (821)..(822)
<223> OTHER INFORMATION: n is a, c, g, or t
<220> FEATURE:
<221> NAME/KEY: misc_feature
<222> LOCATION: (831)..(831)
<223> OTHER INFORMATION: n is a, c, g, or t
<220> FEATURE:
<221> NAME/KEY: misc_feature
<222> LOCATION: (835)..(837)
<223> OTHER INFORMATION: n is a, c, g, or t
<220> FEATURE:
<221> NAME/KEY: misc_feature
<222> LOCATION: (841)..(841)
<223> OTHER INFORMATION: n is a, c, g, or t

<400> SEQUENCE: 34

```
tgcttanntg caagtcgaac ggtaacaggt cttcggatgc tgacgagtgg cgaacgggtg    60
agtaatacat cggaacgtgc ccgatcgtgg gggataacga agcgaaagct ttgctaatac   120
cgcataagat ctaaggatga aagcagggga ccgcaaggcc ttgcgcgaac ggagcggccg   180
atggcagatt aggtagttgg tgggataaaa gcttaccaag ccgacgatct gtagctggtc   240
tgagaggacg accagccaca ctgggactga gacacggccc agactcctac gggaggcagc   300
agtggggaat tttggacaat gggcgaaagc ctgatccagc catgccgcgt gcaggatgaa   360
ggccttcggg ttgtaaactg cttttgtacg gaacgaaaag actctggtta atacctgggg   420
tccatgacgg taccgtaaga ataagcaccg gctaactacg tgccagcagc cgcggtaata   480
cgtagggtgc aagcgttaat cggaattact gggcgtaaag cgtgcgcagg cggttatata   540
agacagatgt gaaatccccg ggctcaacct gggaactgca tttgtgactg tatagctaga   600
gtacggtaga gggggatgga attccgcgtg tagcagtgaa atgcgtagat atgcggagga   660
acaccgatcg cgaangcaat cccctggacc tgtactgacg ctcatgcacg aaagcgtggg   720
gagcaaacag gattagatac cctggnagtc ncgccctaac gatgtcaact nnngttgggt   780
cttcactgac tcagtaacga agctaacgcg tgaagttgac nncctgggga ntacnnncgc   840
nagggttgaa                                                          850
```

<210> SEQ ID NO 35
<211> LENGTH: 859
<212> TYPE: DNA
<213> ORGANISM: Artificial Sequence
<220> FEATURE:
<223> OTHER INFORMATION: FM1-1-7-27F_F12.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (692)..(696)
<223> OTHER INFORMATION: n is a, c, g, or t
<220> FEATURE:
<221> NAME/KEY: misc_feature
<222> LOCATION: (698)..(700)
<223> OTHER INFORMATION: n is a, c, g, or t
<220> FEATURE:
<221> NAME/KEY: misc_feature
<222> LOCATION: (743)..(743)
<223> OTHER INFORMATION: n is a, c, g, or t
<220> FEATURE:
<221> NAME/KEY: misc_feature
<222> LOCATION: (772)..(772)
<223> OTHER INFORMATION: n is a, c, g, or t
<220> FEATURE:
<221> NAME/KEY: misc_feature
<222> LOCATION: (779)..(780)
<223> OTHER INFORMATION: n is a, c, g, or t
<220> FEATURE:
<221> NAME/KEY: misc_feature
<222> LOCATION: (784)..(784)
<223> OTHER INFORMATION: n is a, c, g, or t
<220> FEATURE:
<221> NAME/KEY: misc_feature
<222> LOCATION: (793)..(796)
<223> OTHER INFORMATION: n is a, c, g, or t
<220> FEATURE:
<221> NAME/KEY: misc_feature
<222> LOCATION: (827)..(828)
<223> OTHER INFORMATION: n is a, c, g, or t

<400> SEQUENCE: 35

```
ttanntgcag tcgaacggta acaggtcttc ggatgctgac gagtggcgaa cgggtgagta      60
atacatcgga acgtgcccga tcgtggggga taacgaagcg aaagctttgc taataccgca     120
taagatctaa ggatgaaagc aggggaccgc aaggccttgc gcgaacggag cggccgatgg     180
cagattaggt agttggtggg ataaaagctt accaagccga cgatctgtag ctggtctgag     240
aggacgacca gccacactgg gactgagaca cggcccagac tcctacggga ggcagcagtg     300
gggaattttg gacaatgggc gaaagcctga tccagccatg ccgcgtgcag gatgaaggcc     360
ttcgggttgt aaactgcttt tgtacggaac gaaaagactc tggttaatac ctggggtcca     420
tgacggtacc gtaagaataa gcaccggcta actacgtgcc agcagccgcg gtaatacgta     480
gggtgcaagc gttaatcgga attactgggc gtaaagcgtg cgcaggcggt tatgtaagac     540
agatgtgaaa tccccgggct caacctggga actgcatttg tgactgcata gctagagtac     600
ggcagagggg gatggaattc cgcgtgtagc agtgaaatgc gtagatatgc ggaggaacac     660
cgatggcgaa ggcaatcccc tgggcctgta cnnnnncnnn atgcacgaaa gcgtggggag     720
caaacaggat tagataccct ggnagtccac gccctaacga tgtcaactgg tngttgggnn     780
ttcnctgact cannnngaag ctacgcgtga gttgaccgcc tggggnnta cggccgcagg     840
ttgaaacttc aaaggaatt                                                   859
```

<210> SEQ ID NO 36
<211> LENGTH: 759
<212> TYPE: DNA
<213> ORGANISM: Artificial Sequence
<220> FEATURE:
<223> OTHER INFORMATION: FM-1-8-27F_G01.ab1
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (643)..(643)
<223> OTHER INFORMATION: n is a, c, g, or t
<220> FEATURE:
<221> NAME/KEY: misc_feature
<222> LOCATION: (645)..(646)
<223> OTHER INFORMATION: n is a, c, g, or t
<220> FEATURE:
<221> NAME/KEY: misc_feature
<222> LOCATION: (648)..(654)
<223> OTHER INFORMATION: n is a, c, g, or t
<220> FEATURE:
<221> NAME/KEY: misc_feature
<222> LOCATION: (656)..(657)
<223> OTHER INFORMATION: n is a, c, g, or t
<220> FEATURE:
<221> NAME/KEY: misc_feature
<222> LOCATION: (659)..(659)
<223> OTHER INFORMATION: n is a, c, g, or t
<220> FEATURE:
<221> NAME/KEY: misc_feature
<222> LOCATION: (661)..(662)

<223> OTHER INFORMATION: n is a, c, g, or t
<220> FEATURE:
<221> NAME/KEY: misc_feature
<222> LOCATION: (664)..(684)
<223> OTHER INFORMATION: n is a, c, g, or t
<220> FEATURE:
<221> NAME/KEY: misc_feature
<222> LOCATION: (686)..(692)
<223> OTHER INFORMATION: n is a, c, g, or t
<220> FEATURE:
<221> NAME/KEY: misc_feature
<222> LOCATION: (694)..(696)
<223> OTHER INFORMATION: n is a, c, g, or t
<220> FEATURE:
<221> NAME/KEY: misc_feature
<222> LOCATION: (704)..(706)
<223> OTHER INFORMATION: n is a, c, g, or t

<400> SEQUENCE: 36

```
cttanntgca gtcgaacggt aacaggtctt cggatgctga cgagtggcga acgggtgagt      60
aatacatcgg aacgtgcccg atcgtgggggg ataacgaagc gaaagctttg ctaataccgc    120
ataagatcta aggatgaaag caggggaccg caaggccttg cgcgaacgga gcggccgatg    180
gcagattagg tagttggtgg gataaaagct taccaagccg acgatctgta gctggtctga    240
gaggacgacc agccacactg ggactgagac acggcccaga ctcctacggg aggcagcagt    300
ggggaatttt ggacaatggg cgaaagcctg atccagccat gccgcgtgca ggatgaaggc    360
cttcggggttg taaactgctt ttgtacggaa cgaaaagact ctggttaata cctgggtcc    420
atgacggtac cgtaagaata agcaccggct aactacgtgc cagcagccgc ggtaatacgt    480
agggtgcgag cgttaatcgg aattactggg cgtaaagcgt gcgcaggcgg ttatataaga    540
cagatgtgaa atccccgggc tcaacctggg aactgcattt gtgactgtat agctagagta    600
cggtagaggg ggatggaatt ccgcgtgtag cagtgaaatg cgnanngnnn nnnntnnanc    660
nncnnnnnnn nnnnnnnnnn nnnntnnnnn nnannnacgc aaannnaagc gtggggagca    720
aacaggatta gataccctgg tagtccacgc cctaaacga                           759
```

<210> SEQ ID NO 37
<211> LENGTH: 823
<212> TYPE: DNA
<213> ORGANISM: Artificial Sequence
<220> FEATURE:
<223> OTHER INFORMATION: FM-1-9-27F_G02.ab1
<220> FEATURE:
<221> NAME/KEY: misc_feature
<222> LOCATION: (11)..(12)
<223> OTHER INFORMATION: n is a, c, g, or t
<220> FEATURE:
<221> NAME/KEY: misc_feature
<222> LOCATION: (652)..(653)
<223> OTHER INFORMATION: n is a, c, g, or t
<220> FEATURE:
<221> NAME/KEY: misc_feature
<222> LOCATION: (655)..(656)
<223> OTHER INFORMATION: n is a, c, g, or t
<220> FEATURE:
<221> NAME/KEY: misc_feature
<222> LOCATION: (658)..(658)
<223> OTHER INFORMATION: n is a, c, g, or t
<220> FEATURE:
<221> NAME/KEY: misc_feature
<222> LOCATION: (684)..(685)
<223> OTHER INFORMATION: n is a, c, g, or t
<220> FEATURE:
<221> NAME/KEY: misc_feature
<222> LOCATION: (700)..(701)
<223> OTHER INFORMATION: n is a, c, g, or t
<220> FEATURE:
<221> NAME/KEY: misc_feature

```
<222> LOCATION: (705)..(708)
<223> OTHER INFORMATION: n is a, c, g, or t
<220> FEATURE:
<221> NAME/KEY: misc_feature
<222> LOCATION: (710)..(713)
<223> OTHER INFORMATION: n is a, c, g, or t
<220> FEATURE:
<221> NAME/KEY: misc_feature
<222> LOCATION: (778)..(778)
<223> OTHER INFORMATION: n is a, c, g, or t
<220> FEATURE:
<221> NAME/KEY: misc_feature
<222> LOCATION: (780)..(780)
<223> OTHER INFORMATION: n is a, c, g, or t
<220> FEATURE:
<221> NAME/KEY: misc_feature
<222> LOCATION: (790)..(791)
<223> OTHER INFORMATION: n is a, c, g, or t
<220> FEATURE:
<221> NAME/KEY: misc_feature
<222> LOCATION: (799)..(799)
<223> OTHER INFORMATION: n is a, c, g, or t
<220> FEATURE:
<221> NAME/KEY: misc_feature
<222> LOCATION: (811)..(811)
<223> OTHER INFORMATION: n is a, c, g, or t
<220> FEATURE:
<221> NAME/KEY: misc_feature
<222> LOCATION: (813)..(813)
<223> OTHER INFORMATION: n is a, c, g, or t
<220> FEATURE:
<221> NAME/KEY: misc_feature
<222> LOCATION: (815)..(816)
<223> OTHER INFORMATION: n is a, c, g, or t
<220> FEATURE:
<221> NAME/KEY: misc_feature
<222> LOCATION: (819)..(819)
<223> OTHER INFORMATION: n is a, c, g, or t

<400> SEQUENCE: 37
ggctgcctta nntgcaagtc gaacggtaac aggtcttcgg atgctgacga gtggcgaacg      60
ggtgagtaat acatcggaac gtgcccgatc gtgggggata acgaagcgaa agctttgcta     120
ataccgcata agatctaagg atgaaagcag gggaccgcaa ggccttgcgc gaacggagcg     180
gccgatggca gattaggtag ttggtgggat aaaagcttac caagccgacg atctgtagct     240
ggtctgagag gacgaccagc cacactggga ctgagacacg gcccagactc ctacgggagg     300
cagcagtggg gaattttgga caatgggcga agcctgatcc agccatgccg cgtgcagga     360 tgaaggcctt cggggttgtaa actgcttttg tacggaacga aaagactctg ttaataccct     420
ggggtccatg acggtaccgt aagaataagc accggctaac tacgtgccag cagccgcggt     480
aatacgtagg gtgcaagcgt taatcggaat tactgggcgt aaagcgtgcg caggcggtta     540
tataagacag atgtgaaatc cccgggctca acctgggaac tgcatttgtg actgtatagc     600
tagagtacgt agaggggga tggaattccg cgtgtagcag tgaaatgcgt annanngngg     660
aggaacaccg gatggcgaag gcanncccct ggacctgtan ngacnnnnan nnccgaaag     720 cgtggggagc aaacaggatt agataccctg gtagtcacgc ctaacgatgt cactggtngn     780
tgggtcttcn ntgactcant acgaagctaa ncncnnaant gac                       823

<210> SEQ ID NO 38
<211> LENGTH: 868
<212> TYPE: DNA
<213> ORGANISM: Artificial Sequence
<220> FEATURE:
<223> OTHER INFORMATION: Gam1-1-10-27F_C10.ab1
<220> FEATURE:
<221> NAME/KEY: misc_feature
<222> LOCATION: (2)..(2)
```

```
<223> OTHER INFORMATION: n is a, c, g, or t
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (620)..(626)
<223> OTHER INFORMATION: n is a, c, g, or t
<220> FEATURE:
<221> NAME/KEY: misc_feature
<222> LOCATION: (641)..(641)
<223> OTHER INFORMATION: n is a, c, g, or t
<220> FEATURE:
<221> NAME/KEY: misc_feature
<222> LOCATION: (643)..(650)
<223> OTHER INFORMATION: n is a, c, g, or t
<220> FEATURE:
<221> NAME/KEY: misc_feature
<222> LOCATION: (716)..(716)
<223> OTHER INFORMATION: n is a, c, g, or t
<220> FEATURE:
<221> NAME/KEY: misc_feature
<222> LOCATION: (788)..(790)
<223> OTHER INFORMATION: n is a, c, g, or t
<220> FEATURE:
<221> NAME/KEY: misc_feature
<222> LOCATION: (794)..(794)
<223> OTHER INFORMATION: n is a, c, g, or t
<220> FEATURE:
<221> NAME/KEY: misc_feature
<222> LOCATION: (798)..(798)
<223> OTHER INFORMATION: n is a, c, g, or t
<220> FEATURE:
<221> NAME/KEY: misc_feature
<222> LOCATION: (800)..(800)
<223> OTHER INFORMATION: n is a, c, g, or t
<220> FEATURE:
<221> NAME/KEY: misc_feature
<222> LOCATION: (808)..(808)
<223> OTHER INFORMATION: n is a, c, g, or t
<220> FEATURE:
<221> NAME/KEY: misc_feature
<222> LOCATION: (812)..(813)
<223> OTHER INFORMATION: n is a, c, g, or t
<220> FEATURE:
<221> NAME/KEY: misc_feature
<222> LOCATION: (834)..(836)
<223> OTHER INFORMATION: n is a, c, g, or t
<220> FEATURE:
<221> NAME/KEY: misc_feature
<222> LOCATION: (842)..(842)
<223> OTHER INFORMATION: n is a, c, g, or t
<220> FEATURE:
<221> NAME/KEY: misc_feature
<222> LOCATION: (848)..(848)
<223> OTHER INFORMATION: n is a, c, g, or t
<220> FEATURE:
<221> NAME/KEY: misc_feature
<222> LOCATION: (854)..(855)
<223> OTHER INFORMATION: n is a, c, g, or t
<220> FEATURE:
<221> NAME/KEY: misc_feature
<222> LOCATION: (857)..(857)
<223> OTHER INFORMATION: n is a, c, g, or t

<400> SEQUENCE: 38
tncnntgcaa gtcgagcggc agcgggaaag tagcttgcta cttttgccgg cgagcggcgg      60
acgggtgagt aatgcctggg gatctgccca gtcgaggggg ataactactg gaaacggtag     120
ctaataccgc atacgcccta cggggggaaag caggggacct tcgggccttg cgcgattgga    180
tgaacccagg tgggattagc tagttggtga ggtaacggct caccaaggcg acgatccta     240 gctggtctga gaggatgatc agccacactg gaactgagac acggtccaga ctcctacggg    300
aggcagcagt ggggaatatt gcacaatggg ggaaaccctg atgcagccat gccgcgtgtg    360
```

-continued

```
tgaagaaggc cttcgggttg taaagcactt tcagcgagga ggaaaggtca gtagctaata      420
tctgctggct gtgacgttac tcgcagaaga agcaccggct aactccgtgc cagcagccgc      480
ggtaatacgg agggtgcaag cgttaatcgg aattactggg cgtaaagcgc acgcaggcgg      540
ttggataagt tagatgtgaa agccccgggc tcaacctggg aattgcattt aaaactgtcc      600
agctagagtc ttgtagaggn nnnnnntatt ttccagggtg nannnnnnnn aaatgcgtag      660
agatctggag gaataccggt ggcgaaggcg gcccccctgga caaagactga cgctcngtgc     720
gaaagcgtgg ggagcaaaca ggattagata ccctggtagt ccacgccgta acgatgtcga     780
tttggagnnn tgtntccntn agacgtgntt cnnagctaac gcgttaaatc gacnngggg     840 antacggngc aagnnanctc aaatgaat                                        868
```

```
<210> SEQ ID NO 39
<211> LENGTH: 863
<212> TYPE: DNA
<213> ORGANISM: Artificial Sequence
<220> FEATURE:
<223> OTHER INFORMATION: Gam1-1-11-27F_C11.ab1
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (626)..(627)
<223> OTHER INFORMATION: n is a, c, g, or t
<220> FEATURE:
<221> NAME/KEY: misc_feature
<222> LOCATION: (631)..(631)
<223> OTHER INFORMATION: n is a, c, g, or t
<220> FEATURE:
<221> NAME/KEY: misc_feature
<222> LOCATION: (685)..(685)
<223> OTHER INFORMATION: n is a, c, g, or t
<220> FEATURE:
<221> NAME/KEY: misc_feature
<222> LOCATION: (713)..(717)
<223> OTHER INFORMATION: n is a, c, g, or t

<400> SEQUENCE: 39
taacnntgca agtcgagcgg tagcacagga gagcttgctc tctgggtgac gagcggcgga      60
cgggtgagta atgtctggga aactgcctga tggaggggga taactactgg aaacggtagc     120
taataccgca taacgtcgca agaccaaaga gggggacctt cgggcctctt gccatcagat     180
gtgcccagat gggattagct agtaggtggg gtaacggctc acctaggcga cgatccctag     240
ctggtctgag aggatgacca gccacactgg aactgagaca cggtccagac tcctacggga     300
ggcagcagtg gggaatattg cacaatgggc gcaagcctga tgcagccatg ccgcgtgtat     360
gaagaaggcc ttcgggttgt aaagtacttt cagcggggag gaaggtgttg aggttaataa     420
cctcagcaat tgacgttacc cgcagaagaa gcaccggcta actccgtgcc agcagccgcg     480
gtaatacgga gggtgcaagc gttaatcgga attactgggc gtaaagcgca cgcaggcggt     540
ctgtcaagtc ggatgtgaaa tccccgggct caacctggga actgcattcg aaactggcag     600
gctagagtct tgtagagggg ggtagnnttc nccagggtgt agcggtgaaa tgcgtaggag     660
atctggagga ataccggtgg cgaangcggc ccctgacaa aagactgacg ctnnnnngcg     720
aaagcgtggg gagcaaacag gattagatac cctggtagtc cacgccgtaa cgatgtcgac     780
ttggaggttg tgcccttgag gcgtggcttc cggagctaa cgcgttaagt cgaccggcct     840
gggggagtac gggccgcaag gtt                                             863
```

<210> SEQ ID NO 40
<211> LENGTH: 843
<212> TYPE: DNA
<213> ORGANISM: Artificial Sequence
<220> FEATURE:
<223> OTHER INFORMATION: Gam1-1-12-27F_C12.ab1
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (639)..(640)
<223> OTHER INFORMATION: n is a, c, g, or t
<220> FEATURE:
<221> NAME/KEY: misc_feature
<222> LOCATION: (700)..(704)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (712)..(712)
<223> OTHER INFORMATION: n is a, c, g, or t
<220> FEATURE:
<221> NAME/KEY: misc_feature
<222> LOCATION: (716)..(716)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (731)..(733)
<223> OTHER INFORMATION: n is a, c, g, or t

<400> SEQUENCE: 40

```
cnntgcaagt cgagcggcag cgggaaagta gcttgctact tttgccggcg agcggcggac      60
gggtgagtaa tgcctgggga tctgcccagt cgagggggat aactactgga aacggtagct     120
aataccgcat acgccctacg ggggaaagca ggggaccttc gggccttgcg cgattggatg     180
aacccaggtg ggattagcta gttggtgagg taacggctca ccaaggcgac gatccctagc     240
tggtctgaga ggatgatcag cacactggaa ctgagacacg gtccagactc ctacgggagg     300
cagcagtggg gaatattgca caatggggga acccctgatg cagccatgcc gcgtgtgtga     360
agaaggcctt cgggttgtaa agcactttca gcgaggagga aaggtcagta gctaatatct     420
gctggctgtg acgttactcg cagaagaagc accggctaac tccgtgccag cagccgcggt     480
aatacggagg gtgcaagcgt taatcggaat tactgggcgt aaagcgcacg caggcggttg     540
gataagttag atgtgaaagc cccgggctca acctgagaat tgcatttaaa actgtccagc     600
tagagtcttg tagagggggg tagaattcca ggtgtaggnn tgaaatgcgt agagatctgg     660
aggaataccg gtggcgaagg cggccccctg gacaaagacn nnnngccnca gntgcnaaag     720
gcngtggggg nnncaaacag gattagatac cctggtagtc cacgccctga aacgatgtcg     780
acttggaggt tgtgcccttg aggcgtggct tccggagcta acgcgttaag tcgaccgccc     840
tgg                                                                   843
```

<210> SEQ ID NO 41
<211> LENGTH: 794
<212> TYPE: DNA
<213> ORGANISM: Artificial Sequence
<220> FEATURE:
<223> OTHER INFORMATION: Gam1-1-1-27F_C01.ab1

```
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (613)..(613)
<223> OTHER INFORMATION: n is a, c, g, or t
<220> FEATURE:
<221> NAME/KEY: misc_feature
<222> LOCATION: (616)..(617)
<223> OTHER INFORMATION: n is a, c, g, or t
<220> FEATURE:
<221> NAME/KEY: misc_feature
<222> LOCATION: (657)..(659)
<223> OTHER INFORMATION: n is a, c, g, or t
<220> FEATURE:
<221> NAME/KEY: misc_feature
<222> LOCATION: (683)..(683)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (726)..(726)
<223> OTHER INFORMATION: n is a, c, g, or t
<220> FEATURE:
<221> NAME/KEY: misc_feature
<222> LOCATION: (775)..(775)
<223> OTHER INFORMATION: n is a, c, g, or t
<220> FEATURE:
<221> NAME/KEY: misc_feature
<222> LOCATION: (787)..(787)
<223> OTHER INFORMATION: n is a, c, g, or t

<400> SEQUENCE: 41
gnnacnntgc aagtcgaacg gtagcacaga ggagcttgct ccttgggtga cgagtggcgg      60
acgggtgagt aatgtctggg aaactgcccg atggaggggg ataactactg gaaacggtag     120
ctaataccgc ataacgtcgc aagaccaaag aggggacct tcgggcctct tgccatcgga      180
tgtgcccaga tgggattagc tagtaggtgg ggtaacggct cacctaggcg acgatcccta     240
gctggtctga gaggatgacc agccacactg gaactgagac acggtccaga ctcctacggg     300
aggcagcagt ggggaatatt gcacaatggg cgcaagcctg atgcagccat gccgcgtgta     360
tgaagaaggc cttcgggttg taaagtactt tcagcgagga ggaaggtgtt gtggttaata     420
actgcagcaa ttgacgttac tcgcagaaga agcaccggct aactccgtgc cagcagccgc     480
ggtaatacgg agggtgcaag cgttaatcgg aattactggg cgtaaagcgc acgcaggcgg     540
tctgtcaagt cggatgtgaa atccccgggc tcaacctggg aactgcatcc gaaactggcn     600
gctagagtct tgnagnnggg ggggtagaat tccaggtgta gcggtgaaat gcgtagnnnt     660
ctggaggaat accggtggcg aancggcccc tggacaaana ctgacgctca ntgcgatagc     720
```
gtnggnagca aacaggatta gatacccctgg tagtccacgc cgtaaacgat tgtcnacttg    780
gaggttngtg cctt    794

<210> SEQ ID NO 42
<211> LENGTH: 884
<212> TYPE: DNA
<213> ORGANISM: Artificial Sequence
<220> FEATURE:
<223> OTHER INFORMATION: Gam1-1-13-27F_G06.ab1
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (603)..(605)
<223> OTHER INFORMATION: n is a, c, g, or t
<220> FEATURE:
<221> NAME/KEY: misc_feature
<222> LOCATION: (625)..(629)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (710)..(710)
<223> OTHER INFORMATION: n is a, c, g, or t
<220> FEATURE:
<221> NAME/KEY: misc_feature
<222> LOCATION: (744)..(745)
<223> OTHER INFORMATION: n is a, c, g, or t
<220> FEATURE:
<221> NAME/KEY: misc_feature
<222> LOCATION: (749)..(749)
<223> OTHER INFORMATION: n is a, c, g, or t
<220> FEATURE:
<221> NAME/KEY: misc_feature
<222> LOCATION: (800)..(800)
<223> OTHER INFORMATION: n is a, c, g, or t
<220> FEATURE:
<221> NAME/KEY: misc_feature
<222> LOCATION: (808)..(808)
<223> OTHER INFORMATION: n is a, c, g, or t
<220> FEATURE:
<221> NAME/KEY: misc_feature
<222> LOCATION: (817)..(817)
<223> OTHER INFORMATION: n is a, c, g, or t
<220> FEATURE:
<221> NAME/KEY: misc_feature
<222> LOCATION: (830)..(830)
<223> OTHER INFORMATION: n is a, c, g, or t
<220> FEATURE:
<221> NAME/KEY: misc_feature
<222> LOCATION: (832)..(832)
<223> OTHER INFORMATION: n is a, c, g, or t
<220> FEATURE:
<221> NAME/KEY: misc_feature
<222> LOCATION: (834)..(836)
<223> OTHER INFORMATION: n is a, c, g, or t
<220> FEATURE:
<221> NAME/KEY: misc_feature
<222> LOCATION: (840)..(842)
<223> OTHER INFORMATION: n is a, c, g, or t
<220> FEATURE:
<221> NAME/KEY: misc_feature
<222> LOCATION: (854)..(854)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t

<400> SEQUENCE: 42
tanncatgca gtcgagcggt aacacaggga gcttgctcct gggtgacgag cggcggacgg    60

```
gtgagtaatg tctgggaaac tgcctgatgg aggggataa ctactggaaa cggtagctaa      120
taccgcataa cgtcgcaaga ccaaagaggg ggaccttcgg gcctcttgcc atcagatgtg      180
cccagatggg attagctagt aggtggggta atggctcacc taggcgacga tccctagctg      240
gtctgagagg atgaccagcc acactggaac tgagacacgg tccagactcc tacgggaggc      300
agcagtgggg aatattgcac aatgggcgca agcctgatgc agccatgccg cgtgtatgaa      360
gaaggccttc gggttgtaaa gtactttcag cggggaggaa ggcgataagg ttaataacct      420
tgtcgattga cgttacccgc agaagaagca ccggctaact ccgtgccagc agccgcggta      480
atacggaggg tgcaagcgtt aatcggaatt actgggcgta aagcgcacgc aggcggtctg      540
tcaagtcgga tgtgaaatcc ccgggctcaa cctgggaact gcattcgaaa ctggcaggct      600
aannntttgg taagaggggg ggtannnnnc caggtgtagc ggtgaaatgc gtagagatct      660
ggaggaatac cggtggcgaa ngcggccccc tggacaaaga ctgacgctcn gtgcgaaagc      720
gtggggagca aacaggatta gatnncccng gtagtcacgc cgtaaacgat gtcgacttgg      780
agttgtgccc ttgaggcgtn gcttccgnag ctaacgngtt aagtcgacgn cngnnngagn      840
nngtacggcc gcangttaaa actcaaatga attganggg gccc                        884
```

<210> SEQ ID NO 43
<211> LENGTH: 876
<212> TYPE: DNA
<213> ORGANISM: Artificial Sequence
<220> FEATURE:
<223> OTHER INFORMATION: Gam1-1-15-27F_G08.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (620)..(622)
<223> OTHER INFORMATION: n is a, c, g, or t
<220> FEATURE:
<221> NAME/KEY: misc_feature
<222> LOCATION: (640)..(641)
<223> OTHER INFORMATION: n is a, c, g, or t
<220> FEATURE:
<221> NAME/KEY: misc_feature
<222> LOCATION: (709)..(709)
<223> OTHER INFORMATION: n is a, c, g, or t
<220> FEATURE:
<221> NAME/KEY: misc_feature
<222> LOCATION: (712)..(712)
<223> OTHER INFORMATION: n is a, c, g, or t
<220> FEATURE:
<221> NAME/KEY: misc_feature
<222> LOCATION: (750)..(758)
<223> OTHER INFORMATION: n is a, c, g, or t
<220> FEATURE:
<221> NAME/KEY: misc_feature
<222> LOCATION: (764)..(765)
<223> OTHER INFORMATION: n is a, c, g, or t
<220> FEATURE:
<221> NAME/KEY: misc_feature
<222> LOCATION: (767)..(769)
<223> OTHER INFORMATION: n is a, c, g, or t
<220> FEATURE:
<221> NAME/KEY: misc_feature
<222> LOCATION: (776)..(778)
<223> OTHER INFORMATION: n is a, c, g, or t
<220> FEATURE:
<221> NAME/KEY: misc_feature
<222> LOCATION: (781)..(785)
<223> OTHER INFORMATION: n is a, c, g, or t
<220> FEATURE:
<221> NAME/KEY: misc_feature
<222> LOCATION: (791)..(792)

```
<223> OTHER INFORMATION: n is a, c, g, or t
<220> FEATURE:
<221> NAME/KEY: misc_feature
<222> LOCATION: (796)..(797)
<223> OTHER INFORMATION: n is a, c, g, or t
<220> FEATURE:
<221> NAME/KEY: misc_feature
<222> LOCATION: (801)..(801)
<223> OTHER INFORMATION: n is a, c, g, or t
<220> FEATURE:
<221> NAME/KEY: misc_feature
<222> LOCATION: (803)..(803)
<223> OTHER INFORMATION: n is a, c, g, or t
<220> FEATURE:
<221> NAME/KEY: misc_feature
<222> LOCATION: (807)..(809)
<223> OTHER INFORMATION: n is a, c, g, or t
<220> FEATURE:
<221> NAME/KEY: misc_feature
<222> LOCATION: (811)..(811)
<223> OTHER INFORMATION: n is a, c, g, or t
<220> FEATURE:
<221> NAME/KEY: misc_feature
<222> LOCATION: (814)..(818)
<223> OTHER INFORMATION: n is a, c, g, or t
<220> FEATURE:
<221> NAME/KEY: misc_feature
<222> LOCATION: (824)..(824)
<223> OTHER INFORMATION: n is a, c, g, or t
<220> FEATURE:
<221> NAME/KEY: misc_feature
<222> LOCATION: (828)..(828)
<223> OTHER INFORMATION: n is a, c, g, or t
<220> FEATURE:
<221> NAME/KEY: misc_feature
<222> LOCATION: (830)..(830)
<223> OTHER INFORMATION: n is a, c, g, or t
<220> FEATURE:
<221> NAME/KEY: misc_feature
<222> LOCATION: (835)..(835)
<223> OTHER INFORMATION: n is a, c, g, or t
<220> FEATURE:
<221> NAME/KEY: misc_feature
<222> LOCATION: (840)..(840)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
<221> NAME/KEY: misc_feature
<222> LOCATION: (846)..(847)
<223> OTHER INFORMATION: n is a, c, g, or t
<220> FEATURE:
<221> NAME/KEY: misc_feature
<222> LOCATION: (852)..(852)
<223> OTHER INFORMATION: n is a, c, g, or t
<220> FEATURE:
<221> NAME/KEY: misc_feature
<222> LOCATION: (854)..(854)
<223> OTHER INFORMATION: n is a, c, g, or t
<220> FEATURE:
<221> NAME/KEY: misc_feature
<222> LOCATION: (856)..(856)
<223> OTHER INFORMATION: n is a, c, g, or t
<220> FEATURE:
<221> NAME/KEY: misc_feature
<222> LOCATION: (861)..(861)
<223> OTHER INFORMATION: n is a, c, g, or t
<220> FEATURE:
<221> NAME/KEY: misc_feature
<222> LOCATION: (866)..(866)
<223> OTHER INFORMATION: n is a, c, g, or t
<220> FEATURE:
<221> NAME/KEY: misc_feature
<222> LOCATION: (869)..(869)
<223> OTHER INFORMATION: n is a, c, g, or t
<220> FEATURE:
<221> NAME/KEY: misc_feature
```

<222> LOCATION: (871)..(871)
<223> OTHER INFORMATION: n is a, c, g, or t

<400> SEQUENCE: 43

```
tacnnatgca gtcgagcggt aacacaggga gcttgctcct gggtgacgag cggcggacgg      60
gtgagtaatg tctgggaaac tgcctgatgg aggggggataa ctactggaaa cggtagctaa     120
taccgcataa cgtcgcaaga ccaaagaggg ggaccttcgg gcctcttgcc atcagatgtg     180
cccagatggg attagctagt aggtggggta atggctcacc taggcgacga tccctagctg     240
gtctgagagg atgaccagcc acactggaac tgagacacgg tccagactcc tacgggaggc     300
agcagtgggg aatattgcac aatgggcgca agcctgatgc agccatgccg cgtgtatgaa     360
gaaggccttc gggttgtaaa gcactttcag cgaggaggaa aggttggtag ctaatatctg     420
ccagctgtga cgttactcgc agaagaagca ccggctaact ccgtgccagc agccgcggta     480
atacggaggg tgcaagcgtt aatcggaatt actgggcgta aagcgcacgc aggcggttgg     540
ataagttaga tgtgaaagcc ccgggctcaa cctgggaatt gcatttaaaa ctgtccagct     600
agagtcttgt aagggggggn nnaaattcca ggtgtagcgn ngaaatgcgt agagatctgg     660
aggaataccg gtggcgaagg cggccccctg gacaaaagac tgacgctcnc angtgcgaaa     720
gcgtgggagc aaacaggatt agataccctn nnnnnnnnca cgcnnannnt gatgcnnntt     780
nnnnnggctg nngtcnntga nanacgnnnc ncgnnnnnct agcnactnan tcaancgacn     840
gcnagnncag tncngncggc naggtnaant naaatg                               876
```

<210> SEQ ID NO 44
<211> LENGTH: 887
<212> TYPE: DNA
<213> ORGANISM: Artificial Sequence
<220> FEATURE:
<223> OTHER INFORMATION: Gam1-1-16-27F_G09.ab1
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (600)..(605)
<223> OTHER INFORMATION: n is a, c, g, or t
<220> FEATURE:
<221> NAME/KEY: misc_feature
<222> LOCATION: (626)..(627)
<223> OTHER INFORMATION: n is a, c, g, or t
<220> FEATURE:
<221> NAME/KEY: misc_feature
<222> LOCATION: (629)..(629)
<223> OTHER INFORMATION: n is a, c, g, or t
<220> FEATURE:
<221> NAME/KEY: misc_feature
<222> LOCATION: (631)..(633)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (686)..(686)
<223> OTHER INFORMATION: n is a, c, g, or t
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:

<221> NAME/KEY: misc_feature
<222> LOCATION: (715)..(715)
<223> OTHER INFORMATION: n is a, c, g, or t
<220> FEATURE:
<221> NAME/KEY: misc_feature
<222> LOCATION: (786)..(788)
<223> OTHER INFORMATION: n is a, c, g, or t
<220> FEATURE:
<221> NAME/KEY: misc_feature
<222> LOCATION: (825)..(828)
<223> OTHER INFORMATION: n is a, c, g, or t
<220> FEATURE:
<221> NAME/KEY: misc_feature
<222> LOCATION: (834)..(836)
<223> OTHER INFORMATION: n is a, c, g, or t
<220> FEATURE:
<221> NAME/KEY: misc_feature
<222> LOCATION: (841)..(841)
<223> OTHER INFORMATION: n is a, c, g, or t
<220> FEATURE:
<221> NAME/KEY: misc_feature
<222> LOCATION: (865)..(865)
<223> OTHER INFORMATION: n is a, c, g, or t
<220> FEATURE:
<221> NAME/KEY: misc_feature
<222> LOCATION: (873)..(873)
<223> OTHER INFORMATION: n is a, c, g, or t
<220> FEATURE:
<221> NAME/KEY: misc_feature
<222> LOCATION: (878)..(878)
<223> OTHER INFORMATION: n is a, c, g, or t
<220> FEATURE:
<221> NAME/KEY: misc_feature
<222> LOCATION: (884)..(884)
<223> OTHER INFORMATION: n is a, c, g, or t

<400> SEQUENCE: 44

| | | | | | |
|---|---|---|---|---|---|
| taccntgcaa | gtcgaacggt | agcacagagg | agcttgctcc | ttgggtgacg | agtggcggac | 60 |
| gggtgagtaa | tgtctgggaa | actgcccgat | ggaggggat | aactactgga | aacggtagct | 120 |
| aataccgcat | aacgtcgcaa | gaccaaagag | ggggaccttc | gggcctcttg | ccatcggatg | 180 |
| tgcccagatg | ggattagcta | gtaggtgggg | taacggctca | cctaggcgac | gatccctagc | 240 |
| tggtctgaga | ggatgaccag | ccacactgga | actgagacac | ggtccagact | cctacgggag | 300 |
| gcagcagtgg | ggaatattgc | acaatgggcg | caagcctgat | gcagccatgc | cgcgtgtatg | 360 |
| aagaaggcct | tcgggttgta | aagtactttc | agcgaggagg | aaggtgttgt | ggttaataac | 420 |
| cacagcaatt | gacgttactc | gcagaagaag | caccggctaa | ctccgtgcca | gcagccgcgg | 480 |
| taatacggag | ggtgcaagcg | ttaatcggaa | ttactgggcg | taaagcgcac | gcaggcggtc | 540 |
| tgtcaagtcg | gatgtgaaat | ccccgggctc | aacctgggaa | ctgcatccga | aactggcagn | 600 |
| nnnnattct | ttgtagaggg | gggtannant | nnaggtgta | gcggtgaaat | gcgtagagat | 660 |
| ctggaggaat | accggtggcg | aagngnggcc | ccntgnggac | aaagactgac | gctcngtgcg | 720 |
| aaagcgtggg | gagcaaacag | gattagatac | cctgggtagt | ccacgccgta | aacgatgtcg | 780 |
| acttgnnngt | tgtgcccttg | aggcgtggct | tccggagcta | acgcnnnntc | gacnnggggg | 840 |
| ngtacggccg | caggtaaact | caaangaatt | gangggncc | gccncaa | | 887 |

<210> SEQ ID NO 45
<211> LENGTH: 901
<212> TYPE: DNA
<213> ORGANISM: Artificial Sequence
<220> FEATURE:
<223> OTHER INFORMATION: Gam1-1-17-27F_G10.ab1
<220> FEATURE:
<221> NAME/KEY: misc_feature
<222> LOCATION: (4)..(5)
<223> OTHER INFORMATION: n is a, c, g, or t -continued

```
<220> FEATURE:
<221> NAME/KEY: misc_feature
<222> LOCATION: (634)..(634)
<223> OTHER INFORMATION: n is a, c, g, or t
<220> FEATURE:
<221> NAME/KEY: misc_feature
<222> LOCATION: (650)..(650)
<223> OTHER INFORMATION: n is a, c, g, or t
<220> FEATURE:
<221> NAME/KEY: misc_feature
<222> LOCATION: (665)..(665)
<223> OTHER INFORMATION: n is a, c, g, or t
<220> FEATURE:
<221> NAME/KEY: misc_feature
<222> LOCATION: (673)..(673)
<223> OTHER INFORMATION: n is a, c, g, or t
<220> FEATURE:
<221> NAME/KEY: misc_feature
<222> LOCATION: (713)..(713)
<223> OTHER INFORMATION: n is a, c, g, or t
<220> FEATURE:
<221> NAME/KEY: misc_feature
<222> LOCATION: (745)..(745)
<223> OTHER INFORMATION: n is a, c, g, or t
<220> FEATURE:
<221> NAME/KEY: misc_feature
<222> LOCATION: (749)..(749)
<223> OTHER INFORMATION: n is a, c, g, or t
<220> FEATURE:
<221> NAME/KEY: misc_feature
<222> LOCATION: (751)..(751)
<223> OTHER INFORMATION: n is a, c, g, or t
<220> FEATURE:
<221> NAME/KEY: misc_feature
<222> LOCATION: (753)..(753)
<223> OTHER INFORMATION: n is a, c, g, or t
<220> FEATURE:
<221> NAME/KEY: misc_feature
<222> LOCATION: (755)..(757)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (770)..(770)
<223> OTHER INFORMATION: n is a, c, g, or t
<220> FEATURE:
<221> NAME/KEY: misc_feature
<222> LOCATION: (790)..(790)
<223> OTHER INFORMATION: n is a, c, g, or t
<220> FEATURE:
<221> NAME/KEY: misc_feature
<222> LOCATION: (808)..(808)
<223> OTHER INFORMATION: n is a, c, g, or t
<220> FEATURE:
<221> NAME/KEY: misc_feature
<222> LOCATION: (815)..(817)
<223> OTHER INFORMATION: n is a, c, g, or t
<220> FEATURE:
<221> NAME/KEY: misc_feature
<222> LOCATION: (820)..(821)
<223> OTHER INFORMATION: n is a, c, g, or t
<220> FEATURE:
<221> NAME/KEY: misc_feature
<222> LOCATION: (823)..(824)
<223> OTHER INFORMATION: n is a, c, g, or t
<220> FEATURE:
<221> NAME/KEY: misc_feature
<222> LOCATION: (831)..(834)
<223> OTHER INFORMATION: n is a, c, g, or t
<220> FEATURE:
<221> NAME/KEY: misc_feature
<222> LOCATION: (843)..(844)
<223> OTHER INFORMATION: n is a, c, g, or t
<220> FEATURE:
<221> NAME/KEY: misc_feature
<222> LOCATION: (846)..(846)
```

```
<223> OTHER INFORMATION: n is a, c, g, or t
<220> FEATURE:
<221> NAME/KEY: misc_feature
<222> LOCATION: (849)..(852)
<223> OTHER INFORMATION: n is a, c, g, or t
<220> FEATURE:
<221> NAME/KEY: misc_feature
<222> LOCATION: (857)..(861)
<223> OTHER INFORMATION: n is a, c, g, or t
<220> FEATURE:
<221> NAME/KEY: misc_feature
<222> LOCATION: (871)..(871)
<223> OTHER INFORMATION: n is a, c, g, or t
<220> FEATURE:
<221> NAME/KEY: misc_feature
<222> LOCATION: (881)..(881)
<223> OTHER INFORMATION: n is a, c, g, or t
<220> FEATURE:
<221> NAME/KEY: misc_feature
<222> LOCATION: (890)..(890)
<223> OTHER INFORMATION: n is a, c, g, or t
<220> FEATURE:
<221> NAME/KEY: misc_feature
<222> LOCATION: (892)..(892)
<223> OTHER INFORMATION: n is a, c, g, or t
<220> FEATURE:
<221> NAME/KEY: misc_feature
<222> LOCATION: (894)..(894)
<223> OTHER INFORMATION: n is a, c, g, or t
<220> FEATURE:
<221> NAME/KEY: misc_feature
<222> LOCATION: (896)..(896)
<223> OTHER INFORMATION: n is a, c, g, or t

<400> SEQUENCE: 45
tacnntgcaa gtcgagcggc agcgggaaag tagcttgcta cttttgccgg cgagcggcgg      60
acgggtgagt aatgcctggg gatctgccca gtcgagggg ataactactg gaaacggtag     120
ctaataccgc atacgcccta cggggaaag caggggacct tcgggccttg cgcgattgga     180
tgaacccagg tgggattagc tagttggtga ggtaacggct caccaaggcg acgatccta     240 gctggtctga gaggatgatc agccacactg gaactgagac acggtccaga ctcctacggg     300
aggcagcagt ggggaatatt gcacaatggg ggaaaccctg atgcagccat gccgcgtgtg     360
tgaagaaggc cttcgggttg taaagcactt tcagcgagga ggaaggtca gtagctaata     420 tctgctggct gtgacgttac tcgcagaaga agcaccggct aactccgtgc cagcagccgc     480
ggtaatacgg agggtgcaag cgttaatcgg aattactggg cgtaaagcgc acgcaggcgg     540
ttggataagt tagatgtgaa agccccgggc tcaacctggg aattgcattt aaaactgtcc     600
agctagagtc ttgtagaggg gggtagaatt ccanggtgta gcggtgaaan gcgtagagat     660
ctggnggaat acnggtggcg aaggcggccc cctggacaaa gactgacgct cantgcgaaa     720
gcgtggggag caaacaggat aaatncccng ngntnnncnc cccgtaaacn atgtcgattt     780
ggaaggctgn ggtccttgaa aacgtggntt ccggnnnctn nanncgttaa nnnnacaccc     840
ccnngnggnn nnggagnnnn ncgggccgca nggttaaaac ncaaatgaan tngnangggg     900
g                                                                    901

<210> SEQ ID NO 46
<211> LENGTH: 884
<212> TYPE: DNA
<213> ORGANISM: Artificial Sequence
<220> FEATURE:
<223> OTHER INFORMATION: Gam1-1-18-27F_G11.ab1
<220> FEATURE:
<221> NAME/KEY: misc_feature
<222> LOCATION: (2)..(2)
<223> OTHER INFORMATION: n is a, c, g, or t
```

```
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(8)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (624)..(625)
<223> OTHER INFORMATION: n is a, c, g, or t
<220> FEATURE:
<221> NAME/KEY: misc_feature
<222> LOCATION: (673)..(675)
<223> OTHER INFORMATION: n is a, c, g, or t
<220> FEATURE:
<221> NAME/KEY: misc_feature
<222> LOCATION: (755)..(755)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
<220> FEATURE:
<221> NAME/KEY: misc_feature
<222> LOCATION: (794)..(794)
<223> OTHER INFORMATION: n is a, c, g, or t
<220> FEATURE:
<221> NAME/KEY: misc_feature
<222> LOCATION: (801)..(804)
<223> OTHER INFORMATION: n is a, c, g, or t
<220> FEATURE:
<221> NAME/KEY: misc_feature
<222> LOCATION: (807)..(811)
<223> OTHER INFORMATION: n is a, c, g, or t
<220> FEATURE:
<221> NAME/KEY: misc_feature
<222> LOCATION: (814)..(815)
<223> OTHER INFORMATION: n is a, c, g, or t
<220> FEATURE:
<221> NAME/KEY: misc_feature
<222> LOCATION: (821)..(823)
<223> OTHER INFORMATION: n is a, c, g, or t
<220> FEATURE:
<221> NAME/KEY: misc_feature
<222> LOCATION: (825)..(827)
<223> OTHER INFORMATION: n is a, c, g, or t
<220> FEATURE:
<221> NAME/KEY: misc_feature
<222> LOCATION: (831)..(831)
<223> OTHER INFORMATION: n is a, c, g, or t
<220> FEATURE:
<221> NAME/KEY: misc_feature
<222> LOCATION: (843)..(845)
<223> OTHER INFORMATION: n is a, c, g, or t
<220> FEATURE:
<221> NAME/KEY: misc_feature
<222> LOCATION: (848)..(849)
<223> OTHER INFORMATION: n is a, c, g, or t
<220> FEATURE:
<221> NAME/KEY: misc_feature
<222> LOCATION: (862)..(862)
<223> OTHER INFORMATION: n is a, c, g, or t
<220> FEATURE:
<221> NAME/KEY: misc_feature
<222> LOCATION: (866)..(867)
<223> OTHER INFORMATION: n is a, c, g, or t

<400> SEQUENCE: 46
cngncnnncn ntgcagtcga gcggtaacac agggagcttg ctcctgggtg acgagcggcg      60
gacgggtgag taatgtctgg gaaactgcct gatggagggg gataactact ggaaacggta    120
```

```
gctaataccg cataacgtcg caagaccaaa gagggggacc ttcgggcctc ttgccatcag      180
atgtgcccag atgggattag ctagtaggtg gggtaatggc tcacctaggc gacgatccct      240
agctggtctg agaggatgac cagccacact ggaactgaga cacggtccag actcctacgg      300
gaggcagcag tggggaatat tgcacaatgg gcgcaagcct gatgcagcca tgccgcgtgt      360
atgaagaagg ccttcgggtt gtaaagtact ttcagcgggg aggaaggcga taaggttaat      420
aaccttgtcg attgacgtta cccgcagaag aagcaccggc taactccgtg ccagcagccg      480
cggtaatacg gagggtgcaa gcgttaatcg gaattactgg gcgtaaagcg cacgcaggcg      540
gtctgtcaag tcggatgtga aatccccggg ctcaacctgg gaactgcatt cgaaactggc      600
aggctagagt cttgtagggg gggnnagaat tccaggtgta gcggtgaaat gcgtagagat      660
ctggaggaat acnnntggcg aaggcggccc cctggacaaa gactgacgct cagggtgcga      720
aagcgtgggg agcaaacagg attagatacc ctggnagtcc acgccgtaaa cgatgtcgac      780
ttggaaggtt gngngccctt nnnnggnnnn ngcnntccgg nnncnnnaac nccgttaagt      840
ccnnncgnnc ctgggggaga tnccgnnccg ccaagggtta aaac                      884

<210> SEQ ID NO 47
<211> LENGTH: 806
<212> TYPE: DNA
<213> ORGANISM: Artificial Sequence
<220> FEATURE:
<223> OTHER INFORMATION: Gam1-1-19-27F_G02.ab1
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (673)..(673)
<223> OTHER INFORMATION: n is a, c, g, or t
<220> FEATURE:
<221> NAME/KEY: misc_feature
<222> LOCATION: (702)..(704)
<223> OTHER INFORMATION: n is a, c, g, or t
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (727)..(727)
<223> OTHER INFORMATION: n is a, c, g, or t
<220> FEATURE:
<221> NAME/KEY: misc_feature
<222> LOCATION: (758)..(758)
<223> OTHER INFORMATION: n is a, c, g, or t
<220> FEATURE:
<221> NAME/KEY: misc_feature
<222> LOCATION: (773)..(775)
<223> OTHER INFORMATION: n is a, c, g, or t
<220> FEATURE:
<221> NAME/KEY: misc_feature
<222> LOCATION: (788)..(788)
<223> OTHER INFORMATION: n is a, c, g, or t
<220> FEATURE:
<221> NAME/KEY: misc_feature
<222> LOCATION: (790)..(790)
<223> OTHER INFORMATION: n is a, c, g, or t
<220> FEATURE:
<221> NAME/KEY: misc_feature
<222> LOCATION: (801)..(801)
<223> OTHER INFORMATION: n is a, c, g, or t

<400> SEQUENCE: 47
```

```
tgcnagtcga gcggtagcac agggagcttg ctcctgggtg acgagcggcg gacgggtgag      60
taatgtctgg gaaactgcct gatggagggg gataactact ggaaacggta gctaataccg     120
cataacgtcg caagaccaaa gagggggacc ttcgggcctc ttgccatcag atgtgcccag     180
atgggattag ctagtaggtg gggtaatggc tcacctaggc gacgatccct agctggtctg     240
agaggatgac cagccacact ggaactgaga cacggtccag actcctacgg gaggcagcag     300
tggggaatat tgcacaatgg gcgcaagcct gatgcagcca tgccgcgtgt atgaagaagg     360
ccttcgggtt gtaaagtact ttcagcgggg aggaaggtgt tgaggttaat aacctcagca     420
attgacgtta cccgcagaag aagcaccggc taactccgtg ccagcagccg cggtaatacg     480
gagggtgcaa gcgttaatcg gaattactgg gcgtaaagcg cacgcaggcg gtctgtcaag     540
tcggatgtga atccccggg ctcaacctgg gaactgcatc cgaaactggc aggctagagt      600
cttgtagagg ggggtagaat tccaggtgta gcggtgaaat gcgtagagat ctggaggaat     660
accggtggcg aangcggccc cctggacaaa gactgacgct cnnngcnaaa agcgtgggga     720
gcnaacngga ttagataccc tggtagtcca cgccgtancg atgtcgactt ggnnntgtgc     780
ccttgagngn ggcttccgga nctaac                                          806
```

<210> SEQ ID NO 48
<211> LENGTH: 847
<212> TYPE: DNA
<213> ORGANISM: Artificial Sequence
<220> FEATURE:
<223> OTHER INFORMATION: Gam1-1-20-27F_H01.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (703)..(705)
<223> OTHER INFORMATION: n is a, c, g, or t
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (748)..(748)
<223> OTHER INFORMATION: n is a, c, g, or t

<400> SEQUENCE: 48

```
tacnntgcag tcgagcggta gcacagggag cttgctcctg ggtgacgagc ggcggacggg      60
tgagtaatgt ctgggaaact gcctgatgga gggggataac tactgaaaac ggtagctaat     120
accgcataac gtcgcaagac caaagagggg gaccttcggg cctcttgcca tcagatgtgc     180
ccagatggga ttagctagta ggtgggggtaa tggctcacct aggcgacgat ccctagctgg     240
tctgagagga tgaccagcca cactggaact gagacacggt ccagactcct acgggaggca     300
gcagtgggga atattgcaca atgggcgcaa gcctgatgca gccatgccgc gtgtatgaag     360
aaggccttcg ggttgtaaag tactttcagc ggggaggaag tgttgaggt taataacctc     420 agcaattgac gttacccgca gaagaagcac cggctaactc cgtgccagca gccgcggtaa     480 tacgagggt gcaagcgtta atcggaatta ctgggcgtaa agcgcacgca ggcggtctgt      540
caagtcggat gtgaaatccc cgggctcaac ctgggaactg cattcgaaac tggcaggcta     600
```

```
gagtcttgta gagggggtg gaattcngg tgtagcggtg aaatgcgtag agatctggag      660
gaataccggt ggcgaaggcg gccccctgga caaagactga cgnnncngtg cgaaagcgtg      720
gggagcaaac aggattagat accctggnag tccacgccgt aaacgatgtc gacttggagg      780
ttgtgccctt gaggcgtggc ttccgggagc taacgcgtta agtcgaccgg cctgggggga      840
gtacggg                                                                847
```

```
<210> SEQ ID NO 49
<211> LENGTH: 851
<212> TYPE: DNA
<213> ORGANISM: Artificial Sequence
<220> FEATURE:
<223> OTHER INFORMATION: Gam1-1-21-27F_H02.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (602)..(604)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (710)..(712)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (785)..(785)
<223> OTHER INFORMATION: n is a, c, g, or t
<220> FEATURE:
<221> NAME/KEY: misc_feature
<222> LOCATION: (800)..(800)
<223> OTHER INFORMATION: n is a, c, g, or t
<220> FEATURE:
<221> NAME/KEY: misc_feature
<222> LOCATION: (815)..(815)
<223> OTHER INFORMATION: n is a, c, g, or t
<220> FEATURE:
<221> NAME/KEY: misc_feature
<222> LOCATION: (829)..(829)
<223> OTHER INFORMATION: n is a, c, g, or t
<220> FEATURE:
<221> NAME/KEY: misc_feature
<222> LOCATION: (838)..(839)
<223> OTHER INFORMATION: n is a, c, g, or t
<220> FEATURE:
<221> NAME/KEY: misc_feature
<222> LOCATION: (844)..(844)
<223> OTHER INFORMATION: n is a, c, g, or t
<220> FEATURE:
<221> NAME/KEY: misc_feature
<222> LOCATION: (846)..(846)
<223> OTHER INFORMATION: n is a, c, g, or t

<400> SEQUENCE: 49
tacnntgcag tcgagcggta acacagggag cttgctcctg ggtgacgagc ggcggacggg       60
tgagtaatgt ctgggaaact gcctgatgga gggggataac tactggaaac ggtagctaat      120
accgcataac gtcgcaagac caaagagggg gaccttcggg cctcttgcca tcagatgtgc      180
ccagatggga ttagctagta ggtggggtaa cggctcacct aggcgacgat ccctagctgg      240
```

-continued

```
tctgagagga tgaccagcca cactggaact gagacacggt ccagactcct acgggaggca      300
gcagtgggga atattgcaca atgggcgcaa gcctgatgca gccatgccgc gtgtatgaag      360
aaggccttcg ggttgtaaag tactttcagc ggggaggaag gtgttgaggt taataacctc      420
agcaattgac gttacccgca gaagaagcac cggctaactc cgtgccagca gccgcggtaa      480
tacggagggt gcaagcgtta atcggaatta ctgggcgtaa agcgcacgca ggcggtctgt      540
caagtcggat gtgaaatccc cgggctcaac ctgggaactg cattcgaaac tggcaggcta      600
annntcttng aagaggggggg gtaaaatttc cgggtgtagc ggtgaaatgc gtagagatct      660
ggaggaatac cggtggcgaa ngcggccccc tggacaaaga ctgacgctcn nngngcgaaa      720
gcgtggggag caaacaggat tagatacccct ggtagtccac gccgtaacga tgtcgacttg      780
gagtntgccc ttgagcgtgn ttccggagct aacgngttaa gtcgaccgnc ctggggganna      840 cggncngcaa g                                                          851
```

```
<210> SEQ ID NO 50
<211> LENGTH: 880
<212> TYPE: DNA
<213> ORGANISM: Artificial Sequence
<220> FEATURE:
<223> OTHER INFORMATION: Gam1-1-22-27F_H03.ab1
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (594)..(594)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (601)..(601)
<223> OTHER INFORMATION: n is a, c, g, or t
<220> FEATURE:
<221> NAME/KEY: misc_feature
<222> LOCATION: (604)..(604)
<223> OTHER INFORMATION: n is a, c, g, or t
<220> FEATURE:
<221> NAME/KEY: misc_feature
<222> LOCATION: (651)..(654)
<223> OTHER INFORMATION: n is a, c, g, or t
<220> FEATURE:
<221> NAME/KEY: misc_feature
<222> LOCATION: (716)..(716)
<223> OTHER INFORMATION: n is a, c, g, or t
<220> FEATURE:
<221> NAME/KEY: misc_feature
<222> LOCATION: (814)..(814)
<223> OTHER INFORMATION: n is a, c, g, or t
<220> FEATURE:
<221> NAME/KEY: misc_feature
<222> LOCATION: (853)..(853)
<223> OTHER INFORMATION: n is a, c, g, or t
<220> FEATURE:
<221> NAME/KEY: misc_feature
<222> LOCATION: (867)..(867)
<223> OTHER INFORMATION: n is a, c, g, or t

<400> SEQUENCE: 50
gctacncatg caagtcgaac ggtagcacag aggagcttgc tccttgggtg acgagtggcg       60
gacgggtgag taatgtctgg gaaactgccc gatggagggg gataactact ggaaacggta      120
gctaataccg cataacgtcg caagaccaaa gagggggacc ttcgggcctc ttgccatcgg      180
```

```
atgtgcccag atgggattag ctagtaggtg gggtaacggc tcacctaggc gacgatccct    240
agctggtctg agaggatgac cagccacact ggaactgaga cacggtccag actcctacgg    300
gaggcagcag tgggaatat tgcacaatgg gcgcaagcct gatgcagcca tgccgcgtgt     360
atgaagaagg ccttcgggtt gtaaagtact ttcagcgggg aggaaggcga taaggttaat    420
aaccttgtcg attgacgtta cccgcagaag aagcaccggc taactccgtg ccagcagccg    480
cggtaatacg gagggtgcaa gcgttaatcg gaattactgg gcgtaaagcg cacgcaggcg    540
gtctgtcaag tcggatgtga atccccggg ctcaacctgg gaactgcatt cganagnggc     600
nggntaagag ctcttgtaga gggggtaga attccaggtg tagcgctgaa nnnncgtaga     660
gatctggagg aataccggtg gcgaaggcgg cccctggac aaagactgac gctcangtgc     720
gaaagcgtgg ggagcaatca ggattagata ccctggtagt ccacgccgta acgatgtcg     780 acttggagtt gtgcccttga ggcgtggctt ccgnagctaa cgcgttaagt cgaccgcctg    840
ggggagtacg gcngcaaggt taaaacntca aatgaatttg                          880
```

<210> SEQ ID NO 51
<211> LENGTH: 921
<212> TYPE: DNA
<213> ORGANISM: Artificial Sequence
<220> FEATURE:
<223> OTHER INFORMATION: Gam1-1-2-27F_C02.ab1
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (589)..(596)
<223> OTHER INFORMATION: n is a, c, g, or t
<220> FEATURE:
<221> NAME/KEY: misc_feature
<222> LOCATION: (610)..(610)
<223> OTHER INFORMATION: n is a, c, g, or t
<220> FEATURE:
<221> NAME/KEY: misc_feature
<222> LOCATION: (616)..(619)
<223> OTHER INFORMATION: n is a, c, g, or t
<220> FEATURE:
<221> NAME/KEY: misc_feature
<222> LOCATION: (728)..(729)
<223> OTHER INFORMATION: n is a, c, g, or t
<220> FEATURE:
<221> NAME/KEY: misc_feature
<222> LOCATION: (804)..(805)
<223> OTHER INFORMATION: n is a, c, g, or t
<220> FEATURE:
<221> NAME/KEY: misc_feature
<222> LOCATION: (812)..(812)
<223> OTHER INFORMATION: n is a, c, g, or t
<220> FEATURE:
<221> NAME/KEY: misc_feature
<222> LOCATION: (823)..(825)
<223> OTHER INFORMATION: n is a, c, g, or t
<220> FEATURE:
<221> NAME/KEY: misc_feature
<222> LOCATION: (829)..(829)
<223> OTHER INFORMATION: n is a, c, g, or t
<220> FEATURE:
<221> NAME/KEY: misc_feature
<222> LOCATION: (834)..(834)
<223> OTHER INFORMATION: n is a, c, g, or t
<220> FEATURE:
<221> NAME/KEY: misc_feature
<222> LOCATION: (843)..(847)
<223> OTHER INFORMATION: n is a, c, g, or t
<220> FEATURE:
<221> NAME/KEY: misc_feature
<222> LOCATION: (851)..(851)
<223> OTHER INFORMATION: n is a, c, g, or t
<220> FEATURE:
<221> NAME/KEY: misc_feature
<222> LOCATION: (859)..(859)
<223> OTHER INFORMATION: n is a, c, g, or t
<220> FEATURE:
<221> NAME/KEY: misc_feature
<222> LOCATION: (863)..(864)
<223> OTHER INFORMATION: n is a, c, g, or t
<220> FEATURE:
<221> NAME/KEY: misc_feature
<222> LOCATION: (867)..(867)
<223> OTHER INFORMATION: n is a, c, g, or t
<220> FEATURE:
<221> NAME/KEY: misc_feature
<222> LOCATION: (871)..(871)
<223> OTHER INFORMATION: n is a, c, g, or t
<220> FEATURE:
<221> NAME/KEY: misc_feature
<222> LOCATION: (886)..(886)
<223> OTHER INFORMATION: n is a, c, g, or t
<220> FEATURE:
<221> NAME/KEY: misc_feature
<222> LOCATION: (892)..(892)
<223> OTHER INFORMATION: n is a, c, g, or t
<220> FEATURE:
<221> NAME/KEY: misc_feature
<222> LOCATION: (894)..(894)
<223> OTHER INFORMATION: n is a, c, g, or t
<220> FEATURE:
<221> NAME/KEY: misc_feature
<222> LOCATION: (901)..(905)
<223> OTHER INFORMATION: n is a, c, g, or t
<220> FEATURE:
<221> NAME/KEY: misc_feature
<222> LOCATION: (907)..(908)
<223> OTHER INFORMATION: n is a, c, g, or t
<220> FEATURE:
<221> NAME/KEY: misc_feature
<222> LOCATION: (912)..(914)
<223> OTHER INFORMATION: n is a, c, g, or t
<220> FEATURE:
<221> NAME/KEY: misc_feature
<222> LOCATION: (918)..(918)
<223> OTHER INFORMATION: n is a, c, g, or t

<400> SEQUENCE: 51
ctncnntgca agtcgagcgg cagcgggaaa gtagcttgct acttttgccg gcgagcggcg      60
gacgggtgag taatgtctgg gaaactgcct gatggagggg gataactact ggaaacggta     120
gctaataccg cataacgtcg caagaccaaa gaggggacc ttcgggcctc ttgccatcag     180
atgtgcccag atgggattag ctagtaggtg gggtaacggc tcacctaggc gacgatccct     240
agctggtctg agaggatgac cagccacact ggaactgaga cacggtccag actcctacgg     300
gaggcagcag tggggaatat tgcacaatgg gcgcaagcct gatgcagcca tgccgcgtgt     360
atgaagaagg ccttcgggtt gtaaagtact ttcagcgggg aggaaggtgt tgaggttaat     420
aacctcagca attgacgtta cccgcagaag aagcaccggc taactccgtg ccagcagccg     480
cggtaatacg gagggtgcaa gcgttaatcg gaattactgg gcgtaaagcg cacgcaggcg     540
gtctgtcaag tcggatgtga atccccgggg ctcaacctgg gaactgctnn nnnnnngtgg     600
caggctagan tcttgnnnng gggggtagaa ttccaggtgt agcggtgaaa tgcgtagaga     660
tctggaggaa taccggtggg aaaggcggcc ccctggacaa agactgacgc tcacgtgcga     720
aagcgtgnng agcaaacagg attagatacc ctggtagtcc acgccgtaaa cgatgtcgac     780
ttggaaggtt gtgcccttga ggcnnggctt cngcagctaa ctnnntcant tcanatcgac     840

-continued

```
tgnnnnnggt nagtacggnc gcnnagntta naaactcaaa ttgaantgga cngngggccc    900
nnnnnanncg gnnnggancc a                                              921
```

```
<210> SEQ ID NO 52
<211> LENGTH: 900
<212> TYPE: DNA
<213> ORGANISM: Artificial Sequence
<220> FEATURE:
<223> OTHER INFORMATION: Gam1-1-24-27F_H05.ab1
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (746)..(746)
<223> OTHER INFORMATION: n is a, c, g, or t
<220> FEATURE:
<221> NAME/KEY: misc_feature
<222> LOCATION: (754)..(758)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (826)..(826)
<223> OTHER INFORMATION: n is a, c, g, or t
<220> FEATURE:
<221> NAME/KEY: misc_feature
<222> LOCATION: (838)..(838)
<223> OTHER INFORMATION: n is a, c, g, or t
<220> FEATURE:
<221> NAME/KEY: misc_feature
<222> LOCATION: (857)..(857)
<223> OTHER INFORMATION: n is a, c, g, or t
<220> FEATURE:
<221> NAME/KEY: misc_feature
<222> LOCATION: (880)..(880)
<223> OTHER INFORMATION: n is a, c, g, or t

<400> SEQUENCE: 52
gctanncntg cagtcgagcg gcagcgggaa agtagcttgc tacttttgcc ggcgagcggc    60
ggacgggtga gtaatgcctg gggatctgcc cagtcgaggg ggataactac tggaaacggt   120
agctaatacc gcatgcgccc tacggggaa agcagggac cttcgggcct tgcgcgattg    180
gatgaaccca ggtgggatta gctagttggt gaggtaacgg ctcaccaagg cgacgatccc   240
tagctggtct gagaggatga tcagccacac tggaactgag acacggtcca gactcctacg   300
ggaggcagca gtgggaata ttgcacaatg ggggaaaccc tgatgcagcc atgccgcgtg    360
tgtgaagaag gccttcgggt tgtaaagcac tttcagcgag gaggaaaggt cagtagctaa    420
tatctgctgg ctgtgacgtt actcgcagaa gaagcaccgg ctaactccgt gccagcagcc    480
gcggtaatac ggagggtgca agcgttaatc ggaattactg ggcgtaaagc gcacgcaggc    540
ggttggataa gttagatgtg aaagccccgg gctcaacctg ggaattgcat ttaaaactgt    600
ccagctagag tcttgtagag ggggtgaaa ttccagggtg tagcggtgaa atgcgtagag    660
atctggagga ataccggtgg cgaaggcggc cccctggaca aagactgacg ctcngtgcga    720
aagcgtgggg agcaaacagg attagnatac cctnnnnntc caccnccgta aaccgatgtc    780
```

-continued

```
gatttgggag gctgtgtcct tgagacgtgg cttccggagc taacgncgtt aatcgacngc      840 ctgggggag tacggcngca agggttaaaa cttcaaatgn atttgaacgg ggggcccgcc       900
```

<210> SEQ ID NO 53
<211> LENGTH: 883
<212> TYPE: DNA
<213> ORGANISM: Artificial Sequence
<220> FEATURE:
<223> OTHER INFORMATION: Gam1-1-25-27F_H06.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (710)..(710)
<223> OTHER INFORMATION: n is a, c, g, or t
<220> FEATURE:
<221> NAME/KEY: misc_feature
<222> LOCATION: (744)..(753)
<223> OTHER INFORMATION: n is a, c, g, or t
<220> FEATURE:
<221> NAME/KEY: misc_feature
<222> LOCATION: (755)..(759)
<223> OTHER INFORMATION: n is a, c, g, or t
<220> FEATURE:
<221> NAME/KEY: misc_feature
<222> LOCATION: (833)..(833)
<223> OTHER INFORMATION: n is a, c, g, or t

<400> SEQUENCE: 53

```
tacnntgcag tcgagcggca gcgggaaagt agcttgctac ttttgccggc gagcggcgga       60
cgggtgagta atgcctgggg atctgcccag tcgaggggga taactactgg aaacggtagc      120
taataccgca tgcgccctac gggggaaagc aggggacctt cgggccttgc gcgattggat      180
gaacccaggt gggattagct agttggtgag gtaacggctc accaaggcga cgatccctag      240
ctggtctgag aggatgatca gccacactgg aactgagaca cggtccagac tcctacggga      300
ggcagcagtg gggaatattg cacaatgggg gaaaccctga tgcagccatg ccgcgtgtgt      360
gaagaaggcc ttcgggttgt aaagcacttt cagcgaggag gaaaggttgg tagctaatat      420
ctgccagctg tgacgttact cgcagaagaa gcaccggcta actccgtgcc agcagccgcg      480
gtaatacgga gggtgcaagc gttaatcgga attactgggc gtaaagcgca cgcaggcggt      540
tggataagtt agatgtgaaa gccccgggct caacctggga attgcattta aaactgtcca      600
gctagagtct tgtagagggg ggtagaattc caggtgtagc ggtgaaatgc gtagagatct      660
ggaggaatac cggtggcgaa ngcgcccccc tggacaaaga ctgacgctcn gtgcgaaagc      720
gtggggagca aacaggatta gaannnnnnn nnngnnnnnc gccgtaaacg atgtcgattt      780
ggaggctgtg tccttgagac gtggcttccg gagctaacgc gttaatcgac gcnggggag      840 tacggccgca gttaaactca aatgaaattg acggggccc gcc                        883
```

<210> SEQ ID NO 54
<211> LENGTH: 884
<212> TYPE: DNA
<213> ORGANISM: Artificial Sequence
<220> FEATURE:
<223> OTHER INFORMATION: Gam1-1-26-27F_H07.ab1
<220> FEATURE:
<221> NAME/KEY: misc_feature
<222> LOCATION: (4)..(5)

<223> OTHER INFORMATION: n is a, c, g, or t
<220> FEATURE:
<221> NAME/KEY: misc_feature
<222> LOCATION: (719)..(726)
<223> OTHER INFORMATION: n is a, c, g, or t
<220> FEATURE:
<221> NAME/KEY: misc_feature
<222> LOCATION: (728)..(740)
<223> OTHER INFORMATION: n is a, c, g, or t
<220> FEATURE:
<221> NAME/KEY: misc_feature
<222> LOCATION: (758)..(760)
<223> OTHER INFORMATION: n is a, c, g, or t
<220> FEATURE:
<221> NAME/KEY: misc_feature
<222> LOCATION: (773)..(773)
<223> OTHER INFORMATION: n is a, c, g, or t
<220> FEATURE:
<221> NAME/KEY: misc_feature
<222> LOCATION: (793)..(794)
<223> OTHER INFORMATION: n is a, c, g, or t
<220> FEATURE:
<221> NAME/KEY: misc_feature
<222> LOCATION: (824)..(824)
<223> OTHER INFORMATION: n is a, c, g, or t
<220> FEATURE:
<221> NAME/KEY: misc_feature
<222> LOCATION: (826)..(826)
<223> OTHER INFORMATION: n is a, c, g, or t
<220> FEATURE:
<221> NAME/KEY: misc_feature
<222> LOCATION: (829)..(830)
<223> OTHER INFORMATION: n is a, c, g, or t
<220> FEATURE:
<221> NAME/KEY: misc_feature
<222> LOCATION: (836)..(837)
<223> OTHER INFORMATION: n is a, c, g, or t
<220> FEATURE:
<221> NAME/KEY: misc_feature
<222> LOCATION: (852)..(852)
<223> OTHER INFORMATION: n is a, c, g, or t
<220> FEATURE:
<221> NAME/KEY: misc_feature
<222> LOCATION: (874)..(874)
<223> OTHER INFORMATION: n is a, c, g, or t
<220> FEATURE:
<221> NAME/KEY: misc_feature
<222> LOCATION: (879)..(880)
<223> OTHER INFORMATION: n is a, c, g, or t

<400> SEQUENCE: 54

```
tacnntgcag tcgagcggta acacagggag cttgctcctg ggtgacgagc ggcggacggg     60
tgagtaatgt ctgggaaact gcctgatgga gggggataac tactggaaac ggtagctaat    120
accgcataac gtcgcaaaac caaagagggg gaccttcggg cctcttgcca tcagatgtgc    180
ccagatggga ttagctagta ggtggggtaa tggctcacct aggcgacgat ccctagctgg    240
tctgagagga tgaccagcca cactggaact gagacacggt ccagactcct acggaggca    300 gcagtgggga atactgcaca atgggcgcaa gcctgatgca gccatgccgc gtgtatgaag    360
aaggccttcg ggttgtaaag tactttcagc ggggaggaag gtgttgaggt taataacctc    420
agcaattgac gttacccgca gaagaagcac cggctaactc cgtgccagca gccgcggtaa    480
tacggagggt gcaagcgtta atcggaatta ctgggcgtaa agcgcacgca ggcggtctgt    540
caagtcggat gtgaaatccc cgggctcaac ctggaactg cattcgaaac tggcaggcta    600
gagtcttgta gaggggggta gaattccagg tgtagcggtg aaatgcgtag agatctggag    660
gaataccggt ggcgaaggcg gcccctgga caaagactga cgctcagtgc gaaagcgtnn    720
nnnnnnannn nnnnnnnnnn cctggtagtc cacgccgnnn aaacgaggtc gancttggag    780
ttgtgcccct ganngtggct tccggagcta acgcgtagtc gacncnggnn gtacgnncaa    840
```
gtaaactcaa angaattgac ggggcccgca caancgggnn ggga                884

<210> SEQ ID NO 55
<211> LENGTH: 895
<212> TYPE: DNA
<213> ORGANISM: Artificial Sequence
<220> FEATURE:
<223> OTHER INFORMATION: Gam1-1-27-27F_H08.ab1
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (717)..(721)
<223> OTHER INFORMATION: n is a, c, g, or t
<220> FEATURE:
<221> NAME/KEY: misc_feature
<222> LOCATION: (749)..(749)
<223> OTHER INFORMATION: n is a, c, g, or t
<220> FEATURE:
<221> NAME/KEY: misc_feature
<222> LOCATION: (829)..(829)
<223> OTHER INFORMATION: n is a, c, g, or t
<220> FEATURE:
<221> NAME/KEY: misc_feature
<222> LOCATION: (833)..(833)
<223> OTHER INFORMATION: n is a, c, g, or t
<220> FEATURE:
<221> NAME/KEY: misc_feature
<222> LOCATION: (835)..(836)
<223> OTHER INFORMATION: n is a, c, g, or t
<220> FEATURE:
<221> NAME/KEY: misc_feature
<222> LOCATION: (838)..(838)
<223> OTHER INFORMATION: n is a, c, g, or t
<220> FEATURE:
<221> NAME/KEY: misc_feature
<222> LOCATION: (846)..(847)
<223> OTHER INFORMATION: n is a, c, g, or t
<220> FEATURE:
<221> NAME/KEY: misc_feature
<222> LOCATION: (858)..(859)
<223> OTHER INFORMATION: n is a, c, g, or t
<220> FEATURE:
<221> NAME/KEY: misc_feature
<222> LOCATION: (872)..(873)
<223> OTHER INFORMATION: n is a, c, g, or t
<220> FEATURE:
<221> NAME/KEY: misc_feature
<222> LOCATION: (883)..(884)
<223> OTHER INFORMATION: n is a, c, g, or t
<220> FEATURE:
<221> NAME/KEY: misc_feature
<222> LOCATION: (886)..(886)
<223> OTHER INFORMATION: n is a, c, g, or t
<220> FEATURE:
<221> NAME/KEY: misc_feature
<222> LOCATION: (890)..(890)
<223> OTHER INFORMATION: n is a, c, g, or t
<220> FEATURE:
<221> NAME/KEY: misc_feature
<222> LOCATION: (893)..(893)
<223> OTHER INFORMATION: n is a, c, g, or t

<400> SEQUENCE: 55
taacncntgc agtcgagcgg taacacaggg agcttgctcc tgggtgacga gcggcggacg    60

```
ggtgagtaat gtctgggaaa ctgcctgatg gaggggata  actactggaa acggtagcta    120
ataccgcata acgtcgcaag accaaagagg gggaccttcg ggcctcttgc catcagatgt    180
gcccagatgg gattagctag taggtggggt aacggctcac ctaggcgacg atccctagct    240
ggtctgagag gatgaccagc cacactggaa ctgagacacg gtccagactc ctacgggagg    300
cagcagtggg gaatattgca caatgggcgc aagcctgatg cagccatgcc gcgtgtatga    360
agaaggcctt cgggttgtaa agtactttca gcggggagga aggtgttgag gttaataacc    420
ttgtcaattg acgttacccg cagaagaagc accggctaac tccgtgccag cagccgcggt    480
aatacggagg gtgcaagcgt taatcggaat tactgggcgt aaagcgcacg caggcggtct    540
gtcaagtcgg atgtgaaatc cccgggctca acctgggaac tgcattcgaa actggcaggc    600
tagagtcttg tagaggggg  tagaattcca ggtgtagcgg tgaaatgcgt agagatctgg    660
aggaataccg gtggcgaagg cggcccctg  dacaaagact gacgctcngt gcgaaannnn    720
ngggagcaaa caggattaga taccctggna gtccacgccg taaacgatgt cgacttggag    780
gttgtgccct tgagcgtggc ttccggagct aacgcgttaa gtcgacgcng ggnanntncg    840
gccgcnnagg gttaaacnnc aatggaattg gnncgggggc cgnncncaan cgngg         895
```

<210> SEQ ID NO 56
<211> LENGTH: 882
<212> TYPE: DNA
<213> ORGANISM: Artificial Sequence
<220> FEATURE:
<223> OTHER INFORMATION: Gam1-1-28-27F_H09.ab1
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (699)..(703)
<223> OTHER INFORMATION: n is a, c, g, or t
<220> FEATURE:
<221> NAME/KEY: misc_feature
<222> LOCATION: (705)..(707)
<223> OTHER INFORMATION: n is a, c, g, or t
<220> FEATURE:
<221> NAME/KEY: misc_feature
<222> LOCATION: (710)..(710)
<223> OTHER INFORMATION: n is a, c, g, or t
<220> FEATURE:
<221> NAME/KEY: misc_feature
<222> LOCATION: (832)..(832)
<223> OTHER INFORMATION: n is a, c, g, or t
<220> FEATURE:
<221> NAME/KEY: misc_feature
<222> LOCATION: (839)..(839)
<223> OTHER INFORMATION: n is a, c, g, or t
<220> FEATURE:
<221> NAME/KEY: misc_feature
<222> LOCATION: (857)..(857)
<223> OTHER INFORMATION: n is a, c, g, or t
<220> FEATURE:
<221> NAME/KEY: misc_feature
<222> LOCATION: (866)..(867)
<223> OTHER INFORMATION: n is a, c, g, or t
<220> FEATURE:
<221> NAME/KEY: misc_feature
<222> LOCATION: (879)..(879)
<223> OTHER INFORMATION: n is a, c, g, or t

<400> SEQUENCE: 56

```
gntacncatg caagtcgagc ggtaacacag ggagcttgct cctgggtgac gagcggcgga     60
```

```
cgggtgagta atgtctggga aactgcctga tggaggggga taactactgg aaacggtagc    120
taataccgca taacgtcgca agaccaaaga gggggacctt cgggcctctt gccatcagat    180
gtgcccagat gggattagct agtaggtggg gtaatggctc acctaggcga cgatccctag    240
ctggtctgag aggatgacca gccacactgg aactgagaca cggtccagac tcctacggga    300
ggcagcagtg gggaatattg cacaatgggc gcaagcctga tgcagccatg ccgcgtgtat    360
gaagaaggcc ttcgggttgt aaagtacttt cagcggggag gaaggcgata aggttaataa    420
ccttgtcgat tgacgttacc cgcagaagaa gcaccggcta actccgtgcc agcagccgcg    480
gtaatacgga gggtgcaagc gttaatcgga attactgggc gtaaagcgca cgcaggcggt    540
ctgtcaagtc ggacgtgaaa tccccgggct caacctggga actgcattcg aaactggcag    600
gctagagtct tgtagagggg ggtagaatcc caggtgtagc ggtgaaatgc gtagagatct    660
ggaggaatac cggtggcgaa ggcggccccc tggacaaann nnncnnntcn gtgcgaaagc    720
gtggggagca acaggatta gatacccgg tagtccacgc cgtaaacgat gtcgatttgg    780
aggctgtgtc cttgagacgt ggcttccgga gctaacgcgt taaatcgacg cnggggggant   840 acggccgcaa ggttaaccct caaatnnaat tgacggggnc cc                       882
```

```
<210> SEQ ID NO 57
<211> LENGTH: 938
<212> TYPE: DNA
<213> ORGANISM: Artificial Sequence
<220> FEATURE:
<223> OTHER INFORMATION: Gam1-1-29-27F_H10.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (602)..(603)
<223> OTHER INFORMATION: n is a, c, g, or t
<220> FEATURE:
<221> NAME/KEY: misc_feature
<222> LOCATION: (691)..(694)
<223> OTHER INFORMATION: n is a, c, g, or t
<220> FEATURE:
<221> NAME/KEY: misc_feature
<222> LOCATION: (716)..(716)
<223> OTHER INFORMATION: n is a, c, g, or t
<220> FEATURE:
<221> NAME/KEY: misc_feature
<222> LOCATION: (827)..(828)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t
<220> FEATURE:
<221> NAME/KEY: misc_feature
<222> LOCATION: (886)..(887)
<223> OTHER INFORMATION: n is a, c, g, or t
<220> FEATURE:
<221> NAME/KEY: misc_feature
<222> LOCATION: (894)..(894)
<223> OTHER INFORMATION: n is a, c, g, or t
<220> FEATURE:
<221> NAME/KEY: misc_feature
<222> LOCATION: (909)..(909)
<223> OTHER INFORMATION: n is a, c, g, or t
<220> FEATURE:
<221> NAME/KEY: misc_feature
<222> LOCATION: (916)..(917)
<223> OTHER INFORMATION: n is a, c, g, or t
<220> FEATURE:
<221> NAME/KEY: misc_feature
<222> LOCATION: (919)..(920)
```

```
<223> OTHER INFORMATION: n is a, c, g, or t
<220> FEATURE:
<221> NAME/KEY: misc_feature
<222> LOCATION: (922)..(923)
<223> OTHER INFORMATION: n is a, c, g, or t
<220> FEATURE:
<221> NAME/KEY: misc_feature
<222> LOCATION: (926)..(927)
<223> OTHER INFORMATION: n is a, c, g, or t
<220> FEATURE:
<221> NAME/KEY: misc_feature
<222> LOCATION: (929)..(929)
<223> OTHER INFORMATION: n is a, c, g, or t
<220> FEATURE:
<221> NAME/KEY: misc_feature
<222> LOCATION: (934)..(935)
<223> OTHER INFORMATION: n is a, c, g, or t

<400> SEQUENCE: 57
tacnntgcag tcgagcggca gcgggaaagt agcttgctac ttttgccggc gagcggcgga      60
cgggtgagta atgcctgggg atctgcccaa tcgaggggga taactactgg aaacggtagc    120
taataccgca tacgccctac gggggaaagc agggaccttc gggccttgc gcgattggat     180 gaacccaggt gggattagct agttggtgag gtaacggctc accaaggcga cgatccctag   240
ctggtctgag aggatgatca gccacactgg aactgagaca cggtccagac tcctacggga   300
ggcagcagtg gggaatattg cacaatgggg gaaaccctga tgcagccatg ccgcgtgtgt   360
gaagaaggcc ttcgggttgt aaagcacttt cagcgaggag gaaaggttgg tagctaatat   420
ctgccagctg tgacgttact cgcagaagaa gcaccggcta actccgtgcc agcagccgcg   480
gtaatacgga gggtgcaagc gttaatcgga attactgggc gtaaagcgca cgcaggcggt   540
tggataagtt agatgtgaaa gccccgggct caacctggga attgcattta aaactgtcca   600
gnnagagctc cttgtagagg gggggtaaga attccaggtg tagcggtgaa atgcgtagag   660
atctggagga atacccggtg gcgaaggcg nnnncctgga caaagactga cgctcngtgc    720
gaaagcgtgg ggagcaaaca ggattagata ccctggtagt ccacgccgta aacgatgtcg   780
atttggaagg ctgtgtcctt gagacgtggc cttccggaag ctaaccnncg ttaaatcgac   840
cgccctgggg gagtacgggc cgccaagggt taaaanctcc aaaatnngaa attngaacgg   900 ggggccnc ccaccnnann cnnggnngng gtgnnggc                              938

<210> SEQ ID NO 58
<211> LENGTH: 866
<212> TYPE: DNA
<213> ORGANISM: Artificial Sequence
<220> FEATURE:
<223> OTHER INFORMATION: Gam1-1-30-27F_H11.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
<222> LOCATION: (691)..(692)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (750)..(750)
<223> OTHER INFORMATION: n is a, c, g, or t
```

<220> FEATURE:
<221> NAME/KEY: misc_feature
<222> LOCATION: (785)..(786)
<223> OTHER INFORMATION: n is a, c, g, or t
<220> FEATURE:
<221> NAME/KEY: misc_feature
<222> LOCATION: (790)..(793)
<223> OTHER INFORMATION: n is a, c, g, or t
<220> FEATURE:
<221> NAME/KEY: misc_feature
<222> LOCATION: (802)..(802)
<223> OTHER INFORMATION: n is a, c, g, or t
<220> FEATURE:
<221> NAME/KEY: misc_feature
<222> LOCATION: (846)..(846)
<223> OTHER INFORMATION: n is a, c, g, or t
<220> FEATURE:
<221> NAME/KEY: misc_feature
<222> LOCATION: (857)..(859)
<223> OTHER INFORMATION: n is a, c, g, or t

<400> SEQUENCE: 58
tacnntgcag tcgagcggta gcacaggaga gcttgctctc tgggtgacga gcggcggacg        60
ggtgagtaat gtctgggaaa ctgcctgatg gaggggata actactggaa acggtagcta       120
ataccgcata acgtcgcaag accaaagagg gggaccttcg ggcctcttgc catcagatgt       180
gcccagatgg gattagctag taggtggggt aacggctcac ctaggcgacg atccctagct       240
ggtctgagag gatgaccagc cacactggaa ctgagacacg gtccagactc ctacgggagg       300
cagcagtggg gaatattgca caatgggcgc aagcctgatg cagccatgcc gcgtgtatga       360
agaaggcctt cgggttgtaa agtactttca gcggggagga aggtgttgag gttaataacc       420
tcagcaattg acgttacccg cagaagaagc accggctaac tccgtgccag cagccgcggt       480
aatacggagg gtgcaagcgt taatcggaat tactgggcgt aaagcgcacg caggcggtcc       540
gtcaagtcgg atgtgaaatc cccgggctca acctgggaac tgcattcgaa actggcaggc       600
tagagtcttg tagaggggggg tagaattcca ggtgtagcgg tgaaatgcgt agagatctgg       660
aggaatacng gtggcgaagg cggccccccg nncaaagact gacgctcngt gcgaaagcgt       720
gggggagcaa acaggattag ataccctggn agtccacgcc gtaaacgatg tcgacttgga       780
gttgnngccn nnngaggcgt gnttccgagc tacgcgttag tcgaccgcct gggggagtac       840
ggccgncaag gttaaannnt caaatt                                            866

<210> SEQ ID NO 59
<211> LENGTH: 792
<212> TYPE: DNA
<213> ORGANISM: Artificial Sequence
<220> FEATURE:
<223> OTHER INFORMATION: Gam1-1-32-27F_B01.ab1
<220> FEATURE:
<221> NAME/KEY: misc_feature
<222> LOCATION: (672)..(672)
<223> OTHER INFORMATION: n is a, c, g, or t
<220> FEATURE:
<221> NAME/KEY: misc_feature
<222> LOCATION: (697)..(705)
<223> OTHER INFORMATION: n is a, c, g, or t
<220> FEATURE:
<221> NAME/KEY: misc_feature
<222> LOCATION: (711)..(713)
<223> OTHER INFORMATION: n is a, c, g, or t
<220> FEATURE:
<221> NAME/KEY: misc_feature
<222> LOCATION: (789)..(790)
<223> OTHER INFORMATION: n is a, c, g, or t

<400> SEQUENCE: 59

```
tgcagtcgag cggtaacaca gggagcttgc tcctgggtga cgagcggcgg acgggtgagt    60
aatgtctggg aaactgcctg atggagggggg ataactactg gaaacggtag ctaataccgc  120
ataacgtcgc aagaccaaag aggggggacct tcgggcctct tgccatcaga tgtgcccaga  180
tgggattagc tagtaggtgg ggtaatggct cacctaggcg acgatcccta gctggtctga  240
gaggatgacc agccacactg gaactgagac acggtccaga ctcctacggg aggcagcagt  300
ggggaatatt gcacaatggg cgcaagcctg atgcagccat gccgcgtgta tgaagaaggc  360 cttcggggttg taaagtactt tcagcgggga ggaaggcgat aaggttaata accttgtcga  420
ttgacgttac ccgcagaaga agcaccggct aactccgtgc cagcagccgc ggtaatacgg  480
agggtgcaag cgttaatcgg aattactggg cgtaaagcgc acgcaggcgg tctgtcaagt  540
cggatgtgaa atccccgggc tcaacctggg aactgcattc gaaactggca ggctagagtc  600
ttgtagaggg gggtagaatt ccaggtgtag cggtgaaatg cgtagagatc tggaggaata  660
ccggtggcga angcggcccc ctggacaaag actgacnnnn nnnnngcgaa nnncgtgggg  720
agcaaacagg attagatacc ctggtagtcc acgccgtaaa cgatgtcgac ttggaggttg  780
tgcccttgnn gg                                                      792
```

```
<210> SEQ ID NO 60
<211> LENGTH: 792
<212> TYPE: DNA
<213> ORGANISM: Artificial Sequence
<220> FEATURE:
<223> OTHER INFORMATION: Gam1-1-3-27F_H02.ab1
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (675)..(675)
<223> OTHER INFORMATION: n is a, c, g, or t
<220> FEATURE:
<221> NAME/KEY: misc_feature
<222> LOCATION: (704)..(704)
<223> OTHER INFORMATION: n is a, c, g, or t
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (729)..(731)
<223> OTHER INFORMATION: n is a, c, g, or t
<220> FEATURE:
<221> NAME/KEY: misc_feature
<222> LOCATION: (733)..(733)
<223> OTHER INFORMATION: n is a, c, g, or t
<220> FEATURE:
<221> NAME/KEY: misc_feature
<222> LOCATION: (789)..(789)
<223> OTHER INFORMATION: n is a, c, g, or t

<400> SEQUENCE: 60
tgcnagtcga acggtagcac agaggagctt gctccttggg tgacgagtgg cggacgggtg    60
agtaatgtct gggaaactgc cgatggaggg ggataacta ctggaaacgg tagctaatac   120
cgcataacgt cgcaagacca aagagggggga ccttcgggcc tcttgccatc ggatgtgccc   180
agatgggatt agctagtagg tggggtaacg gctcacctag gcgacgatcc ctagctggtc   240
tgagaggatg accagccaca ctggaactga gacacggtcc agactcctac gggaggcagc   300 agtgggggaat attgcacaat gggcgcaagc ctgatgcagc catgccgcgt gtatgaagaa   360
ggccttcggg ttgtaaagta ctttcagcgg ggaggaaggc gataaggtta ataaccttgt   420
```

```
cgattgacgt tacccgcaga agaagcaccg gctaactccg tgccagcagc cgcggtaata    480
cggagggtgc aagcgttaat cggaattact gggcgtaaag cgcacgcagg cggtctgtca    540
agtcggatgt gaaatccccg ggctcaacct gggaactgca ttcgaaactg gcaggctaga    600
gtcttgtaga gggggtaga attccaggtg tagcggtgaa atgcgtagag atctggagga    660
ataccggtgg cgaangcggc ccctggaca aagactgacg ctcnggngcg aaagcgtggg    720
gagcaatcnn nantagatac cctggtagtc cacgccgtaa acgatgtcga cttggaggtt    780
gtgcccttna gg                                                        792
```

```
<210> SEQ ID NO 61
<211> LENGTH: 828
<212> TYPE: DNA
<213> ORGANISM: Artificial Sequence
<220> FEATURE:
<223> OTHER INFORMATION: Gam1-1-33-27F_B02.ab1
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (701)..(703)
<223> OTHER INFORMATION: n is a, c, g, or t
<220> FEATURE:
<221> NAME/KEY: misc_feature
<222> LOCATION: (743)..(743)
<223> OTHER INFORMATION: n is a, c, g, or t
<220> FEATURE:
<221> NAME/KEY: misc_feature
<222> LOCATION: (758)..(758)
<223> OTHER INFORMATION: n is a, c, g, or t
<220> FEATURE:
<221> NAME/KEY: misc_feature
<222> LOCATION: (771)..(775)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t
<220> FEATURE:
<221> NAME/KEY: misc_feature
<222> LOCATION: (787)..(789)
<223> OTHER INFORMATION: n is a, c, g, or t
<220> FEATURE:
<221> NAME/KEY: misc_feature
<222> LOCATION: (791)..(794)
<223> OTHER INFORMATION: n is a, c, g, or t
<220> FEATURE:
<221> NAME/KEY: misc_feature
<222> LOCATION: (799)..(799)
<223> OTHER INFORMATION: n is a, c, g, or t
<220> FEATURE:
<221> NAME/KEY: misc_feature
<222> LOCATION: (801)..(801)
<223> OTHER INFORMATION: n is a, c, g, or t
<220> FEATURE:
<221> NAME/KEY: misc_feature
<222> LOCATION: (809)..(809)
<223> OTHER INFORMATION: n is a, c, g, or t
<220> FEATURE:
<221> NAME/KEY: misc_feature
<222> LOCATION: (812)..(812)
<223> OTHER INFORMATION: n is a, c, g, or t
<220> FEATURE:
<221> NAME/KEY: misc_feature
<222> LOCATION: (817)..(817)
<223> OTHER INFORMATION: n is a, c, g, or t
<220> FEATURE:
<221> NAME/KEY: misc_feature
<222> LOCATION: (819)..(819)
<223> OTHER INFORMATION: n is a, c, g, or t
<220> FEATURE:
```

-continued

<221> NAME/KEY: misc_feature
<222> LOCATION: (822)..(822)
<223> OTHER INFORMATION: n is a, c, g, or t
<220> FEATURE:
<221> NAME/KEY: misc_feature
<222> LOCATION: (824)..(825)
<223> OTHER INFORMATION: n is a, c, g, or t

<400> SEQUENCE: 61

```
tgnnntcgag cggtaacaca gggagcttgc tcctgggtga cgagcggcgg acgggtgagt      60
aatgtctggg aaactgcctg atggaggggg ataactactg gaaacggtag ctaataccgc     120
ataacgtcgc aagaccaaag aggggggacct tcgggcctct tgccatcaga tgtgcccaga    180
tgggattagc tagtaggtgg ggtaacggct cacctaggcg acgatcccta gctggtctga    240
gaggatgacc agccacactg gaactgagac acggtccaga ctcctacggg aggcagcagt    300
ggggaatatt gcacaatggg cgcaagcctg atgcagccat gccgcgtgta tgaagaaggc    360
cttcggggttg taaagtactt tcagcgggga ggaaggtgtt gaggttaata acctcagcaa   420
ttgacgttac ccgcagaaga agcaccggct aactccgtgc cagcagccgc ggtaatacgg    480
agggtgcaag cgttaatcgg aattactggg cgtaaagcgc acgcaggcgg tctgtcaagt    540
cggatgtgaa atccccgggc tcaacctggg aactgcattc gaaactggca ggctagagtc    600
ttgtagaggg gggtagaatt ccaggtgtag cggtgaaatg cgtagagatc tggaggaata    660
ccggtggcga aggcggcccc ctggacaaag actgacgctc nnntgcgaaa gcgtggggag    720
caaacaggat tagataccct ggnagtccac gccgtaacg atgtcgactt nnnnntngtg    780
cccttgnnng nnnntccgna nctaacgcnt tnagtcnanc gncnnggg                 828
```

<210> SEQ ID NO 62
<211> LENGTH: 755
<212> TYPE: DNA
<213> ORGANISM: Artificial Sequence
<220> FEATURE:
<223> OTHER INFORMATION: Gam1-1-35-27F_B04.ab1
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (671)..(673)
<223> OTHER INFORMATION: n is a, c, g, or t
<220> FEATURE:
<221> NAME/KEY: misc_feature
<222> LOCATION: (683)..(686)
<223> OTHER INFORMATION: n is a, c, g, or t
<220> FEATURE:
<221> NAME/KEY: misc_feature
<222> LOCATION: (689)..(689)
<223> OTHER INFORMATION: n is a, c, g, or t
<220> FEATURE:
<221> NAME/KEY: misc_feature
<222> LOCATION: (700)..(702)
<223> OTHER INFORMATION: n is a, c, g, or t
<220> FEATURE:
<221> NAME/KEY: misc_feature
<222> LOCATION: (706)..(706)
<223> OTHER INFORMATION: n is a, c, g, or t
<220> FEATURE:
<221> NAME/KEY: misc_feature
<222> LOCATION: (717)..(718)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
<220> FEATURE:
<221> NAME/KEY: misc_feature
<222> LOCATION: (722)..(722)
<223> OTHER INFORMATION: n is a, c, g, or t
<220> FEATURE:
<221> NAME/KEY: misc_feature
<222> LOCATION: (724)..(724)
<223> OTHER INFORMATION: n is a, c, g, or t
<220> FEATURE:
<221> NAME/KEY: misc_feature
<222> LOCATION: (740)..(740)
<223> OTHER INFORMATION: n is a, c, g, or t
<220> FEATURE:
<221> NAME/KEY: misc_feature
<222> LOCATION: (743)..(743)
<223> OTHER INFORMATION: n is a, c, g, or t
<220> FEATURE:
<221> NAME/KEY: misc_feature
<222> LOCATION: (746)..(746)
<223> OTHER INFORMATION: n is a, c, g, or t
<220> FEATURE:
<221> NAME/KEY: misc_feature
<222> LOCATION: (748)..(748)
<223> OTHER INFORMATION: n is a, c, g, or t
<220> FEATURE:
<221> NAME/KEY: misc_feature
<222> LOCATION: (750)..(751)
<223> OTHER INFORMATION: n is a, c, g, or t

<400> SEQUENCE: 62
gcnngtcgag cggtaacaca gggagcttgc tcctgggtga cgagcggcgg acgggtgagt    60
aatgtctggg aaactgcctg atggaggggg ataactactg gaaacggtag ctaataccgc   120
ataacgtcgc aagaccaaag aggggqacct tcgggcctct tgccatcaga tgtgcccaga   180
tgggattagc tagtaggtgg ggtaatggct caccctaggcg acgatcccta gctggtctga   240
gaggatgacc agccacactg gaactgagac acggtccaga ctcctacggg aggcagcagt   300
ggggaatatt gcacaatggg cgcaagcctg atgcagccat gccgcgtgta tgaagaaggc   360 cttcggggttg taaagtactt tcagcgggga ggaaggcgat aaggttaata accttgtcga   420
ttgacgttac ccgcagaaga agcaccggct aactccgtgc cagcagccgc ggtaatacgg   480
agggtgcaag cgttaatcgg aattactggg cgtaaagcgc acgcaggcgg ttggataagt   540
tagatgtgaa agccccgggc tcaacctggg aactgcattc gaaactggca ggctagagtc   600
ttgtagaggg gggtagaatt ccaggtgtag cggtgaaatg cgtagagatc tggaggaata   660
ccggtggcga nnnggccccc tgnnnnaana ctgacgctcn nntgcaaaag cgtgggnngn   720
ancnggatta gataccctgn tantcncncn naaac   755

<210> SEQ ID NO 63
<211> LENGTH: 780
<212> TYPE: DNA
<213> ORGANISM: Artificial Sequence
<220> FEATURE:
<223> OTHER INFORMATION: Gam1-1-36-27F_B05.ab1
<220> FEATURE:
<221> NAME/KEY: misc_feature
<222> LOCATION: (664)..(664)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
<222> LOCATION: (704)..(705)
<223> OTHER INFORMATION: n is a, c, g, or t
<220> FEATURE:
<221> NAME/KEY: misc_feature
<222> LOCATION: (727)..(727)
<223> OTHER INFORMATION: n is a, c, g, or t
<220> FEATURE:

<221> NAME/KEY: misc_feature
<222> LOCATION: (763)..(763)
<223> OTHER INFORMATION: n is a, c, g, or t
<220> FEATURE:
<221> NAME/KEY: misc_feature
<222> LOCATION: (774)..(778)
<223> OTHER INFORMATION: n is a, c, g, or t

<400> SEQUENCE: 63

```
agtcgagcgg tagcacaggg agcttgctcc tgggtgacga gcggcggacg ggtgagtaat      60
gtctgggaaa ctgcctgatg gaggggggata actactggaa acggtagcta ataccgcata    120
acgtcgcaag accaaagagg gggaccttcg ggcctcttgc catcagatgt gcccagatgg     180
gattagctag taggtggggt aatggctcac ctagacgacg atccctagct ggtctgagag     240
gatgaccagc cacactggaa ctgagacacg gtccagactc ctacgggagg cagcagtggg     300
gaatattgca caatgggcgc aagcctgatg cagccatgcc gcgtgtatga agaaggcctt     360
cggggttgtaa agtactttca gcggggagga aggtgttgag gttaataacc tcagcaattg    420
acgttacccg cagaagaagc accggctaac tccgtgccag cagccgcggt aatacggagg     480
gtgcaagcgt taatcggaat tactgggcgt aaagcgcacg caggcggtct gtcaagtcgg     540
atgtgaaatc cccgggctca acctgggaac tgcattcgaa actggcaggc tagagtcttg     600
tagagggggg tagaattcca ggtgtagcgg tgaaatgcgt agagatctgg aggaataccg     660
gtgncgaang cggcccctg dacaaagact gacgctcagg tgcnnaagcg tggggagcaa      720
acaggantag ataccctggt agtccacgcc gtaaacgatg tcnacttgga ggtnnnnncc    780
```

<210> SEQ ID NO 64
<211> LENGTH: 854
<212> TYPE: DNA
<213> ORGANISM: Artificial Sequence
<220> FEATURE:
<223> OTHER INFORMATION: Gam1-1-37-27F_B06.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (673)..(673)
<223> OTHER INFORMATION: n is a, c, g, or t
<220> FEATURE:
<221> NAME/KEY: misc_feature
<222> LOCATION: (702)..(704)
<223> OTHER INFORMATION: n is a, c, g, or t
<220> FEATURE:
<221> NAME/KEY: misc_feature
<222> LOCATION: (732)..(732)
<223> OTHER INFORMATION: n is a, c, g, or t
<220> FEATURE:
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (758)..(759)
<223> OTHER INFORMATION: n is a, c, g, or t
<220> FEATURE:
<221> NAME/KEY: misc_feature
<222> LOCATION: (767)..(767)
<223> OTHER INFORMATION: n is a, c, g, or t
<220> FEATURE:
<221> NAME/KEY: misc_feature
<222> LOCATION: (772)..(775)
<223> OTHER INFORMATION: n is a, c, g, or t
<220> FEATURE:
<221> NAME/KEY: misc_feature
<222> LOCATION: (779)..(779)
<223> OTHER INFORMATION: n is a, c, g, or t

```
<220> FEATURE:
<221> NAME/KEY: misc_feature
<222> LOCATION: (784)..(784)
<223> OTHER INFORMATION: n is a, c, g, or t
<220> FEATURE:
<221> NAME/KEY: misc_feature
<222> LOCATION: (788)..(789)
<223> OTHER INFORMATION: n is a, c, g, or t
<220> FEATURE:
<221> NAME/KEY: misc_feature
<222> LOCATION: (792)..(794)
<223> OTHER INFORMATION: n is a, c, g, or t
<220> FEATURE:
<221> NAME/KEY: misc_feature
<222> LOCATION: (797)..(798)
<223> OTHER INFORMATION: n is a, c, g, or t
<220> FEATURE:
<221> NAME/KEY: misc_feature
<222> LOCATION: (800)..(800)
<223> OTHER INFORMATION: n is a, c, g, or t
<220> FEATURE:
<221> NAME/KEY: misc_feature
<222> LOCATION: (816)..(816)
<223> OTHER INFORMATION: n is a, c, g, or t
<220> FEATURE:
<221> NAME/KEY: misc_feature
<222> LOCATION: (819)..(820)
<223> OTHER INFORMATION: n is a, c, g, or t
<220> FEATURE:
<221> NAME/KEY: misc_feature
<222> LOCATION: (822)..(822)
<223> OTHER INFORMATION: n is a, c, g, or t
<220> FEATURE:
<221> NAME/KEY: misc_feature
<222> LOCATION: (827)..(829)
<223> OTHER INFORMATION: n is a, c, g, or t
<220> FEATURE:
<221> NAME/KEY: misc_feature
<222> LOCATION: (834)..(834)
<223> OTHER INFORMATION: n is a, c, g, or t
<220> FEATURE:
<221> NAME/KEY: misc_feature
<222> LOCATION: (838)..(840)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
<221> NAME/KEY: misc_feature
<222> LOCATION: (850)..(850)
<223> OTHER INFORMATION: n is a, c, g, or t
<220> FEATURE:
<221> NAME/KEY: misc_feature
<222> LOCATION: (852)..(853)
<223> OTHER INFORMATION: n is a, c, g, or t

<400> SEQUENCE: 64
tgcnngtcga gcggtaacac agggagcttg ctcctgggtg acgagcggcg gacgggtgag      60
taatgtctgg gaaactgcct gatggagggg gataactact ggaaacggta gctaataccg     120
cataacgtcg caagaccaaa gaggggggacc ttcgggcctc ttgccatcag atgtgcccag    180
atgggattag ctagtaggtg gggtaatggc tcacctaggc gacgatccct agctggtctg    240
agaggatgac cagccacact ggaactgaga cacggtccag actcctacgg gaggcagcag    300
tggggaatat tgcacaatgg gcgcaagcct gatgcagcca tgccgcgtgt atgaagaagg    360
ccttcgggtt gtaaagtact ttcagcgggg aggaaggcga taaggttaat aaccttgtcg    420
attgacgtta cccgcagaag aagcaccggc taactccgtg ccagcagccg cggtaatacg    480
gagggtgcaa gcgttaatcg gaattactgg gcgtaaagcg cacgcaggcg gtctgtcaag    540
tcggatgtga atccccggg ctcaacctgg gaactgcatt cgaaactggc aggctagagt     600
```

-continued cttgtagagg ggggtagaat tccaggtgta gcggtggaat gcgtagagat ctggaggaat    660
accggtggcg aangcggccc cctggacaaa gactgacgct cnnngtgcga aagcgtgggg    720
agcaaacagg antanatacc ctggtagtcc acgccgtnnc gatgtcnact tnnnnttgng    780
cccntganng tnnntcnnan ctaacgcgtt aagtcnacnn cngggnnna cggncgcnnn    840 gtnaaactcn anng    854

<210> SEQ ID NO 65
<211> LENGTH: 830
<212> TYPE: DNA
<213> ORGANISM: Artificial Sequence
<220> FEATURE:
<223> OTHER INFORMATION: Gam1-1-38-27F_B07.ab1
<220> FEATURE:
<221> NAME/KEY: misc_feature
<222> LOCATION: (3)..(6)
<223> OTHER INFORMATION: n is a, c, g, or t
<220> FEATURE:
<221> NAME/KEY: misc_feature
<222> LOCATION: (648)..(665)
<223> OTHER INFORMATION: n is a, c, g, or t
<220> FEATURE:
<221> NAME/KEY: misc_feature
<222> LOCATION: (668)..(670)
<223> OTHER INFORMATION: n is a, c, g, or t
<220> FEATURE:
<221> NAME/KEY: misc_feature
<222> LOCATION: (675)..(688)
<223> OTHER INFORMATION: n is a, c, g, or t
<220> FEATURE:
<221> NAME/KEY: misc_feature
<222> LOCATION: (690)..(692)
<223> OTHER INFORMATION: n is a, c, g, or t
<220> FEATURE:
<221> NAME/KEY: misc_feature
<222> LOCATION: (701)..(701)
<223> OTHER INFORMATION: n is a, c, g, or t
<220> FEATURE:
<221> NAME/KEY: misc_feature
<222> LOCATION: (756)..(756)
<223> OTHER INFORMATION: n is a, c, g, or t
<220> FEATURE:
<221> NAME/KEY: misc_feature
<222> LOCATION: (764)..(764)
<223> OTHER INFORMATION: n is a, c, g, or t
<220> FEATURE:
<221> NAME/KEY: misc_feature
<222> LOCATION: (769)..(772)
<223> OTHER INFORMATION: n is a, c, g, or t
<220> FEATURE:
<221> NAME/KEY: misc_feature
<222> LOCATION: (790)..(791)
<223> OTHER INFORMATION: n is a, c, g, or t
<220> FEATURE:
<221> NAME/KEY: misc_feature
<222> LOCATION: (793)..(793)
<223> OTHER INFORMATION: n is a, c, g, or t
<220> FEATURE:
<221> NAME/KEY: misc_feature
<222> LOCATION: (797)..(797)
<223> OTHER INFORMATION: n is a, c, g, or t
<220> FEATURE:
<221> NAME/KEY: misc_feature
<222> LOCATION: (800)..(800)
<223> OTHER INFORMATION: n is a, c, g, or t
<220> FEATURE:
<221> NAME/KEY: misc_feature
<222> LOCATION: (802)..(802)
<223> OTHER INFORMATION: n is a, c, g, or t
<220> FEATURE:
<221> NAME/KEY: misc_feature
<222> LOCATION: (806)..(809)
<223> OTHER INFORMATION: n is a, c, g, or t
<220> FEATURE:
<221> NAME/KEY: misc_feature
<222> LOCATION: (818)..(818)
<223> OTHER INFORMATION: n is a, c, g, or t
<220> FEATURE:
<221> NAME/KEY: misc_feature
<222> LOCATION: (825)..(827)
<223> OTHER INFORMATION: n is a, c, g, or t

<400> SEQUENCE: 65

```
tgnnnntcga gcggtaacac agggagcttg ctcctgggtg acgagcggcg gacgggtgag      60
taatgtctgg gaaactgcct gatggagggg gataactact ggaaacggta gctaataccg     120
cataacgtcg caagaccaaa gaggggggacc ttcgggcctc ttgccatcag atgtgcccag    180
atgggattag ctagtaggtg gggtaacggc tcacctaggc gacgatccct agctggtctg    240
agaggatgac cagccacact ggaactgaga cacggtccag actcctacgg gaggcagcag    300
tggggaatat tgcacaatgg gcgcaagcct gatgcagcca tgccgcgtgt atgaagaagg    360
ccttcgggct gtaaagtact ttcagcgggg aggaaggcga taaggttaat aaccttgtcg    420
attgacgtta cccgcagaag aagcaccggc taactccgtg ccagcagccg cggtaatacg    480
gagggtgcaa gcgttaatcg gaattactgg gcgtaaagcg cacgcaggcg gtctgtcaag    540
tcggatgtga atccccggg ctcaacctgg gaactgcatt cgaaactggc aggctagagt    600
cttgtagagg ggggtagaat tccaggtgta gcggtgaaat gcgtagannn nnnnnnnnn     660
nnnnnccnnn ccccnnnnnn nnnnnnnnan nngacgctca ngtgcgaaag cgtggggagc    720
aaacaggatt agataccctg gtagtccacg ccgtancgat gtcnacttnn nngttgtgcc    780
cttgaggcgn ngnttcnggn anctannnng ttaagtcnac cgccnnnggg               830
```

<210> SEQ ID NO 66
<211> LENGTH: 703
<212> TYPE: DNA
<213> ORGANISM: Artificial Sequence
<220> FEATURE:
<223> OTHER INFORMATION: Gam1-1-39-27F_B08.ab1
<220> FEATURE:
<221> NAME/KEY: misc_feature
<222> LOCATION: (23)..(28)
<223> OTHER INFORMATION: n is a, c, g, or t
<220> FEATURE:
<221> NAME/KEY: misc_feature
<222> LOCATION: (674)..(674)
<223> OTHER INFORMATION: n is a, c, g, or t
<220> FEATURE:
<221> NAME/KEY: misc_feature
<222> LOCATION: (676)..(676)
<223> OTHER INFORMATION: n is a, c, g, or t

<400> SEQUENCE: 66

```
gcaagtcgag cggtagcaca ggnnnnnntg ctctctgggt gacgagcggc ggacgggtga     60
gtaatgtctg ggaaactgcc tgatggaggg ggataactac tggaaacggt agctaatacc   120
gcataacgtc gcaagaccaa agagggggac cttcgggcct cttgccatca gatgtgccca   180
gatgggatta gctagtaggt ggggtaacgg ctcacctagg cgacgatccc tagctggtct   240
gagaggatga ccagccacac tggaactgag acacggtcca gactcctacg ggaggcagca   300
gtggggaata ttgcacaatg ggcgcaagcc tgatgcagcc atgccgcgtg tatgaagaag   360
gccttcgggt tgtaaagtac tttcagcggg gaggaaggtg ttgaggttaa taacctcagc   420
aattgacgtt acccgcagaa gaagcaccgg ctaactccgt gccagcagcc gcggtaatac   480
ggagggtgca agcgttaatc ggaattactg ggcgtaaagc gcacgcaggc ggtctgtcaa   540
gtcggatgtg aaatccccgg gctcaacctg ggaactgcat tcgaaactgg caggctagag   600
```

-continued

```
tcttgtagag gggggtagaa ttccaggtgt agcggtgaaa tgcgtagaga tctggaggaa      660
taccggtggc gaangnggc cccctggaca aagactgacg ctc                        703
```

<210> SEQ ID NO 67
<211> LENGTH: 777
<212> TYPE: DNA
<213> ORGANISM: Artificial Sequence
<220> FEATURE:
<223> OTHER INFORMATION: Gam1-1-40-27F_B09.ab1
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (700)..(702)
<223> OTHER INFORMATION: n is a, c, g, or t
<220> FEATURE:
<221> NAME/KEY: misc_feature
<222> LOCATION: (704)..(704)
<223> OTHER INFORMATION: n is a, c, g, or t
<220> FEATURE:
<221> NAME/KEY: misc_feature
<222> LOCATION: (706)..(707)
<223> OTHER INFORMATION: n is a, c, g, or t
<220> FEATURE:
<221> NAME/KEY: misc_feature
<222> LOCATION: (729)..(732)
<223> OTHER INFORMATION: n is a, c, g, or t
<220> FEATURE:
<221> NAME/KEY: misc_feature
<222> LOCATION: (734)..(736)
<223> OTHER INFORMATION: n is a, c, g, or t
<220> FEATURE:
<221> NAME/KEY: misc_feature
<222> LOCATION: (744)..(744)
<223> OTHER INFORMATION: n is a, c, g, or t
<220> FEATURE:
<221> NAME/KEY: misc_feature
<222> LOCATION: (754)..(756)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (775)..(776)
<223> OTHER INFORMATION: n is a, c, g, or t

<400> SEQUENCE: 67

```
caagtcnngn ggtagcacag ggagcttgct cctgggtgac gagcggcgga cgggtgagta      60
atgtctggga aactgcctga tggagggga taactactgg aaacggtagc taataccgca      120
taacgtcgca agaccaaaga gggggacctt cgggcctctt gccatcagat gtgcccagat      180
gggattagct agtaggtggg gtaatggctc acctagacga cgatccctag ctggtctgag      240
aggatgacca gccacactgg aactgagaca cggtccagac tcctacggga ggcagcagtg      300
gggaatattg cacaatgggc gcaagcctga tgcagccatg ccgcgtgtat gaagaaggcc      360
ttcgggttgt aaagtacttt cagcggggag aaggtgttg aggttaataa cctcagcaat      420
tgacgttacc cgcagaagaa gcaccggcta actccgtgcc agcagccgcg gtaatacgga      480
gggtgcaagc gttaatcgga attactgggc gtaaagcgca cgcaggcggt ctgtcaagtc      540
ggatgtgaaa tccccgggct caacctggga actgcattcg aaactggcag gctagagtct      600
tgtagagggg ggtagaattc caggtgtagc ggtgaaatgc gtagagatct ggaggaatac      660
```
cggtggcgaa ggcggccccc tggacaaaga ctgacgctcn nngncnnaag cgtggggagc    720
aaacaggann nnannncctg gtantccacg ccgnnnacga tgtcnacttg gaggnng       777

<210> SEQ ID NO 68
<211> LENGTH: 895
<212> TYPE: DNA
<213> ORGANISM: Artificial Sequence
<220> FEATURE:
<223> OTHER INFORMATION: Gam1-1-4-27F_C04.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (613)..(614)
<223> OTHER INFORMATION: n is a, c, g, or t
<220> FEATURE:
<221> NAME/KEY: misc_feature
<222> LOCATION: (691)..(692)
<223> OTHER INFORMATION: n is a, c, g, or t
<220> FEATURE:
<221> NAME/KEY: misc_feature
<222> LOCATION: (694)..(694)
<223> OTHER INFORMATION: n is a, c, g, or t
<220> FEATURE:
<221> NAME/KEY: misc_feature
<222> LOCATION: (697)..(697)
<223> OTHER INFORMATION: n is a, c, g, or t
<220> FEATURE:
<221> NAME/KEY: misc_feature
<222> LOCATION: (701)..(701)
<223> OTHER INFORMATION: n is a, c, g, or t
<220> FEATURE:
<221> NAME/KEY: misc_feature
<222> LOCATION: (703)..(705)
<223> OTHER INFORMATION: n is a, c, g, or t
<220> FEATURE:
<221> NAME/KEY: misc_feature
<222> LOCATION: (771)..(776)
<223> OTHER INFORMATION: n is a, c, g, or t
<220> FEATURE:
<221> NAME/KEY: misc_feature
<222> LOCATION: (781)..(784)
<223> OTHER INFORMATION: n is a, c, g, or t
<220> FEATURE:
<221> NAME/KEY: misc_feature
<222> LOCATION: (787)..(790)
<223> OTHER INFORMATION: n is a, c, g, or t
<220> FEATURE:
<221> NAME/KEY: misc_feature
<222> LOCATION: (793)..(794)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (814)..(821)
<223> OTHER INFORMATION: n is a, c, g, or t
<220> FEATURE:
<221> NAME/KEY: misc_feature
<222> LOCATION: (828)..(830)
<223> OTHER INFORMATION: n is a, c, g, or t
<220> FEATURE:
<221> NAME/KEY: misc_feature
<222> LOCATION: (843)..(845)

<223> OTHER INFORMATION: n is a, c, g, or t
<220> FEATURE:
<221> NAME/KEY: misc_feature
<222> LOCATION: (850)..(850)
<223> OTHER INFORMATION: n is a, c, g, or t
<220> FEATURE:
<221> NAME/KEY: misc_feature
<222> LOCATION: (855)..(856)
<223> OTHER INFORMATION: n is a, c, g, or t
<220> FEATURE:
<221> NAME/KEY: misc_feature
<222> LOCATION: (860)..(860)
<223> OTHER INFORMATION: n is a, c, g, or t
<220> FEATURE:
<221> NAME/KEY: misc_feature
<222> LOCATION: (862)..(862)
<223> OTHER INFORMATION: n is a, c, g, or t
<220> FEATURE:
<221> NAME/KEY: misc_feature
<222> LOCATION: (868)..(868)
<223> OTHER INFORMATION: n is a, c, g, or t
<220> FEATURE:
<221> NAME/KEY: misc_feature
<222> LOCATION: (878)..(879)
<223> OTHER INFORMATION: n is a, c, g, or t
<220> FEATURE:
<221> NAME/KEY: misc_feature
<222> LOCATION: (887)..(887)
<223> OTHER INFORMATION: n is a, c, g, or t
<220> FEATURE:
<221> NAME/KEY: misc_feature
<222> LOCATION: (891)..(891)
<223> OTHER INFORMATION: n is a, c, g, or t

<400> SEQUENCE: 68

```
tacnntgcaa gtcgagcggt agcacaggag agcttgctct ctgggtgacg agcggcggac      60
gggtgagtaa tgtctgggaa actgcctgat ggagggggat aactactgga aacggtagct     120
aataccgcat aacgtcgcaa gaccaaagag ggggaccttc gggcctcttg ccatcagatg     180
tgcccagatg ggattagcta gtaggtgggg taacggctca cctaggcgac gatccctagc     240
tggtctgaga ggatgaccag ccacactgga actgagacac ggtccagact cctacgggag     300
gcagcagtgg ggaatattgc acaatggggg aaaccctgat gcagccatgc cgcgtgtgtg     360
aagaaggcct tcgggttgta aagcactttc agcgaggagg aaaggttggt agctaatatc     420
tgccagctgt gacgttactc gcagaagaag caccggctaa ctccgtgcca gcagccgcgg     480
taatacggag ggtgcaagcg ttaatcggaa ttactgggcg taaagcgcac gcaggcggtt     540
ggataagtta gatgtgaaag ccccgggctc aacctgggaa ttgcatttaa aactgtccag     600
ctagantcna ganngggggg ggtagattcc aggtgtagcg gtgaaatgcg tagagatctg     660
gaggaatacc ggtggcgaag gcggccccct nngnaanaaa nannngacgc tcaggcgcga     720
aagcgtgggg agcaaacagg attagatacc ctggtagtcc acgccgtaaa nnnnnngtct     780
nnnnttnnnn ggnnggctgt gtcntgagac gtcnnnnnnn nctacgcnnn aatcgaacgc     840
tgnnntacgn gcagnnaaan tnaatganga cggggccnnc acagcgngga ncatg          895
```

<210> SEQ ID NO 69
<211> LENGTH: 925
<212> TYPE: DNA
<213> ORGANISM: Artificial Sequence
<220> FEATURE:
<223> OTHER INFORMATION: Gam1-1-5-27F_C05.ab1
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature -continued

```
<222> LOCATION: (603)..(603)
<223> OTHER INFORMATION: n is a, c, g, or t
<220> FEATURE:
<221> NAME/KEY: misc_feature
<222> LOCATION: (605)..(605)
<223> OTHER INFORMATION: n is a, c, g, or t
<220> FEATURE:
<221> NAME/KEY: misc_feature
<222> LOCATION: (607)..(607)
<223> OTHER INFORMATION: n is a, c, g, or t
<220> FEATURE:
<221> NAME/KEY: misc_feature
<222> LOCATION: (614)..(614)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (629)..(629)
<223> OTHER INFORMATION: n is a, c, g, or t
<220> FEATURE:
<221> NAME/KEY: misc_feature
<222> LOCATION: (703)..(703)
<223> OTHER INFORMATION: n is a, c, g, or t
<220> FEATURE:
<221> NAME/KEY: misc_feature
<222> LOCATION: (706)..(706)
<223> OTHER INFORMATION: n is a, c, g, or t
<220> FEATURE:
<221> NAME/KEY: misc_feature
<222> LOCATION: (710)..(710)
<223> OTHER INFORMATION: n is a, c, g, or t
<220> FEATURE:
<221> NAME/KEY: misc_feature
<222> LOCATION: (713)..(713)
<223> OTHER INFORMATION: n is a, c, g, or t
<220> FEATURE:
<221> NAME/KEY: misc_feature
<222> LOCATION: (772)..(773)
<223> OTHER INFORMATION: n is a, c, g, or t
<220> FEATURE:
<221> NAME/KEY: misc_feature
<222> LOCATION: (787)..(787)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
<220> FEATURE:
<221> NAME/KEY: misc_feature
<222> LOCATION: (799)..(800)
<223> OTHER INFORMATION: n is a, c, g, or t
<220> FEATURE:
<221> NAME/KEY: misc_feature
<222> LOCATION: (805)..(806)
<223> OTHER INFORMATION: n is a, c, g, or t
<220> FEATURE:
<221> NAME/KEY: misc_feature
<222> LOCATION: (823)..(823)
<223> OTHER INFORMATION: n is a, c, g, or t
<220> FEATURE:
<221> NAME/KEY: misc_feature
<222> LOCATION: (825)..(826)
<223> OTHER INFORMATION: n is a, c, g, or t
<220> FEATURE:
<221> NAME/KEY: misc_feature
<222> LOCATION: (842)..(842)
<223> OTHER INFORMATION: n is a, c, g, or t
<220> FEATURE:
<221> NAME/KEY: misc_feature
<222> LOCATION: (847)..(848)
<223> OTHER INFORMATION: n is a, c, g, or t
<220> FEATURE:
<221> NAME/KEY: misc_feature
<222> LOCATION: (850)..(851)
<223> OTHER INFORMATION: n is a, c, g, or t
<220> FEATURE:
```

<221> NAME/KEY: misc_feature
<222> LOCATION: (858)..(858)
<223> OTHER INFORMATION: n is a, c, g, or t
<220> FEATURE:
<221> NAME/KEY: misc_feature
<222> LOCATION: (860)..(860)
<223> OTHER INFORMATION: n is a, c, g, or t
<220> FEATURE:
<221> NAME/KEY: misc_feature
<222> LOCATION: (867)..(867)
<223> OTHER INFORMATION: n is a, c, g, or t
<220> FEATURE:
<221> NAME/KEY: misc_feature
<222> LOCATION: (872)..(872)
<223> OTHER INFORMATION: n is a, c, g, or t
<220> FEATURE:
<221> NAME/KEY: misc_feature
<222> LOCATION: (884)..(884)
<223> OTHER INFORMATION: n is a, c, g, or t
<220> FEATURE:
<221> NAME/KEY: misc_feature
<222> LOCATION: (892)..(892)
<223> OTHER INFORMATION: n is a, c, g, or t
<220> FEATURE:
<221> NAME/KEY: misc_feature
<222> LOCATION: (896)..(896)
<223> OTHER INFORMATION: n is a, c, g, or t
<220> FEATURE:
<221> NAME/KEY: misc_feature
<222> LOCATION: (908)..(908)
<223> OTHER INFORMATION: n is a, c, g, or t
<220> FEATURE:
<221> NAME/KEY: misc_feature
<222> LOCATION: (910)..(910)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t

<400> SEQUENCE: 69

```
gcctacnntg caagtcgagc ggtagcacag ggagcttgct cctgggtgac gagcggcgga      60
cgggtgagta atgtctggga aactgcctga tggaggggga taactactgg aaacggtagc     120
taataccgca taacgtcgca agaccaaaga gggggacctt cgggcctctt gccatcagat     180
gtgcccagat gggattagct agtaggtggg gtaatggctc acctaggcga cgatccctag     240
ctggtctgag aggatgacca gccacactgg aactgagaca cggtccagac ttctacggga     300
ggcagcagtg gggaatattg cacaatgggc gcaagcctga tgcagccatg ccgcgtgtat     360
gaagaaggcc ttcgggttgt aaagtacttt cagcggggag gaaggtgttg aggttaataa     420
cctcagcaat tgacgttacc cgcagaagaa gcaccggcta actccgtgcc agcagccgcg     480
gtaatacgga gggtgcaagc gttaatcgga attactgggc gtaaagcgca cgcaggcggt     540
ctgtcaagtc ggatgtgaaa tccccgggct caacctggga actgcattcg aaactggcag     600
ccnananttc ttgnagaggg gggtagnant ccaggtgtag cggtgaaatg cgtagagatc     660
tggaggaata ccggtggcga aggcggcccc ctggacaaaa acnganctcn tcngtgcga      720
aagcgtgggg agcaaacagg attagatacc ctggtagtcc acgccgtaaa cnnatgtcga     780
cttggangtt gngcccttnn aggcnnggct tccggaagct aancnncgtt aagttcgacc     840
gnccggnngn ngtacgtncn gccagcnatg gntacaaact tcanaatgaa tnggangggg     900
cggcccgncn caagggcggn tgggg                                          925
```

<210> SEQ ID NO 70
<211> LENGTH: 900
<212> TYPE: DNA
<213> ORGANISM: Artificial Sequence -continued

```
<220> FEATURE:
<223> OTHER INFORMATION: Gam1-1-6-27F_C06.ab1
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (728)..(737)
<223> OTHER INFORMATION: n is a, c, g, or t
<220> FEATURE:
<221> NAME/KEY: misc_feature
<222> LOCATION: (742)..(742)
<223> OTHER INFORMATION: n is a, c, g, or t
<220> FEATURE:
<221> NAME/KEY: misc_feature
<222> LOCATION: (744)..(746)
<223> OTHER INFORMATION: n is a, c, g, or t
<220> FEATURE:
<221> NAME/KEY: misc_feature
<222> LOCATION: (748)..(749)
<223> OTHER INFORMATION: n is a, c, g, or t
<220> FEATURE:
<221> NAME/KEY: misc_feature
<222> LOCATION: (754)..(754)
<223> OTHER INFORMATION: n is a, c, g, or t
<220> FEATURE:
<221> NAME/KEY: misc_feature
<222> LOCATION: (756)..(756)
<223> OTHER INFORMATION: n is a, c, g, or t
<220> FEATURE:
<221> NAME/KEY: misc_feature
<222> LOCATION: (761)..(761)
<223> OTHER INFORMATION: n is a, c, g, or t
<220> FEATURE:
<221> NAME/KEY: misc_feature
<222> LOCATION: (764)..(764)
<223> OTHER INFORMATION: n is a, c, g, or t
<220> FEATURE:
<221> NAME/KEY: misc_feature
<222> LOCATION: (773)..(773)
<223> OTHER INFORMATION: n is a, c, g, or t
<220> FEATURE:
<221> NAME/KEY: misc_feature
<222> LOCATION: (798)..(798)
<223> OTHER INFORMATION: n is a, c, g, or t
<220> FEATURE:
<221> NAME/KEY: misc_feature
<222> LOCATION: (803)..(804)
<223> OTHER INFORMATION: n is a, c, g, or t
<220> FEATURE:
<221> NAME/KEY: misc_feature
<222> LOCATION: (808)..(808)
<223> OTHER INFORMATION: n is a, c, g, or t
<220> FEATURE:
<221> NAME/KEY: misc_feature
<222> LOCATION: (814)..(815)
<223> OTHER INFORMATION: n is a, c, g, or t
<220> FEATURE:
<221> NAME/KEY: misc_feature
<222> LOCATION: (837)..(839)
<223> OTHER INFORMATION: n is a, c, g, or t
<220> FEATURE:
<221> NAME/KEY: misc_feature
<222> LOCATION: (841)..(844)
<223> OTHER INFORMATION: n is a, c, g, or t
<220> FEATURE:
<221> NAME/KEY: misc_feature
<222> LOCATION: (847)..(850)
<223> OTHER INFORMATION: n is a, c, g, or t
<220> FEATURE:
<221> NAME/KEY: misc_feature
<222> LOCATION: (854)..(855)
<223> OTHER INFORMATION: n is a, c, g, or t
<220> FEATURE:
```

<221> NAME/KEY: misc_feature
<222> LOCATION: (871)..(871)
<223> OTHER INFORMATION: n is a, c, g, or t
<220> FEATURE:
<221> NAME/KEY: misc_feature
<222> LOCATION: (881)..(882)
<223> OTHER INFORMATION: n is a, c, g, or t
<220> FEATURE:
<221> NAME/KEY: misc_feature
<222> LOCATION: (886)..(886)
<223> OTHER INFORMATION: n is a, c, g, or t
<220> FEATURE:
<221> NAME/KEY: misc_feature
<222> LOCATION: (888)..(888)
<223> OTHER INFORMATION: n is a, c, g, or t
<220> FEATURE:
<221> NAME/KEY: misc_feature
<222> LOCATION: (891)..(891)
<223> OTHER INFORMATION: n is a, c, g, or t
<220> FEATURE:
<221> NAME/KEY: misc_feature
<222> LOCATION: (894)..(894)
<223> OTHER INFORMATION: n is a, c, g, or t
<220> FEATURE:
<221> NAME/KEY: misc_feature
<222> LOCATION: (896)..(896)
<223> OTHER INFORMATION: n is a, c, g, or t

<400> SEQUENCE: 70

```
gcctacnntg caagtcgagc ggtaacacag ggagcttgct cctgggtgac gagcggcgga      60
cgggtgagta acgtctggga aactgcctga tggagggggA taactactgg aaacggtagc     120
taataccgca taacgtcgca agaccaaaga gggggacctt cgggcctctt gccatcagat     180
gtgcccagat gggattagct agtaggtggg gtaacggctc acctaggcga cgatccctag     240
ctggtctgag aggatgacca gccacactgg aactgagaca cggtccagac tcctacggga     300
ggcagcagtg gggaatattg cacaatgggc gcaagcctga tgcagccatg ccgcgtgtat     360
gaagaaggcc ttcgggttgt aaagtacttt cagcggggag gaaggtgttg aggttaataa     420
cctcagcaat tgacgttacc cgcagaagaa gcaccggcta actccgtgcc agcagccgcg     480
gtaatacgga gggtgcaagc gttaatcgga attactgggc gtaaagcgca cgcaggcggt     540
ctgtcaagtc ggatgtgaaa tccccgggct caacctggga actgcattcg aaactggcag     600
gctagagtct tgtagagggg ggtagaattc caggtgtagc ggtgaaatgc gtagagatct     660
ggaggaatac cggtggcgaa ggcggcccc tggacaaaga ctgacgctca ngtgcgaaag     720
cgtgggnnn nnnnnntta ancnnncnnt ggtncnccac nccnataaca cgnatgtcga     780
cttggaaggt tgtgcccntg agnngtgntt tccnnagcta acgcgtttaa gtcgacnnng     840
nnnntannnn gcannaaact caatgattga nggggcccgc nncaancngg nggnancatg     900
```

<210> SEQ ID NO 71
<211> LENGTH: 892
<212> TYPE: DNA
<213> ORGANISM: Artificial Sequence
<220> FEATURE:
<223> OTHER INFORMATION: Gam1-1-7-27F_C07.ab1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (673)..(675)
<223> OTHER INFORMATION: n is a, c, g, or t
<220> FEATURE:
<221> NAME/KEY: misc_feature
<222> LOCATION: (751)..(751)
<223> OTHER INFORMATION: n is a, c, g, or t
<220> FEATURE:
<221> NAME/KEY: misc_feature
<222> LOCATION: (800)..(801)
<223> OTHER INFORMATION: n is a, c, g, or t
<220> FEATURE:
<221> NAME/KEY: misc_feature
<222> LOCATION: (835)..(835)
<223> OTHER INFORMATION: n is a, c, g, or t
<220> FEATURE:
<221> NAME/KEY: misc_feature
<222> LOCATION: (859)..(859)
<223> OTHER INFORMATION: n is a, c, g, or t
<220> FEATURE:
<221> NAME/KEY: misc_feature
<222> LOCATION: (874)..(874)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t
<220> FEATURE:
<221> NAME/KEY: misc_feature
<222> LOCATION: (878)..(880)
<223> OTHER INFORMATION: n is a, c, g, or t
<220> FEATURE:
<221> NAME/KEY: misc_feature
<222> LOCATION: (888)..(888)
<223> OTHER INFORMATION: n is a, c, g, or t

<400> SEQUENCE: 71

```
ctannatgca agtcgagcgg taacacaggg agcttgctcc tgggtgacga gcggcggacg      60
ggtgagtaat gtctgggaaa ctgcctgatg gaggggata actactggaa acggtagcta     120
ataccgcata acgtcgcaag accaaagagg gggaccttcg ggcctcttgc catcagatgt     180
gcccagatgg gattagctag taggtggggt aacggctcac ctaggcgacg atccctagct     240
ggtctgagag gatgaccagc cacactggaa ctgagacacg gtccagactc ctacgggagg     300
cagcagtggg gaatattgca caatgggcgc aagcctgatg cagccatgcc gcgtgtatga     360
agaaggcctt cgggttgtaa agtactttca gcggggagga aggcgataag gttaataacc     420
ttgtcgattg acgttacccg cagaagaagc accggctaac tccgtgccag cagccgcggt     480
aatacgaagg gtgcaagcgt taatcggaat tactgggcgt aaagcgcacg caggcggtct     540
gtcaagtcgg atgtgaaatc cccgggctca acctgggaac tgcattcgaa actggcaggc     600
tagagtcttg taaggggggg gtagaattcc aggtgtagcg gtgaaatgcg tagagatctg     660
gaggaatacc ggnnncgaag gcggccccct ggacaaagac tgacgctcag gtgcgaaagc     720
gtggggagca aacaggatta gataccctgg nagtccacgc cgtaaacgat gtcgacttgg     780
agttgtgccc ttgagcgtgn ntccggagct aacgcgttaa gtcgacgctg gggantacgg     840
cgcaggttaa actcaaatna attgacgggg gccngncnnn agcgggtngg ga             892
```

<210> SEQ ID NO 72
<211> LENGTH: 938
<212> TYPE: DNA
<213> ORGANISM: Artificial Sequence
<220> FEATURE:
<223> OTHER INFORMATION: Gam1-1-8-27F_C08.ab1
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(8)

```
<223> OTHER INFORMATION: n is a, c, g, or t
<220> FEATURE:
<221> NAME/KEY: misc_feature
<222> LOCATION: (614)..(614)
<223> OTHER INFORMATION: n is a, c, g, or t
<220> FEATURE:
<221> NAME/KEY: misc_feature
<222> LOCATION: (616)..(616)
<223> OTHER INFORMATION: n is a, c, g, or t
<220> FEATURE:
<221> NAME/KEY: misc_feature
<222> LOCATION: (697)..(701)
<223> OTHER INFORMATION: n is a, c, g, or t
<220> FEATURE:
<221> NAME/KEY: misc_feature
<222> LOCATION: (703)..(703)
<223> OTHER INFORMATION: n is a, c, g, or t
<220> FEATURE:
<221> NAME/KEY: misc_feature
<222> LOCATION: (709)..(709)
<223> OTHER INFORMATION: n is a, c, g, or t
<220> FEATURE:
<221> NAME/KEY: misc_feature
<222> LOCATION: (800)..(802)
<223> OTHER INFORMATION: n is a, c, g, or t
<220> FEATURE:
<221> NAME/KEY: misc_feature
<222> LOCATION: (815)..(815)
<223> OTHER INFORMATION: n is a, c, g, or t
<220> FEATURE:
<221> NAME/KEY: misc_feature
<222> LOCATION: (817)..(817)
<223> OTHER INFORMATION: n is a, c, g, or t
<220> FEATURE:
<221> NAME/KEY: misc_feature
<222> LOCATION: (828)..(828)
<223> OTHER INFORMATION: n is a, c, g, or t
<220> FEATURE:
<221> NAME/KEY: misc_feature
<222> LOCATION: (830)..(834)
<223> OTHER INFORMATION: n is a, c, g, or t
<220> FEATURE:
<221> NAME/KEY: misc_feature
<222> LOCATION: (836)..(836)
<223> OTHER INFORMATION: n is a, c, g, or t
<220> FEATURE:
<221> NAME/KEY: misc_feature
<222> LOCATION: (856)..(856)
<223> OTHER INFORMATION: n is a, c, g, or t
<220> FEATURE:
<221> NAME/KEY: misc_feature
<222> LOCATION: (860)..(860)
<223> OTHER INFORMATION: n is a, c, g, or t
<220> FEATURE:
<221> NAME/KEY: misc_feature
<222> LOCATION: (874)..(874)
<223> OTHER INFORMATION: n is a, c, g, or t
<220> FEATURE:
<221> NAME/KEY: misc_feature
<222> LOCATION: (877)..(877)
<223> OTHER INFORMATION: n is a, c, g, or t
<220> FEATURE:
<221> NAME/KEY: misc_feature
<222> LOCATION: (907)..(907)
<223> OTHER INFORMATION: n is a, c, g, or t
<220> FEATURE:
<221> NAME/KEY: misc_feature
<222> LOCATION: (919)..(921)
<223> OTHER INFORMATION: n is a, c, g, or t
<220> FEATURE:
<221> NAME/KEY: misc_feature
<222> LOCATION: (923)..(924)
<223> OTHER INFORMATION: n is a, c, g, or t
<220> FEATURE:
<221> NAME/KEY: misc_feature
<222> LOCATION: (929)..(929)
<223> OTHER INFORMATION: n is a, c, g, or t
<220> FEATURE:
<221> NAME/KEY: misc_feature
```

<222> LOCATION: (932)..(932)
<223> OTHER INFORMATION: n is a, c, g, or t
<220> FEATURE:
<221> NAME/KEY: misc_feature
<222> LOCATION: (934)..(935)
<223> OTHER INFORMATION: n is a, c, g, or t

<400> SEQUENCE: 72

```
gntancnntg caagtcgagc ggcagcggga aagtagcttg ctactttgc cggcgagcgg      60
cggacgggtg agtaatgcct ggggatctgc ccagtcgagg gggataacta ctggaaacgg    120
tagctaatac cgcatacgcc ctacggggga aagcagggga ccttcgggcc ttgcgcgatt    180
ggatgaaccc aggtgggatt agctagttgg tgaggtaacg gctcaccaag gcgacgatcc    240
ctagctggtc tgagaggatg atcagccaca ctggaactga gacacggtcc agactcctac    300
gggaggcagc agtggggaat attgcacaat gggggaaacc ctgatgcagc catgccgcgt    360
gtgtgaagaa ggccttcggg ttgtaaagca ctttcagcga ggaggaaagg tcagtagcta    420
atatctgctg gctgtgacgt tactcgcaga agaagcaccg gctaactccg tgccagcagc    480
cgcggtaata cggagggtgc aagcgttaat cggaattact gggcgtaaag cgcacgcagg    540
cggttggata agttagatgt gaaagccccg ggctcaacct gggaattgca tttaaaactg    600
tccagctaga gttngntaga gggggggta gaattccagg tgtagcggtg aaatgcgtag    660
agatctggag gaataccggt ggcgaaaggg cggcccnnnn nanaaaaant gagacgctca    720
ggtgcgaaag cgtgggggag caaacaggat ttagataccc tggtagtcca cgccgtaaac    780
gatgtcgatt tggaaggctn nngtccttga agacntngcc tcccggancn nnnngncgtt    840
aattcaatcg acctgnctgn gtgcagtacg gacngcnaag attaaaacct caaatgaaat    900
ttgaacnggg ggcccgccnn nanncgggng gnanncca                            938
```

<210> SEQ ID NO 73
<211> LENGTH: 894
<212> TYPE: DNA
<213> ORGANISM: Artificial Sequence
<220> FEATURE:
<223> OTHER INFORMATION: Gam1-1-9-27F_C09.ab1
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (624)..(628)
<223> OTHER INFORMATION: n is a, c, g, or t
<220> FEATURE:
<221> NAME/KEY: misc_feature
<222> LOCATION: (655)..(656)
<223> OTHER INFORMATION: n is a, c, g, or t
<220> FEATURE:
<221> NAME/KEY: misc_feature
<222> LOCATION: (659)..(659)
<223> OTHER INFORMATION: n is a, c, g, or t
<220> FEATURE:
<221> NAME/KEY: misc_feature
<222> LOCATION: (670)..(670)

<223> OTHER INFORMATION: n is a, c, g, or t
<220> FEATURE:
<221> NAME/KEY: misc_feature
<222> LOCATION: (719)..(719)
<223> OTHER INFORMATION: n is a, c, g, or t
<220> FEATURE:
<221> NAME/KEY: misc_feature
<222> LOCATION: (783)..(783)
<223> OTHER INFORMATION: n is a, c, g, or t
<220> FEATURE:
<221> NAME/KEY: misc_feature
<222> LOCATION: (842)..(842)
<223> OTHER INFORMATION: n is a, c, g, or t

<400> SEQUENCE: 73

```
gnnancnntg cnagtcgagc ggtagcacag gagagcttgc tctctgggtg acgagcggcg      60
gacgggtgag taatgtctgg gaaactgcct gatggagggg gataactact ggaaacggta     120
gctaataccg cataacgtcg caagaccaaa gaggggggacc ttcgggcctc ttgccatcag    180
atgtgcccag atgggattag ctagtaggtg gggtaacggc tcacctaggc gacgatccct    240
agctggtctg agaggatgac cagccacact ggaactgaga cacggtccag actcctacgg    300
gaggcagcag tggggaatat tgcacaatgg gcgcaagcct gatgcagcca tgccgcgtgt    360
atgaagaagg ccttcgggtt gtaaagtact ttcagcgggg aggaaggtgt tgaggttaat    420
aacctcagca attgacgtta cccgcagaag aagcaccggc taactccgtg ccagcagccg    480
cggtaatacg gagggtgcaa gcgttaatcg gaattactgg gcgtaaagcg cacgcaggcg    540
gtctgtcaag tcggatgtga atccccgggg ctcaacctgg gaactgcatt cgaaactggc    600
aggctagagt cttgtagagg ggtnnnnnat ttcgggggtg aagggtgaa atggnntana    660
agatcggggn agaaaatacc ggtggcgaag gcggccccct ggacaaagac tgacgctcng    720
tgcgaaagcg tggggagcaa acaggattag ataccctggt agtccacgcc gtaaacgatg    780
tcnacttgga ggttgtgccc ttgaggcgtg gcttccggag ctaacgcgtt agtcgaccgc    840
cnggggagt acggccgcaa ggttaaaact caaatggaat ttgacggggg cccg           894
```

<210> SEQ ID NO 74
<211> LENGTH: 813
<212> TYPE: DNA
<213> ORGANISM: Artificial Sequence
<220> FEATURE:
<223> OTHER INFORMATION: Gam1-1-41-27F_B10.ab1
<220> FEATURE:
<221> NAME/KEY: misc_feature
<222> LOCATION: (694)..(710)
<223> OTHER INFORMATION: n is a, c, g, or t
<220> FEATURE:
<221> NAME/KEY: misc_feature
<222> LOCATION: (732)..(732)
<223> OTHER INFORMATION: n is a, c, g, or t
<220> FEATURE:
<221> NAME/KEY: misc_feature
<222> LOCATION: (751)..(751)
<223> OTHER INFORMATION: n is a, c, g, or t
<220> FEATURE:
<221> NAME/KEY: misc_feature
<222> LOCATION: (754)..(754)
<223> OTHER INFORMATION: n is a, c, g, or t
<220> FEATURE:
<221> NAME/KEY: misc_feature
<222> LOCATION: (760)..(760)
<223> OTHER INFORMATION: n is a, c, g, or t
<220> FEATURE:
<221> NAME/KEY: misc_feature
<222> LOCATION: (766)..(766)
<223> OTHER INFORMATION: n is a, c, g, or t
<220> FEATURE:
<221> NAME/KEY: misc_feature
<222> LOCATION: (772)..(772)
<223> OTHER INFORMATION: n is a, c, g, or t
<220> FEATURE:
<221> NAME/KEY: misc_feature
<222> LOCATION: (777)..(779)
<223> OTHER INFORMATION: n is a, c, g, or t
<220> FEATURE:
<221> NAME/KEY: misc_feature
<222> LOCATION: (783)..(785)
<223> OTHER INFORMATION: n is a, c, g, or t
<220> FEATURE:
<221> NAME/KEY: misc_feature
<222> LOCATION: (795)..(796)
<223> OTHER INFORMATION: n is a, c, g, or t
<220> FEATURE:
<221> NAME/KEY: misc_feature
<222> LOCATION: (798)..(799)
<223> OTHER INFORMATION: n is a, c, g, or t
<220> FEATURE:
<221> NAME/KEY: misc_feature
<222> LOCATION: (801)..(801)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (809)..(809)
<223> OTHER INFORMATION: n is a, c, g, or t

<400> SEQUENCE: 74

```
tgcaagtcga gcggcagcgg gaaagtagct tgctactttt gccggcgagc ggcggacggg    60
tgagtaatgc ctggggatct gcccagtcga gggggataac tactgaaaac ggtagctaat   120
accgcatacg ccctacgggg gaaagcaggg gaccttcggg ccttgcgcga ttggatgaac   180
ccaggtggga ttagctagtt ggtgaggtaa cggctcacca aggcgacgat ccctagctgg   240
tctgagagga tgatcagcca cactggaact gagacacggt ccagactcct acgggaggca   300
gcagtgggga atattgcaca atgggcgcaa gcctgatgca gccatgctgc gtgtatgaag   360
aaggccttcg ggttgtaaag tactttcagc ggggaggaag gtgttgaggt taataaccte   420
agcaattgac gttacccgca gaagaagcac cggctaactc cgtgccagca gccgcggtaa   480
tacggagggt gcaagcgtta atcggaatta ctgggcgtaa agcgcacgca ggcggtctgt   540
caagtcggat gtgaaatccc cgggctcaac ctgggaactg cattcgaaac tggcaggcta   600
gagtcttgta gaggggggta gaattccagg tgtagcggtg aaatgcgtag agatctggag   660
gaataccggt ggcgaaggcg ccccctggac aannnnnnnn nnnnnnnnnn gcgaaagcgt   720
ggggagcaaa cnggattaga taccctggta ntcnacgccn taaacnatgt cnacttnnng   780
gtnnngccct tgagnngnng nttncgganc taa                                813
```

<210> SEQ ID NO 75
<211> LENGTH: 803
<212> TYPE: DNA
<213> ORGANISM: Artificial Sequence
<220> FEATURE:
<223> OTHER INFORMATION: Gam1-1-42-27F_B11.ab1
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (673)..(673)
<223> OTHER INFORMATION: n is a, c, g, or t
<220> FEATURE:
<221> NAME/KEY: misc_feature
<222> LOCATION: (702)..(704)

```
<223> OTHER INFORMATION: n is a, c, g, or t
<220> FEATURE:
<221> NAME/KEY: misc_feature
<222> LOCATION: (726)..(732)
<223> OTHER INFORMATION: n is a, c, g, or t
<220> FEATURE:
<221> NAME/KEY: misc_feature
<222> LOCATION: (734)..(735)
<223> OTHER INFORMATION: n is a, c, g, or t
<220> FEATURE:
<221> NAME/KEY: misc_feature
<222> LOCATION: (737)..(739)
<223> OTHER INFORMATION: n is a, c, g, or t
<220> FEATURE:
<221> NAME/KEY: misc_feature
<222> LOCATION: (742)..(742)
<223> OTHER INFORMATION: n is a, c, g, or t
<220> FEATURE:
<221> NAME/KEY: misc_feature
<222> LOCATION: (769)..(769)
<223> OTHER INFORMATION: n is a, c, g, or t
<220> FEATURE:
<221> NAME/KEY: misc_feature
<222> LOCATION: (773)..(779)
<223> OTHER INFORMATION: n is a, c, g, or t
<220> FEATURE:
<221> NAME/KEY: misc_feature
<222> LOCATION: (782)..(782)
<223> OTHER INFORMATION: n is a, c, g, or t
<220> FEATURE:
<221> NAME/KEY: misc_feature
<222> LOCATION: (789)..(789)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
<220> FEATURE:
<221> NAME/KEY: misc_feature
<222> LOCATION: (795)..(798)
<223> OTHER INFORMATION: n is a, c, g, or t

<400> SEQUENCE: 75
tgcnagtcga gcggtaacac agggagcttg ctcctgggtg acgagcggcg gacgggtgag      60
taatgtctgg gaaactgcct gatggagggg gataactact ggaaacggta gctaataccg     120
cataacgtcg caagaccaaa gagggggacc ttcgggcctc ttgccatcag atgtgcccag     180
atgggattag ctagtaggtg gggtaatggc tcacctaggc gacgatccct agctggtctg     240
agaggatgac cagccacact ggaactgaga cacggtccag actcctacgg gaggcagcag     300
tggggaatat tgcacaatgg gcgcaagcct gatgcagcca tgccgcgtgt atgaagaagg     360
ccttcgggtt gtaaagtact ttcagcgggg aggaaggcga taaggttaat aaccttgtcg     420
attgacgtta cccgcagaag aagcaccggc taactccgtg ccagcagccg cggtaatacg     480
gagggtgcaa gcgttaatcg gaattactgg gcgtaaagcg cacgcaggcg gttggataag     540
ttagatgtga aagccccggg ctcaacctgg gaactgcatt cgaaactggc aggctagagt     600
cttgtagagg ggggtagaat tccaggtgta gcggtgaaat gcgtagagat ctggaggaat     660
accggtggcg aangcggccc cctggacaaa gactgacgct cnnntgcgaa agcgtgggga     720
gcaaannnnn nntnnannnc cntggtagtc cacgccgtaa acgatgtcna ctnnnnnnnt     780
gngcccttna gncgnnnntt ccg                                             803

<210> SEQ ID NO 76
<211> LENGTH: 777
<212> TYPE: DNA
<213> ORGANISM: Artificial Sequence
<220> FEATURE:
<223> OTHER INFORMATION: Gam1-1-43-27F_B12.ab1
```

```
<220> FEATURE:
<221> NAME/KEY: misc_feature
<222> LOCATION: (3)..(6)
<223> OTHER INFORMATION: n is a, c, g, or t
<220> FEATURE:
<221> NAME/KEY: misc_feature
<222> LOCATION: (680)..(680)
<223> OTHER INFORMATION: n is a, c, g, or t
<220> FEATURE:
<221> NAME/KEY: misc_feature
<222> LOCATION: (709)..(711)
<223> OTHER INFORMATION: n is a, c, g, or t
<220> FEATURE:
<221> NAME/KEY: misc_feature
<222> LOCATION: (734)..(736)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (761)..(764)
<223> OTHER INFORMATION: n is a, c, g, or t
<220> FEATURE:
<221> NAME/KEY: misc_feature
<222> LOCATION: (773)..(774)
<223> OTHER INFORMATION: n is a, c, g, or t
<220> FEATURE:
<221> NAME/KEY: misc_feature
<222> LOCATION: (776)..(776)
<223> OTHER INFORMATION: n is a, c, g, or t

<400> SEQUENCE: 76
ctnnnntgca gtcgagcggt agcacaggag agcttgctct ctgggtgacg agcggcggac      60
gggtgagtaa tgtctgggaa actgcctgat ggaggggat aactactgga aacggtagct     120
aataccgcat aacgtcgcaa gaccaaagag ggggaccttc gggcctcttg ccatcagatg     180
tgcccagatg ggattagcta gtaggtgggg taacggctca cctaggcgac gatccctagc     240
tggtctgaga ggatgaccag ccacactgga actgagacac ggtccagact cctacgggag     300
gcagcagtgg ggaatattgc acaatgggcg caagcctgat gcagccatgc cgcgtgtatg     360
aagaaggcct tcgggttgta aagtactttc agcggggagg aaggtgttga ggttaataac     420
ctcagcaatt gacgttaccc gcagaagaag caccggctaa ctccgtgcca gcagccgcgg     480
taatacggag ggtgcaagcg ttaatcggaa ttactgggcg taaagcgcac gcaggcggtc     540
tgtcaagtcg gatgtgaaat ccccgggctc aacctgggaa ctgcattcga aactggcagg     600
ctagagtctt gtagagggg gtagaattcc aggtgtagcg gtgaaatgcg tagagatctg     660
gaggaatacc ggtggcgaan gcggcccct ggacaaagac tgacgctcnn ntgcgaaagc     720
gtggggagca acnnnatta gatacctgg tagtccacnc nnnnaacgat gtnnant      777

<210> SEQ ID NO 77
<211> LENGTH: 793
<212> TYPE: DNA
<213> ORGANISM: Artificial Sequence
<220> FEATURE:
<223> OTHER INFORMATION: GS1-1-1-27F_H01.ab1
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (679)..(680)
<223> OTHER INFORMATION: n is a, c, g, or t
<220> FEATURE:
<221> NAME/KEY: misc_feature
<222> LOCATION: (684)..(684)
```

```
<223> OTHER INFORMATION: n is a, c, g, or t
<220> FEATURE:
<221> NAME/KEY: misc_feature
<222> LOCATION: (687)..(689)
<223> OTHER INFORMATION: n is a, c, g, or t
<220> FEATURE:
<221> NAME/KEY: misc_feature
<222> LOCATION: (691)..(693)
<223> OTHER INFORMATION: n is a, c, g, or t
<220> FEATURE:
<221> NAME/KEY: misc_feature
<222> LOCATION: (695)..(695)
<223> OTHER INFORMATION: n is a, c, g, or t
<220> FEATURE:
<221> NAME/KEY: misc_feature
<222> LOCATION: (697)..(698)
<223> OTHER INFORMATION: n is a, c, g, or t
<220> FEATURE:
<221> NAME/KEY: misc_feature
<222> LOCATION: (701)..(701)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (713)..(713)
<223> OTHER INFORMATION: n is a, c, g, or t
<220> FEATURE:
<221> NAME/KEY: misc_feature
<222> LOCATION: (718)..(720)
<223> OTHER INFORMATION: n is a, c, g, or t
<220> FEATURE:
<221> NAME/KEY: misc_feature
<222> LOCATION: (722)..(726)
<223> OTHER INFORMATION: n is a, c, g, or t
<220> FEATURE:
<221> NAME/KEY: misc_feature
<222> LOCATION: (728)..(734)
<223> OTHER INFORMATION: n is a, c, g, or t
<220> FEATURE:
<221> NAME/KEY: misc_feature
<222> LOCATION: (786)..(786)
<223> OTHER INFORMATION: n is a, c, g, or t

<400> SEQUENCE: 77
cctacnntgc agtcgaacgg taacagaaag cagcttgctg ctttgctgac gagtggcgga      60
cgggtgagta atgtctggga aactgcctga tggaggggga taactactgg aaacggtagc     120
taataccgca taacgtcttc ggaccaaagt gggggacctt cgggcctcat gccatcagat     180
gtgcccagat gggattagct agtaggtggg gtaatggctc acctaggcga cgatccctag     240
ctggtctgag aggatgacca gccacactgg aactgagaca cggtccagac tcctacggga     300
ggcagcagtg gggaatattg cacaatgggc gcaagcctga tgcagccatg ccgcgtgtat     360
gaagaaggcc ttcgggttgt aaagtacttt cagcgaggag gaaggcgtta aggttaataa     420
ccttagtgat tgacgttact cgcagaagaa gcaccggcta actccgtgcc agcagccgcg     480
gtaatacgga gggtgcaagc gttaatcgga attactgggc gtaaagcgca cgcaggcggt     540
ctgtcaagtc ggatgtgaaa tccccgggct caacctggga actgcattcg aaactggcaa     600
gctagagtct tgtagagggg ggtagaattc caggtgtagc ggtgaaatgc gtagagatct     660
ggaggaatac cggtggcgnn gccncannng nnnangnngc ngacgctggg ngngagannn     720
cnnnnngnnn nnncaggat tagataccct ggtagtccac gccgtaacga tgtcgacttg     780
gaggtnttcc ctt                                                        793
```

```
<210> SEQ ID NO 78
<211> LENGTH: 885
<212> TYPE: DNA
<213> ORGANISM: Artificial Sequence
<220> FEATURE:
<223> OTHER INFORMATION: GS1-1-2-27F_H02.ab1
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (679)..(679)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (702)..(703)
<223> OTHER INFORMATION: n is a, c, g, or t
<220> FEATURE:
<221> NAME/KEY: misc_feature
<222> LOCATION: (705)..(706)
<223> OTHER INFORMATION: n is a, c, g, or t
<220> FEATURE:
<221> NAME/KEY: misc_feature
<222> LOCATION: (708)..(711)
<223> OTHER INFORMATION: n is a, c, g, or t
<220> FEATURE:
<221> NAME/KEY: misc_feature
<222> LOCATION: (716)..(716)
<223> OTHER INFORMATION: n is a, c, g, or t
<220> FEATURE:
<221> NAME/KEY: misc_feature
<222> LOCATION: (733)..(735)
<223> OTHER INFORMATION: n is a, c, g, or t
<220> FEATURE:
<221> NAME/KEY: misc_feature
<222> LOCATION: (740)..(740)
<223> OTHER INFORMATION: n is a, c, g, or t
<220> FEATURE:
<221> NAME/KEY: misc_feature
<222> LOCATION: (744)..(744)
<223> OTHER INFORMATION: n is a, c, g, or t
<220> FEATURE:
<221> NAME/KEY: misc_feature
<222> LOCATION: (750)..(751)
<223> OTHER INFORMATION: n is a, c, g, or t
<220> FEATURE:
<221> NAME/KEY: misc_feature
<222> LOCATION: (753)..(753)
<223> OTHER INFORMATION: n is a, c, g, or t
<220> FEATURE:
<221> NAME/KEY: misc_feature
<222> LOCATION: (764)..(764)
<223> OTHER INFORMATION: n is a, c, g, or t
<220> FEATURE:
<221> NAME/KEY: misc_feature
<222> LOCATION: (805)..(805)
<223> OTHER INFORMATION: n is a, c, g, or t
<220> FEATURE:
<221> NAME/KEY: misc_feature
<222> LOCATION: (808)..(809)
<223> OTHER INFORMATION: n is a, c, g, or t
<220> FEATURE:
<221> NAME/KEY: misc_feature
<222> LOCATION: (811)..(817)
<223> OTHER INFORMATION: n is a, c, g, or t
<220> FEATURE:
<221> NAME/KEY: misc_feature
<222> LOCATION: (830)..(830)
<223> OTHER INFORMATION: n is a, c, g, or t
<220> FEATURE:
<221> NAME/KEY: misc_feature
<222> LOCATION: (834)..(834)
```

<223> OTHER INFORMATION: n is a, c, g, or t
<220> FEATURE:
<221> NAME/KEY: misc_feature
<222> LOCATION: (846)..(846)
<223> OTHER INFORMATION: n is a, c, g, or t
<220> FEATURE:
<221> NAME/KEY: misc_feature
<222> LOCATION: (849)..(850)
<223> OTHER INFORMATION: n is a, c, g, or t
<220> FEATURE:
<221> NAME/KEY: misc_feature
<222> LOCATION: (859)..(859)
<223> OTHER INFORMATION: n is a, c, g, or t
<220> FEATURE:
<221> NAME/KEY: misc_feature
<222> LOCATION: (878)..(879)
<223> OTHER INFORMATION: n is a, c, g, or t

<400> SEQUENCE: 78

```
ctacnntgca agtcgagcgg tagcacaggg agcttgctcc tgggtgacga gcggcggacg      60
ggtgagtaat gtctgggaaa ctgcctgatg gaggggata actactggaa acggtagcta     120
ataccgcata acgtcttcgg accaaagtgg gggaccttcg ggcctcatgc catcagatgt     180
gcccagatgg gattagctag taggtggggt aatggctcac ctaggcgacg atccctagct     240
ggtctgagag gatgaccagc cacactggaa ctgagacacg gtccagactc ctacgggagg     300
cagcagtggg gagtattgca caatgggcgc aagcctgatg cagccatgcc gcgtgtatga     360
agaaggcctt cgggttgtaa agtactttca gcgaggagga aggcgttaag gttaataacc     420
ttagcgattg acgttactcg cagaagaagc accggctaac tccgtgccag cagccgcggt     480
aatacggagg gtgcaagcgt taatcggaat tactgggcgt aaagcgcacg caggcggttt     540
gtcaagtcgg atgtgaaatc cccgggctca acctgggaac tgcattcgaa actggcaagc     600
tagagtcttg tagaggggg tagaattcca ggtgtagcgg tgaaatgcgt agagatctgg     660
aggaataccg gtggcgaang cggccccctg dacaaagant gnngnngnnn ngggnaggg     720
ggagggaga acnnaggan taanataccn ngngtagtcc accnccgtaa acgatgtcga     780
cttggaaggt tgttcccttg aggantgnnt nnnnnnntaa cgccgttaan tccnccgcct     840
ggggantann gccgcaagnt aaacctcaaa atgaaatnna cggggg              885
```

<210> SEQ ID NO 79
<211> LENGTH: 832
<212> TYPE: DNA
<213> ORGANISM: Artificial Sequence
<220> FEATURE:
<223> OTHER INFORMATION: GS1-1-3-27F_H03.ab1
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (706)..(712)
<223> OTHER INFORMATION: n is a, c, g, or t
<220> FEATURE:
<221> NAME/KEY: misc_feature
<222> LOCATION: (714)..(718)
<223> OTHER INFORMATION: n is a, c, g, or t
<220> FEATURE:
<221> NAME/KEY: misc_feature
<222> LOCATION: (722)..(723)
<223> OTHER INFORMATION: n is a, c, g, or t
<220> FEATURE:
<221> NAME/KEY: misc_feature
<222> LOCATION: (728)..(734)
<223> OTHER INFORMATION: n is a, c, g, or t
<220> FEATURE:
<221> NAME/KEY: misc_feature

```
<222> LOCATION: (737)..(737)
<223> OTHER INFORMATION: n is a, c, g, or t
<220> FEATURE:
<221> NAME/KEY: misc_feature
<222> LOCATION: (749)..(749)
<223> OTHER INFORMATION: n is a, c, g, or t
<220> FEATURE:
<221> NAME/KEY: misc_feature
<222> LOCATION: (763)..(763)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (790)..(790)
<223> OTHER INFORMATION: n is a, c, g, or t
<220> FEATURE:
<221> NAME/KEY: misc_feature
<222> LOCATION: (807)..(808)
<223> OTHER INFORMATION: n is a, c, g, or t
<220> FEATURE:
<221> NAME/KEY: misc_feature
<222> LOCATION: (821)..(821)
<223> OTHER INFORMATION: n is a, c, g, or t

<400> SEQUENCE: 79
ggctacnntg caagtcgaac ggtaacagaa agcagcttgc tgctttgctg acgagtggcg      60
gacgggtgag taatgtctgg gaaactgcct gatggagggg gataactact ggaaacggta     120
gctaataccg cataacgtct tcggaccaaa gtgggggacc ttcgggcctc atgccatcag     180
atgtgcccag atgggattag ctagtaggtg gggtaatggc tcacctaggc gacgatccct     240
agctggtctg agaggatgac cagccacact ggaactgaga cacggtccag actcctacgg     300
gaggcagcag tggggaatat tgcacaatgg gcgcaagcct gatgcagcca tgccgcgtgt     360
atgaagaagg ccttcgggtt gtaaagtact ttcagcgagg aggaaggcgt taaggttaat     420
aaccttagtg attgacgtta ctcgcagaag aagcaccggc taactccgtg ccagcagccg     480
cggtaatacg gagggtgcaa gcgttaatcg gaattactgg gcgtaaagcg cacgcaggcg     540
gtctgtcaag tcggatgtga atccccggg ctcaacctgg gaactgcatt cgaaactgac     600
aggctagagt cttgtagagg ggggtagaat tccaggtgta gcggtgaaat gcgtagagat     660
ctggaggaat accggtggcg aaggcggccc cctggacaaa gactgnnnnn nnannnnnaa     720
gnngggnnnn nnnnacngga ttagatccnc tggtagtcca cgncngtaaa cgatgtcgac     780
ttggaaggtn gtgcccttga ggcgtgnntc cggagctacg ngttaagtcg ac             832

<210> SEQ ID NO 80
<211> LENGTH: 865
<212> TYPE: DNA
<213> ORGANISM: Artificial Sequence
<220> FEATURE:
<223> OTHER INFORMATION: GS1-1-4-27F_H04.ab1
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (647)..(652)
<223> OTHER INFORMATION: n is a, c, g, or t
<220> FEATURE:
<221> NAME/KEY: misc_feature
<222> LOCATION: (654)..(655)
<223> OTHER INFORMATION: n is a, c, g, or t
<220> FEATURE:
<221> NAME/KEY: misc_feature
<222> LOCATION: (657)..(657)
```

-continued

```
<223> OTHER INFORMATION: n is a, c, g, or t
<220> FEATURE:
<221> NAME/KEY: misc_feature
<222> LOCATION: (664)..(667)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
<222> LOCATION: (672)..(672)
<223> OTHER INFORMATION: n is a, c, g, or t
<220> FEATURE:
<221> NAME/KEY: misc_feature
<222> LOCATION: (694)..(694)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (752)..(752)
<223> OTHER INFORMATION: n is a, c, g, or t
<220> FEATURE:
<221> NAME/KEY: misc_feature
<222> LOCATION: (756)..(756)
<223> OTHER INFORMATION: n is a, c, g, or t
<220> FEATURE:
<221> NAME/KEY: misc_feature
<222> LOCATION: (759)..(760)
<223> OTHER INFORMATION: n is a, c, g, or t
<220> FEATURE:
<221> NAME/KEY: misc_feature
<222> LOCATION: (762)..(762)
<223> OTHER INFORMATION: n is a, c, g, or t
<220> FEATURE:
<221> NAME/KEY: misc_feature
<222> LOCATION: (764)..(764)
<223> OTHER INFORMATION: n is a, c, g, or t
<220> FEATURE:
<221> NAME/KEY: misc_feature
<222> LOCATION: (768)..(770)
<223> OTHER INFORMATION: n is a, c, g, or t
<220> FEATURE:
<221> NAME/KEY: misc_feature
<222> LOCATION: (772)..(777)
<223> OTHER INFORMATION: n is a, c, g, or t
<220> FEATURE:
<221> NAME/KEY: misc_feature
<222> LOCATION: (783)..(783)
<223> OTHER INFORMATION: n is a, c, g, or t
<220> FEATURE:
<221> NAME/KEY: misc_feature
<222> LOCATION: (788)..(788)
<223> OTHER INFORMATION: n is a, c, g, or t
<220> FEATURE:
<221> NAME/KEY: misc_feature
<222> LOCATION: (791)..(791)
<223> OTHER INFORMATION: n is a, c, g, or t
<220> FEATURE:
<221> NAME/KEY: misc_feature
<222> LOCATION: (801)..(801)
<223> OTHER INFORMATION: n is a, c, g, or t
<220> FEATURE:
<221> NAME/KEY: misc_feature
<222> LOCATION: (805)..(805)
<223> OTHER INFORMATION: n is a, c, g, or t
<220> FEATURE:
<221> NAME/KEY: misc_feature
<222> LOCATION: (810)..(812)
<223> OTHER INFORMATION: n is a, c, g, or t
<220> FEATURE:
<221> NAME/KEY: misc_feature
<222> LOCATION: (814)..(814)
<223> OTHER INFORMATION: n is a, c, g, or t
<220> FEATURE:
<221> NAME/KEY: misc_feature
```

<222> LOCATION: (818)..(822)
<223> OTHER INFORMATION: n is a, c, g, or t
<220> FEATURE:
<221> NAME/KEY: misc_feature
<222> LOCATION: (830)..(832)
<223> OTHER INFORMATION: n is a, c, g, or t
<220> FEATURE:
<221> NAME/KEY: misc_feature
<222> LOCATION: (837)..(839)
<223> OTHER INFORMATION: n is a, c, g, or t
<220> FEATURE:
<221> NAME/KEY: misc_feature
<222> LOCATION: (843)..(844)
<223> OTHER INFORMATION: n is a, c, g, or t
<220> FEATURE:
<221> NAME/KEY: misc_feature
<222> LOCATION: (846)..(846)
<223> OTHER INFORMATION: n is a, c, g, or t
<220> FEATURE:
<221> NAME/KEY: misc_feature
<222> LOCATION: (852)..(853)
<223> OTHER INFORMATION: n is a, c, g, or t
<220> FEATURE:
<221> NAME/KEY: misc_feature
<222> LOCATION: (857)..(859)
<223> OTHER INFORMATION: n is a, c, g, or t

<400> SEQUENCE: 80
ctacctgcaa gtcgaacggt aacaggaagc agcttgctgc ttcgccgacg agtggcggac      60
gggtgagtaa tgtctgggaa actgcctgat ggagggggat aactactgga aacggtagct     120
aataccgcat aacgtcttcg gaccaaagag ggggaccttc gggcctcttg ccatcagatg     180
tgcccagatg ggattagcta gtaggtgggg taatggctca cctaggcgac gatccctagc     240
tggtctgaga ggatgaccag ccacactgga actgagacac ggtccagact cctacgggag     300
gcagcagtgg ggaatattgc acaatgggcg caagcctgat gcagccatgc cgcgtgtatg     360
aagaaggcct tcgggttgta aagtactttc agcgaggagg aaggcgttaa ggttaataac     420
cttagcgatt gacgttactc gcagaagaag caccggctaa ctccgtgcca gcagccgcgg     480
taatacggag ggtgcaagcg ttaatcggaa ttactgggcg taaagcgcac gcaggcggtc     540
tgtcaagtcg gatgtgaaat ccccgggctc aacctgggaa ctgcattcga actgacagg      600 ctagagtctt gtagaggggg gtagaattcc aggtgtagcg gtgangnnnn nncnncnggg     660
gggnnnngng cngccggggg cccccgcgaa aaancaaaga ctgacgctca ngtgcgaaag     720
cgtggggagc aaacaggatt agataccctg gnaatnccnn cncnaaannn annnnnnttt     780
ggnaggtngg ncctcttga ngggnggggn nntncggnnn nnaacgctan nnagtcnnna      840
ccnncnagcg gnnggnnnt acggc                                           865

<210> SEQ ID NO 81
<211> LENGTH: 868
<212> TYPE: DNA
<213> ORGANISM: Artificial Sequence
<220> FEATURE:
<223> OTHER INFORMATION: GS1-1-5-27F_H05.ab1
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (749)..(749)
<223> OTHER INFORMATION: n is a, c, g, or t
<220> FEATURE:
<221> NAME/KEY: misc_feature
<222> LOCATION: (762)..(763)
<223> OTHER INFORMATION: n is a, c, g, or t
<220> FEATURE:

<221> NAME/KEY: misc_feature
<222> LOCATION: (777)..(781)
<223> OTHER INFORMATION: n is a, c, g, or t
<220> FEATURE:
<221> NAME/KEY: misc_feature
<222> LOCATION: (793)..(793)
<223> OTHER INFORMATION: n is a, c, g, or t
<220> FEATURE:
<221> NAME/KEY: misc_feature
<222> LOCATION: (797)..(797)
<223> OTHER INFORMATION: n is a, c, g, or t
<220> FEATURE:
<221> NAME/KEY: misc_feature
<222> LOCATION: (824)..(824)
<223> OTHER INFORMATION: n is a, c, g, or t
<220> FEATURE:
<221> NAME/KEY: misc_feature
<222> LOCATION: (830)..(830)
<223> OTHER INFORMATION: n is a, c, g, or t
<220> FEATURE:
<221> NAME/KEY: misc_feature
<222> LOCATION: (833)..(833)
<223> OTHER INFORMATION: n is a, c, g, or t
<220> FEATURE:
<221> NAME/KEY: misc_feature
<222> LOCATION: (835)..(836)
<223> OTHER INFORMATION: n is a, c, g, or t
<220> FEATURE:
<221> NAME/KEY: misc_feature
<222> LOCATION: (852)..(852)
<223> OTHER INFORMATION: n is a, c, g, or t
<220> FEATURE:
<221> NAME/KEY: misc_feature
<222> LOCATION: (854)..(854)
<223> OTHER INFORMATION: n is a, c, g, or t
<220> FEATURE:
<221> NAME/KEY: misc_feature
<222> LOCATION: (856)..(858)
<223> OTHER INFORMATION: n is a, c, g, or t
<220> FEATURE:
<221> NAME/KEY: misc_feature
<222> LOCATION: (860)..(860)
<223> OTHER INFORMATION: n is a, c, g, or t

<400> SEQUENCE: 81

```
ctaccntgca gtcgagcggt agcacaggga gcttgctcct gggtgacgag cggcggacgg      60
gtgagtaatg tctgggaaac tgcctgatgg aggggataac tactggaaac ggtagctaa     120 taccgcataa cgtcttcgga ccaaagtggg ggaccttcgg gcctcatgcc atcagatgtg    180
cccagatggg attagctagt aggtgaggta atggctcacc taggcgacga tccctagctg    240
gtctgagagg atgaccagcc acactggaac tgagacacgg tccagactcc tacgggaggc    300
agcagtgggg aatattgcac aatgggcgca agcctgatgc agccatgccg cgtgtatgaa    360
gaaggccttc gggttgtaaa gtactttcag cgaggaggaa ggcgttaagg ttaataacct    420
tagcgattga cgttactcgc agaagaagca ccggctaact ccgtgccagc agccgcggta    480
atacggaggg tgcaagcgtt aatcggaatt actgggcgta aagcgcacgc aggcggtctg    540
tcaagtcgga tgtgaaatcc ccgggctcaa cctgggaact gcattcgaaa ctgacaggct    600
agagtcttgt agagggggt agaattccag gtgtagcggt gaaatgcgta gagatctgga    660
ggaataccgg tggcgaaggc ggcccctgg acaaagactg acgctcaggt gcgaaagcgt    720
ggggagcaaa caggattaga taccctggna gtccacgccg tnncgatgtc gacttgnnnn    780
ngttcccttg agngtgnttc cggagctacg cgttagtcga cgcnggggan tangnncagt    840
aaactcaaat gnantnnncn gggggccc                                       868
```